US011654343B2

(12) United States Patent
Lee

(10) Patent No.: US 11,654,343 B2
(45) Date of Patent: May 23, 2023

(54) EXERCISE HISTORY MANAGING DEVICE, EXERCISE HISTORY MANAGING METHOD, AND COMPUTER PROGRAM FOR EXECUTING SAME IN COMPUTER

(71) Applicant: Ki Won Lee, Seoul (KR)

(72) Inventor: Ki Won Lee, Seoul (KR)

( * ) Notice: Subject to any disclaimer, the term of this patent is extended or adjusted under 35 U.S.C. 154(b) by 0 days.

(21) Appl. No.: 17/296,930

(22) PCT Filed: Nov. 26, 2019

(86) PCT No.: PCT/KR2019/016354
§ 371 (c)(1),
(2) Date: May 25, 2021

(87) PCT Pub. No.: WO2020/111722
PCT Pub. Date: Jun. 4, 2020

(65) Prior Publication Data
US 2022/0023737 A1    Jan. 27, 2022

(30) Foreign Application Priority Data

Nov. 26, 2018  (KR) .......................... 10-2018-0147697
Dec. 28, 2018  (KR) .......................... 10-2018-0173081

(51) Int. Cl.
*A63B 71/06*       (2006.01)
*G06F 3/04817*     (2022.01)
(Continued)

(52) U.S. Cl.
CPC ........ *A63B 71/0619* (2013.01); *G06F 3/0484* (2013.01); *G06F 3/04817* (2013.01);
(Continued)

(58) Field of Classification Search
None
See application file for complete search history.

(56) References Cited

U.S. PATENT DOCUMENTS 6,312,363 B1 *  11/2001  Watterson .......... A63B 22/0235
                                                    482/54
9,563,450 B1 *   2/2017  Totale ................. G06F 9/44589
(Continued)

FOREIGN PATENT DOCUMENTS

KR    10-2015-0128970 A    11/2015
KR    10-2016-0049090 A     5/2016
(Continued)

OTHER PUBLICATIONS

International Search Report and Written Opinion dated Mar. 4, 2020 in International Application No. PCT/KR2019/016354, in 11 pages. (English translation of ISR in 3 pages).

*Primary Examiner* — Daniel Rodriguez
*Assistant Examiner* — Gabriel Mercado
(74) *Attorney, Agent, or Firm* — Knobbe, Martens, Olson & Bear, LLP

(57) ABSTRACT

The application relates to an exercise history managing device. In one aspect, the device includes a map data providing unit configured to provide, to a user terminal, map data about a specific area requested by the user terminal. The device may also include a user relation managing unit configured to manage a relationship between each user and the other users. The device may further include an exercise information managing unit configured to receive information about at least one of an exercise name that is input through the user terminal, a first category obtained by classifying exercises belonging to each exercise name according to a first condition, a second category obtained by classifying an exercise belonging to the first category according to a second condition, and a specific exercise belonging to the second category, store the information, and retrieve exercise information in response to a request from the user terminal.

41 Claims, 98 Drawing Sheets

(51) Int. Cl.
*G06F 3/0484* (2022.01)
*G06F 3/04847* (2022.01)
*G16H 20/30* (2018.01)

(52) U.S. Cl.
CPC .... *G06F 3/04847* (2013.01); *A63B 2071/065* (2013.01); *G16H 20/30* (2018.01)

(56) References Cited

U.S. PATENT DOCUMENTS

| | | | | |
|---|---|---|---|---|
| 2003/0142125 | A1* | 7/2003 | Salmimaa | H04M 1/72454 715/733 |
| 2004/0229729 | A1* | 11/2004 | Albert | A63B 24/0062 482/8 |
| 2009/0217201 | A1* | 8/2009 | Bocking | G06Q 10/109 715/810 |
| 2010/0267521 | A1* | 10/2010 | Matsunaga | G16H 20/30 482/9 |
| 2011/0060988 | A1* | 3/2011 | Mysliwy | G06F 3/0482 715/702 |
| 2012/0182431 | A1* | 7/2012 | Asanov | A63F 13/335 348/207.1 |
| 2012/0191147 | A1* | 7/2012 | Rao | G16H 20/17 607/3 |
| 2012/0283855 | A1* | 11/2012 | Hoffman | A63B 24/0062 700/91 |
| 2013/0035220 | A1* | 2/2013 | Adams | A63B 21/156 482/129 |
| 2014/0214446 | A1* | 7/2014 | Nusbaum | G09B 19/00 705/2 |
| 2015/0182839 | A1* | 7/2015 | Taylor | A63B 22/001 482/52 |
| 2015/0185967 | A1* | 7/2015 | Ly | G06F 3/0488 715/720 |
| 2015/0287338 | A1* | 10/2015 | Wells | G09B 23/288 702/19 |
| 2015/0306457 | A1* | 10/2015 | Crankson | A43C 19/00 700/91 |
| 2015/0317063 | A1* | 11/2015 | Felt | G06F 3/0488 715/835 |
| 2017/0289340 | A1 | 10/2017 | Wong et al. | |
| 2018/0064991 | A1* | 3/2018 | Yanev | A63B 21/154 |
| 2019/0060708 | A1* | 2/2019 | Fung | G06F 3/012 |
| 2020/0047027 | A1* | 2/2020 | Ward | A63B 24/0021 |
| 2020/0139187 | A1* | 5/2020 | Kennington | A63B 21/154 |
| 2020/0267191 | A1* | 8/2020 | Pankey | G06F 3/0482 |

FOREIGN PATENT DOCUMENTS

| | | |
|---|---|---|
| KR | 10-2016-0139922 A | 12/2016 |
| KR | 10-2018-0098515 A | 8/2018 |

* cited by examiner

FIG. 80
"LIVING AND LOVING" IS FATE AND NATURAL INSTINCT OF HUMAN BEINGS.
EXERCISE IS ONLY WAY TO INCREASE PROBABILITIES OF THOSE TWO TOGETHER
 BECAUSE WHEN YOU EXERCISE MOVE    YOU BECOME HEALTHY LIVE   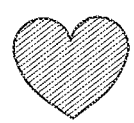 AND BEAUTIFUL LOVE

EXERCISE HISTORY MANAGING DEVICE, EXERCISE HISTORY MANAGING METHOD, AND COMPUTER PROGRAM FOR EXECUTING SAME IN COMPUTER

The present application is a U.S. national phase application under 35 U.S.C. § 371 of International Application No. PCT/KR2019/016354, filed on Nov. 26, 2019, which claims the benefit of Korean Patent Application Nos. 1 0-201 8-01 47697 and 10-2018-0173081 filed on Nov. 26, 2018 and Dec. 28, 2018, respectively, in the Korean Intellectual Property Office, the entire disclosure of each of which is incorporated herein by reference.

TECHNICAL FIELD

The present disclosure relates to an exercise history managing device, an exercise history managing method, and a computer program for executing the same in a computer.

BACKGROUND ART

Most people, who sign up for a gym to exercise, have a hard time keeping up with their initial determination after a few days. In particular, in the case of exercise performed by themselves, such as Weight Training, people easily get bored and have difficulty in continuing the exercise because they do not feel the meaning of the exercise day by day.

In this case, one piece of advice from a person who is successfully and consistently performing an exercise is saying people to come to a gym on days when they don't want to exercise and to just watch people without exercising. This is because, in many cases, people have the experience of regaining their motivations to exercise just by watching people who exercise hard.

It is known that human beings described as social animals are known to have a tendency to match their behavior to the behavior of another person, particularly the behavior of a group. The behavior of unconsciously matching oneself with the person being communicated with can be easily observed in everyday life. Further, researchers from various academic fields are exploring the effect of other people's actions on individuals, examples of which include a study in the field of anthropology on the sense of unity and sublimation, which are testified by a group dance that exists in various cultures in common, a study on the "mirror neurons" of primates, published in 1999 by neuroscientist Marco Iacoboni, and the like.

DESCRIPTION OF EMBODIMENTS

Technical Problem

Embodiments of the present disclosure are directed to providing an exercise history managing device, an exercise history managing method, and a computer program for executing the same in a computer, allowing users to share exercise records with each other to increase the motivation to exercise.

Solution to Problem

One aspect of the present disclosure provides an exercise history managing device including: a map data providing unit configured to provide, to a user terminal, map data about a specific area requested by the user terminal; a user relation managing unit configured to manage a relationship between each user and the other users; an exercise information managing unit configured to receive information about at least one of an exercise name that is input through the user terminal, a first category obtained by classifying exercises belonging to each exercise name according to a first condition, a second category obtained by classifying an exercise belonging to the first category according to a second condition, and a specific exercise belonging to the second category, store the information, and retrieve exercise information in response to a request from the user terminal and provide the same to the user terminal; and an exercise log managing unit configured to receive predetermined exercise log information transmitted from the user terminal, store the same, and retrieve exercise log in response to a request from the user terminal and provide the retrieved exercise log information to the user terminal.

Advantageous Effects

Embodiments of the present disclosure allow users to share exercise records with each other to increase the motivation to exercise.

BRIEF DESCRIPTION OF DRAWINGS

FIGS. 74 to 80 are views illustrating a photo zoom-in page of the exercise history management system according to an embodiment of the present disclosure and an icon "like" displayed on the photo zoom-in page.

MODES OF DISCLOSURE

Figure 1:
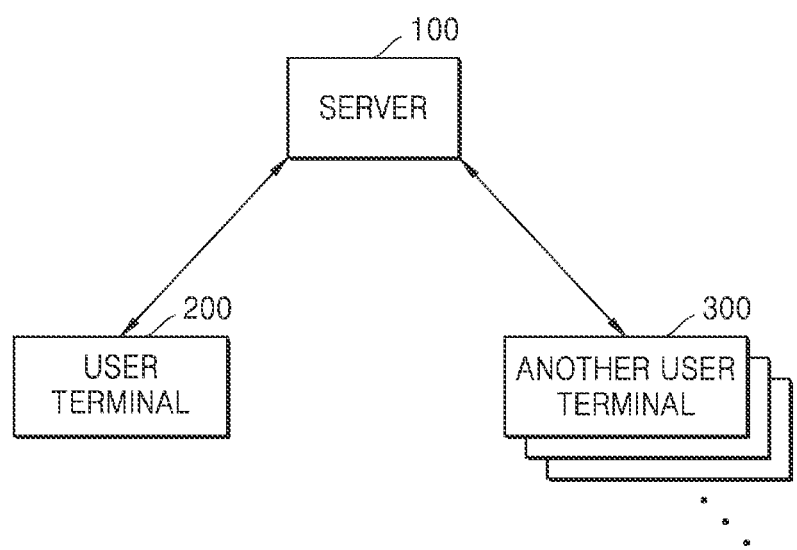
FIG. 1 is a diagram illustrating a configuration of an exercise history management system according to an embodiment of the present disclosure.

Detailed descriptions of the present disclosure will be made below with reference to the accompanying drawings illustrating specific embodiments in which the present disclosure may be implemented by way of example. These embodiments are described in detail to be sufficient for those skilled in the art to implement the present disclosure. It should be understood that various embodiments of the present disclosure are different from each other but are not necessarily mutually exclusive. For example, the specific shapes, structures, and characteristics described herein may be changed from one embodiment to another embodiment and implemented without departing from the spirit and scope of the present disclosure. It should also be understood that the locations or arrangements of individual components in each embodiment may also be varied without departing from the spirit and scope of the present disclosure. Accordingly, the following detailed description is not to be construed as limiting, and it should be understood that the scope of the present disclosure encompasses the scope claimed by the claims and all scopes equivalent thereto. Like reference numerals in the drawings denote like elements throughout the specification.

Hereinafter, various embodiments of the present disclosure will be described in detail with reference to the accompanying drawings so that those skilled in the art can easily implement the present disclosure.

FIG. 1 is a diagram illustrating a configuration of an exercise history management system according to an embodiment of the present disclosure.

Referring to FIG. 1, the exercise history management system according to an embodiment of the present disclosure includes a service server 100, a user terminal 200, and another user terminal 300. Here, the service server 100 may be an example of an exercise history managing device of the present disclosure, and the user terminal 200 may be an example of a display control device of the present disclosure The service server 100 according to an embodiment of the present disclosure may control the user terminal 200 to display an exercise log and manage an exercise history. That is, the service server 100 may provide map data about a specific area, which is requested by the user terminal 200, to the user terminal 200. In addition, the service server 100 may receive predetermined user information transmitted from the user terminal 200, store the user information, and, in response to a request from the user terminal 200, retrieve the user information and provide the retrieved user information to the user terminal 200. In addition, the service server 100 may store and manage a relationship between each user and other users. In addition, the service server 100 may receive information about gyms from the user terminal 200, store the received information, and, in response to a request from the user terminal 200, retrieve the gym information and provide the retrieved information to the user terminal 200. In addition, the service server 100 may receive exercise information, store the received exercise information, and, in response to a request from the user terminal 200, retrieve the exercise information and provide the retrieved exercise information to the user terminal 200. In addition, the service server 100 may receive predetermined exercise log information transmitted from the user terminal 200, store the exercise log information, and, information in response to a request from the user terminal 200, retrieve the exercise log and provide the retrieved exercise log information to the user terminal 200.

The user terminal 200 refers to a communication terminal capable of using an application that is provided by the service server 100 in a wired or wireless communication environment. Here, the user terminal 200 may be a portable terminal of the user. In more detail, the user terminal 200 may include a computer (e.g., a desktop, a laptop, a tablet, or the like), a media computing platform (e.g., a cable or satellite set-top box, a digital video recorder, or the like), a handheld computing device (e.g., a personal digital assistant (PDA), an email client, or the like), any form of mobile phone, a form of wearable device that is used while being attached to and worn on a user's body, or any other type of computing or communication platform, but the present disclosure is not limited thereto.

Meanwhile, the service server 100 may also communicate with another user terminal 300 used by the other users other than the user himself/herself. The description of the user terminal 200 made above may be applied to another user terminal 300 as it is. However, in the present specification, for convenience of description, a terminal of each of the other users is classified and referred to as another user terminal 300 from a point of the user of the user terminal 200, which uses the exercise history managing method of the present disclosure. Accordingly, a user of another user terminal 300 may also be the user of the user terminal 200 described herein.

Meanwhile, the service server 100, the user terminal 200, and another user terminal 300 may communicate with each other through a communication network. In this case, the communication network refers to a communication network that provides a connection path so that the user terminals 200 and 300 are connected to the service server 100 and then transmits and receives data thereto and therefrom. The communication network may include, for example, a wired network such as a local area network (LAN), a wide area network (WAN), a metropolitan area network (MAN), and an integrated service digital network (ISDN), and a wireless network such as a wireless LAN, a code division multiple access (CDMA) network, a Bluetooth network, and a satellite communication network, but the present disclosure is not limited thereto.

Figure 2:
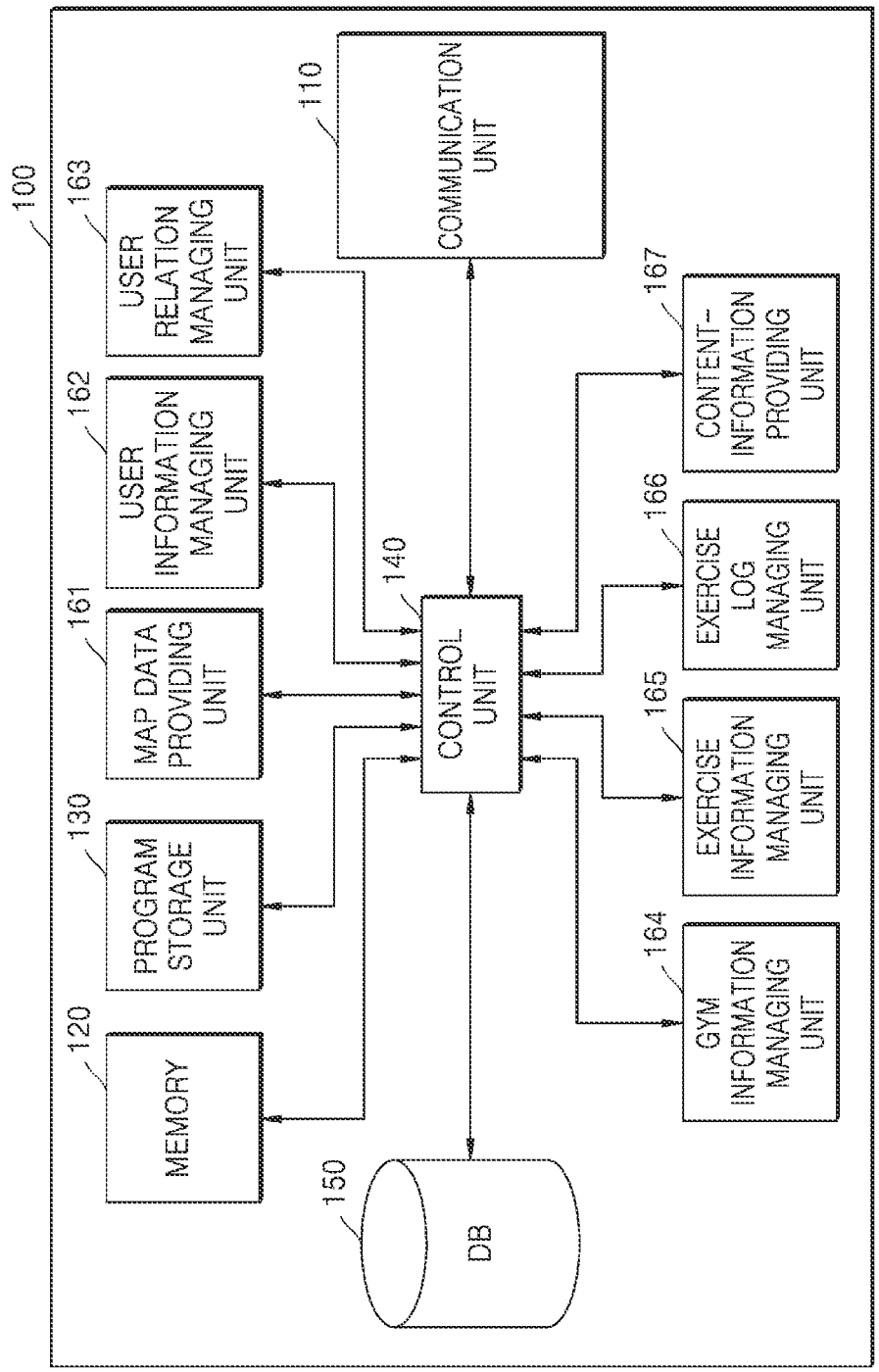
FIG. 2 is a block diagram illustrating an example of an internal configuration of an exercise history managing device shown in FIG. 1.

FIG. 2 is a block diagram illustrating an example of an internal configuration of the service server 100 shown in FIG. 1.

Referring to FIG. 2, the service server 100 may include a communication unit 110, a memory 120, a program storage unit 130, a control unit 140, a database 150, a map data providing unit 161, a user information managing unit 162, a user relation managing unit 163, a gym information managing unit 164, an exercise information managing unit 165, an exercise log managing unit 166, and a content-information providing unit 167.

The communication unit 110 provides a communication interface necessary for providing a transmission/reception signal between the service server 100 and the user terminals 200 and 300 in the form of packet data. Here, the communication unit 110 may be a device including hardware and software necessary for transmitting and receiving a signal, such as a control signal or a data signal, to and from another network device through a wired or wireless connection.

The memory 120 performs a function of temporarily or permanently storing data to be processed by the control unit 140. Here, the memory 120 may include a magnetic storage medium or flash storage medium, but the scope of the present disclosure is not limited thereto.

The program storage unit 130 may store a program composed of commands instructing all processes executed by the control unit 140, which will be described below, according to an embodiment of the present disclosure.

The control unit 140 is a type of central processing unit and controls the entire process of managing the exercise history, such as receiving an exercise log from the user terminal and providing the exercise log of the user terminal and/or other users to the user terminal. That is, the control unit 140 may perform a function of executing control software installed in the program storage unit 130 and controlling each unit in the service server 100 to provide information such as the exercise history to the user terminal 200.

Here, the control unit 140 may include any type of devices which are capable of processing data, such as a processor. Here, a processor may refer to, for example, a data processing device embedded in hardware that has a physically structured circuit to perform a function expressed by codes or commands included in a program. Examples of the data processing device embedded in the hardware may include processing devices such as a microprocessor, a central processing unit (CPU), a processor core, a multiprocessor, an application-specific integrated circuit (ASIC), and a field-programmable gate array (FPGA), but the scope of the present disclosure is not limited thereto.

The database 150 may include a user database that stores user information, a map information database that stores map information, a user relationship information database that stores user relationship information, a gym information database that stores gym information, an exercise information database that stores exercise information, an exercise log database that stores exercise logs, and a content-information database that stores content information.

The map data providing unit 161 may serve to provide map data about a specific area, which is requested by the user terminal 200, to the user terminal 200. Here, the specific area may be an area corresponding to a gym location, which is included in the data transmitted from the user terminal 200, or may be an area including a current location of the user terminal 200. Alternatively, when the use of location information is not selected in the user terminal 200 (e.g., a global positioning system (GPS) is turned off), the specific area may be an area corresponding to the map data most recently received by the user.

The user information managing unit 162 may receive predetermined user information transmitted from the user terminal 200, store the user information, and retrieve the user information in response to a request from the user terminal 200 and provide the retrieved user information to the user terminal 200. Here, the user information may include user authentication information (e.g., an email, a password, or the like), user personal information (e.g., a name of the user, a gender, a birth month, a photo, an exercise count, the number of users who have been pooled (followed) by me, the number of users who have been pooled me, user comments, and the like), user's preferred exercise information, user's gym information, and the like. Furthermore, the user information may further include a date badge (e.g., a badge of a "birthday exerciser," and "Eve exerciser," or the like), a city badge (e.g., a badge indicating the country, city, or the like in which the exercise was performed), and the like.

The user relation managing unit 163 manages the relationship between each user and other users, and may be referred to as a component that provides a type of social network service. That is, the user relation managing unit 163 manages a series of processes such as requesting, accepting, rejecting, and storing a pooling (or following) relationship between the users.

The gym information managing unit 164 may receive information about gyms, store the received information, and retrieve the gym information in response to a request from the user terminal 200 and provide the retrieved gym information to the user terminal 200. Here, the gym information may include a name, a location, a photo, possible exercises, provided exercise equipment, registered users, and the like of the gym.

The exercise information managing unit 165 may receive information about exercises, store the received information, and retrieve the exercise information in response to a request from the user terminal 200 and provide the retrieved exercise information to the user terminal 200. Here, the exercise information may include pieces of information on exercise names, first categories obtained by classifying the exercises belonging to each exercise name according to a first condition, second categories obtained by classifying the exercises belonging to the first category according to a second condition, and specific exercises belonging to the second category.

For example, when Weight Training is taken as an example of the exercise name, a first category of Weight Training may include a core exercise, a lower body exercise, an upper body-pull exercise, an upper body-push exercise, a whole-body exercise, and the like.

Further, information on an operation order and a part on which the exercise is performed of each specific exercise may also be included as information on each specific exercise.

The exercise log managing unit 166 may receive predetermined exercise log information transmitted from the user terminal 200, store the exercise log information, and retrieve the exercise log information in response to a request from the user terminal 200 and provide the retrieved exercise log information to the user terminal 200. Here, the exercise log may include the name of exercise performed (per set), the weight of the exercise, an exercise count (per set), exercise duration (per set), comments, and the like. Here, the exercise log managing unit 166 may provide an exercise log of another user to the user terminal 200 so that the exercise log of another user is displayed on the user terminal 200 as an image representing an exercise. In addition, the exercise log managing unit 166 may provide each user terminal 200 with exercise logs of other users currently exercising, other users exercising in a preferred gym of the user, and other users having a pooling relationship with the user.

The content-information providing unit 167 may receive information about contents, store the received information, and retrieve the content information in response to a request from the user terminal 200 and provide the retrieved content information to the user terminal 200.

Further, although not shown in the drawings, the service server 100 according to an embodiment of the present disclosure may further include a memory, an input/output unit, a program storage unit, and a control unit.

The functions and configurations of each component of the service server 100 will be described in more detail in a description of each screen of an application to be described below.

Figure 3:
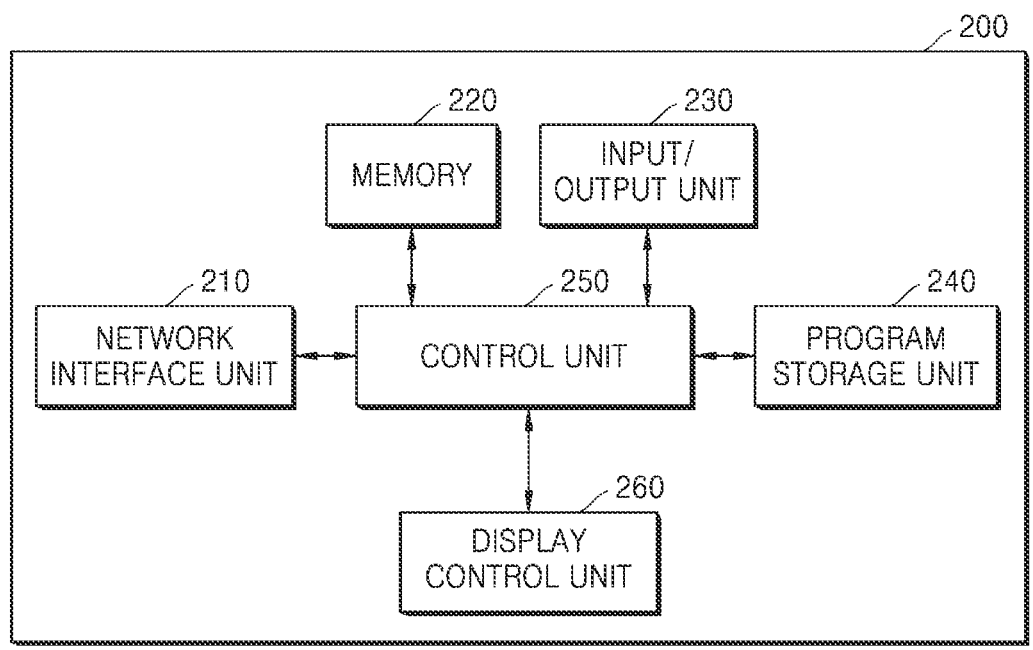
FIG. 3 is a block diagram illustrating an example of an internal configuration of a display control device shown in FIG. 1.

FIG. 3 is a block diagram illustrating an example of an internal configuration of the display control device shown in FIG. 1.

The user terminal 200 of the present disclosure includes a network interface unit 210, a memory 220, an input/output unit 230, a program storage unit 240, a control unit 250, a display control unit 260, and the like.

In more detail, the network interface unit 210 provides a communication interface necessary for receiving data such as the exercise log, the user information, the map data, and the like from the service server 100 in conjunction with a communication network.

The memory 220 performs a function of temporarily storing data processed by the control unit 250 or temporarily storing the exercise log, the map data, and the like transmitted to the user terminal 200.

The input/output unit 230 may be configured as a touch recognition display controller or one of other various input/output controllers. In an example, the touch recognition display controller provides an output interface and an input interface between the device and the user. The touch recognition display controller transmits and receives electrical signals to and from the control unit. In addition, the touch recognition display controller may display a visual output to the user, and the visual output may include text, graphics, an image, a video, and a combination thereof. The input/output unit 230 may be, for example, a display member such as an organic light-emitting display (OLED) or a liquid crystal display (LCD) having a touch recognition function.

The program storage unit 240 includes control software performing an operation of receiving the exercise log and the map data from the service server 100, an operation of displaying data such as the exercise log and the map data on the input/output unit 230 of the user terminal 200, an operation of receiving a user input signal, and the like.

The control unit 250 is a type of central processing unit, and controls the entire process of providing an exercise history management service in the user terminal 200. That is, the control unit 250 executes the control software installed in the program storage unit 240, and controls the display control unit 260 to provide various services, e.g., displaying the exercise log and/or map data on the input/output unit 230 of the user terminal 200.

The display control unit 260 controls pages displayed on the input/output unit 230 on the basis of the input of the recognized user.

The detailed functions and roles of the display control unit 260 will be described in more detail in the description of each screen of the application to be described below.

In an embodiment, the display control unit 260 may control such that a map page is displayed on the user terminal. As will be described below with reference to FIGS. 4 to 7, a map page 1100 may include a recommended-users display area 1110, a map display area 1120, and a gym display area 1130. Suggested users retrieved by a predetermined algorithm are displayed on the recommended-users display area 1110. Predetermined map data is displayed on the map display area 1120. Information on the selected gym is displayed on the gym display area 1130.

Here, for the convenience of user input, the display control unit 260 may control such that the suggested-users display area overlapping and displayed on the map display area 1120 is not displayed while the user input is being made on the map page. In addition, when the user input is stopped in this state, the recommended-users display area 1110 may be controlled to be displayed again.

In an embodiment, the display control unit 260 may control such that a pool page is displayed on the user terminal. As will be described below with reference to FIGS. 8 to 11, a pool page 1200 may include a user's-in-exercise display area 1210, a my-exercise-state display area 1220, and a user's-not-in-exercise display area 1230.

On the users-in-exercise display area 1210, information on users, who are currently exercising, among the users pooled by the user himself/herself may be displayed, and real-time exercise motions of the users who are exercising may be displayed.

A user's own exercise state may be displayed on the my-exercise-state display area 1220.

On the users-not-in-exercise display area 1230, information on users, who are not currently exercising, among the users pooled by the user himself/herself may be displayed, and in particular, the information on the users who are not currently exercising may be displayed in rows. Here, a time machine icon 1235 may be further displayed in each user area of the users-not-in-exercise display area 1230. When the time machine icon 1235 is selected, a time machine mode may be performed.

In an embodiment, the display control unit 260 may control such that a contents page is displayed on the user terminal. As will be described below with reference to FIGS. 12 to 14, specialized information (anatomy, kinematics, and the like) that beginners need to know in order to exercise may be displayed on a contents page 1300. The contents page 1300 may be provided in the form of a list divided by section.

In an embodiment, the display control unit 260 may control such that an exercise log input area is displayed on the user terminal. As will be described below with reference to FIGS. 15 to 18 and 19 to 24, an exercise log input area 1400 may include an exercise log display portion 1410, an exercise log input and transmission portion 1420, and an input value selection portion 1430.

The exercise log display portion 1410 is an area in which a previously performed exercise is recorded. In more detail, the exercise log display portion 1410 includes one or more exercise log-by-date display portions 1411. In addition, each of the exercise log-by-date display portions 1411 includes one or more individual exercise log display portions 1412. Each of the individual exercise log display portions 1412 may include an exercise name display portion 1413 and an exercise amount display portion 1414. Here, sets of a weight x count of the performed exercise may be sequentially displayed on the exercise amount display portion 1414. The individual exercise log display portions 1412 may be displayed in a compact form, and one thereof is selected, records for each set for the corresponding individual exercise may be displayed in more detail in a drop-down manner. This will be described in more detail with reference to FIGS. 15 to 18.

The exercise log input and transmission portion 1420 includes an exercise name input portion 1421 through which the name of exercise, in which a log is to be recorded, is input, an exercise weight input portion 1422 through which the weight of the exercise is input, an exercise count input portion 1423 through which the number of exercises is input, a comment input portion 1424, and a transmission portion 1425 used for transmitting the above-mentioned items to the server.

Figure 19:
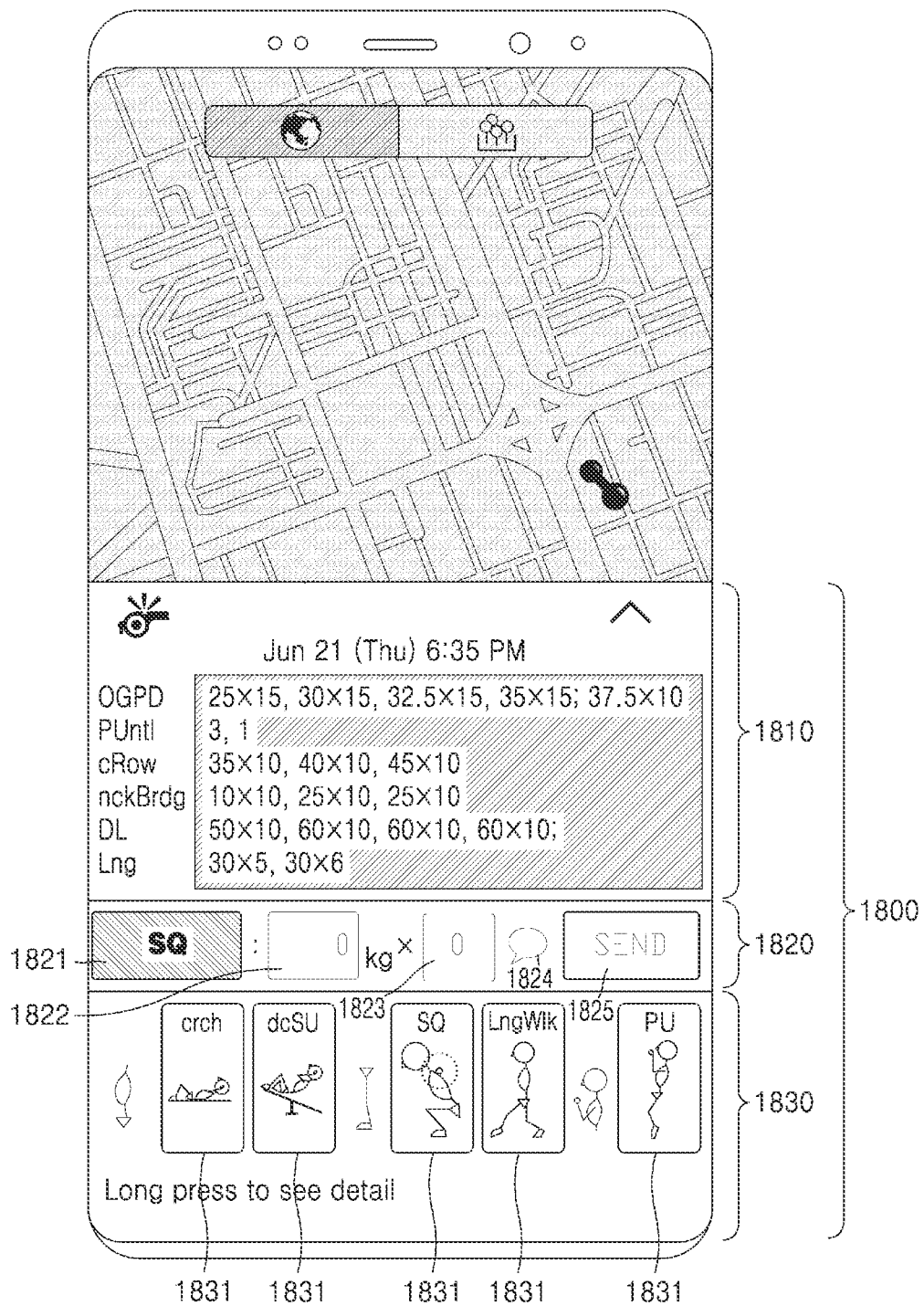
FIGS. 19 to 24 are views illustrating an exercise log input area displayed on the user terminal of the exercise history management system according to an embodiment of the present disclosure.

Referring to FIG. 19, an input value selection portion 1830 is an area on which input values, which change as input items of an exercise log input and transmission portion 1820 are changed, are displayed. In a state in which an exercise name input portion 1821 is selected from the exercise log input and transmission portion 1820, one or more exercise name display portions 1831 may be displayed on the input value selection portion 1830.

Here, when each of the exercise name display portions 1831 is selected, the name or abbreviation of the corresponding exercise may be displayed on the exercise name input portion 1821 of the exercise log input and transmission portion 1820.

Figure 22:
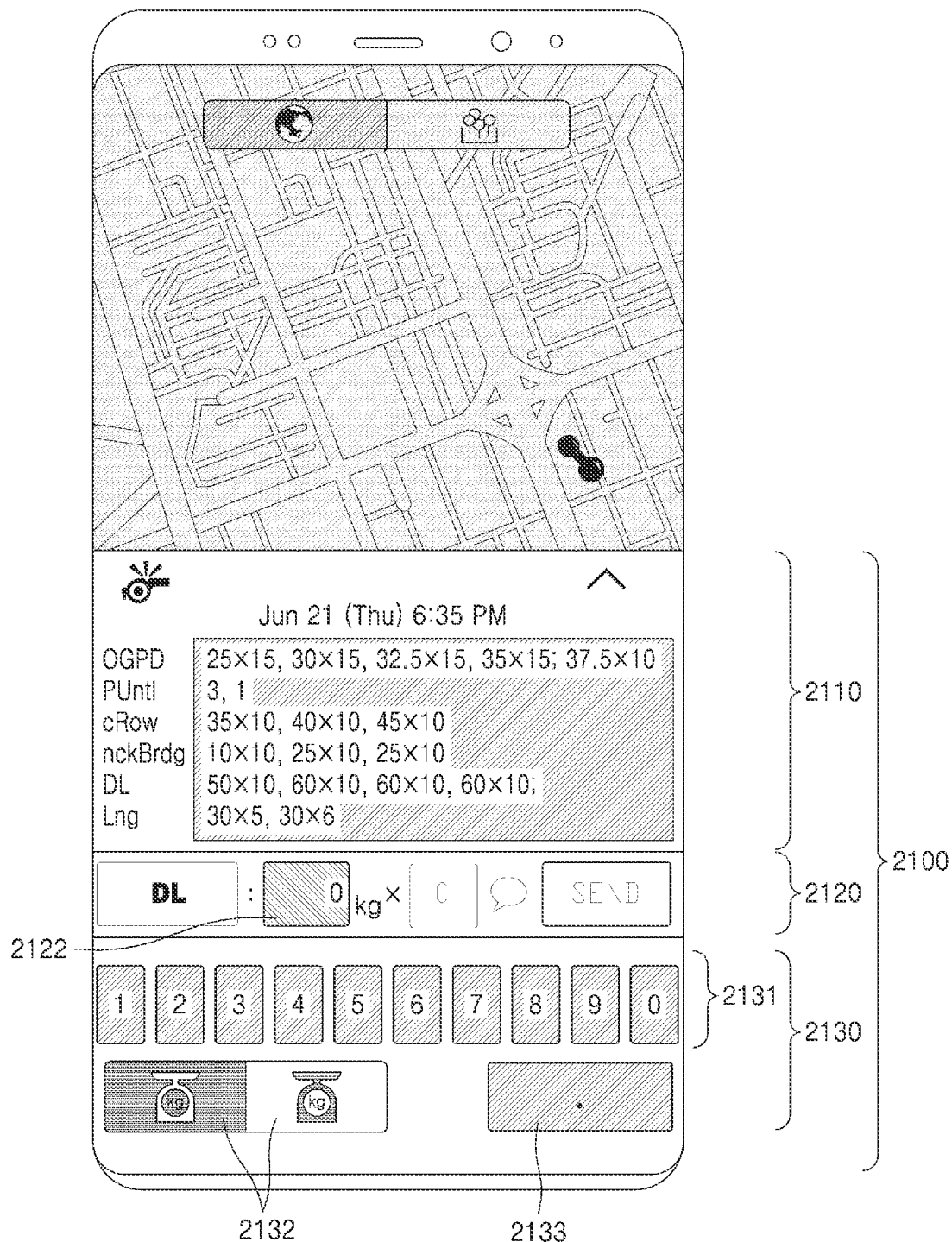

Meanwhile, as shown in FIG. 22, when an exercise weight input portion 2122 is selected from an exercise log input and transmission portion 2120, an exercise weight display portion 2131 is displayed on an input value selection portion 2130. Further, a unit-of-weight selection portion 2132 and a decimal point selection portion 2133 may be further displayed on the input value selection portion 2130. Here, the unit-of-weight selection portion 2132 may be provided in the form of a segmented control window and may be provided to change a unit of weight into a kilogram (kg) scale or a pound (lb) scale.

Figure 23:
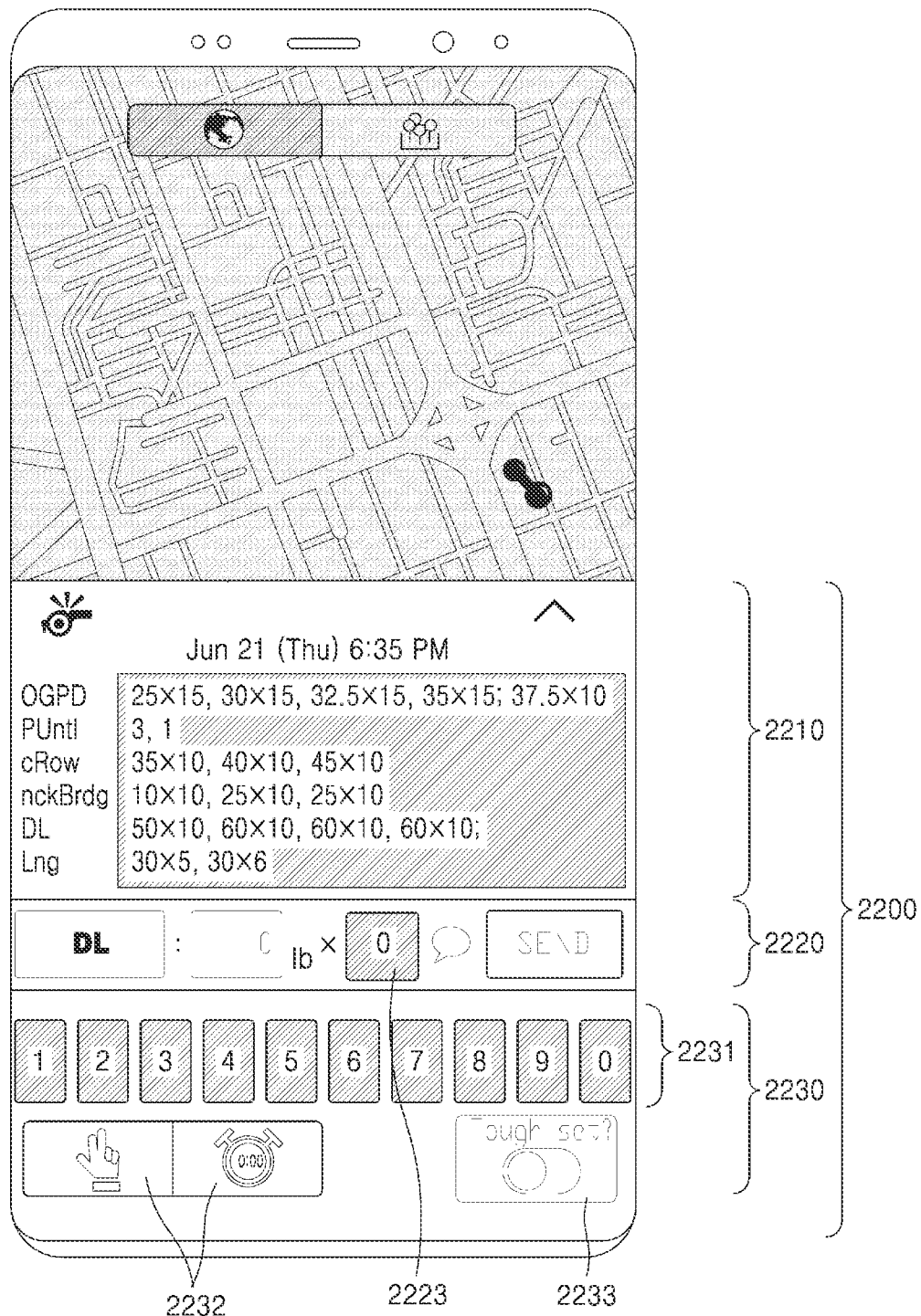

Meanwhile, as shown in FIG. 23, when an exercise count input portion 2223 is selected from an exercise log input and transmission portion 2220, an exercise count display portion 2231 is displayed on an input value selection portion 2230. In addition, a count/duration selection portion 2232 and a tough set input portion 2233 may be further displayed on the input value selection portion 2230. Here, the count/duration selection portion 2232 is provided in the form of a segmented control window to allow the user to select whether the exercise name is a counting exercise or a duration exercise (e.g., an isometric exercise) that maintains the same posture. Here, in the case of the duration exercise, a mark ["], indicating units of seconds, may be displayed on the exercise count input portion 2223.

The input value selection portion will be described in more detail with reference to FIGS. 19 to 24.

In an embodiment, the display control unit 260 may control such that a user-preferred exercise setup page is displayed on the user terminal. As will be described below with reference to FIGS. 25 to 27, a user-preferred exercise setup page 2300 includes a preferred exercise display portion 2310 and a preferred exercise selection portion 2320. An exercise name display portion 2330 and a first category selection portion 2340 may be displayed on the preferred exercise selection portion 2320 of each exercise name.

Here, the name of the corresponding exercise name is displayed on the exercise name display portion 2330 (e.g., Weight Training, Running, or the like). In addition, first categories obtained by classifying exercises belonging to the corresponding exercise name according to a first condition are displayed on the first category selection portion 2340 in the form of icons. Here, the first categories of the corresponding exercise name may be displayed in a first direction (transverse direction on a screen) on the first category selection portion 2340.

When one of a plurality of displayed first categories is selected, second categories 2451 obtained by classifying the exercises, which are belonging to the selected first category, according to a second condition are displayed on a second category selection portion 2450. Here, icons of the second categories of the corresponding exercise name may be displayed in the first direction (transverse direction on the screen) on the second category selection portion 2450.

When one of a plurality of displayed second categories is selected, one or more specific exercises belonging to the selected second category are displayed on a specific exercise selection portion 2460. Here, one or more specific exercises may be sequentially displayed in a second direction (longitudinal direction on the screen). Here, an on/off button of each of the specific exercises may be turned on to select the corresponding specific exercise.

In an embodiment, the display control unit 260 may control such that an exercise log input area is displayed on the user terminal. As will be described below with reference to FIGS. 28 to 31, an exercise log input area 2600 includes an exercise log display portion 2610, an exercise log input and transmission portion 2620, and an input value selection portion 2630. Here, a start/end signal transmission portion 2611 used for transmitting an exercise start/end signal is displayed at a left upper end of the exercise log display portion 2610. In a situation in which the user is not exercising, a whistle icon is displayed on the start/end signal transmission portion 2611. When the user presses the whistle icon, the whistle icon is linked to the exercise start declaration page 2700 of FIG. 29.

In an embodiment, the display control unit 260 may control such that a sign-in page is displayed on the user terminal. As will be described below with reference to FIGS. 32 to 37, an email input portion 3010 and an email transmission portion 3020 are displayed on a sign-in page 3000. This will be described in more detail with reference to FIGS. 32 to 37.

In an embodiment, the display control unit 260 may control such that a member sign-up page is displayed on the user terminal. As will be described below with reference to FIG. 38 to 43, an email input portion 3110 and an email transmission portion 3120 are displayed on a member sign-up page 3100. This will be described in more detail with reference to FIGS. 38 to 43.

In an embodiment, the display control unit 260 may control such that a user information input page is displayed on the user terminal. As will be described below with reference to FIGS. 44 to 49, a user information input page 3200 includes a user image input portion 3210, a user's date pf birth input portion 3220, a user name input portion 3230, a terms display portion 3240, a user gender input portion 3250, and a user information transmission portion 3260. Here, a predetermined color may be already displayed on a border excluding the user's input portions. Here, in the user information input page of the present disclosure, each time each piece of information is input, an area to which the corresponding input portion belongs is displayed in different colors, brightness, and contrast so that an area in which information is not input is clearly expressed.

In an embodiment, the display control unit 260 may control such that a my-gym setup page is displayed on the user terminal. As will be described below with reference to FIGS. 50 to 53, a my-gym setup page 3300 includes a gym list display area 3310, a map display area 3320, and a gym information display area 3330. In addition, the my-gym setup page 3300 may further include a my-gym setup button 3340.

In an embodiment, the display control unit 260 may control such that a user page is displayed on the user terminal. As will be described below with reference to FIGS. 54 to 59, a user image, an exercise count, the number of users who have been pooled (followed) by me, the number of users who have been pooled me, user comments, and the like may be displayed on a user information display portion 3710.

<Map Page>

Figure 4:
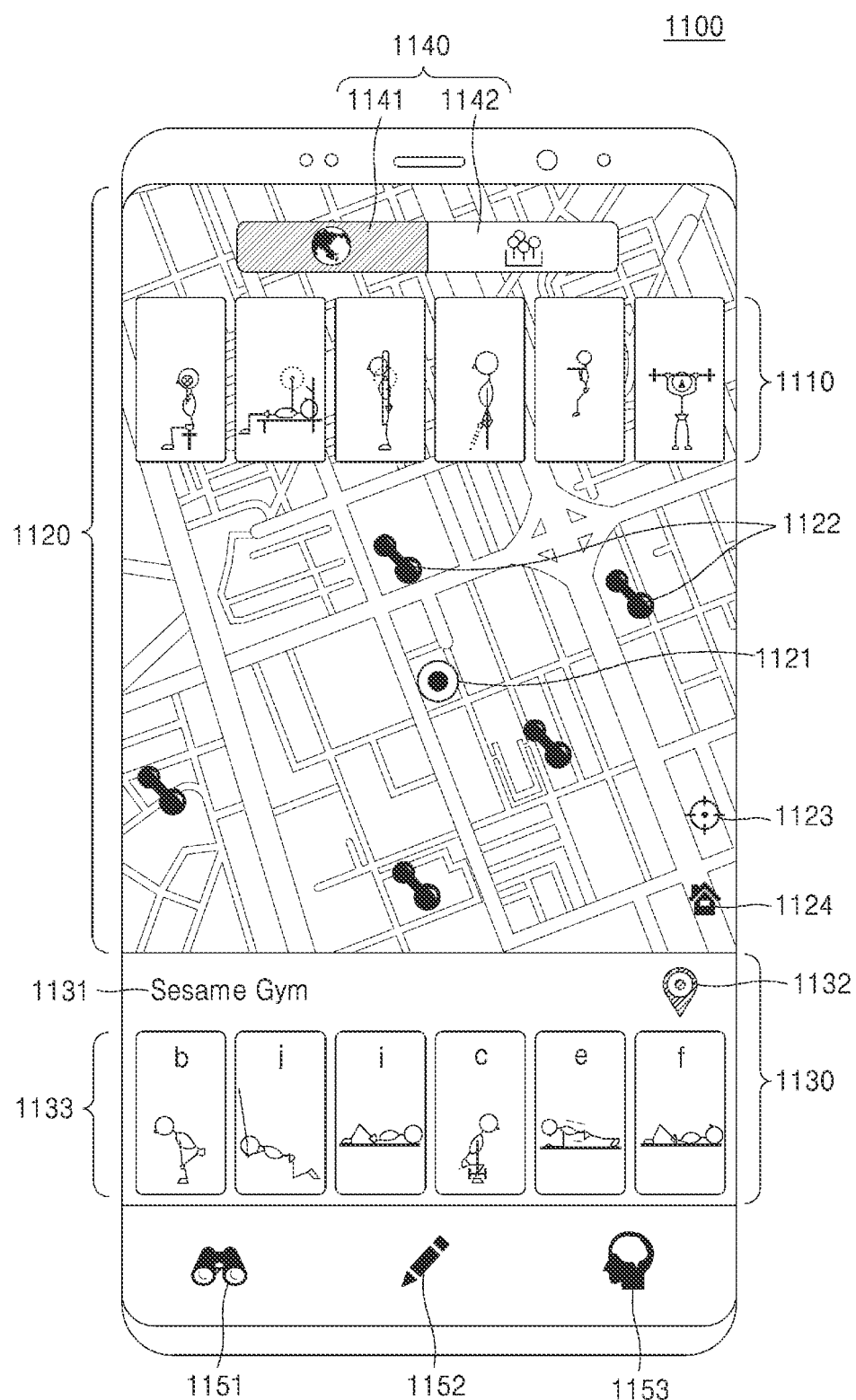
FIGS. 4 to 7 are views illustrating a map page displayed on a user terminal of the exercise history management system according to an embodiment of the present disclosure.

FIG. 4 is a view illustrating a map page displayed on the user terminal of the exercise history management system according to an embodiment of the present disclosure.

The map page 1100 may be an initial screen of the application, which is provided to the user terminal 200 by an exercise history management system 1.

The map page 1100 includes the recommended-users display area 1110, the map display area 1120, and the gym display area 1130.

In addition, a segmented control button 1140, allowing the map page 1100 to be switched to and from the pool page 1200 (see FIG. 8), is displayed at an upper end of the map page 1100. The segmented control button 1140 includes a map page selection button 1141 and a pool page selection button 1142. The map page selection button 1141 on the left of the segmented control button 1140 is selected by default. Here, when the pool page selection button 1142 at the right is selected, the page is switched to the pool page 1200 (see FIG. 8).

That is, a separate navigation bar is not provided at an upper portion of the map page 1100, and the map page 1100 is configured to be moved to the left and right using the segmented control button 1140. Here, when the pool page selection button 1142 is selected, the pool page 1200 (see FIG. 8) may be horizontally moved and displayed on the screen.

In addition, three tab buttons are displayed at a lower end of the map page 1100. Among the three tabs at the lower end, a first tab on the left is a social network linking tab 1151 linking the map page 1100 and a social network page linked to the pool page 1200, a second tab on the center is an exercise log input tab 1152 linked to a page for inputting an exercise history, and a third tab on the right is a content tab 1153 displaying various contents related to an exercise.

Suggested users retrieved by a predetermined algorithm are displayed on the recommended-users display area 1110. That is, users matching the corresponding users, which are extracted among all users currently using the app in consideration of the time, name, pattern, location, or the like of the exercise, is displayed on the recommended-users display area 1110.

Predetermined map data is displayed on the map display area 1120. At the time when the application is executed, a current location 1121 of the user terminal 200 is displayed at the center of a screen in the map display area 1120, and nearby gyms 1122 are displayed at respective locations.

Meanwhile, a button 1123 for displaying the current location on the center of the screen and a button 1124 for displaying my gym on the center of the screen may be displayed on a right lower end of the map display area 1120. When the button 1124 for displaying my gym on the center of the screen is selected, a preset my gym may be displayed at the center of the map display area 1120, and information corresponding to my gym may be displayed on the gym display area 1130.

Information about the selected gym is displayed on the gym display area 1130. At the time when the application is executed, information on a gym, which is closest to my location, may be displayed on the gym display area 1130. When one of the gyms 1122, which are displayed on the map display area 1120, is selected, information about the selected gyms may be displayed on the gym display area 1130.

In more detail, a selected gym name display area 1131 and a button 1132 for displaying the corresponding gym on the center of the map may be displayed may be displayed on an upper end of the gym display area 1130. In addition, a user-in-exercise display area 1133, on which motion information of the user currently exercising in the gym is displayed, is displayed at a lower end of the gym display area 1130. A corresponding exercise and an exercise count generated according to the exercise log transmitted by the corresponding users may be displayed on the user-in-exercise display area 1133.

Figure 5:
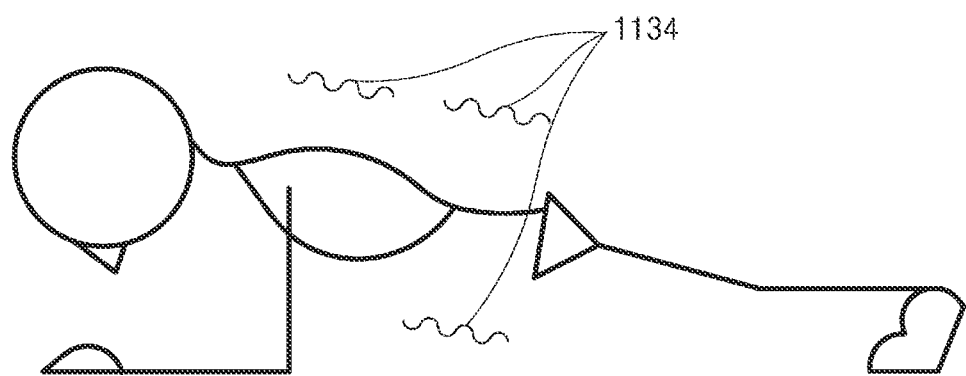

Here, in the case of a duration exercise that lasts for a predetermined period of time rather than a counting exercise expressed by a count number, a shaking icon 1134 may be displayed as shown in FIG. 5.

Figure 6:
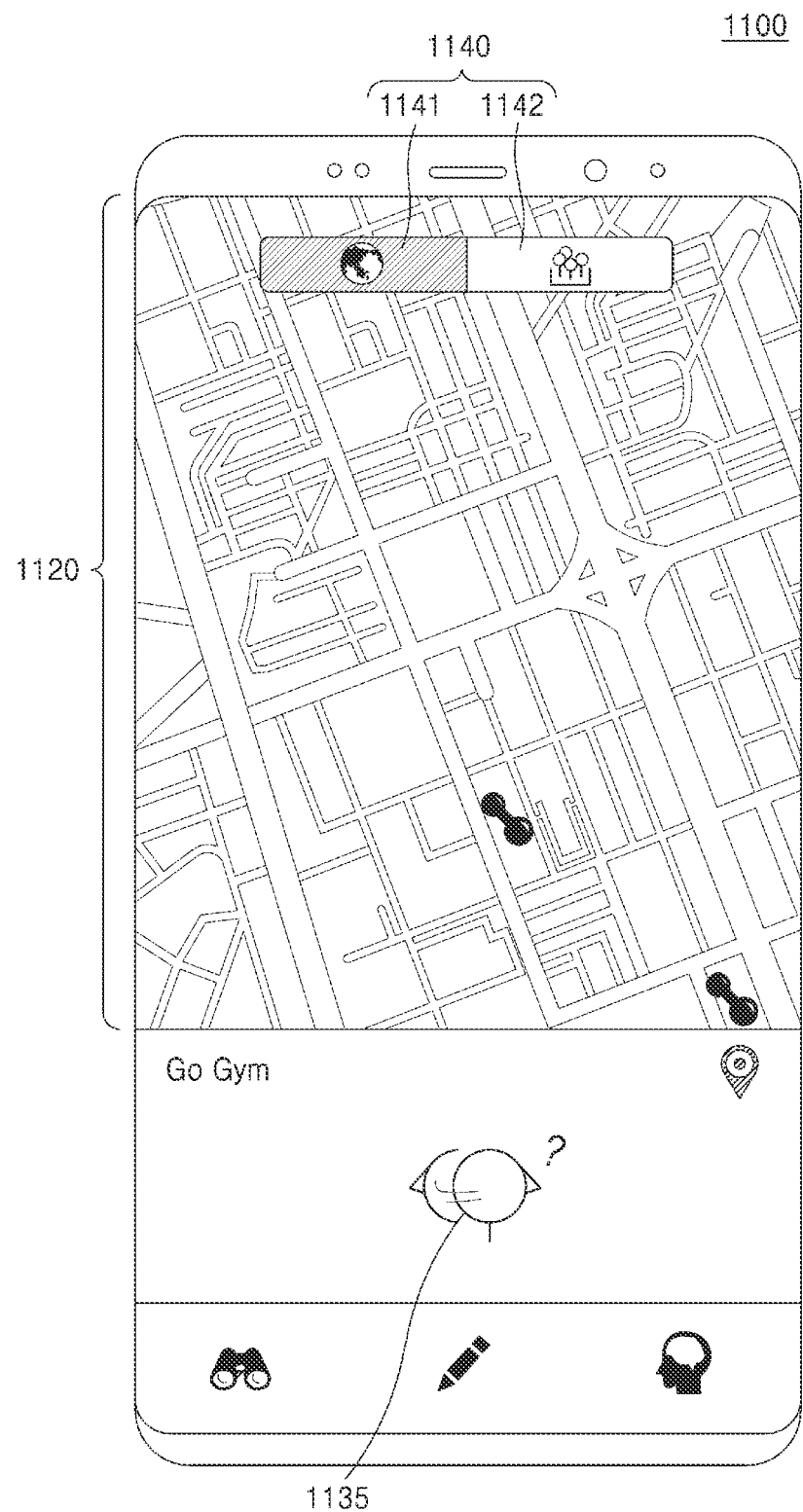

Meanwhile, when no one is currently exercising in the corresponding gym, a looking around icon 1135 may be displayed as shown in FIG. 6.

Figure 7:
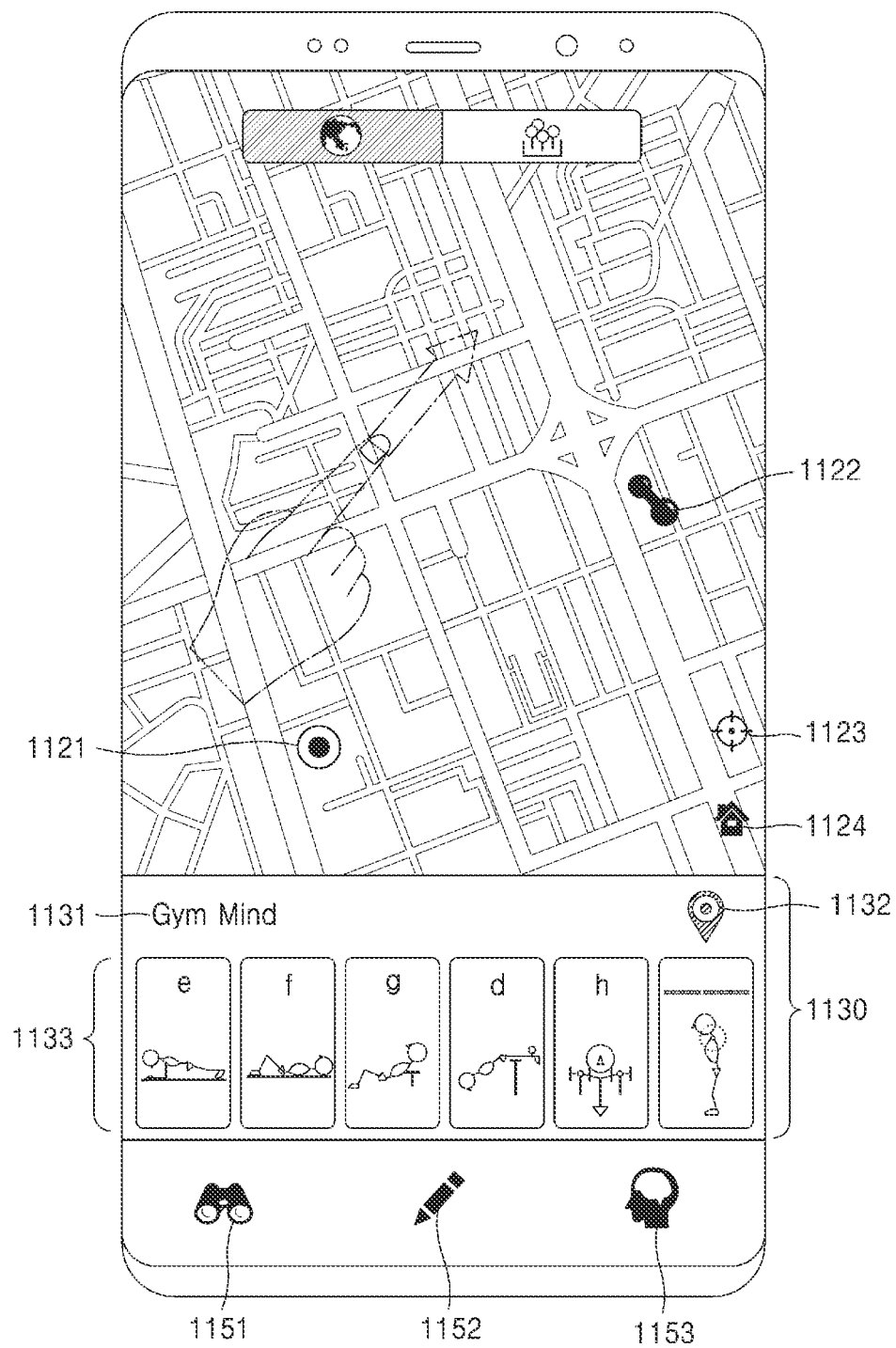

FIG. 7 is a view illustrating a state in which a user input is being made on the map page.

Referring to FIG. 7, for the convenience of user input, the recommended-users display area 1110 (see FIG. 4) overlapping and displayed on the map display area 1120 may be controlled not to be displayed while the user input is being made on the map page. In addition, when the user input is stopped at this point, the recommended-users display area 1110 (see FIG. 4) may be displayed again.

<Pool Page>

Figure 8:
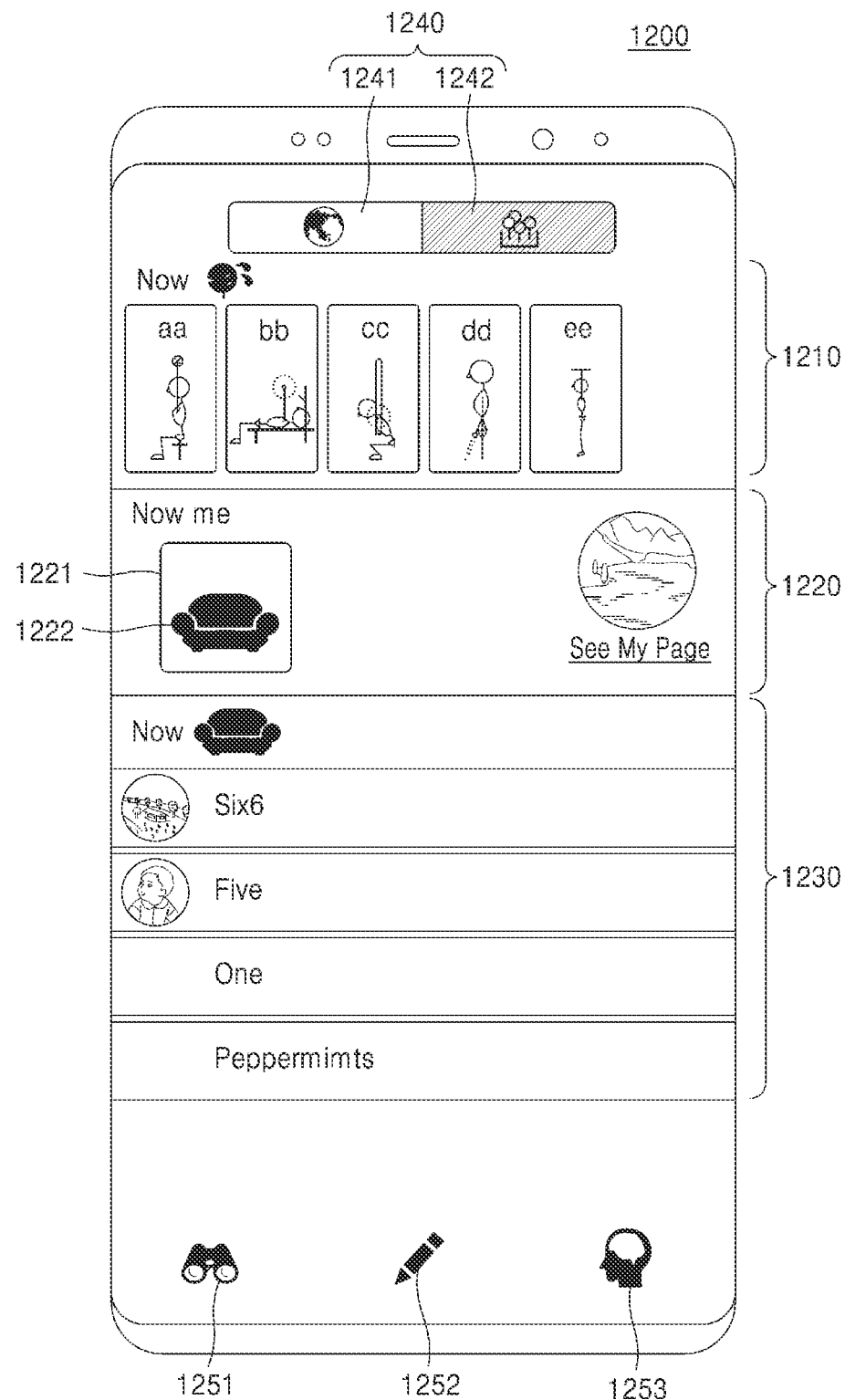
FIGS. 8 to 11 are views illustrating a pool page displayed on the user terminal of the exercise history management system according to an embodiment of the present disclosure.

FIG. 8 is a view illustrating a pool page displayed on the user terminal of the exercise history management system according to an embodiment of the present disclosure.

The current exercise states of users who are pooled by the user himself/herself may be displayed on the pool page 1200. According to the present disclosure, the term "pooling" may be a concept similar to the term "following" in other apps. In the present disclosure, there may be two pools. That is, the pools may include a human pool (for people who followed by me) and an exercise pool (for frequent exercises selected by me, i.e., user's preferred exercises).

The pool page 1200 includes the users-in-exercise display area 1210, the my-exercise-state display area 1220, and the users-not-in-exercise display area 1230.

In addition, the segmented control button 1240, allowing the map page 1100 (see FIG. 4) to be switched to and from the pool page 1200, is displayed on the upper end of the pool page 1200. The segmented control button 1240 includes a map page selection button 1241 and a pool page selection button 1242.

On the users-in-exercise display area 1210, information on users, who are currently exercising, among the users pooled by the user himself/herself may be displayed, and real-time exercise motions of the users who are currently exercising may be displayed.

Figure 9:
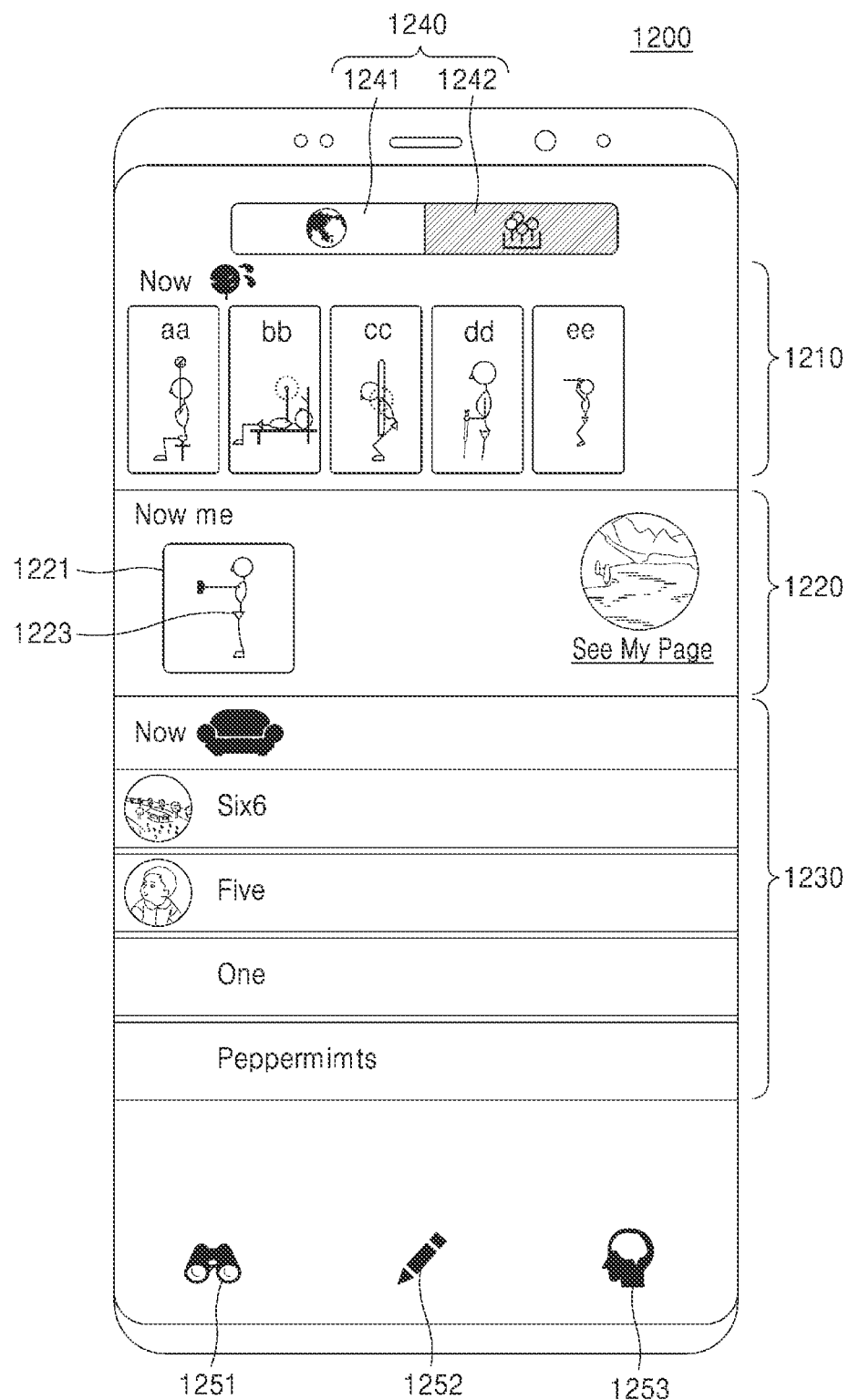

A user's own exercise state is displayed on the my-exercise-state display area 1220. When the user himself/herself is not yet exercising, as shown in FIG. 8, a sofa icon 1222 may be displayed on an exercise display area 1221 to indicate that the user is in rest. Meanwhile, when the user himself/herself is exercising, an exercise motion 1223 that is being performed by the user may be displayed on the exercise display area 1221 as shown in FIG. 9.

When the user does not exercise for more than a predetermined period of time (e.g., one week or more), a potato may be displayed on the sofa icon 1222, and as the period of time for which the user does not exercise increases, an icon in the shape of a potato sprout and growing may be displayed. That is, when the user himself/herself does not exercise for a predetermined period of time, the user may be motivated to exercise by making the potato sprout and allowing other users to recognize the fact that the user himself/herself is not exercising.

Further, although not shown in the drawings, a numerical value indicating the date the most recently performed exercise was performed, the average number of exercises per month this year, and the like may also be displayed on the my-exercise-state display area 1220.

On the users-not-in-exercise display area 1230, information on users, who are not currently exercising, among the users pooled by the user himself/herself may be displayed, and in particular, the information on the users who are not currently exercising may be displayed in rows.

In addition, three tab buttons are displayed at a lower end of the pool page 1200. Among the three tabs at the lower end, a first tab on the left is a social network linking tab 1251 linking the map page 1100 (see FIG. 4) and a social network page linked to the pool page 1200, a second tab on the center is an exercise log input tab 1252 linked to a page for inputting an exercise history, and a third tab on the right is a content tab 1253 displaying various contents related to an exercise.

Figure 10:
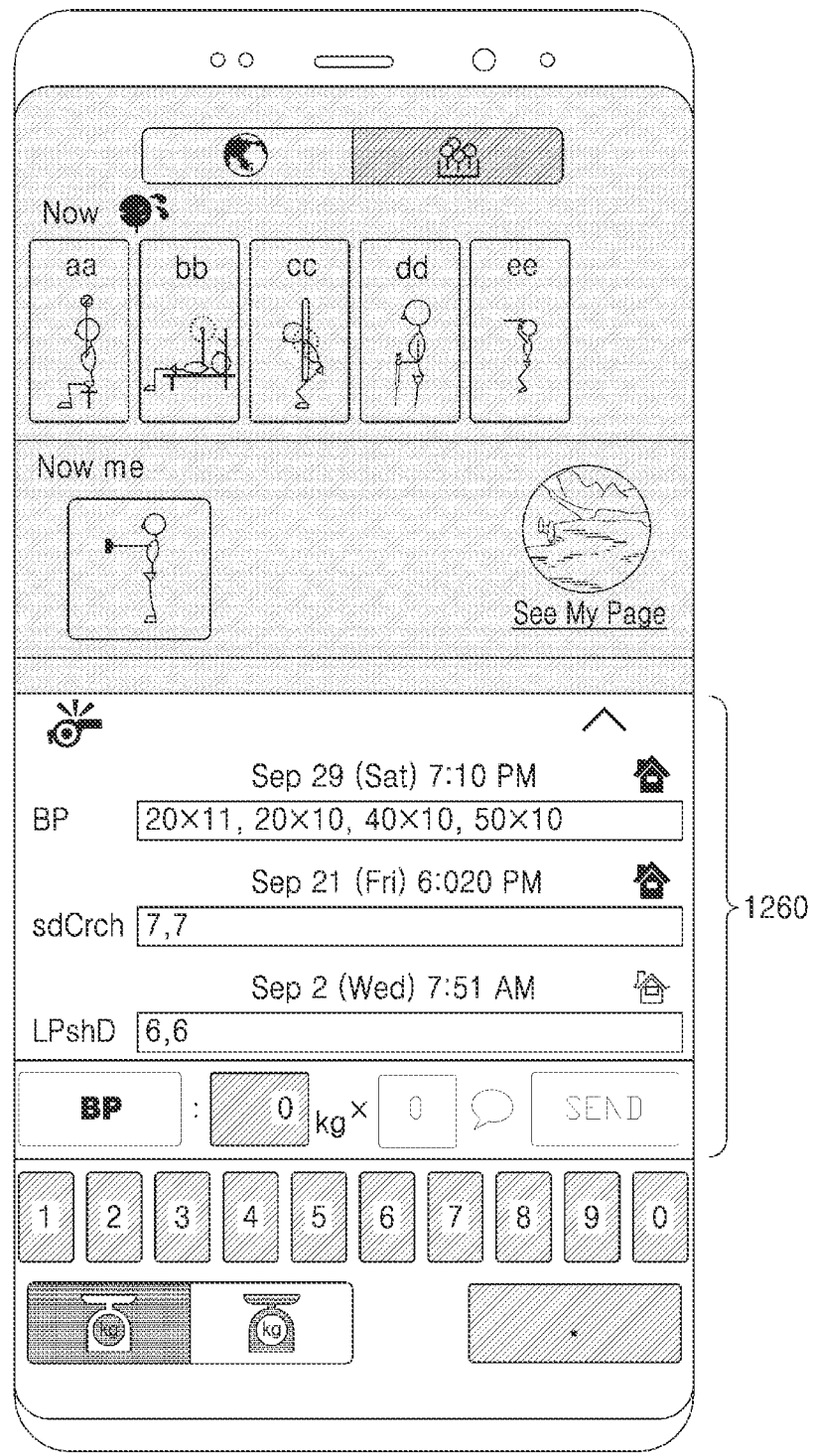

Meanwhile, when the exercise log input tab 1252 at the lower end of the pool page 1200 is selected, an exercise log input portion 1260 is displayed on a portion of the pool page 1200 as shown in FIG. 10. The exercise log input portion 1260 and the input of an exercise log through the exercise log input portion 1260 will be described in more detail below. At this point, on a lower portion of the pool page 1200, the exercise log input portion 1260 may be displayed, and on an upper portion of the pool page 1200, the users-in-exercise display area 1210 and the my-exercise-state display area 1220 may be displayed as they are.

Figure 11:
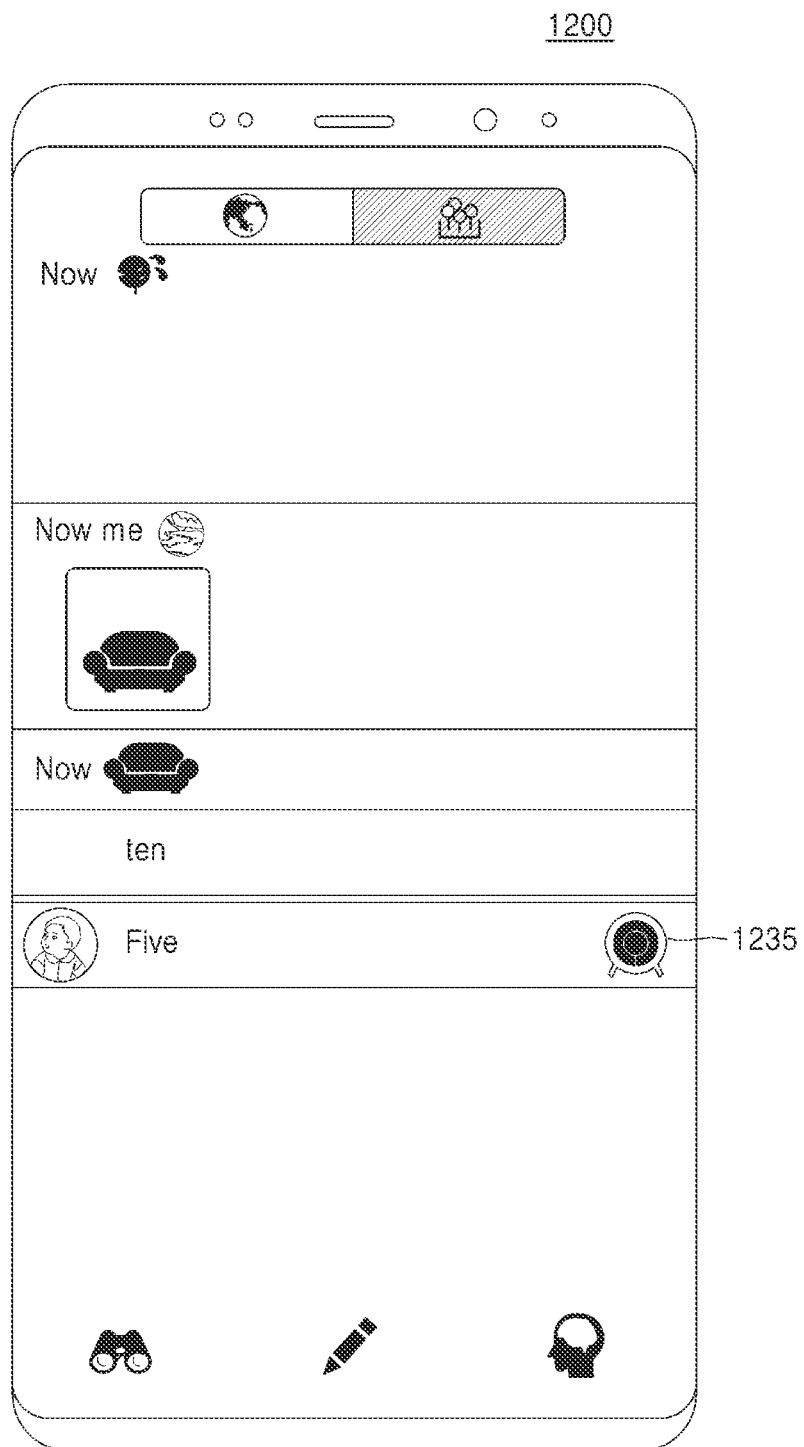

Meanwhile, as shown in FIG. 11, the time machine icon 1235 may be further displayed in each of the user's areas of the users-not-in-exercise display area 1230. When the time machine icon 1235 is selected, a time machine mode may be performed.

Here, the time machine mode refers to a function that makes it look like "exercising" even when a user who has been pooled by the user himself/herself has finished exercising, and makes it look like he/she is exercising with the user himself/herself. When the user himself/herself sets the time machine mode to "On," a recent exercise state of another user exercising in the time machine mode may be displayed as the time machine icon 1235 in each user area of the users-not-in-exercise display area 1230. In addition, when the user himself/herself starts exercising, the most recent exercise of another user exercising in the time machine mode may be displayed on the users-in-exercise display area 1210 at the same tempo (as if another user started at the time same as me). Of course, the users currently exercising may also be displayed on the users-in-exercise display area 1210. Here, the users (who not actually exercising) displayed as being in the time machine mode may be displayed together with the time machine icon 1235 (see FIG. 11).

Meanwhile, although not shown in the drawings, when a user who is exercising is displayed on the upper end (that is, when the user pooled by the user himself/herself starts exercising), the user himself/herself may be notified by a push notification even when the app is not used.

<Contents Page>

Figure 12:
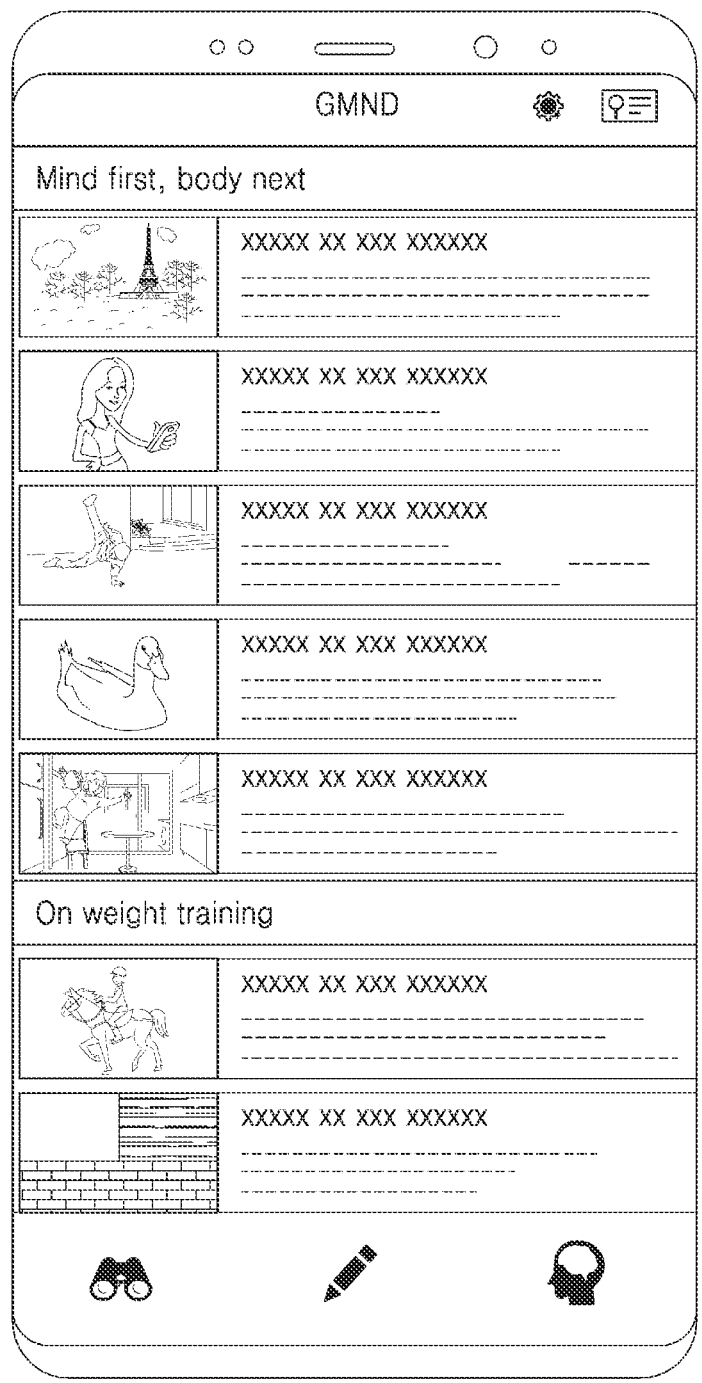
FIGS. 12 to 14 are views illustrating a contents page displayed on the user terminal of the exercise history management system according to an embodiment of the present disclosure.

FIG. 12 is a view illustrating a contents page displayed on the user terminal of the exercise history management system according to an embodiment of the present disclosure. When the content tab 1153 (see FIG. 4) is selected from the map page 1100 (see FIG. 4), the page is switched to the contents page of FIG. 12.

Information (anatomy, kinematics, and the like) that beginners need to know in order to exercise may be display on the contents page 1300. The contents page 1300 may be provided in the form of a list divided by section.

Figure 13:
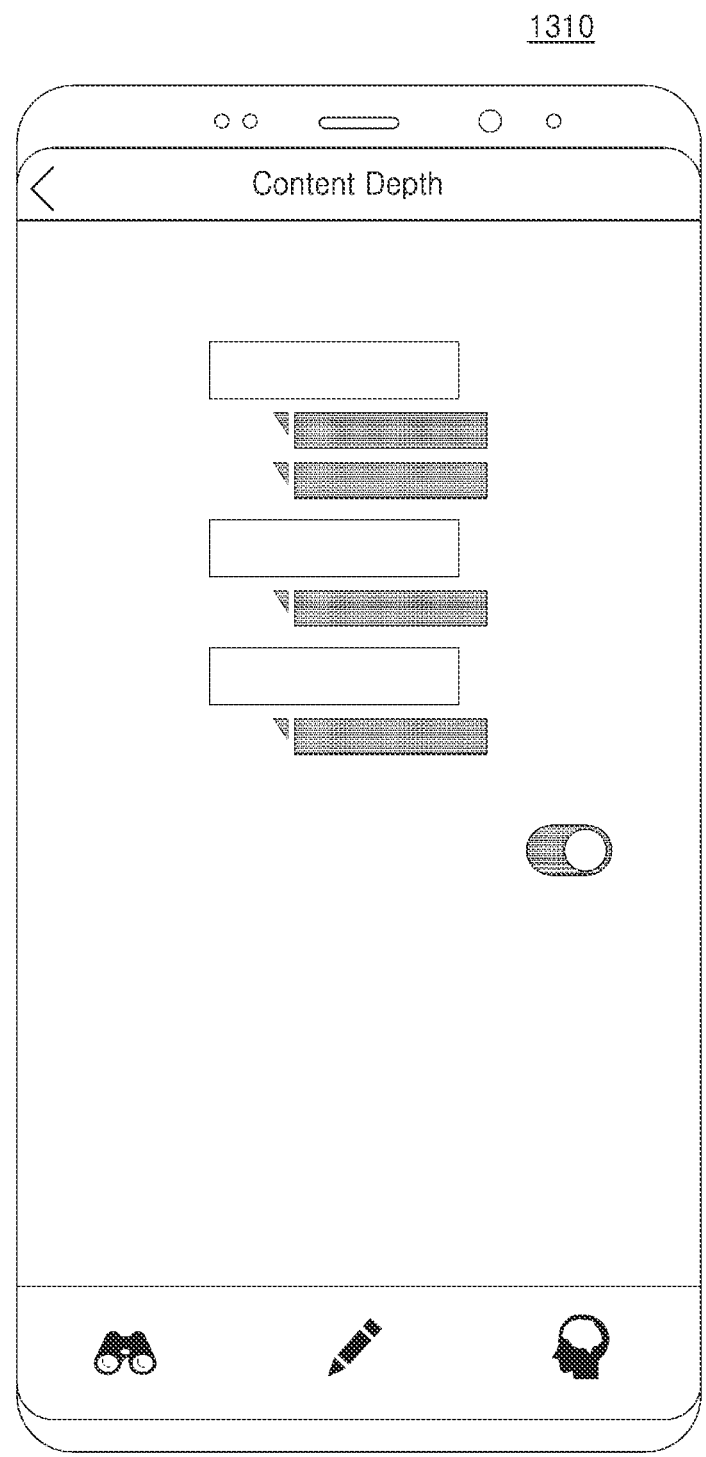

As shown in FIG. 13, the contents page 1300 may also be provided such that all contents are displayed in a list form (bore me mode).

Figure 14:
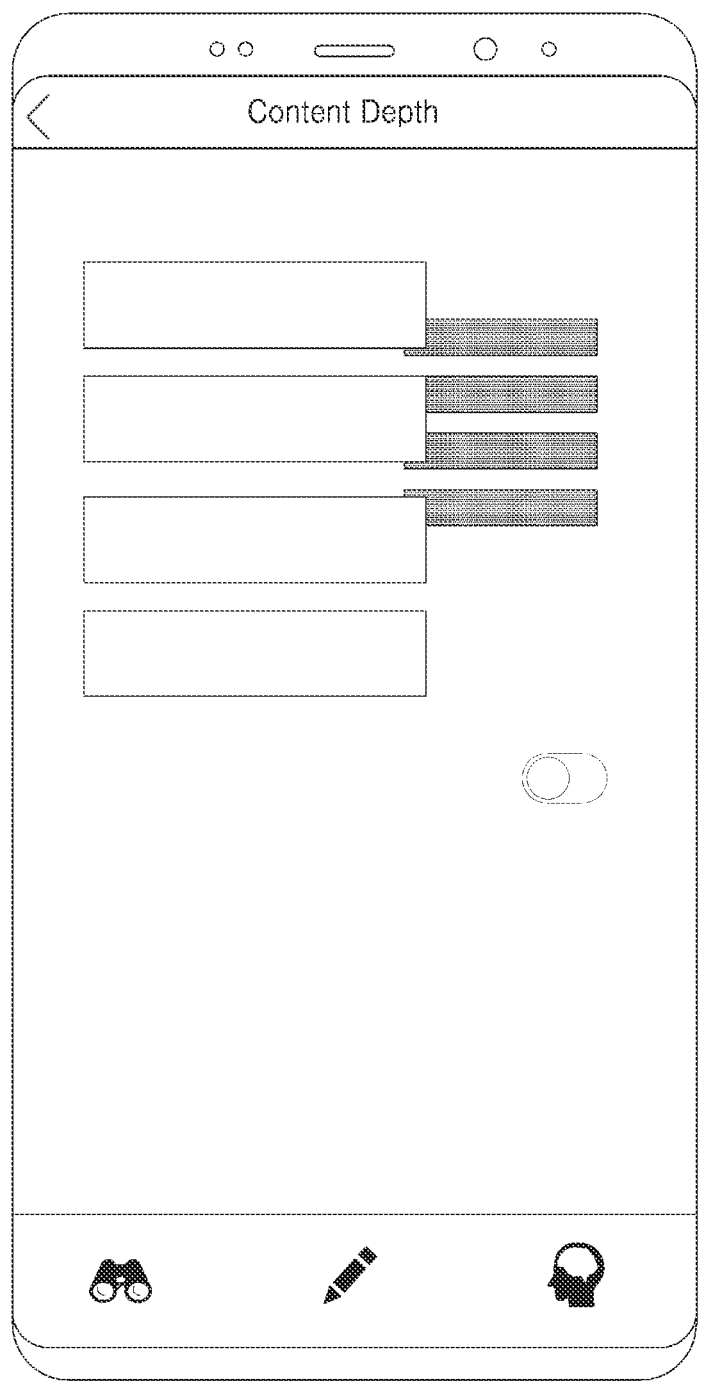

Alternatively, as shown in FIG. 14, the contents page 1300 may be provided to display only core posts and to be accessed through a link at a lower end of the post without displaying detailed information on the list (just basics mode).

Meanwhile, although not shown in the drawings, the contents page of the present disclosure may further include a dashboard for displaying the progress of reading or new posts. That is, the dashboard may be additionally provided to lead content consumption, such as indicating what percentage of the total posts have been read, notifying the creation of new posts, and displaying popular posts.

<Exercise Log Input Area-Exercise Log Display Portion>

Figure 15:
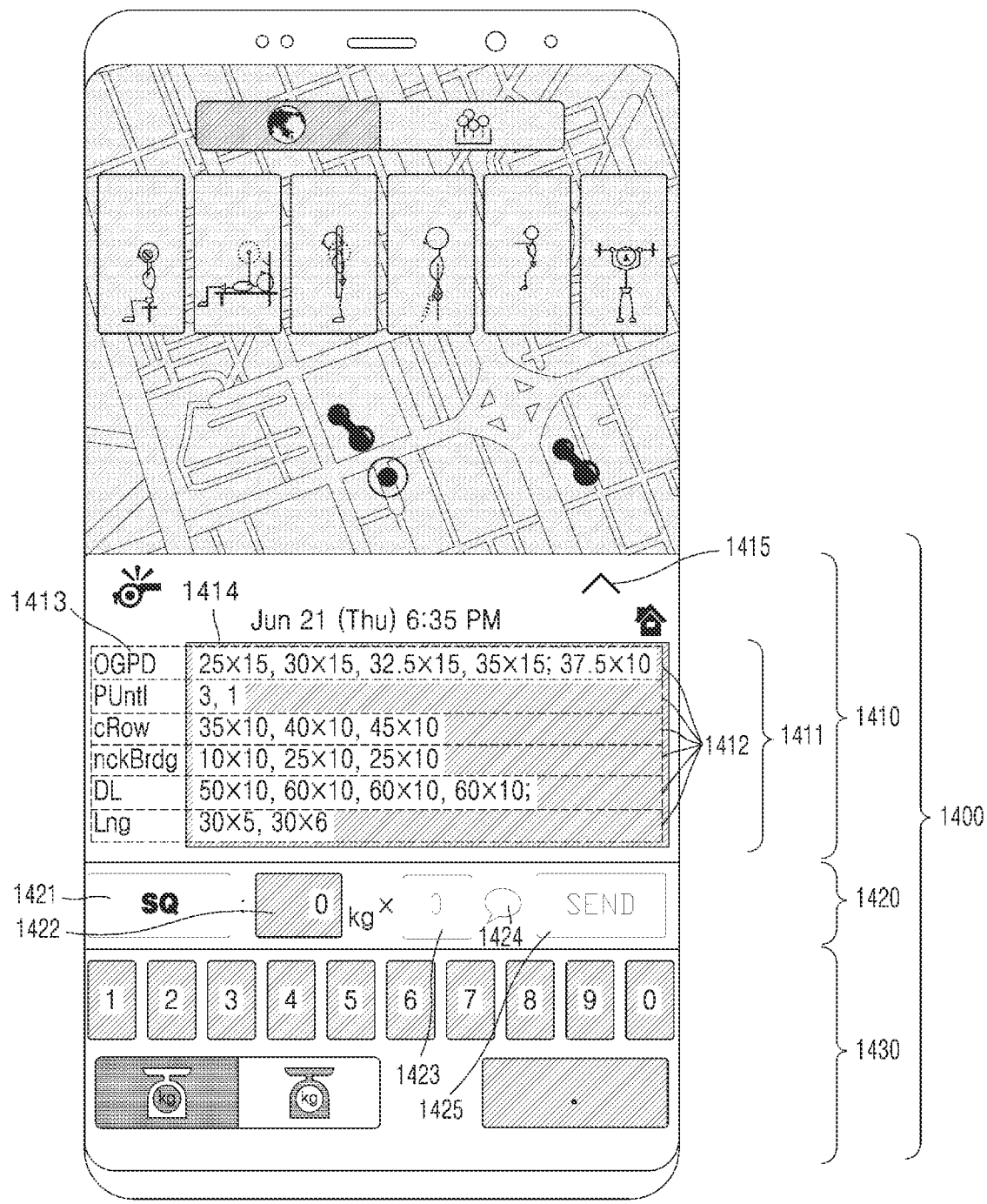
FIGS. 15 to 18 are views illustrating an exercise log input area displayed on the user terminal of the exercise history management system according to an embodiment of the present disclosure.

FIG. 15 is a view illustrating an exercise log input area displayed on the user terminal of the exercise history management system according to an embodiment of the present disclosure. When the exercise log input tab 1152 (see FIG. 4) is selected from the map page 1100 (see FIG. 4), the exercise log input area 1400 may be displayed as shown in FIG. 15.

In more detail, when the exercise log input tab 1152 (see FIG. 4) is selected from the map page 1100 (see FIG. 4), the exercise log input area 1400 may be displayed in a manner of moving up from a lower side of a screen to occupy a lower portion of the screen as shown in FIG. 15.

The exercise log input area 1400 includes the exercise log display portion 1410, the exercise log input and transmission portion 1420, and the input value selection portion 1430.

The exercise log display portion 1410 is an area in which a previously performed exercise is recorded. In more detail, the exercise log display portion 1410 includes one or more exercise log-by-date display portions 1411. In addition, each of the exercise log-by-date display portions 1411 includes one or more individual exercise log display portions 1412.

Each of the individual exercise log display portions 1412 may include the exercise name display portion 1413 and the exercise amount display portion 1414. In more detail, the exercise name display portion 1413 may be disposed on a left side of the individual exercise log display portion 1412 to display the name of exercise (e.g., OGPD, PUntl, cRow, and the like). In addition, the exercise amount display portion 1414 may be disposed on a right side of the individual exercise log display portion 1412, and sets of a weight x count of the performed exercise may be sequentially displayed on the exercise amount display portion 1414. This will be described in more detail later.

The exercise log input and transmission portion 1420 includes the exercise name input portion 1421 through which the name of exercise, in which log is to be recorded, is input, the exercise weight input portion 1422 through which the weight of the exercise is input, the exercise count input portion 1423 through which the number of exercises is input, the comment input portion 1424, and the transmission portion 1425 for transmitting the above-mentioned items to the server.

The input value selection portion 1430 is an area on which input values, which changed as the input item of the exercise log input and transmission portion 1420 is changed, are displayed. This will be described in more detail later.

Figure 16:
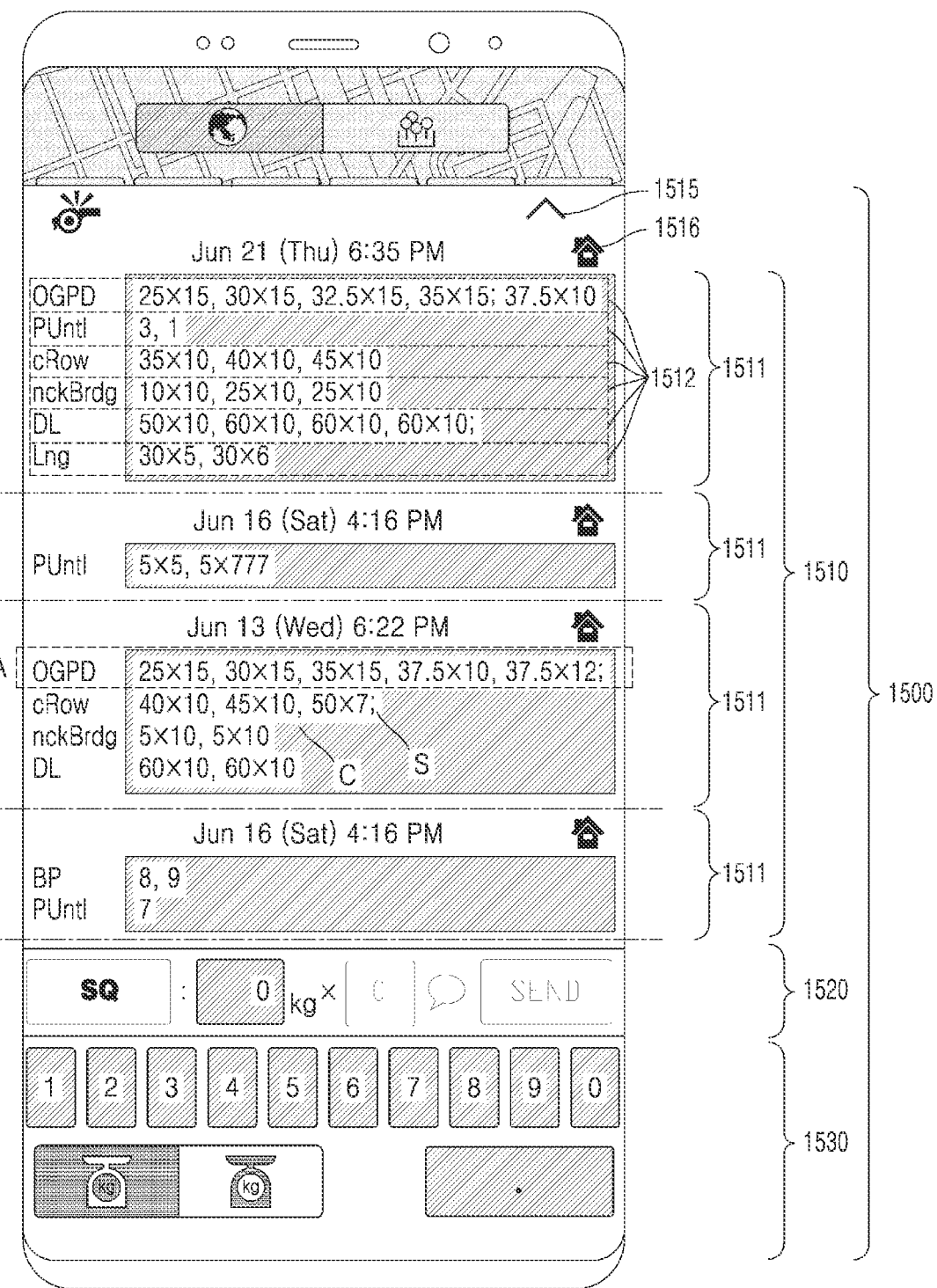

In a state in which the page is displayed as shown in FIG. 15, when an expand button 1415 is pressed, an exercise log input area 1500 is enlarged and displayed as shown in FIG. 16. In particular, an exercise log display portion 1510 is enlarged and displayed in more detail as compared with FIG. 15, and an exercise log input and transmission portion 1520 and an input value selection portion 1530 may be displayed in the same manner as in FIG. 15.

In more detail, the enlarged exercise log display portion 1510 includes one or more exercise log-by-date display portions 1511. In addition, each of the exercise log-by-date display portions includes one or more individual exercise log display portions 1512.

Meanwhile, when a gym shortcut button 1516 is displayed on each of the exercise log-by-date display portions 1511 is selected, the gym shortcut button 1516 may be linked to a page of the gym where the corresponding exercise was performed.

In FIG. 16, the individual exercise log display portions 1512 are displayed in a compact form. In the case of displaying in the compact form as shown in FIG. 16, a separation between sets is indicated by a comma C, but a tough set may be indicated by a semicolon S.

Figure 17:
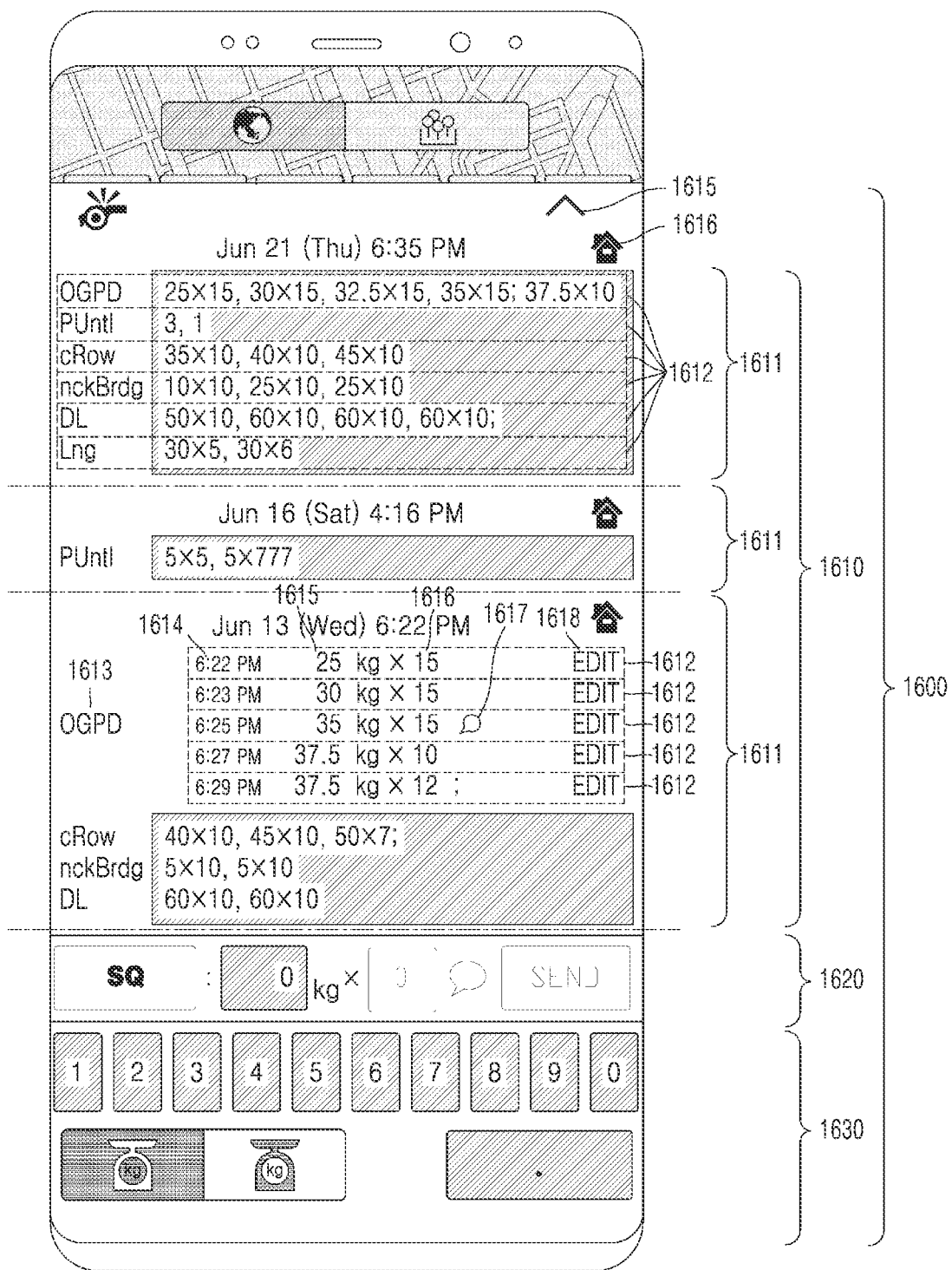

In this state, when one of the individual exercise log display portions 1512 is selected (for example, when area A of FIG. 16 is selected), as shown in FIG. 17, records for each set of the corresponding individual exercise may be displayed in more detail in a drop-down manner. In FIG. 17, records for the individual exercise are expanded downward in a drop-down manner and are displayed in a manner that each set is displayed on one line.

As shown in FIG. 17, when the records for the individual exercise are displayed in a drop-down manner, an individual exercise log display portion 1611 is displayed again in a state of including one or more exercise-log-for-each-set display portions 1612.

In more detail, the individual exercise log display portion 1611 includes an exercise name display portion 1613 displaying the name of exercise and one or more exercise-log-for-each-set display portions 1612. In addition, each of the exercise-log-for-each-set display portions 1612 may include an exercise duration display portion 1614 that displays the time at which the exercise of the corresponding set is performed, an exercise weight display portion 1615 that displays the weight of the exercise of the corresponding set, an exercise count display portion 1616 that displays the number of exercises of the corresponding set, a comment input portion 1617 for inputting a memo for the corresponding set, and an edit button 1618 used to change to a record edit mode for the corresponding set.

Figure 18:
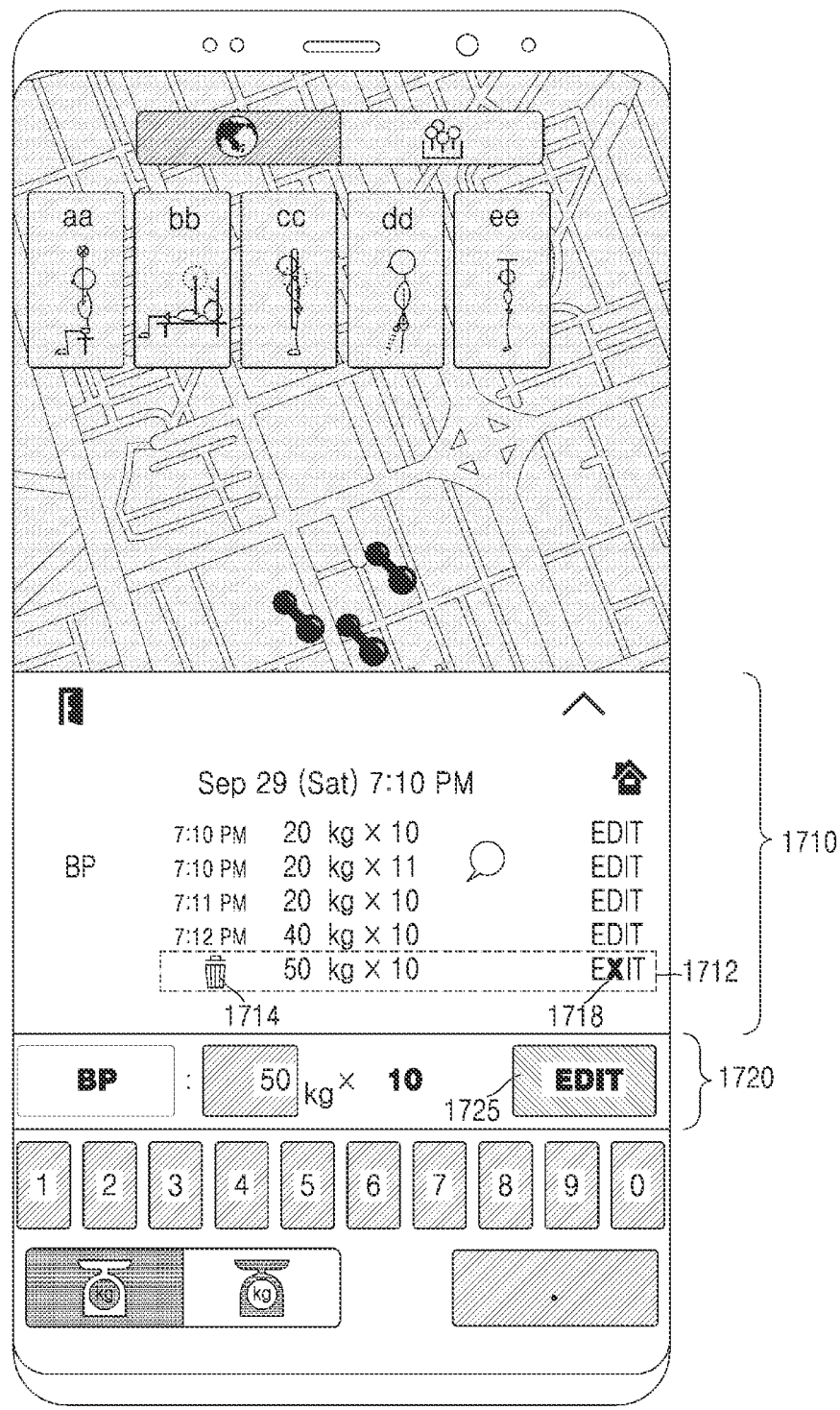

In this state, when the edit button 1618 is selected, an edit screen for each set is displayed as shown in FIG. 18.

In this screen of an exercise-log-for-each-set display portion 1712, the edit button 1618 (see FIG. 16), which is being displayed as "EDIT" in FIG. 16, is changed into an EXIT 1718 and displayed, and the exercise duration display portion 1614 (see FIG. 16) is changed into a recycle bin icon 1714 and displayed.

In addition, an exercise log input and transmission portion 1720 displayed on a middle portion of the screen is changed into an editing window for the exercise records for each set, and the weight, count, and the like of the set to be edited are displayed on the exercise log input and transmission portion 1720.

When an EDIT button 1725 of the exercise log input and transmission portion 1720 is pressed, the edit is reflected, and an EXIT button 1718 is pressed to cancel the edit. Alternatively, instead of pressing the EXIT button 1718, another part of the exercise log display window may be pressed to return to a SEND mode.

<Exercise Log Input Area—Input Value Selection Portion>

FIG. 19 is a view illustrating an exercise log input area displayed on the user terminal of the exercise history management system according to an embodiment of the present disclosure. When the exercise log input tab 1152 (see FIG. 4) is selected from the map page 1100 (see FIG. 4), an exercise log input area 1800 may be displayed as shown in FIG. 19.

FIG. 19 is a view illustrating an initial screen of the exercise log input area. Referring to FIG. 19, the exercise log input area 1800 includes an exercise log display portion 1810, the exercise log input and transmission portion 1820, and the input value selection portion 1830.

The exercise log input and transmission portion 1820 includes an exercise name input portion 1821 through which the name of exercise, in which a log is to be recorded, is input, an exercise weight input portion 1822 through which the weight of the exercise is input, an exercise count input portion 1823 through which the number of exercises is input, a comment input portion 1824, and a transmission portion 1825 used for transmitting the above-mentioned items to the server.

Here, when the comment input portion 1824 is selected, a comment input window (not shown) is displayed in a pop-up form to allow a comment to be input, and when the comment is input, the comment input portion 1824 is displayed in a different color or the border of the comment input portion 1824 is displayed in a dark color. In the way, whether or not a comment is inputted is indicated.

Here, the transmission portion 1825 may respond to a change in an input value. For example, when the input value is zero, there is no meaning of the input, and thus the transmission portion 1825 is deactivated, and when the input value is changed to a valid value, the transmission portion 1825 is activated to indicate that the transmission is allowed.

Further, although not shown in the drawings, it may be configured such that, when the transmission portion 1825 is pressed, an alarm is activated according to a preset break time.

Meanwhile, in a state in which the exercise name input portion 1821 is selected from the exercise log input and transmission portion 1820, one or more exercise name display portions 1831 may be displayed on the input value selection portion 1830.

Here, the setting of the exercise name display portions 1831 will be described in more detail.

Figure 20:
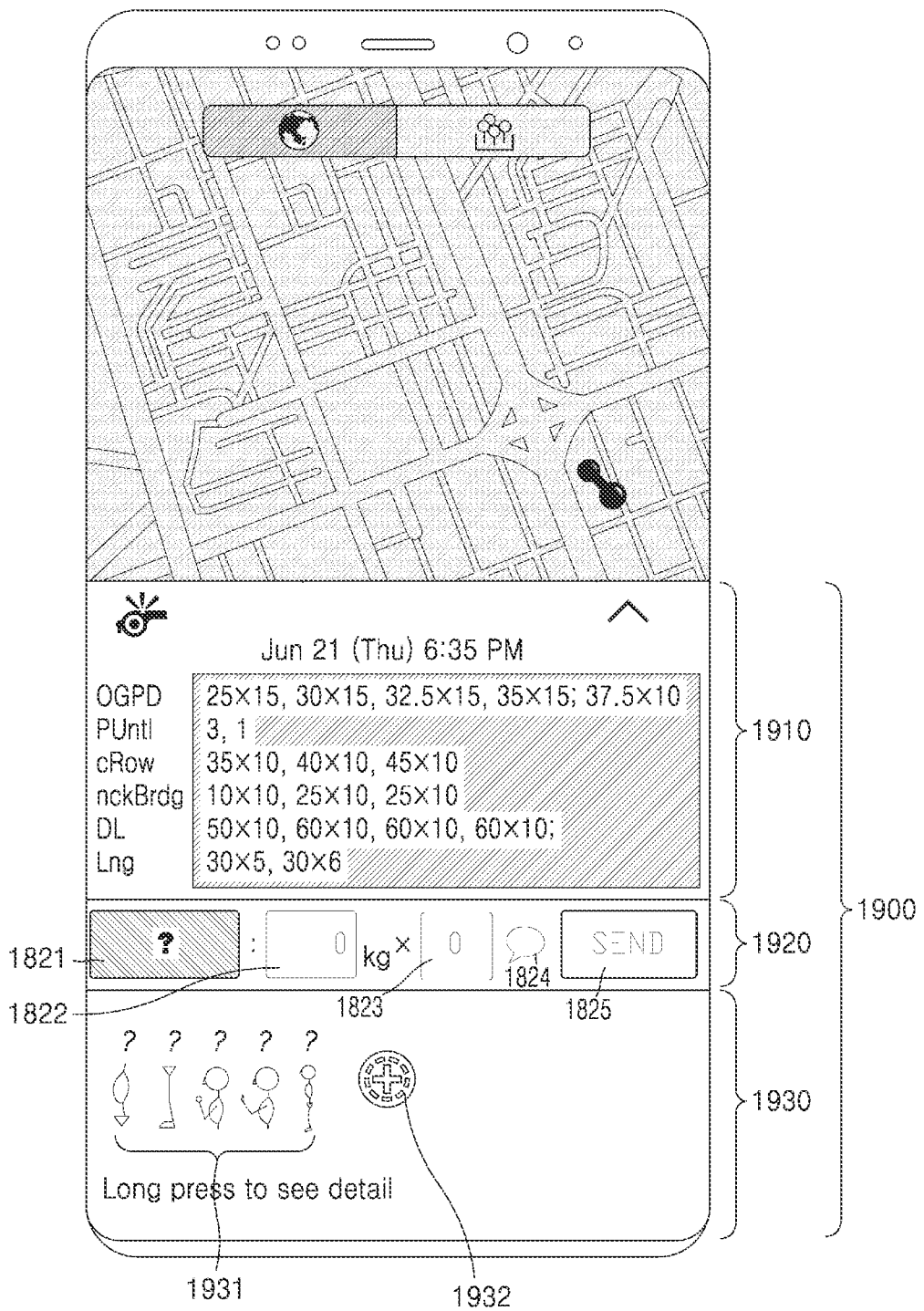

FIG. 20 is a view illustrating an initial screen of an exercise log input mode.

As shown in FIG. 20, when the application is executed for the first time, exercised-part blanked categories 1931 are displayed. In this state, when an exercise is added to the corresponding part by pressing an add button 1932 on the right to switch to the user-preferred exercise setup page 2300 (see FIG. 25) and setting the user's preferred exercise, a mark "?" disappears as shown in FIG. 19, and the user's preferred exercises may be displayed in ways such as images and abbreviations on the corresponding exercise name display portions 1831.

Once the user's preferred exercise is stored, as shown in FIG. 19, the user's preferred exercises previously selected by the user may be displayed on the exercise name display portions 1831, may be organized and displayed by category. Exercises that are initially set after the application is loaded, or the order in which the exercises are arranged at a lower end of the page may be presented differently depending on the frequency and pattern of the exercise and the recently performed exercises.

Here, when each of the exercise name display portions 1831 is selected, the name or abbreviation of the corresponding exercise may be displayed on the exercise name input portion 1821 of the exercise log input and transmission portion 1820.

Alternatively, when a predetermined input, which is different from a general input such as a long press or a force touch, is performed on each of the exercise name display portions 1831, the exercise log input area 1800 disappears upward, and a detailed introduction page 2000 for the corresponding exercise may be displayed while moving upward.

Figure 21:
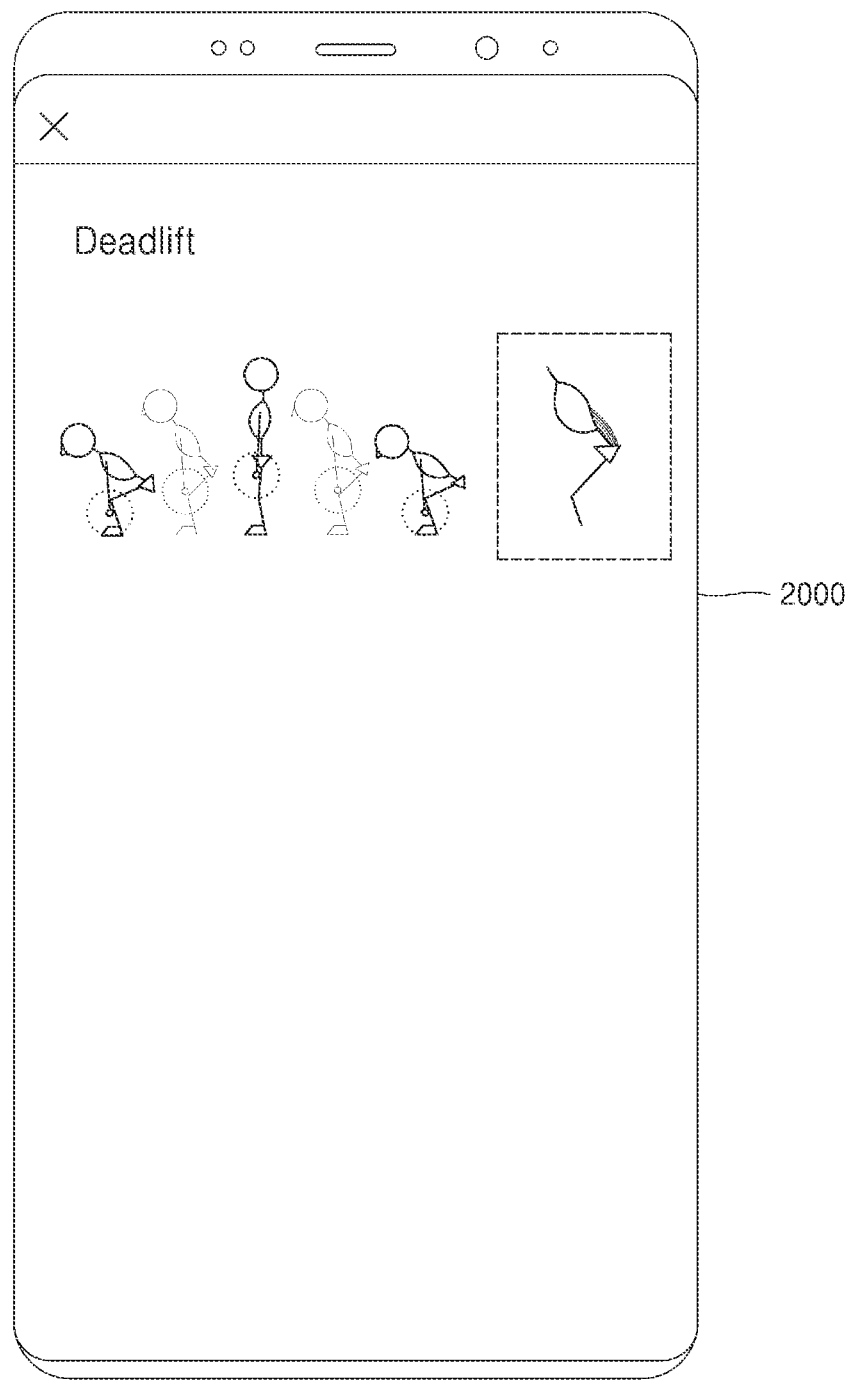

Referring to FIG. 21, detailed information (an operation order, a part on which the exercise is performed, or the like) about the selected specific exercise may be displayed on the detailed introduction page 2000 of the exercise. Here, although not shown in the drawings, various detailed information such as how frequently the corresponding exercise was performed and the maximum weight information (a date, a count, or the like) for the corresponding exercise may be additionally displayed on the detailed introduction page 2000 of the exercise.

Meanwhile, as shown in FIG. 22, when the exercise weight input portion 2122 is selected from the exercise log input and transmission portion 2120, the exercise weight display portion 2131 is displayed on the input value selection portion 2130. Here, the exercise weight display portion 2131 is shown as a numbered button shape in the drawing, but in addition to this, various input methods are possible. In addition, the unit-of-weight selection portion 2132 and the decimal point selection portion 2133 may be further displayed on the input value selection portion 2130. Here, the unit-of-weight selection portion 2132 may be provided in the form of a segmented control window and may be provided to change a unit of weight into a kilogram (kg) scale or a pound (lb) scale.

In most gyms, a single exercise device, for example, a lat pulldown machine, has only one name of unit, which is either lb or kg. Most gyms have free weights in only one unit of "kg" and "lb" per weight. Accordingly, for those who are exercising at the corresponding gym for the first time, when the exercise name display portion 1831 (see FIG. 19) is pressed and a specific exercise code is entered in the exercise name input portion 1821 (see FIG. 19), the unit of weight in the exercise log input and transmission portion 1820 (see FIG. 19) may be automatically suggested among "kg" and "lb" through the past exercise records at the corresponding gym of the corresponding exerciser.

Here, when the exercise weight input portion 2122 is selected, the exercise weight input portion 2122 may be initialized to display "0" while the exercise weight display portion 2131 is displayed on the input value selection portion 2130. This is for the exercise weight input portion 2122 to quickly display "0" without using a backspace button.

Meanwhile, as shown in FIG. 23, when the exercise count input portion 2223 is selected from the exercise log input and transmission portion 2220, the exercise count display portion 2231 is displayed on the input value selection portion 2230. Here, the exercise count display portion 2231 is shown as a numbered button shape in the drawing, but in addition to this, various input methods are possible. In addition, the count/duration selection portion 2232 may be further displayed on the input value selection portion 2230. Here, the count/duration selection portion 2232 is provided in the form of a segmented control window to allow the user to select whether the exercise name is a counting exercise or a duration exercise (e.g., an isometric exercise) that maintains the same posture. Here, in the case of the duration exercise, a mark ("), indicating units of seconds, may be displayed on the exercise count input portion 2223.

Figure 24:
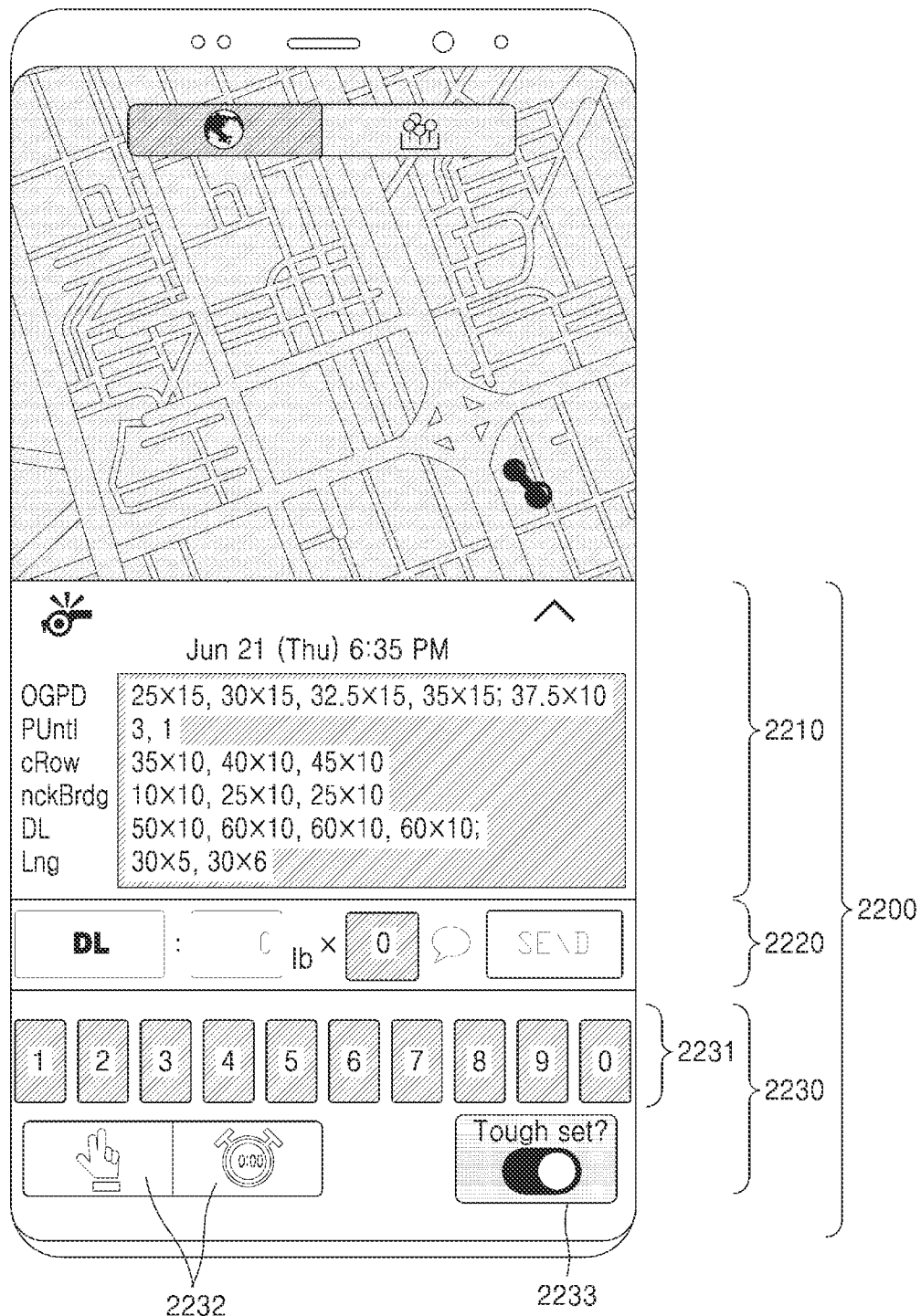

In addition, the tough set input portion 2233 may be further displayed on the input value selection portion 2230. Here, a tough set refers to a set that the user was able to complete with maximal or near-maximal effort. Here, when the user turns the tough set input portion 2233 on to display the tough set, the tough set input portion 2233 may be displayed by being changed as shown in FIG. 24.

When the performed exercise set is recorded as the tough set by the tough set input portion 2233 as described above, a specific mark may be added when the corresponding exercise is displayed on the exercise display area 1221 (see FIG. 9) or the like. For example, a sweat mark may be added to the exercise motion icon 1223 (see FIG. 9), or a predetermined icon may be displayed on one side of the exercise posture icon 1223 (see FIG. 9).

In addition, when such a tough set is continuously performed, the degree of difficulty of the corresponding set is calculated and a specific mark may be displayed.

For example, when the tough set is performed twice in succession, and the second set is performed by increasing the number of times with the same weight (for example, 8 times-→10 times), the second set is judged as a "very difficult set," and thus a specific mark may be displayed (for example, a cell background screen may flicker like an ambulance). As a result, when the tough set is completed, by analyzing the exercise log information and displaying a specific mark, the motivation to exercise may be further increased. Meanwhile, when the exercise count input portion 2223 is selected, the exercise count input portion 2223 may be initialized to display "0" while the exercise count display portion 2231 is displayed on the input value selection portion 2230. This is for the exercise count input portion 2223 to quickly display "o" without using a backspace button.

Meanwhile, the exercise log input and transmission portion 2220 may be limited such that the exercise weight is input to a total of seven digits, and the exercise count is input to a total of three digits (in a case in which the weight has a decimal point, the weight may be limited to six digits excluding the decimal point.). That is, by limiting the input range in consideration of the number of times that general people can exercise and the unit of weight of the exercise device, the occurrence of erroneous input may be prevented.

Meanwhile, the exercise log input and transmission portion 2220 may be set such that the decimal point may be entered when the exercise weight is input but the decimal point is not allowed to be entered when the exercise count/duration is input. This is because the decimal point is not required for inputting the exercise count and the decimal point is not required when the duration is input in units of seconds.

That is, when the weight is input, the input value selection portion 2130 has the unit-of-weight selection portion 2132 and the decimal point selection portion 2133, and when the count/duration is input, the input value selection portion 2130 is changed to the input value selection portion 2230 having the count/duration selection portion 2232 and the tough set input portion 2233. This is because, in general, people input in the order of weight=→number, and in the present disclosure, since it is possible to input a decimal point only when the weight is input, it is intuitive to judge whether the performed exercise was a tough set when entering the exercise count.

Meanwhile, when the exercise displayed on the exercise name display portion 1831 (see FIG. 19) is changed, the unit ("kg" or "lb") is maintained as it is, but the exercise weight input portion 1822 (see FIG. 19) or the exercise count input portion 1823 (see FIG. 19) may be reset to display "0." This is because when the name of exercise is changed the weight and count of the exercise are considered to be changed.

According to the present disclosure, when an item to be entered is pressed in the exercise log input and transmission portion 1820, items displayed on the input value selection portion 1830 are changed and provided, so that the name, weight, and count of the exercise to be recorded may be quickly, accurately, and intuitively entered. In particular, the unit, the count/duration, and the like are changeable in one screen, and when the exercise weight input portion 1822 or the exercise count input portion 1823 is selected, the exercise weight input portion 1822 or the exercise count input portion 1823 is reset to display "0," so that user convenience may be further improved.

Meanwhile, in the present embodiment, the weight and the count are entered assuming that the exercise name is Weight Training, and thus, the exercise weight input portion 1822 (see FIG. 19) and the exercise count input portion 1823 (see FIG. 19) are displayed on the exercise log input and transmission portion 1820 (see FIG. 19), and as the exercise weight input portion 1822 or the exercise count input portion 1823 is selected, the exercise weight display portion 2131 (see FIG. 22) for inputting the exercise weight is displayed on the input value selection portion 2130, or the exercise count display portion 2231 (see FIG. 23) for inputting the exercise count is displayed.

However, the spirit of the present disclosure is not limited thereto, and the input value selection portion may be variously changed according to items and categories. For example, when the selected exercise name or category is Running, the weight input is unnecessary, and configurations of the exercise log input and transmission portion and the input value selection portion may be changed such that only the exercise duration is input. In addition, for example, in the case of a running machine, the weight input portion may be changed into a difficulty level input window (such as an inclination or speed of the running machine), and the configuration and shape of a count/duration input portion may also be changed according to the corresponding exercise. Furthermore, even in the same exercise name, the input window may be changed and displayed according to the name of exercise. That is, the shape and configuration of the input window may be changed and displayed according to not only the exercise name but also the pattern in which the corresponding exercise is performed.

<User-Preferred Exercise Setup Page→

Figure 25:
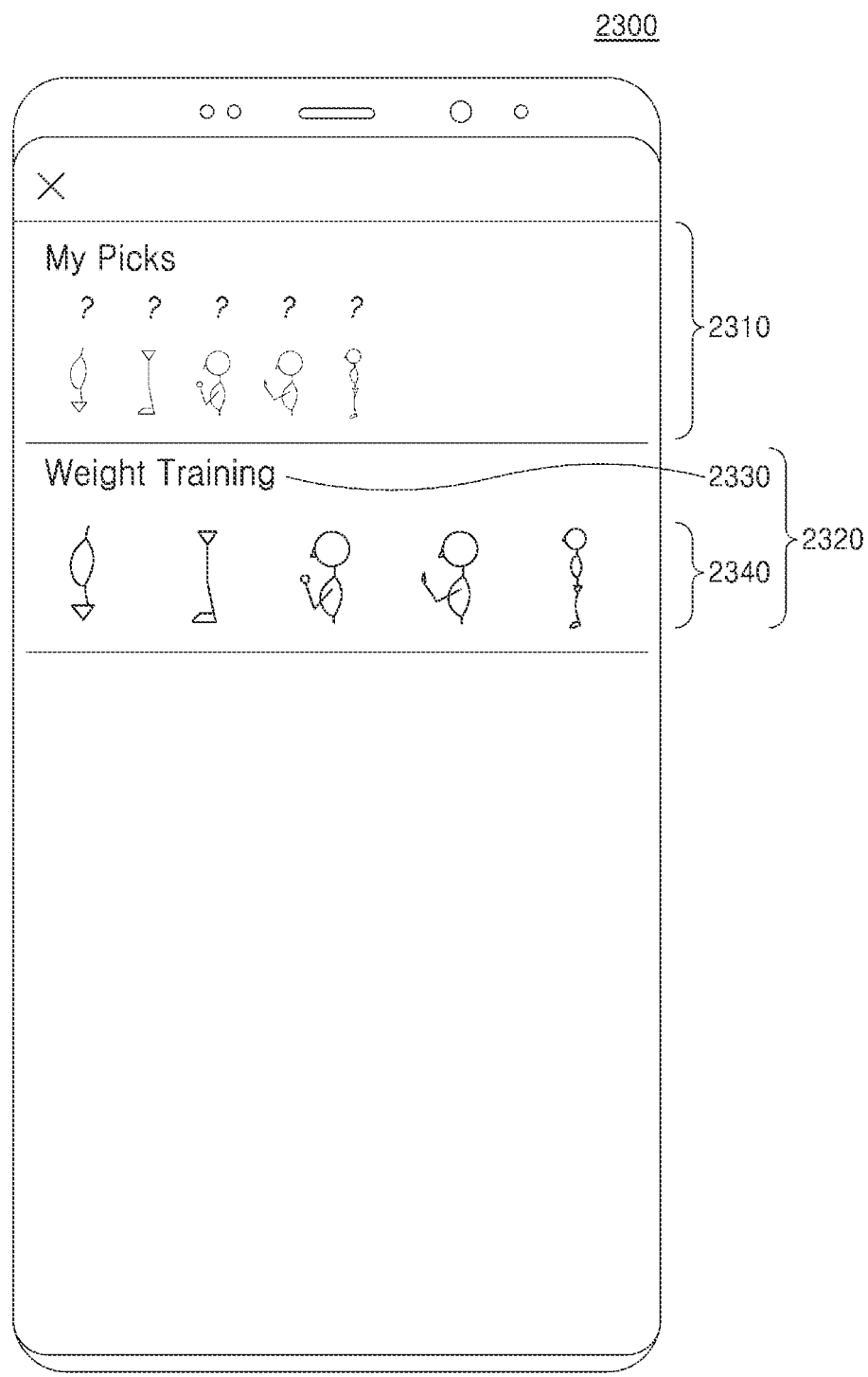
FIGS. 25 to 27 are views illustrating a user-preferred exercise setup page displayed on the user terminal of the exercise history management system according to an embodiment of the present disclosure.

FIG. 25 is a view illustrating a user-preferred exercise setup page displayed on the user terminal of the exercise history management system according to an embodiment of the present disclosure.

Referring to FIG. 25, the user-preferred exercise setup page 2300 includes the preferred exercise display portion 2310 and the preferred exercise selection portion 2320.

Here, FIG. 25 illustrates a screen (i.e., an initialized screen) at the time when the user-preferred exercise setup page 2300 is accessed for the first time after signing up for the service. Since preferred exercises are not yet set, a mark "?" is displayed on an upper end of each of first category icons of the preferred exercise display portion 2310. In addition, at least one preferred exercise selection portion 2320 is displayed on the preferred exercise selection portion 2320 for each exercise name.

In addition, the exercise name display portion 2330 and the first category selection portion 2340 are displayed on the preferred exercise selection portion 2320 for each exercise name. Here, the name of the corresponding exercise name is displayed on the exercise name display portion 2330 (e.g., Weight Training, Running, or the like). Here, when the exercise name display portion 2330 is pressed, other selectable exercise names may be listed. In addition, first categories obtained by classifying exercises belonging to the corresponding exercise name according to a first condition are displayed on the first category selection portion 2340 in the form of icons. In FIG. 25, a core exercise, a lower body exercise, an upper body-pull exercise, an upper body-push exercise, a whole-body exercise, and the like are displayed in the form of icons as the first category of Weight Training. Here, the first categories of the corresponding exercise name may be displayed in the first direction (transverse direction on the screen) on the first category selection portion 2340. Here, FIG. 25 illustrates a state before the exercise names are selected so that only icons for the first categories of each exercise name are displayed.

Figure 26:
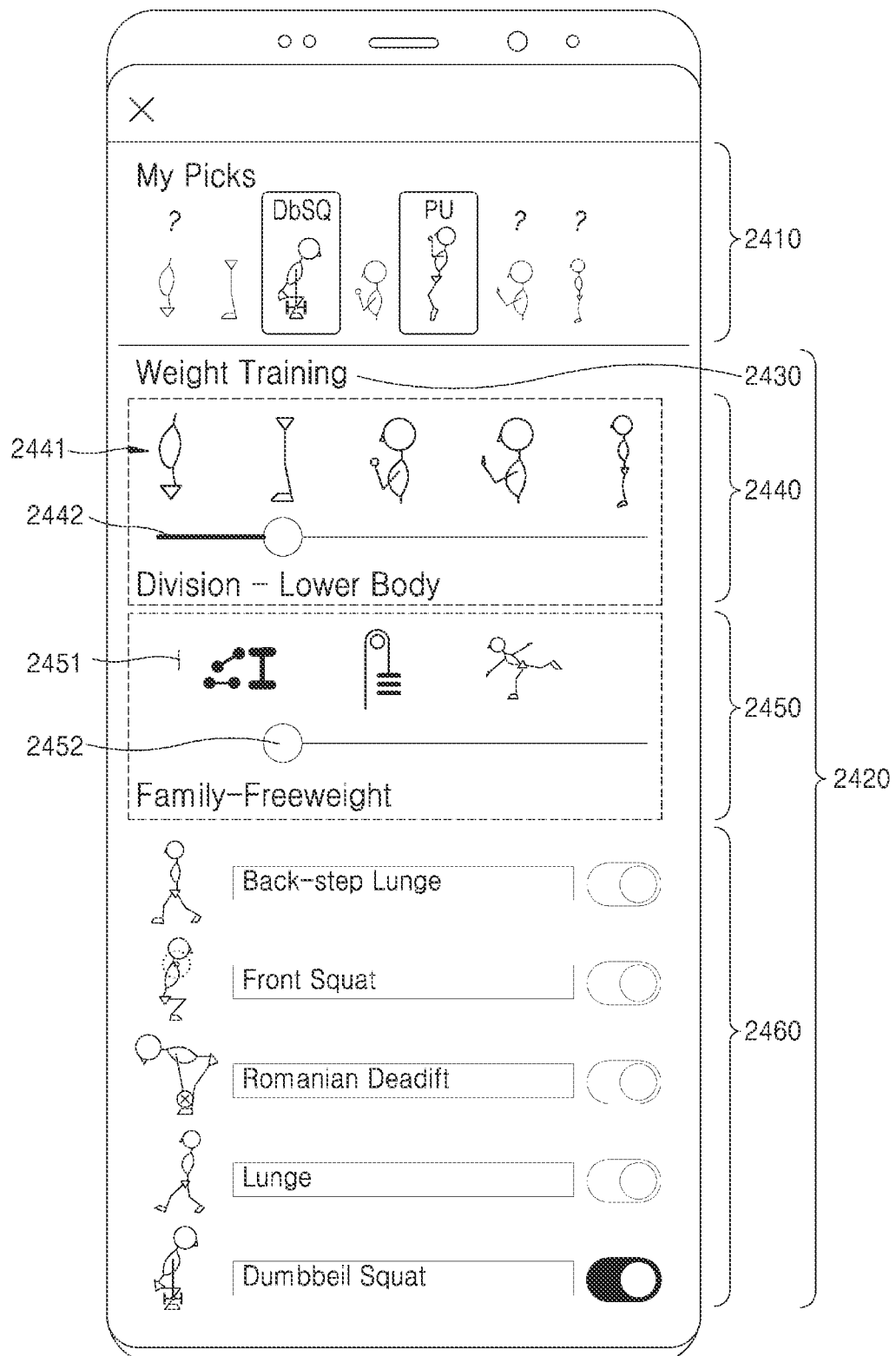

Here, when a specific icon is selected from the first category selection portion 2340, first categories of the corresponding exercise name and subcategories thereof may be sequentially delectably displayed as shown in FIG. 26.

FIG. 26 is a view illustrating a process of setting a user-preferred exercise in the user-preferred exercise setup page.

Referring to FIG. 26, a user-preferred exercise setup page 2400 includes a preferred exercise display portion 2410 and a preferred exercise selection portion 2420. In addition, an exercise name display portion 2430, a first category selection portion 2440, the second category selection portion 2450, and the specific exercise selection portion 2460 are displayed on the preferred exercise selection portion 2420.

First categories 2441 obtained by classifying exercises belonging to the corresponding exercise name according to a first condition are displayed on the first category selection portion 2440. Here, the first category may also be referred to as a "division." Here, icons of the first categories of the corresponding exercise name may be displayed in the first direction (transverse direction on the screen) on the first category selection portion 2440.

The first category may be selected by the following method. First, one icon in the first category selection portion 2440 may be tapped to select a desired first category. Alternatively, a slider 2442 of the first category selection portion 2440 may be dragged to select a desired first category. Alternatively, a desired first category may be selected by tapping one icon in the preferred exercise display portion 2410.

When one of the plurality of displayed first categories is selected, the second categories 2451 obtained by classifying exercises belonging to the selected first category according to a second condition are displayed on the second category selection portion 2450. Here, the second category may also be referred to as a "family." Here, icons of the second categories of the corresponding exercise name may be displayed in the first direction (transverse direction on the screen) on the second category selection portion 2450.

The second category may be selected by the following method. First, one icon may be tapped from the second category selection portion 2450 to select a desired second category. Alternatively, a slider 2452 of the second category selection portion 2450 may be dragged to select a desired category.

When one of the plurality of displayed second categories is selected, one or more specific exercises belonging to the selected second category are displayed on the specific exercise selection portion 2460. Here, one or more specific exercises may be sequentially displayed in the second direction (longitudinal direction on the screen). Here, an on/off button of each of the specific exercises may be turned on to select the corresponding specific exercise.

When the specific exercise is selected, the selected specific exercise is included and displayed on one side of the corresponding first category icon of the preferred exercise display portion 2410, and when the specific exercise is included in the corresponding first category, the mark "?" displayed on the upper side of the first category icon may disappear. In another aspect, when all the icons have the mark "?" in the category, it means that there is no user-preferred exercise, and this may be interpreted as that the user is not exercising the whole body evenly. Thus, by displaying the mark "?," the user may be guided to exercise evenly for each part.

Here, when a predetermined input different from a general input such as a long press or a force touch is performed on each specific exercise displayed on the preferred exercise display portion 2410, the corresponding preferred exercise display portion 2410 may be deleted.

Figure 27:
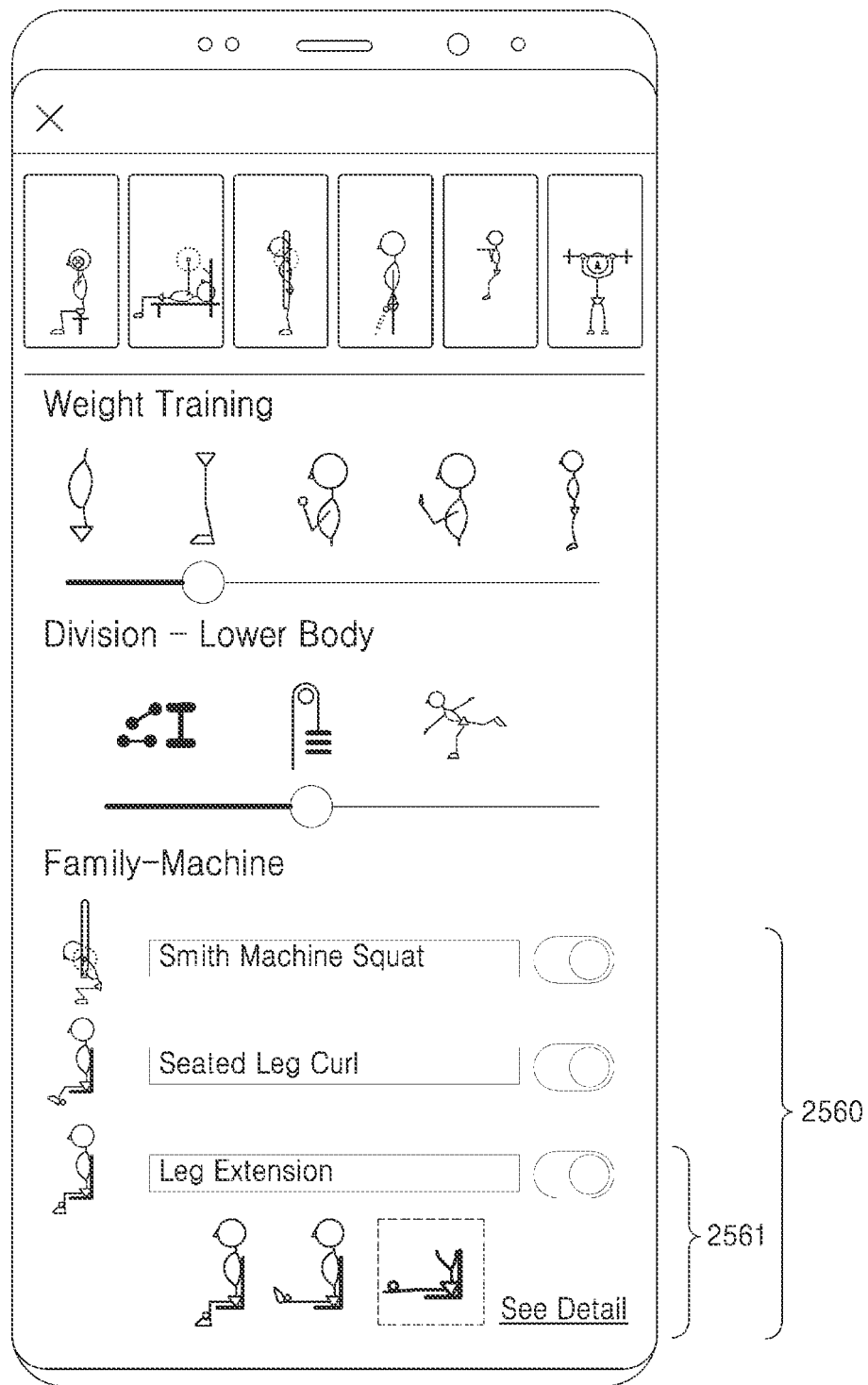

FIG. 27 is a view illustrating an exercise detailed information page of the user-preferred exercise setup page.

When a specific exercise is selected from a specific exercise selection portion 2560, as shown in FIG. 27, a height of a cell of the selected specific exercise is increased, and detailed information (a motion and a part on which the exercise is performed) about the selected specific exercise is displayed. When a button of "See Detail" is pressed to obtain more detailed information, the detailed introduction page 2000 (see FIG. 21) for the corresponding exercise may be displayed.

Here, in a user-preferred exercise setup page provided by an exercise history management system according to an embodiment of the present disclosure, the preferred exercise may be easily selected step by step on one screen. That is, first categories are displayed in the first direction (transverse direction on a screen). When one of the first categories is selected, second categories corresponding to the selected first category are displayed in the first direction (transverse direction on the screen).

When one of the second categories is selected, specific exercises corresponding to the selected second category are displayed in the second direction (longitudinal direction on the screen). As a result, specific exercises to be added may be found with the minimum number of clicks on a small screen.

Further, according to the present disclosure, a user may more easily select a preferred exercise by arranging the exercises in the order of a name (kind)/a first category (division)/a second category (family)/a specific exercise (member exercise).

<Exercise Log Input Area-Whistle View→

Figure 28:
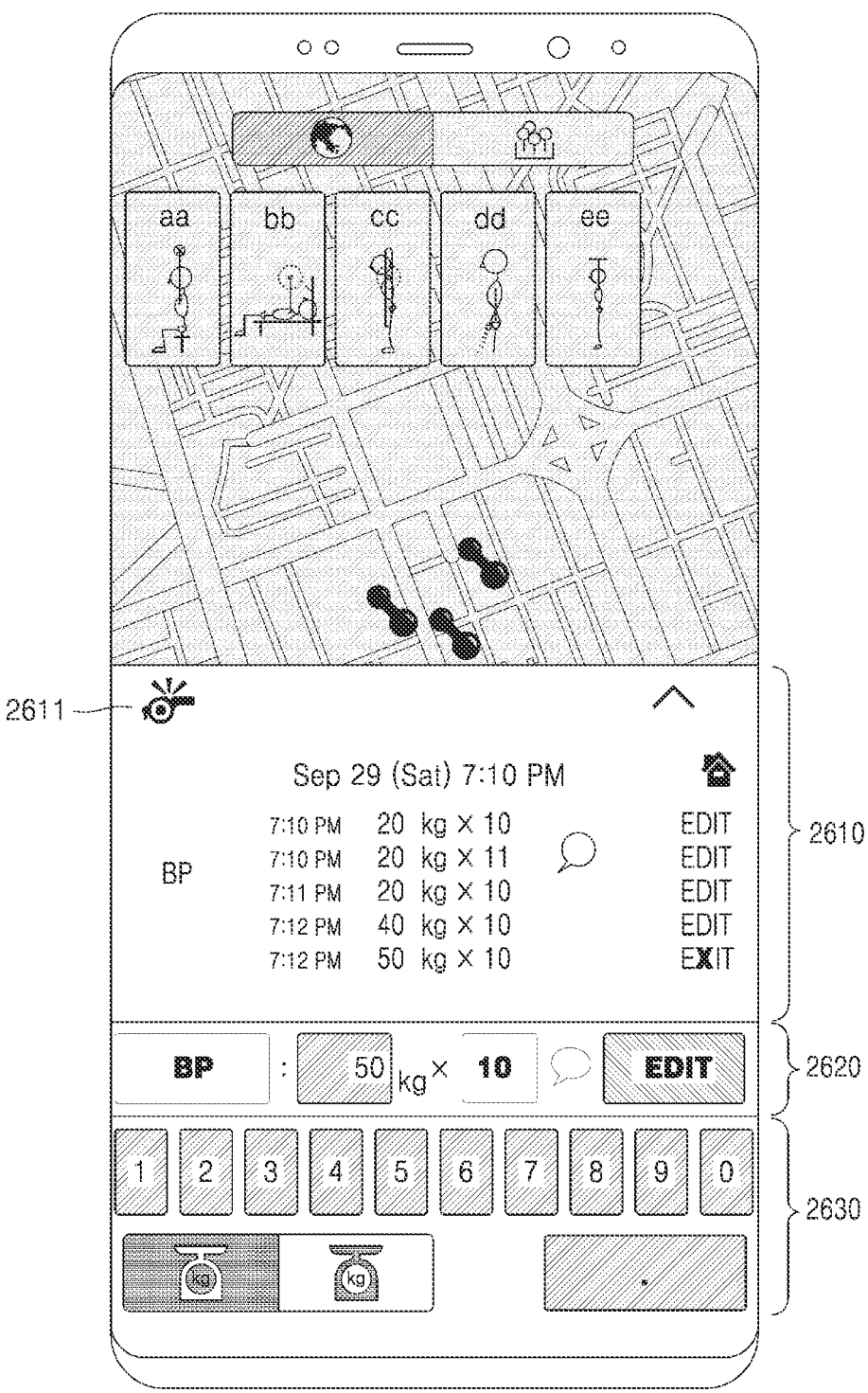
FIGS. 28 to 31 are views illustrating an exercise log input area displayed on the user terminal of the exercise history management system according to an embodiment of the present disclosure.
Figure 29:
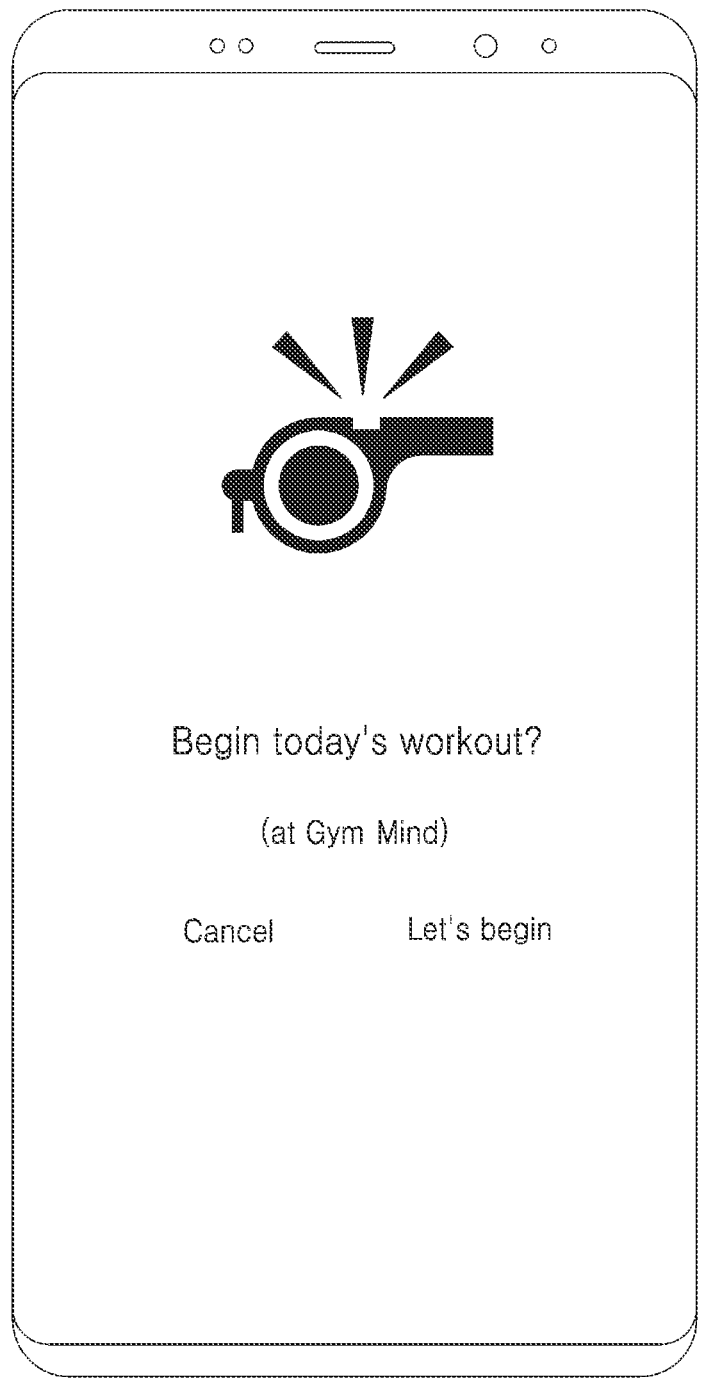

FIG. 28 is a view illustrating an exercise log input area displayed on the user terminal of the exercise history management system according to an embodiment of the present disclosure. When the exercise log input tab 1152 (see FIG. 4) is selected from the map page 1100 (see FIG. 4), an exercise log input area 2600 may be displayed as shown in FIG. 28.

In more detail, when the exercise log input tab 1152 (see FIG. 4) is selected from the map page 1100 (see FIG. 4), the exercise log input area 2600 may be displayed in a manner of moving up from a lower side of a screen to occupy a lower portion of the screen as shown in FIG. 28.

The exercise log input area 2600 includes the exercise log display portion 2610 and the exercise log input and transmission portion 2620. The input value selection portion 2630 may be included.

Here, the start/end signal transmission portion 2611 used for transmitting an exercise start/end signal is displayed at a left upper end of the exercise log display portion 2610.

First, in a situation in which the user is not exercising, a whistle icon is displayed on the start/end signal transmission portion 2611. When the user presses the whistle icon, the whistle icon is linked to the exercise start declaration page 2700 of FIG. 29. When the user presses the exercise log input and transmission portion 2620 without declaring a start while entering the exercise log (that is, without pressing a "Let's begin" button in FIG. 29), a transmission/reception logic does not operate, and the exercise log input and transmission portion 2620 may be linked to the exercise start declaration page 2700 first.

For reference, in order for the exercise log to be transmitted, it may be required that certain predetermined conditions are satisfied. For example, the predetermined conditions may include conditions such as a state in which "my gym" should be selected in advance, which will be described below, or an exercise start is declared in the exercise start declaration page 2700.

Figure 30:
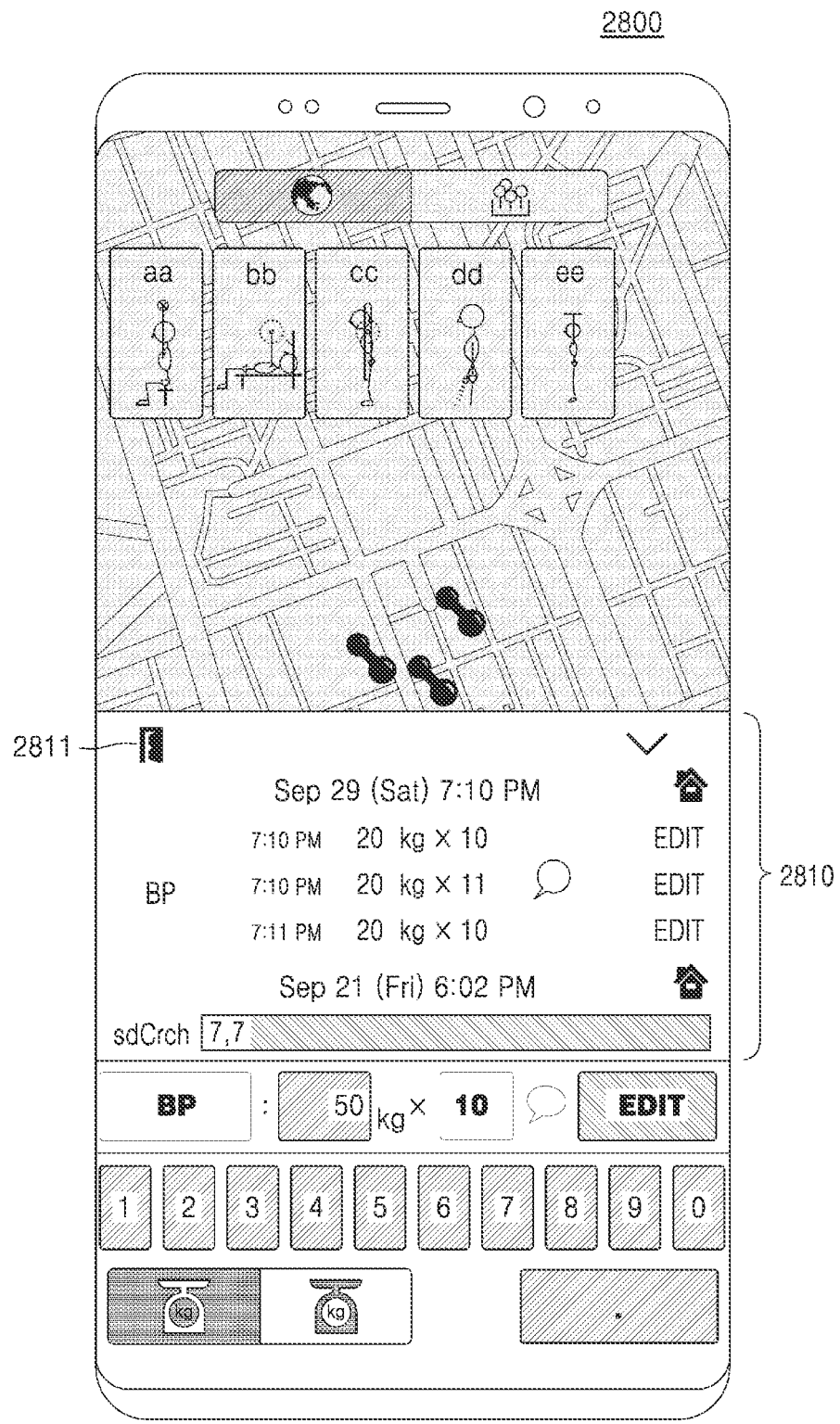
Figure 31:
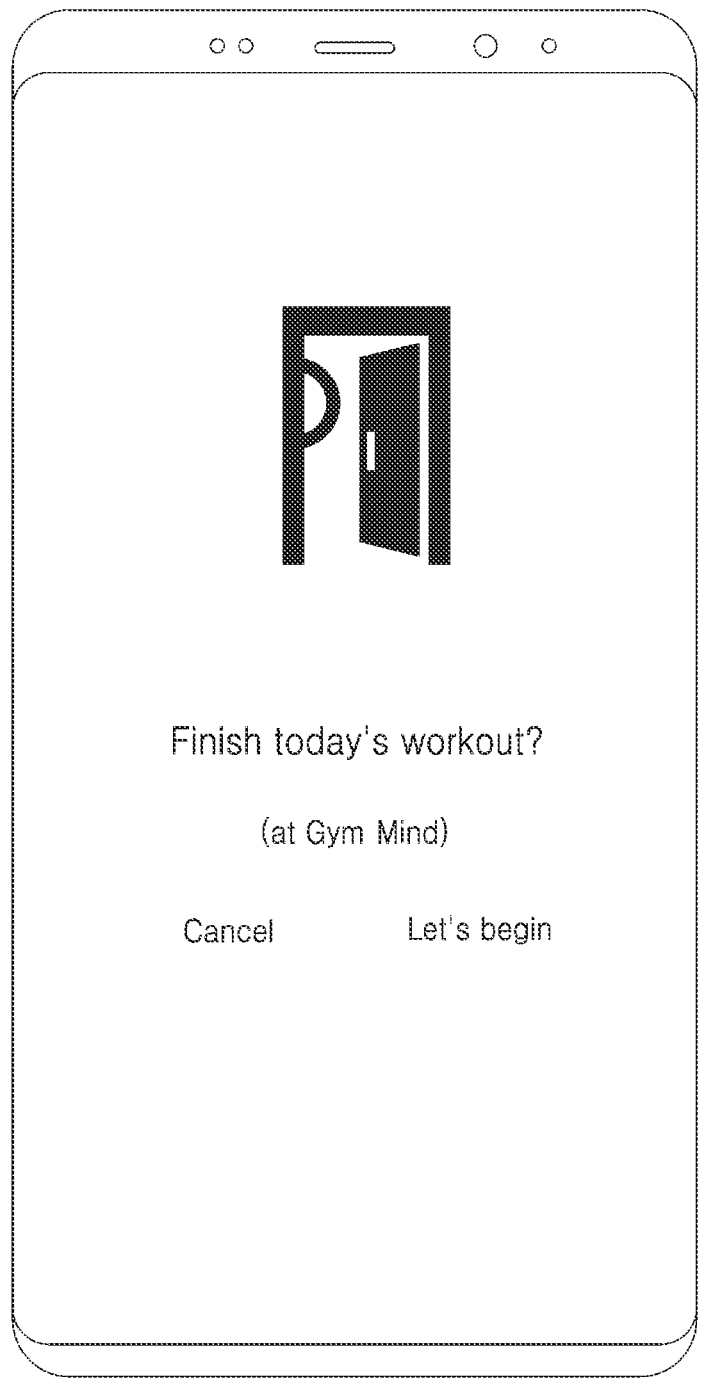

When the exercise start is declared, an end icon is displayed on a start/end signal transmission portion 2811 as shown in FIG. 30. When the user presses the end icon, the end icon is linked to an exercise end declaration page 2900.

Meanwhile, the end of the exercise will be described below in more detail.

Although not shown in the drawings, an embodiment of the present disclosure provides a duration exercise notice function for an aerobic exercise or the like.

An exercise having a duration such as an aerobic exercise, yoga, filament, or the like may include a "notice function" that may notice the duration of exercise in advance. For example, when "30 minutes" is entered as an exercise notice time in the input value selection portion 2230 (see FIG. 23) and transmitted to the server before performing the exercise, an image of the corresponding exercise may be displayed on the recommended-users display area 1110 (see FIG. 4) or the user-in-exercise display area 1133 (see FIG. 4) of the map page 1100 (see FIG. 4), or the users-in-exercise display area 1210 (see FIG. 8) of the pool page 1200 (see FIG. 8).

Here, when the image of the corresponding exercise is displayed on the user display areas (1110 of FIG. 4, 1133 of FIG. 4, and 1210 of FIG. 8), a remaining time from the exercise notice time may be displayed together with an image of an exercise motion, and the remaining time may be counted down. In addition, an alarm may be given to the user when the notice time has elapsed. In addition, when the notice time has elapsed, the image of the exercise motion may be changed (for example, an image of a person running may be changed into an image of a person sweating).

Meanwhile, the shape of the content displayed on the start/end signal transmission portion 2811 may be changed before and after the notice time. For example, an abort button may be displayed when the exercise is finished before the notice time elapses, and an end button, which is displayed when the target is accomplished, may be displayed when the exercise is finished after the notice time has elapsed.

However, in an actual gym, although 30 minutes is set as a notice time of the exercise, there may be cases in which the exercise is not actually performed that much. That is, even while the user is not exercising, the user display areas (1110 of FIG. 4, 1133 of FIG. 4, and 1210 of FIG. 8) may be displayed as "in exercise."

In order to resolve the above-described problem, after the notice time elapses, an icon may be differently displayed on the user display areas (1110 of FIG. 4, 1133 of FIG. 4, and 1210 of FIG. 8) or the like depending on whether the end button is pressed.

That is, the image of the exercise in the user display area stops moving when the notice time has elapsed, and when a predetermined time elapses, an end process is performed and the image of the exercise is removed from the user display area even when the user does not press the end button separately.

On the other hand, in a case in which the user directly presses the end button during the notice time after performing the exercise (after a target time has elapsed), when the server determines that the completion is valid after identifying the user's location or the like, the server may cause a separate image to be displayed in the user display area indicating that the exercise has been successfully completed. For example, images of rest and cool-down, which are displayed only when the exercise is normally ended, may be displayed.

Here, the notice time of the exercise may be restricted for each exercise. That is, it is possible to limit the notice time of the exercise for each exercise, such as 1 hour for aerobic exercise and 2 hours for yoga. Meanwhile, it is possible to restrict such that the notice time of the exercise is enabled only when a specific exercise is performed. For example, it is also possible to place restrictions on the order of the exercises so that the exercise, which requires the notice time, may be performed only by performing a strength exercise in advance.

<Exercise Online Sign-in Page→

FIGS. 32 to 37 are views illustrating a sign-in page of the exercise history management system according to an embodiment of the present disclosure.

Figure 32:
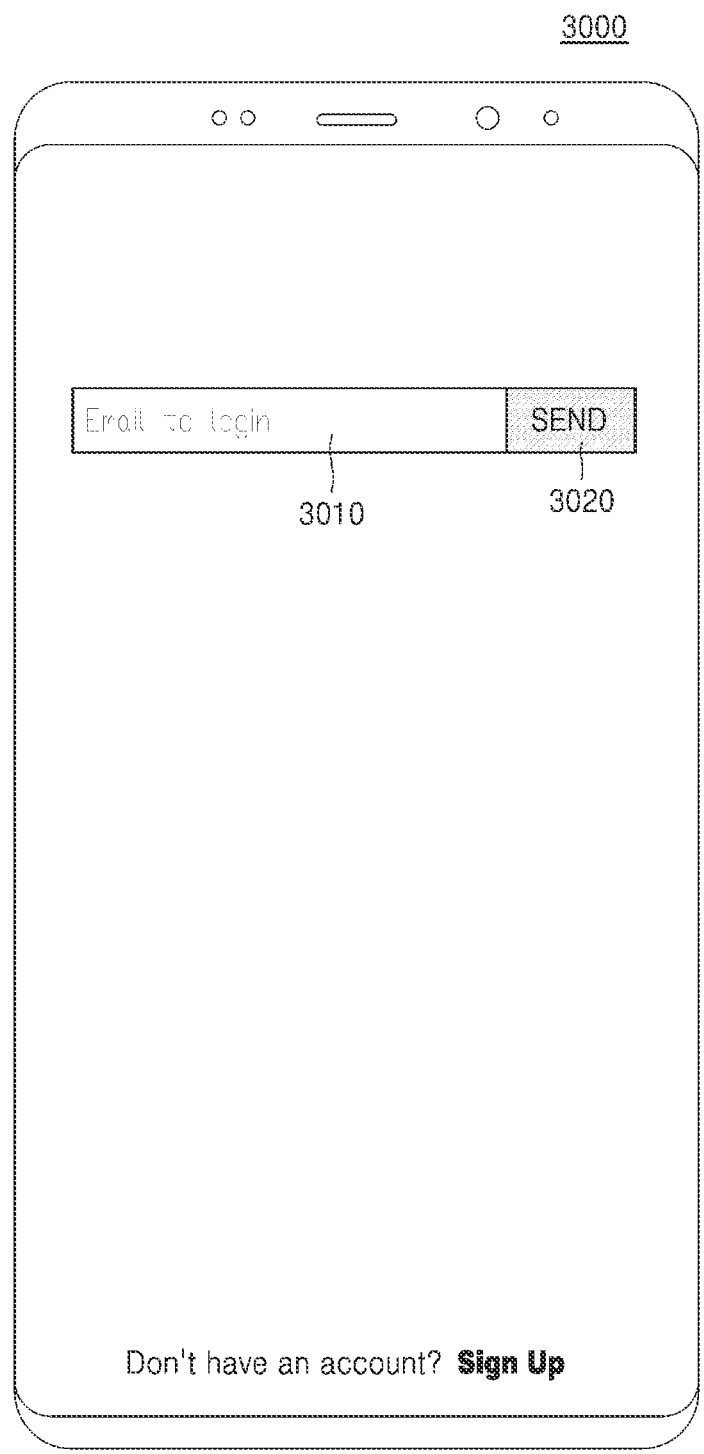
FIGS. 32 to 37 are views illustrating a sign-in page of the exercise history management system according to an embodiment of the present disclosure.

First, referring to FIG. 32, the email input portion 3010 and the email transmission portion 3020 are displayed on the sign-in page 3000 of the exercise history management system.

The email transmission portion 3020 may be deactivated until an email address is input to the email input portion 3010. In addition, when the user inputs the email address to the email input portion 3010 and the input email address has a correct email format (for example, "@" is included), the email transmission portion 3020 may be activated.

Figure 33:
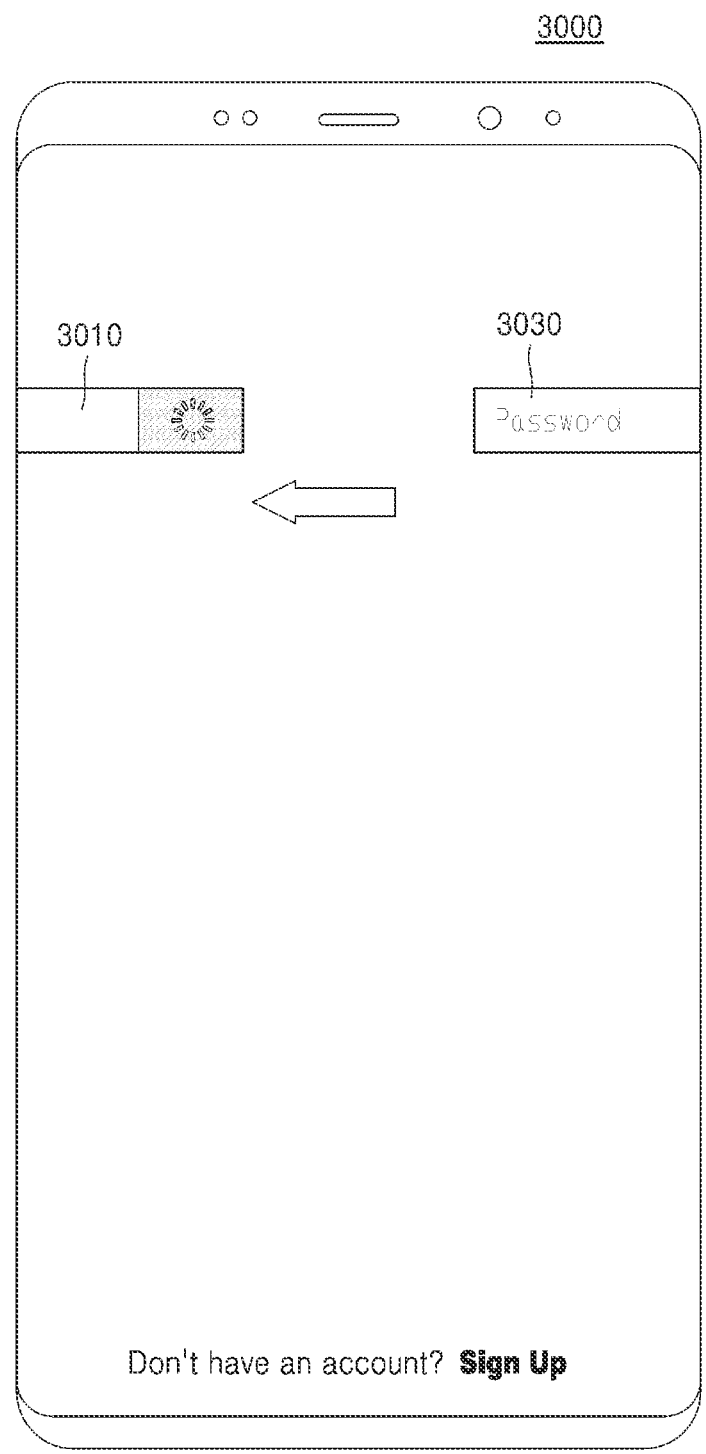

When the user presses the activated email transmission portion 3020, the email input portion 3010 is switched to a password input window. That is, when the user presses the activated email transmission portion 3020, as shown in FIGS. 33 and 34, the email input portion 3010 and the email transmission portion 3020 disappear while moving in one direction (an arrow direction of FIG. 33), and a password input portion 3030 and a password transmission portion 3040 appear while moving in one direction (the arrow direction of FIG. 33).

The password transmission portion 3040 may be deactivated until a password is input to the password input portion 3030. In addition, when the user inputs the password to the password input portion 3030, the password transmission portion 3040 may be activated.

Figure 35:
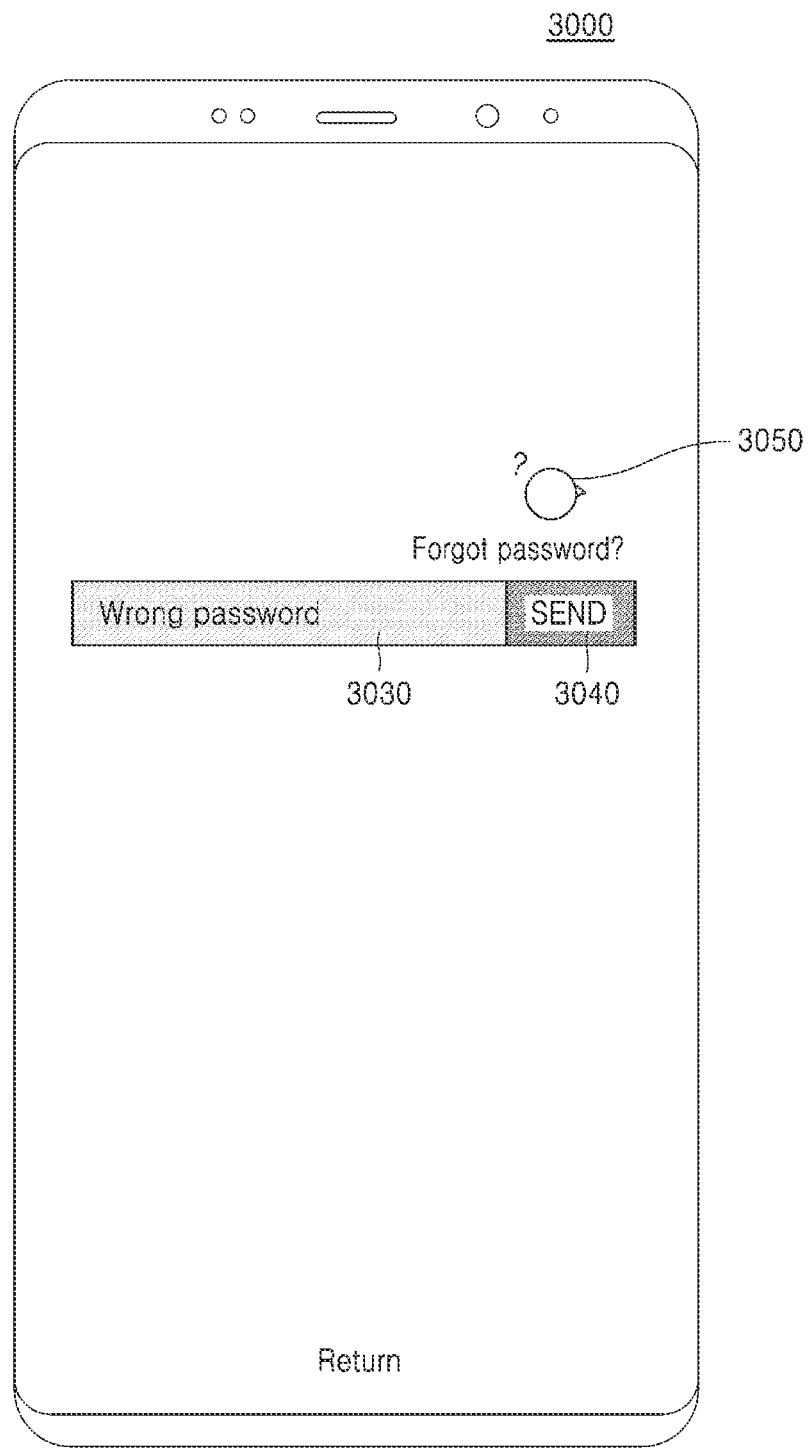
Figure 36:
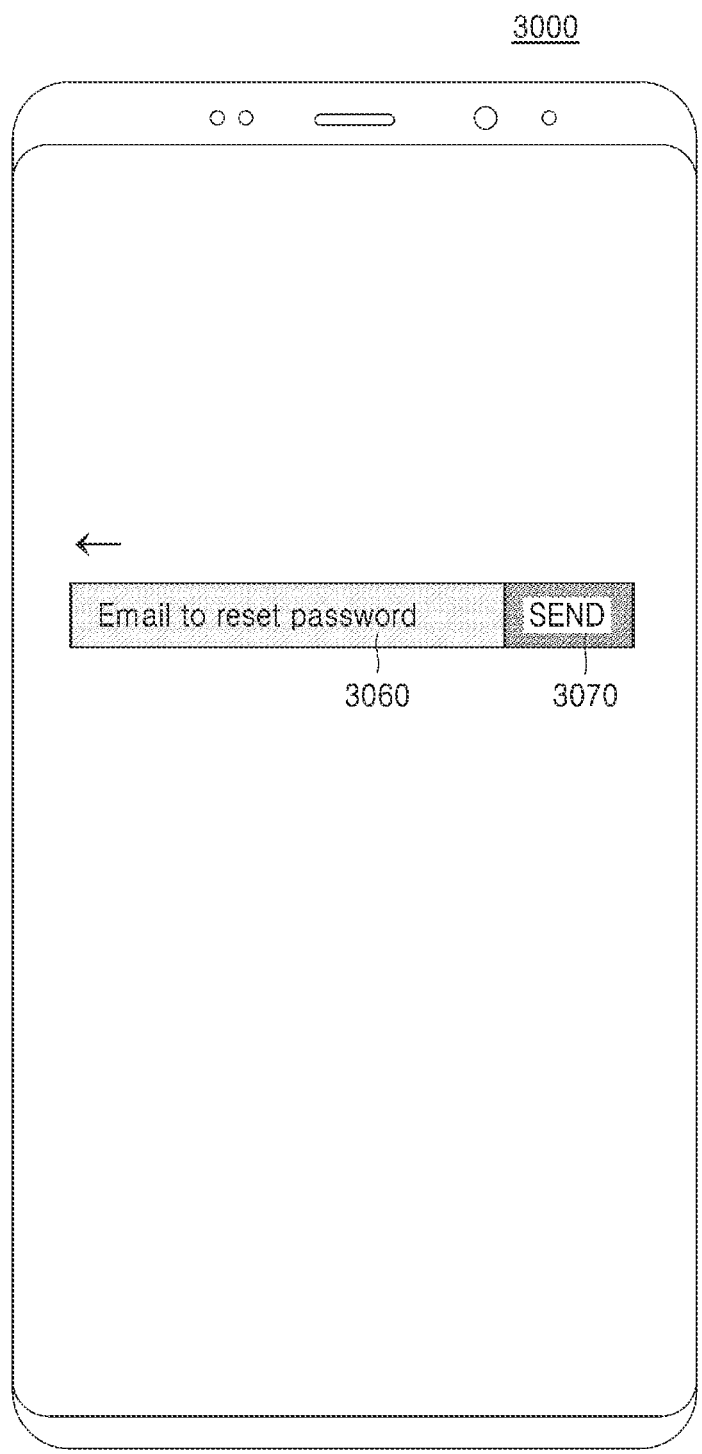

When the input password is a wrong password, an input error message is displayed on the password input portion 3030 as shown in FIG. 35. At this point, the password input portion 3030 may be displayed in a changed color. At this point, the password transmission portion 3040 may be activated. In addition, a password reset request portion 3050 may be displayed at one side of the password transmission portion 3040, and when the password reset request portion 3050 is pressed, the password reset request portion 3050 may be linked to a password reset page of FIG. 36. When the email address to which the reset password is to be transmitted is input to an email input portion 3060 of FIG. 36, and then an email transmission portion 3070 is pressed, the password that is reset to correspond to the email address may be transmitted.

Figure 34:
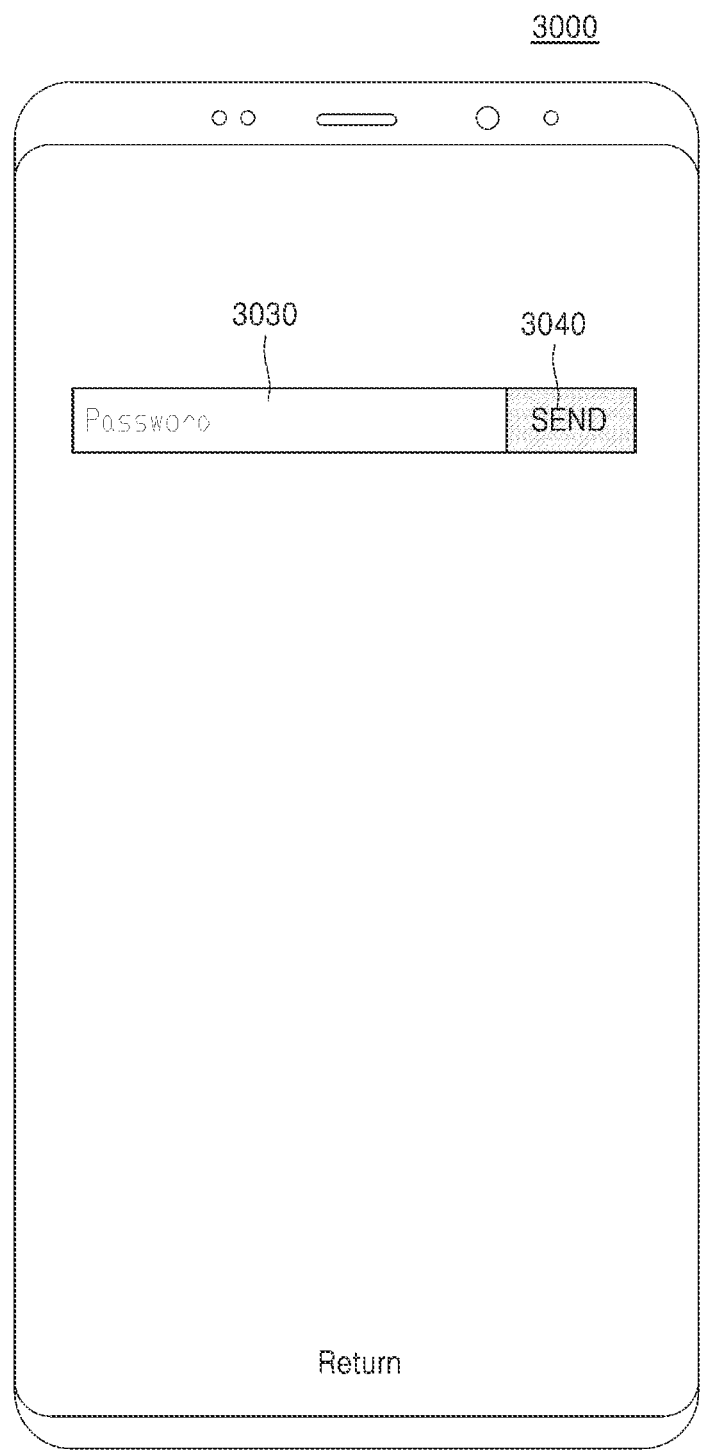

Meanwhile, when the password input portion 3030 on which the input error message is displayed is pressed in the state of FIG. 35, the state may return to the state of the password input window shown in FIG. 34.

Figure 37:
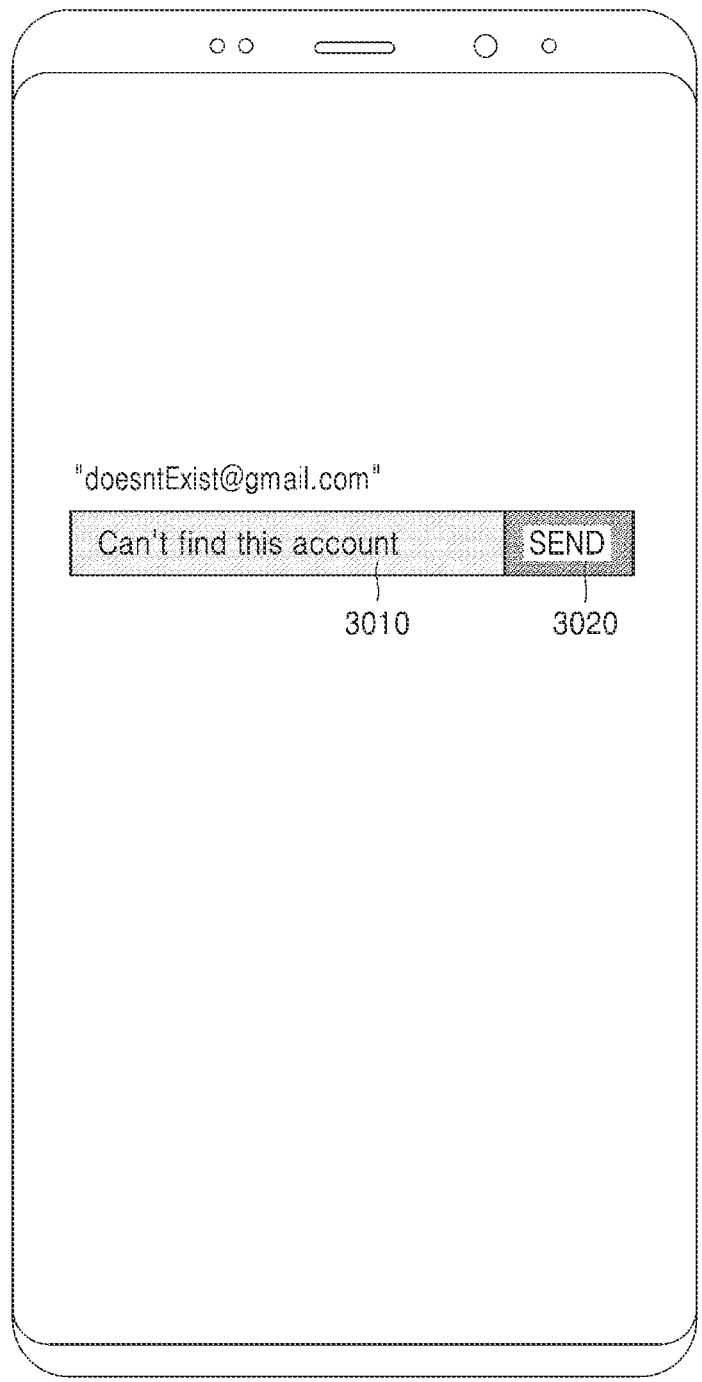

Meanwhile, when the email address, which is input in FIG. 32, is an email address that does not exist in a user database (DB), as shown in FIG. 37, the input email address moves while animating upward of the email input portion 3010, and an error message is displayed in the email input portion 3010, and when the error message displayed in the email input portion 3010 is clicked, the page may return to the page of FIG. 32.

The above-described sign-in page of the exercise history management system according to an embodiment of the present disclosure may show an email, password input and transmission, and an error message in one line, so that the effect of allowing users to use the sign-in page with a simple design and high immersion may be obtained.

<One-Line Exercise Member Sign-Up Page→

FIGS. 38 to 43 are views illustrating a member sign-up page of the exercise history management system according to an embodiment of the present disclosure.

Figure 38:
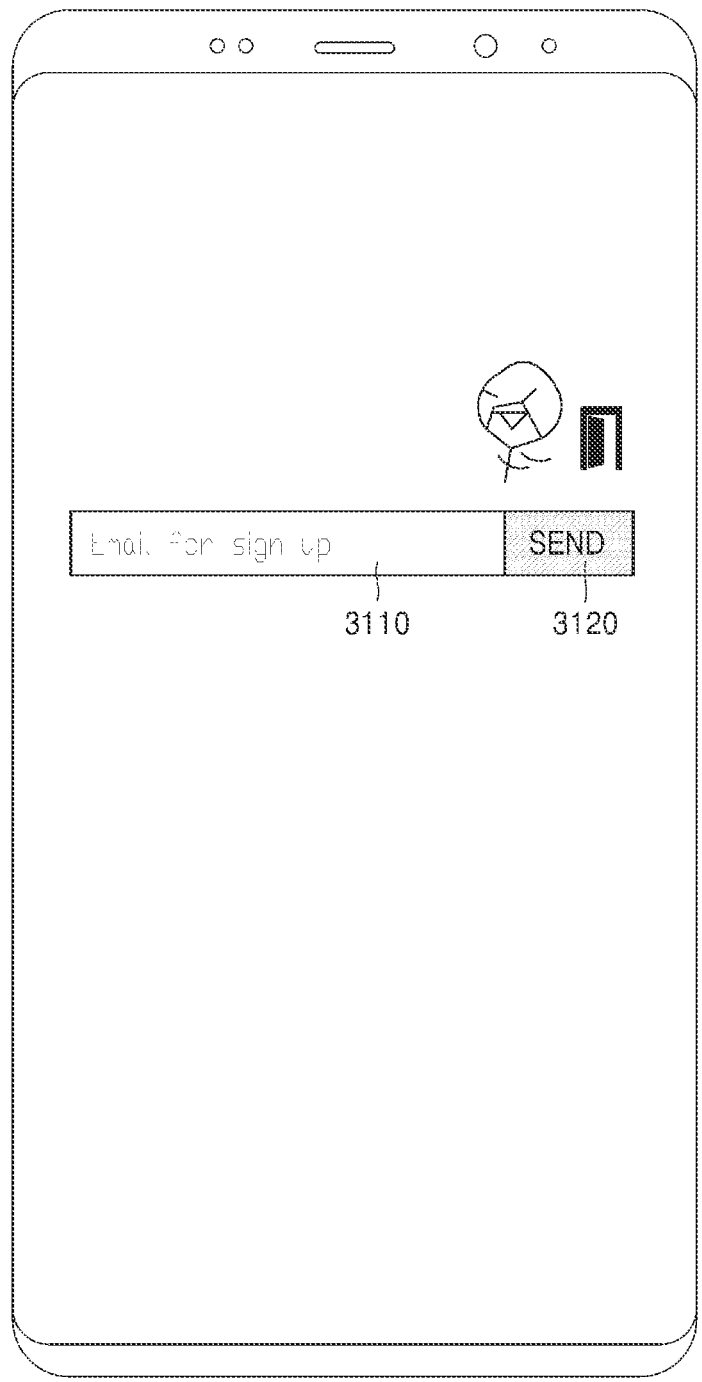
FIGS. 38 to 43 are views illustrating a member sign-up page of the exercise history management system according to an embodiment of the present disclosure.

First, referring to FIG. 38, the email input portion 3110 and the email transmission portion 3120 are displayed on the member sign-up page 3100 of the exercise history management system.

The email transmission portion 3120 may be deactivated until an email address is input to the email input portion 3110. In addition, when the user inputs the email address to the email input portion 3110 and the input email address has a correct email format (for example, "@" is included), the email transmission portion 3120 may be activated.

Figure 39:
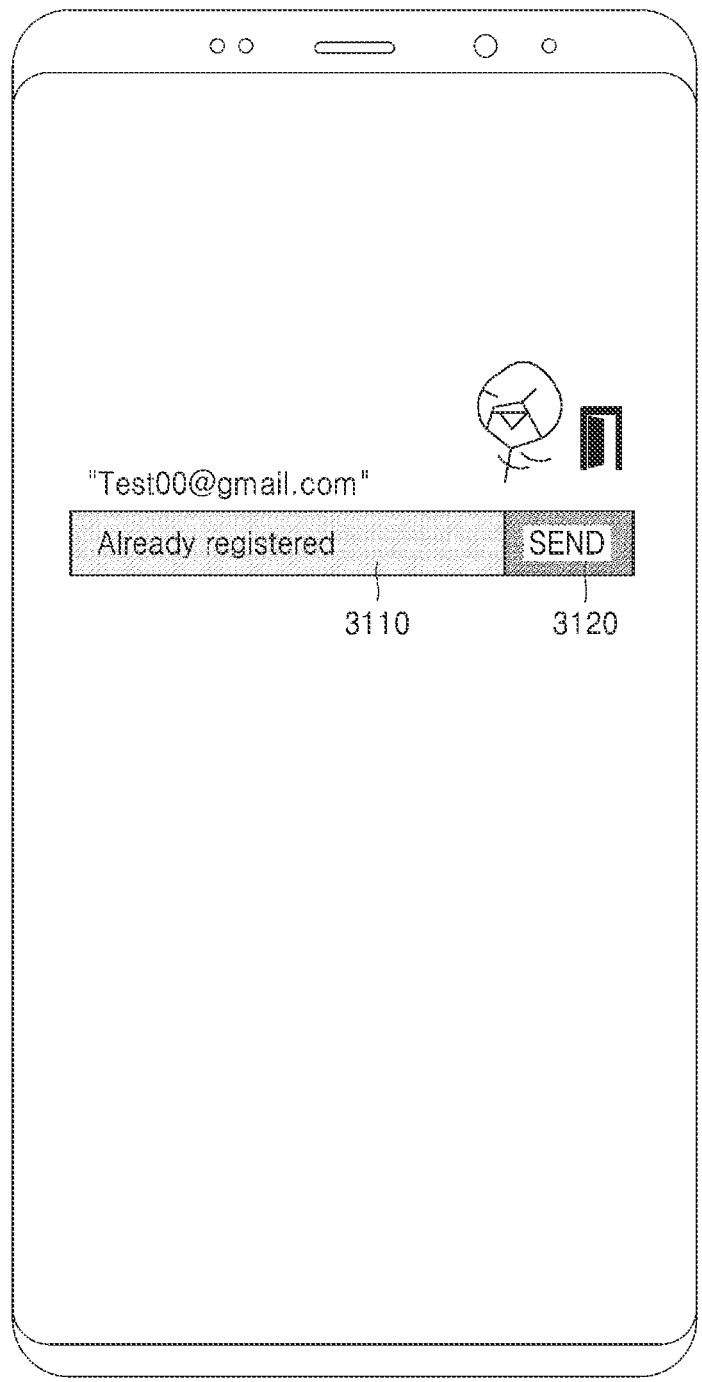

When the input email address is the email address that already exists in the user DB, as shown in FIG. 39, the input email address moves while animating upward of the email input portion 3110, and an error message may be displayed in the email input portion 3110. Here, when the error message displayed on the email input portion 3110 is clicked, the page may be switched to the sign-in page of FIG. 32.

Meanwhile, in FIG. 38, when the user presses the activated email transmission portion 3120, the email input portion 3110 is switched to a password input window. That is, when the user presses the activated email transmission portion 3120, the email input portion 3110 and the email transmission portion 3120 disappear while moving in one direction, and a password input portion 3130 and a password transmission portion 3140 appear while moving in one direction, so that the password input portion 3130 and the password transmission portion 3140 are displayed on the screen as shown in FIG. 40.

Figure 40:
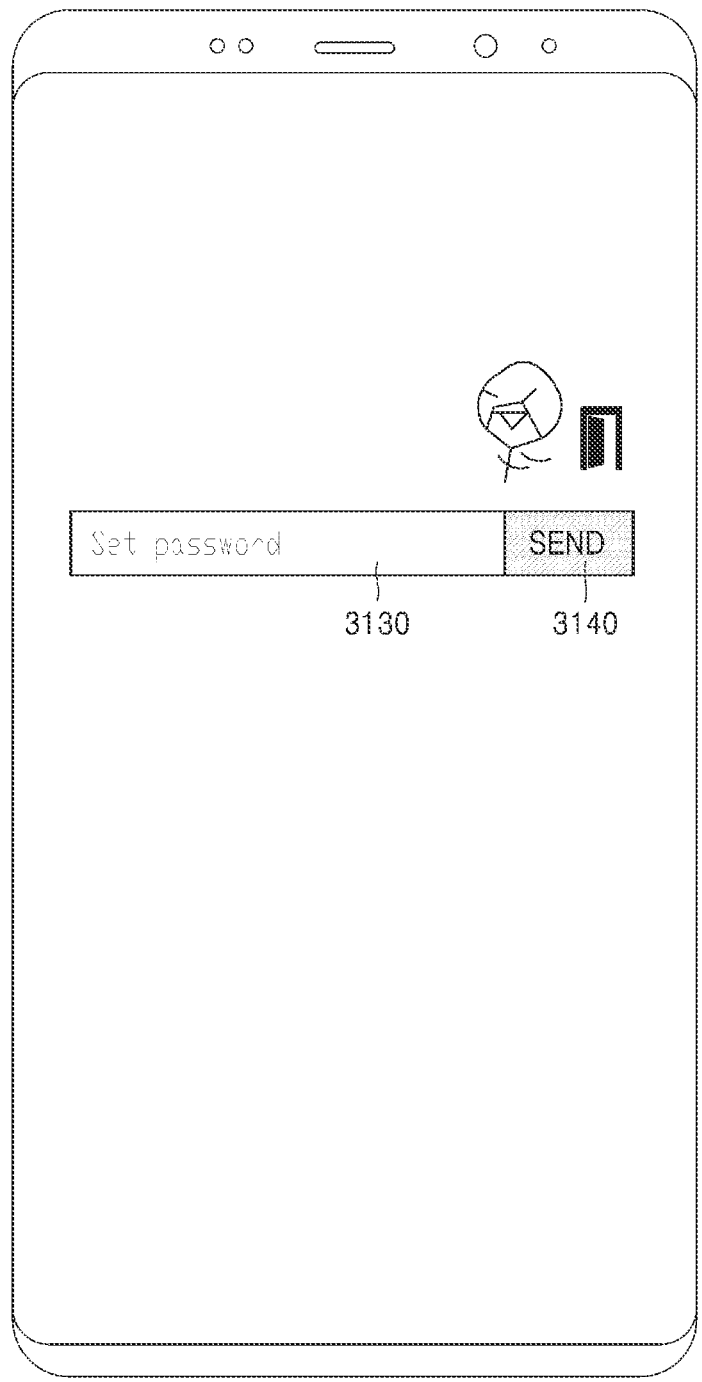
Figure 41:
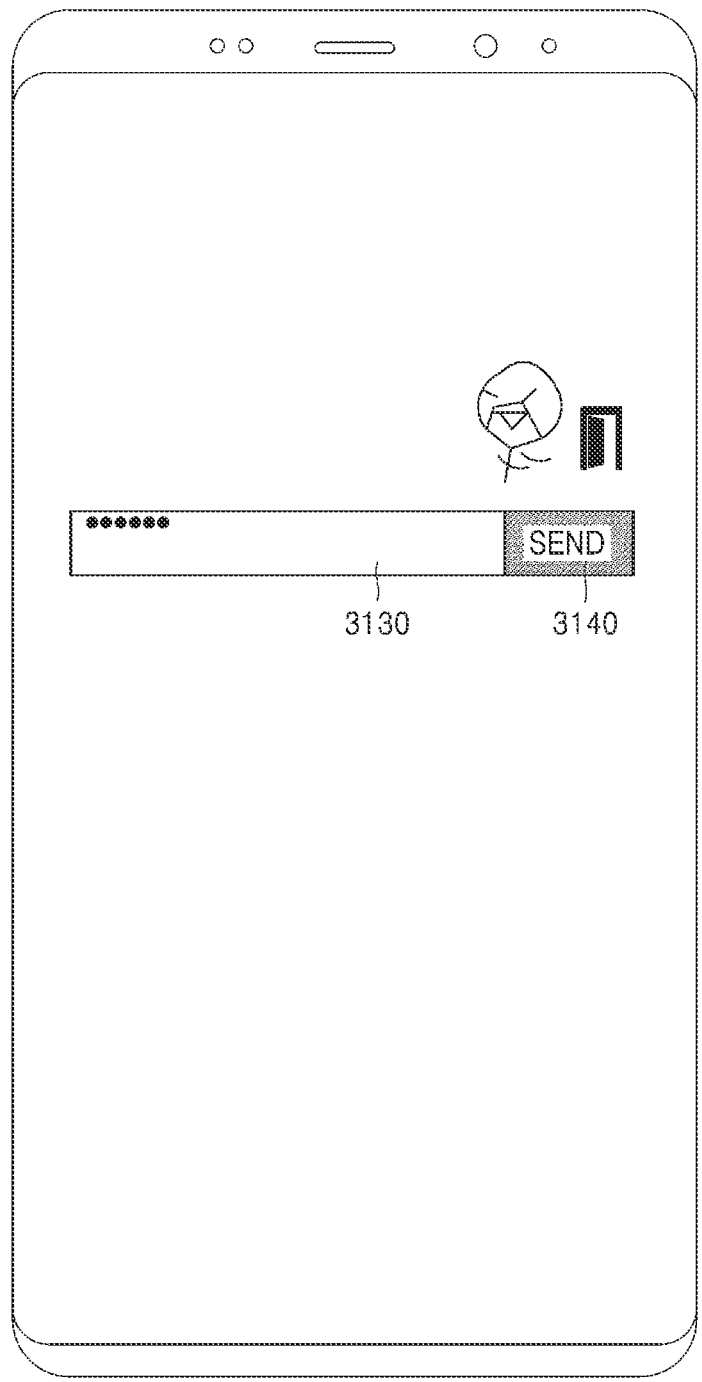

As shown in FIG. 40, the password transmission portion 3140 may be deactivated until a password is input to the password input portion 3130. In addition, when the user inputs the password to the password input portion 3130 and the input password is shorter than a preset minimum password length, the phrase "Weak password" may be displayed. In addition, when the input password has a length equal to or greater than the preset minimum password length, the password transmission portion 3140 may be activated as shown in FIG. 41. At this point, when the password transmission portion 3140 is pressed but the input password violates preset password rules (for example, the password includes special characters or the like), an error message may be displayed.

Figure 42:
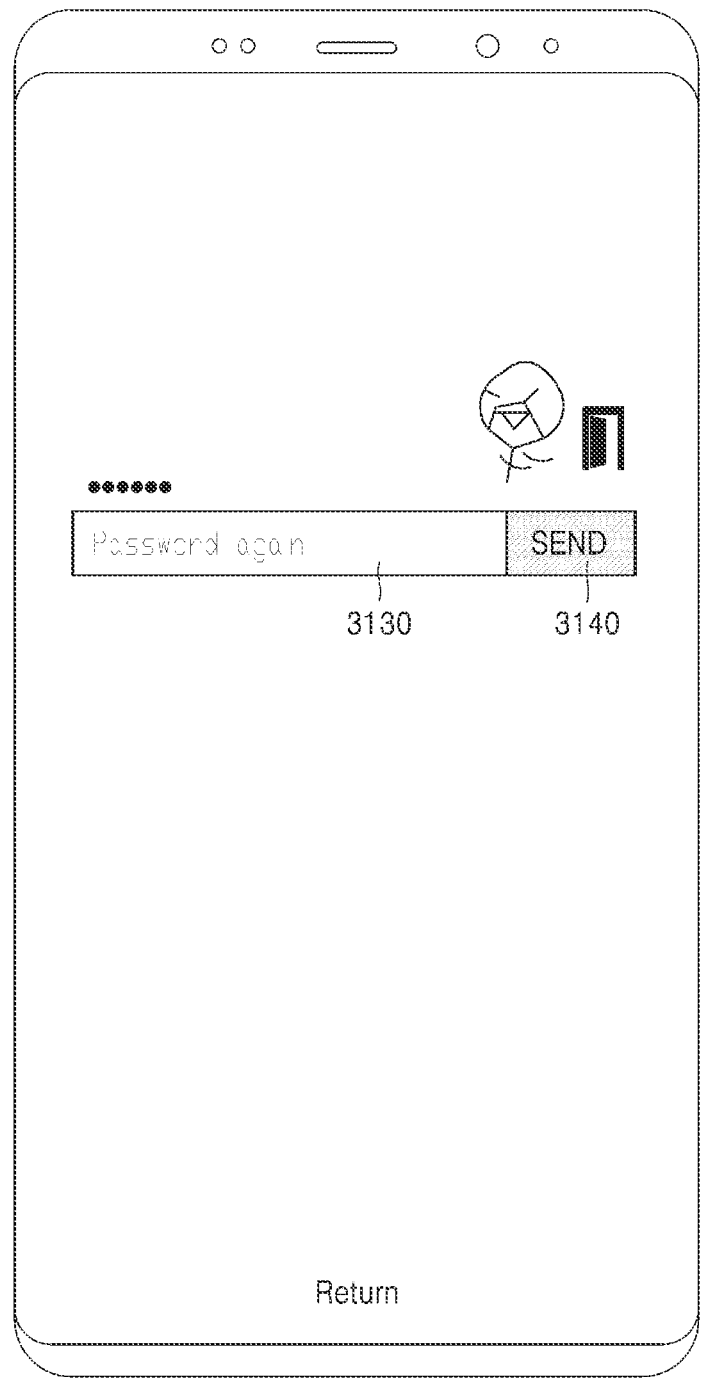
Figure 43:
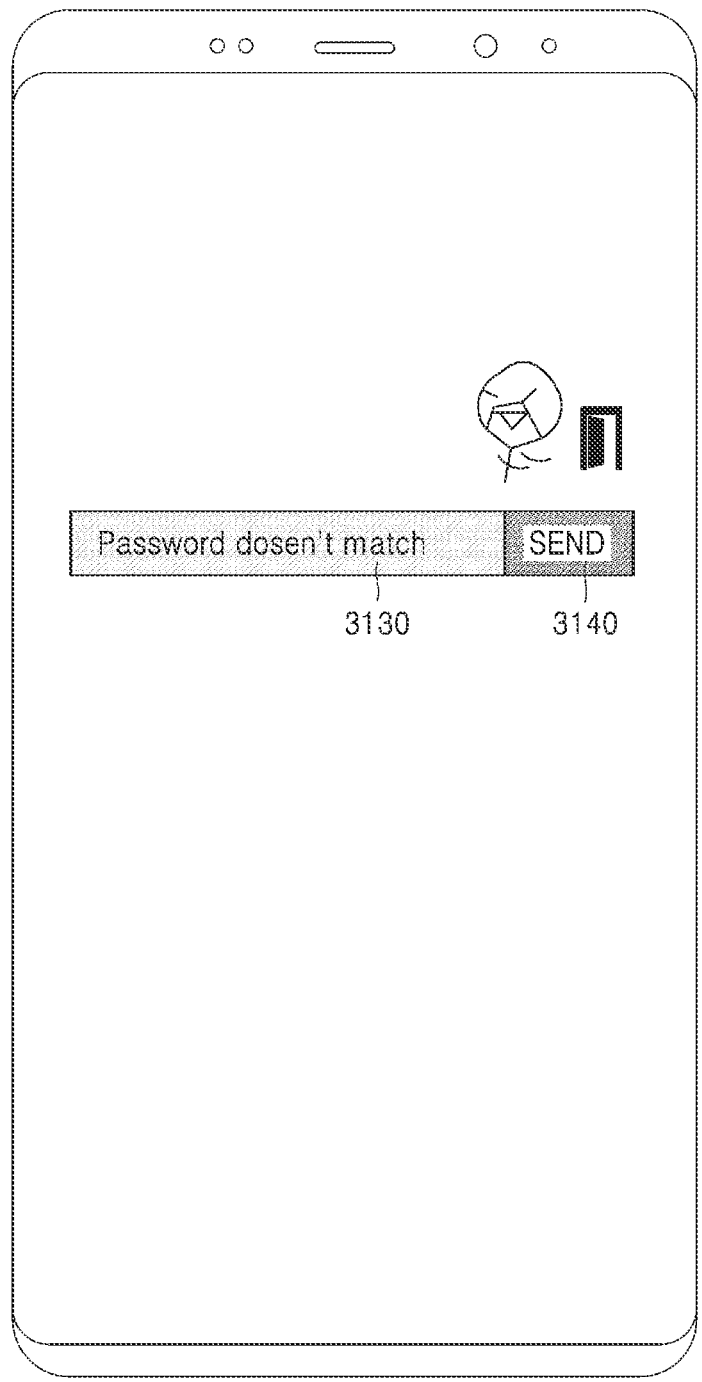

When the input password is an appropriate password corresponding to the rules, as shown in FIG. 42, the input password is moved while animating upward of the password input portion 3130, and a message, notifying a password needs to be re-input, is displayed in the password input portion 3130.

Figure 44:
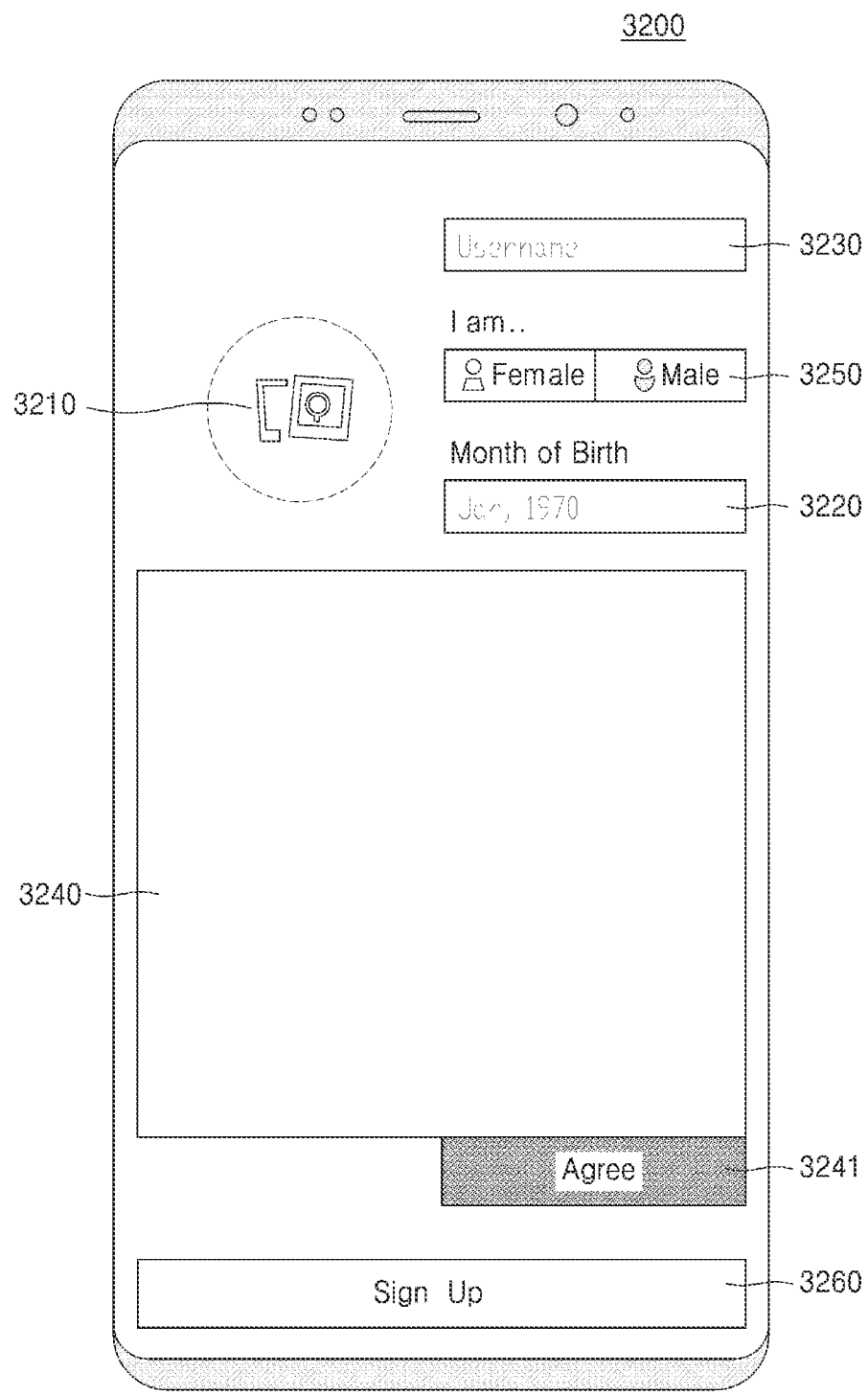
FIGS. 44 to 49 are views illustrating a user information input page of the exercise history management system according to an embodiment of the present disclosure.

In this state, when the password is re-input to the password input portion 3130 and the re-input password matches the previously input password, the page is switched to a registration information/terms page (see FIG. 44). On the other hand, when the re-input password does not match the previously input password, an input error message is displayed on the password input portion 3130. At this point, the password input portion 3130 may be displayed in a changed color. At this point, the password transmission portion 3140 may be activated.

The member sign-up page of the exercise history management system according to an embodiment of the present disclosure may show an email, password input and transmission, and an error message in one line, so that the effect of allowing users to use the sign-in page with a simple design and high immersion may be obtained.

<User Information Input Page→

FIGS. 44 to 49 are views illustrating a user information input page of the exercise history management system according to an embodiment of the present disclosure.

First, referring to FIG. 44, the user information input page 3200 of the exercise history management system includes the user image input portion 3210, the user's date pf birth input portion 3220, the user name input portion 3230, the terms display portion 3240, the user gender input portion 3250, and the user information transmission portion 3260. Here, a predetermined color may be already displayed on a border excluding the user's input portions.

Here, in the user information input page of the present disclosure, each time each piece of information is input, an area to which the corresponding input portion belongs is displayed in different colors, brightness, and contrast so that an area in which information is not input is clearly expressed.

Figure 45:
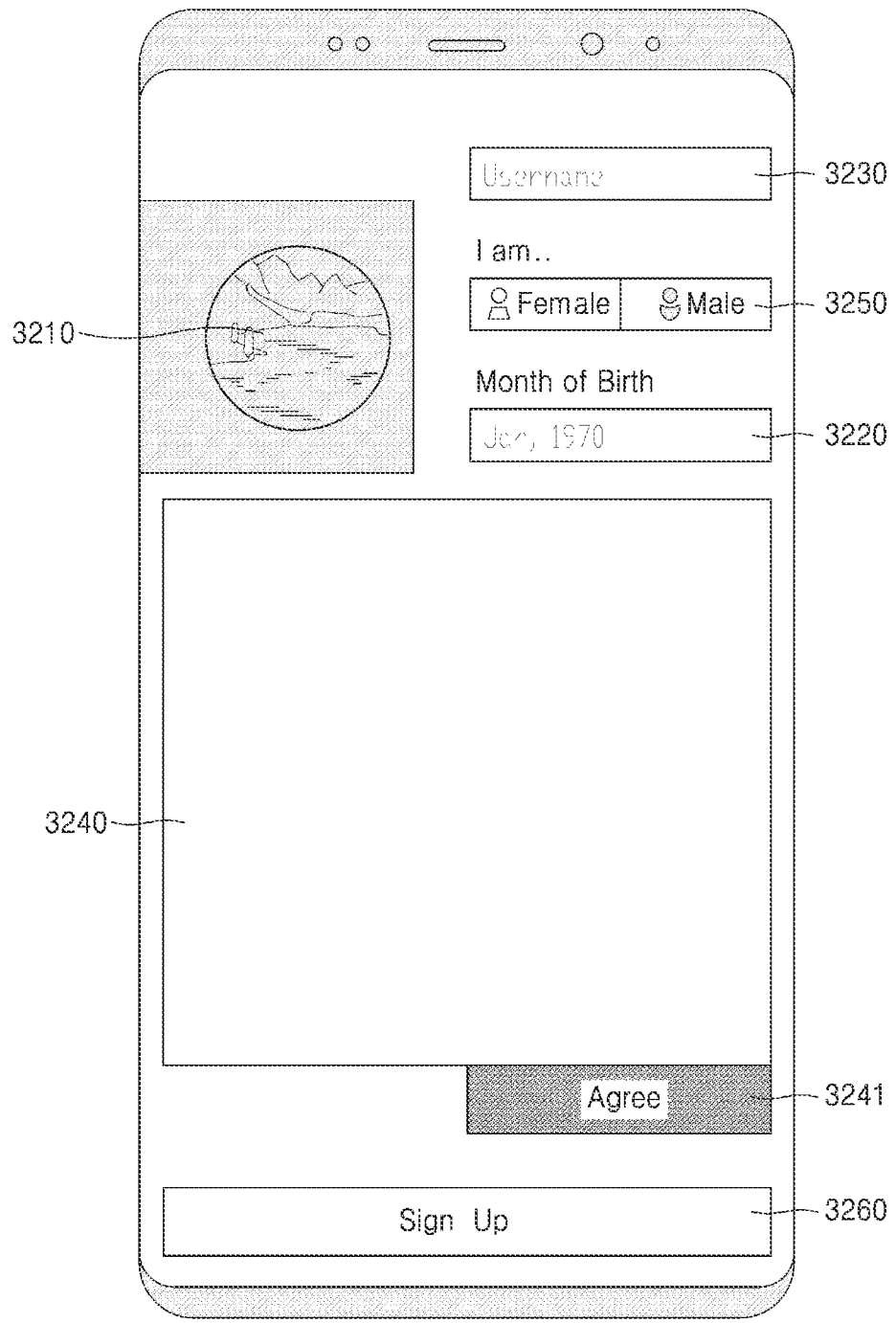

First, when a user image is input to the user image input portion 3210, a color of the area of the user image input portion 3210 is changed as shown in FIG. 45.

Figure 46:
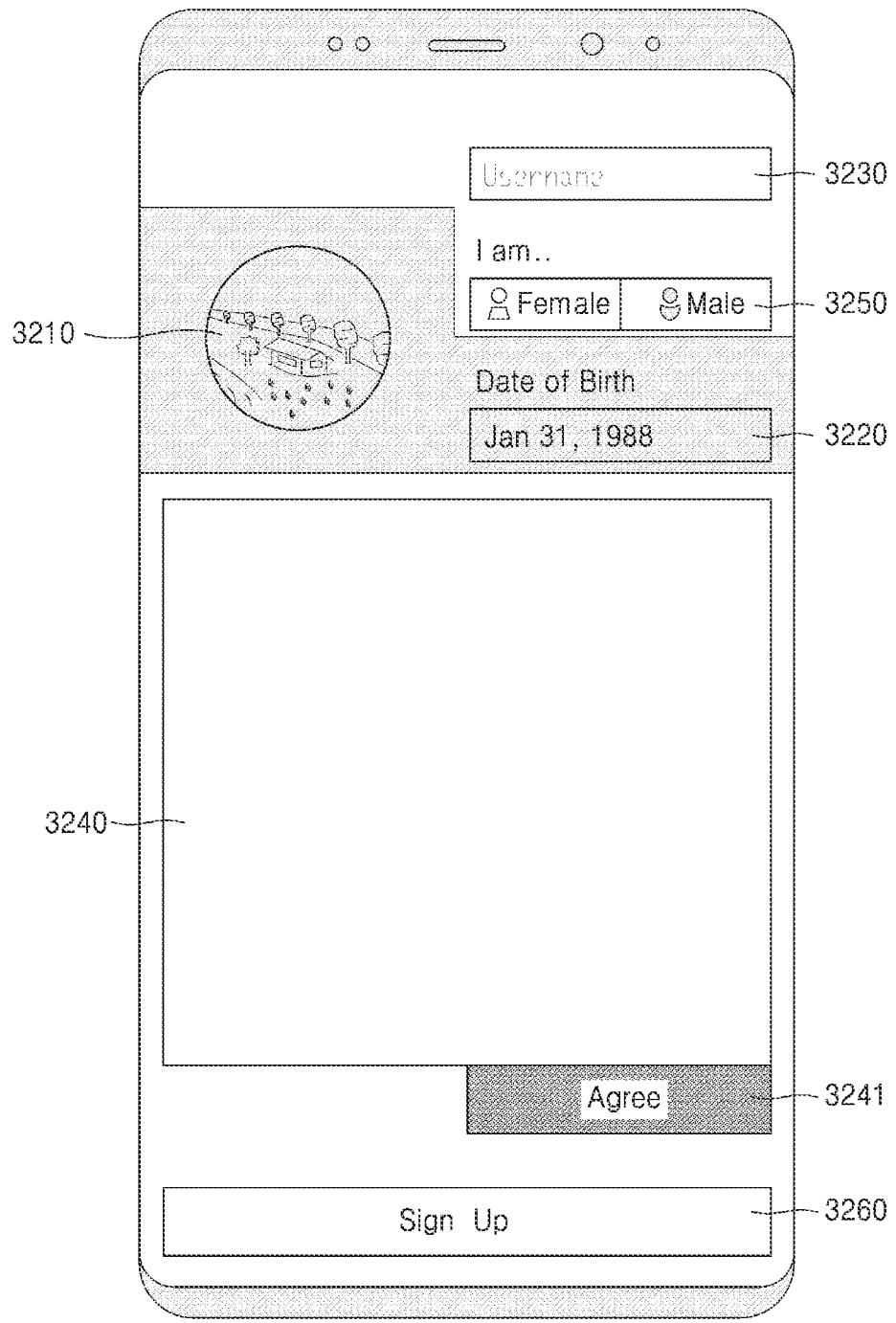

Next, when a birth month of the user is input to the user's date pf birth input portion 3220, a color of the area of the user's date pf birth input portion 3220 is changed as shown in FIG. 46.

Figure 47:
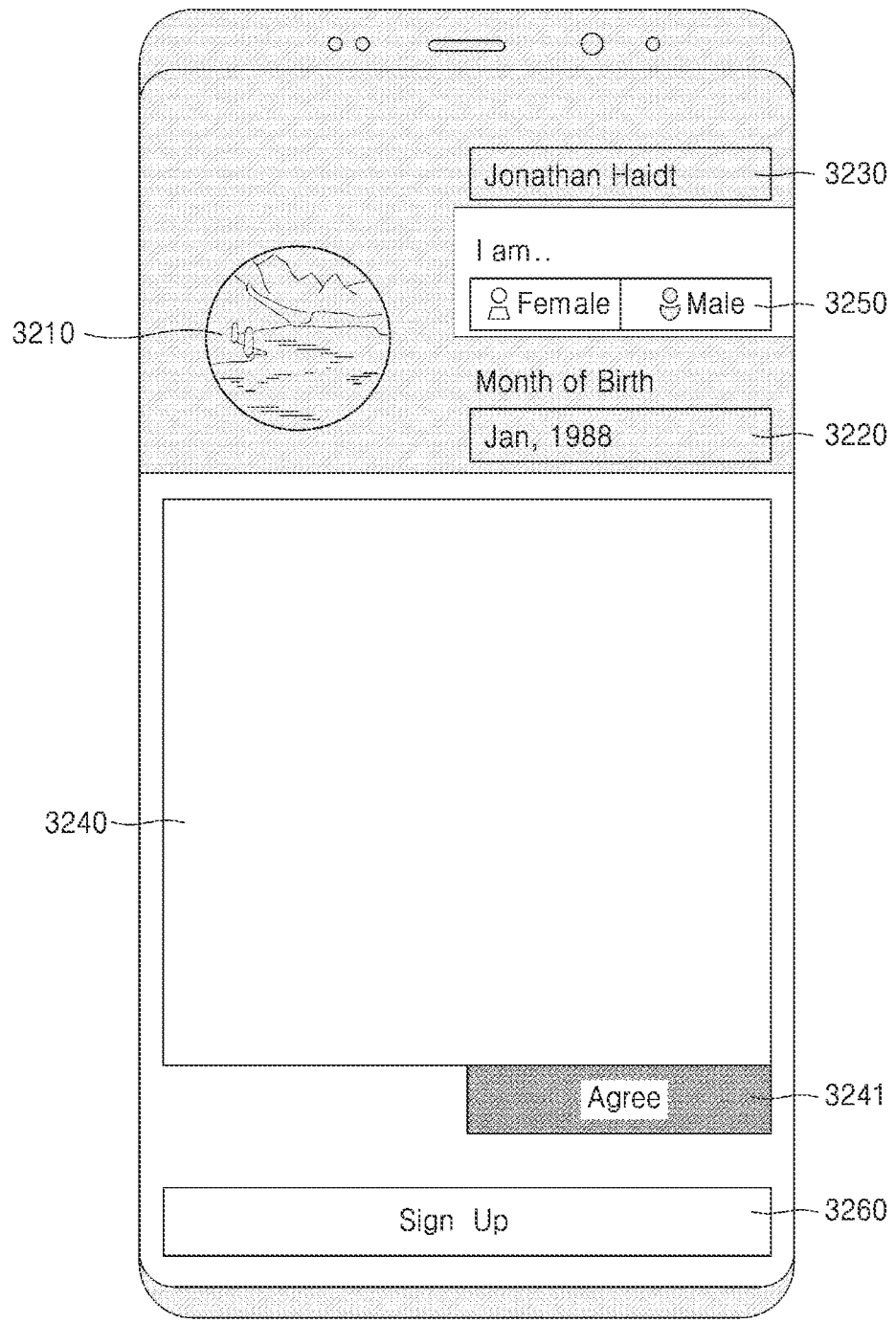

Next, when a name of the user is input to the user name input portion 3230, a color of the area of the user name input portion 3230 is changed as shown in FIG. 47.

Figure 48:
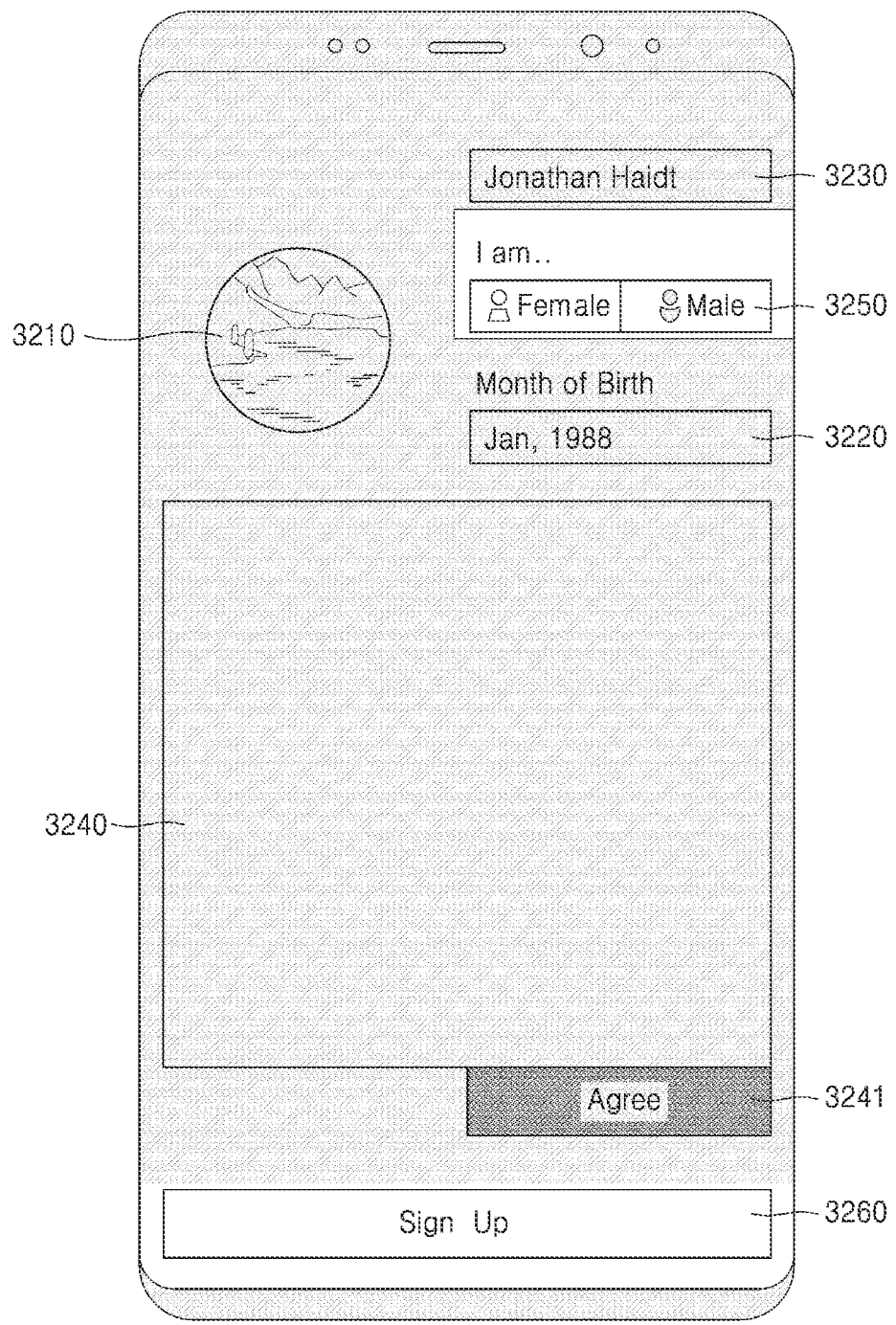

Next, when an agreement button 3241 is clicked on the terms display portion 3240, as shown in FIG. 48, a color of the area of the terms display portion 3240 is changed. At this point, when the agreement button 3241 is clicked, a mark "Agree" may be changed to a mark "Agreed" and displayed. In this state, the gender has not been entered, and thus, it is possible to intuitively and clearly identify which information has not been input.

Figure 49:
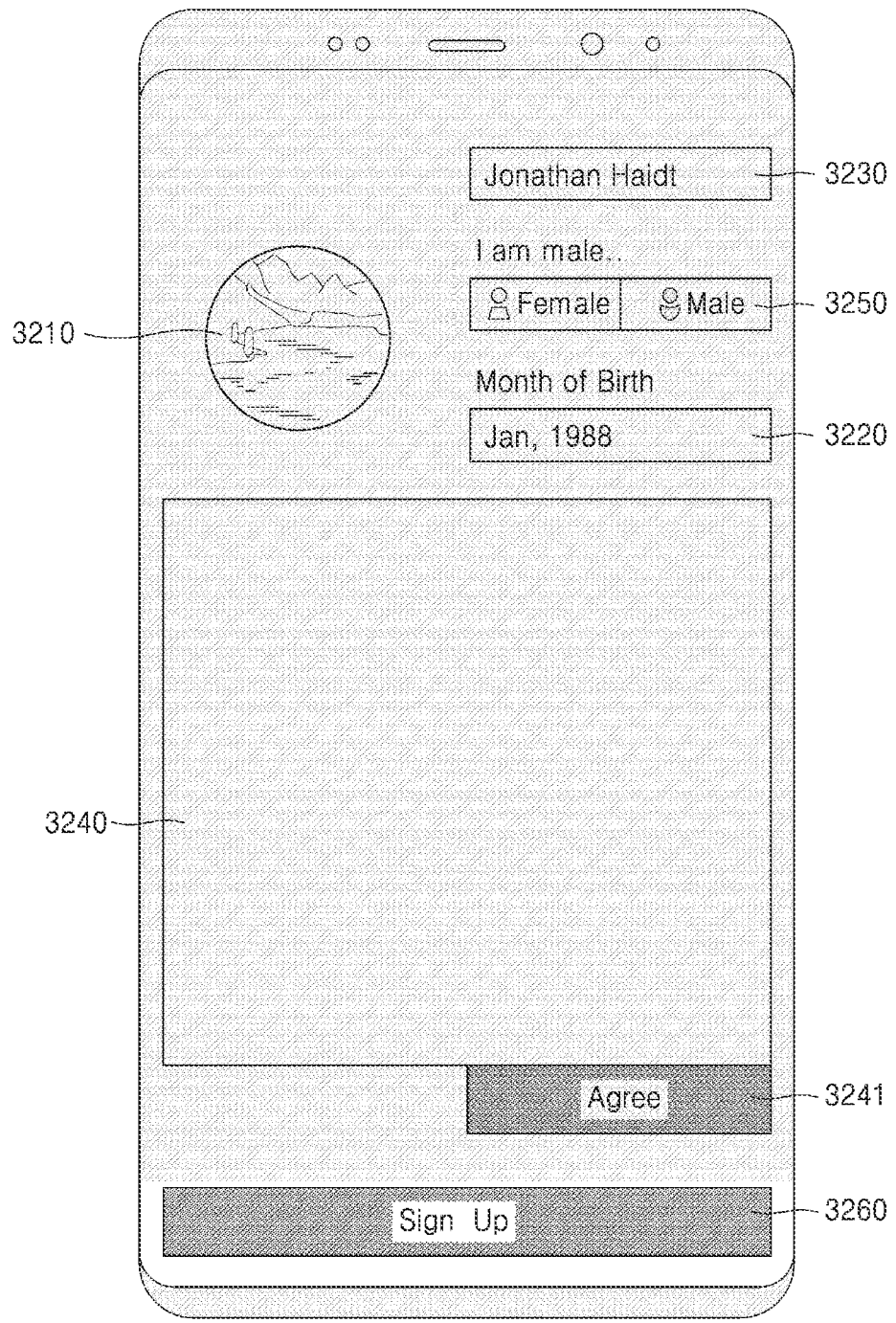
Figure 50:
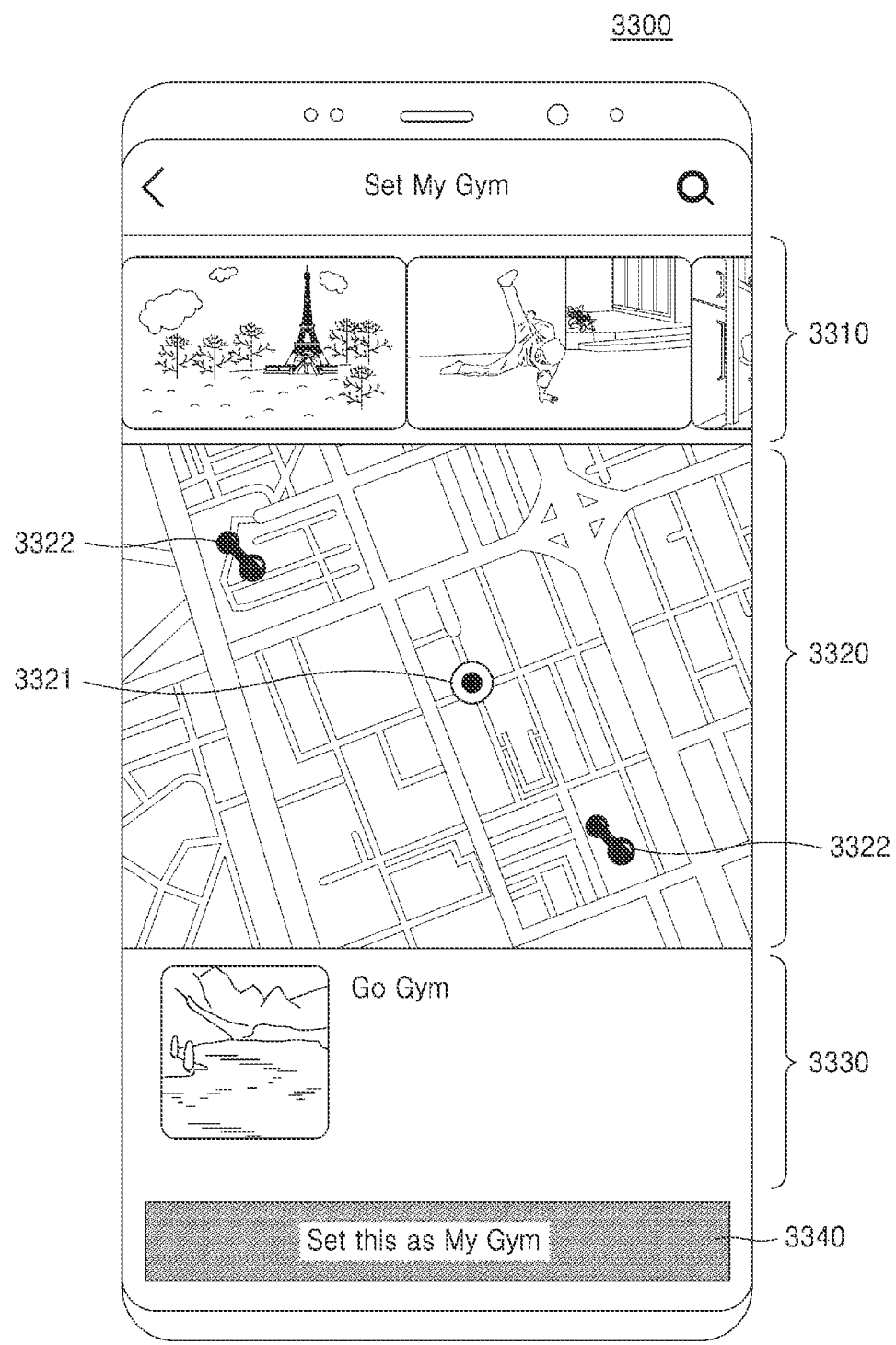
FIGS. 50 to 53 are views illustrating a my-gym setup page of the exercise history management system according to an embodiment of the present disclosure.
Figure 51:
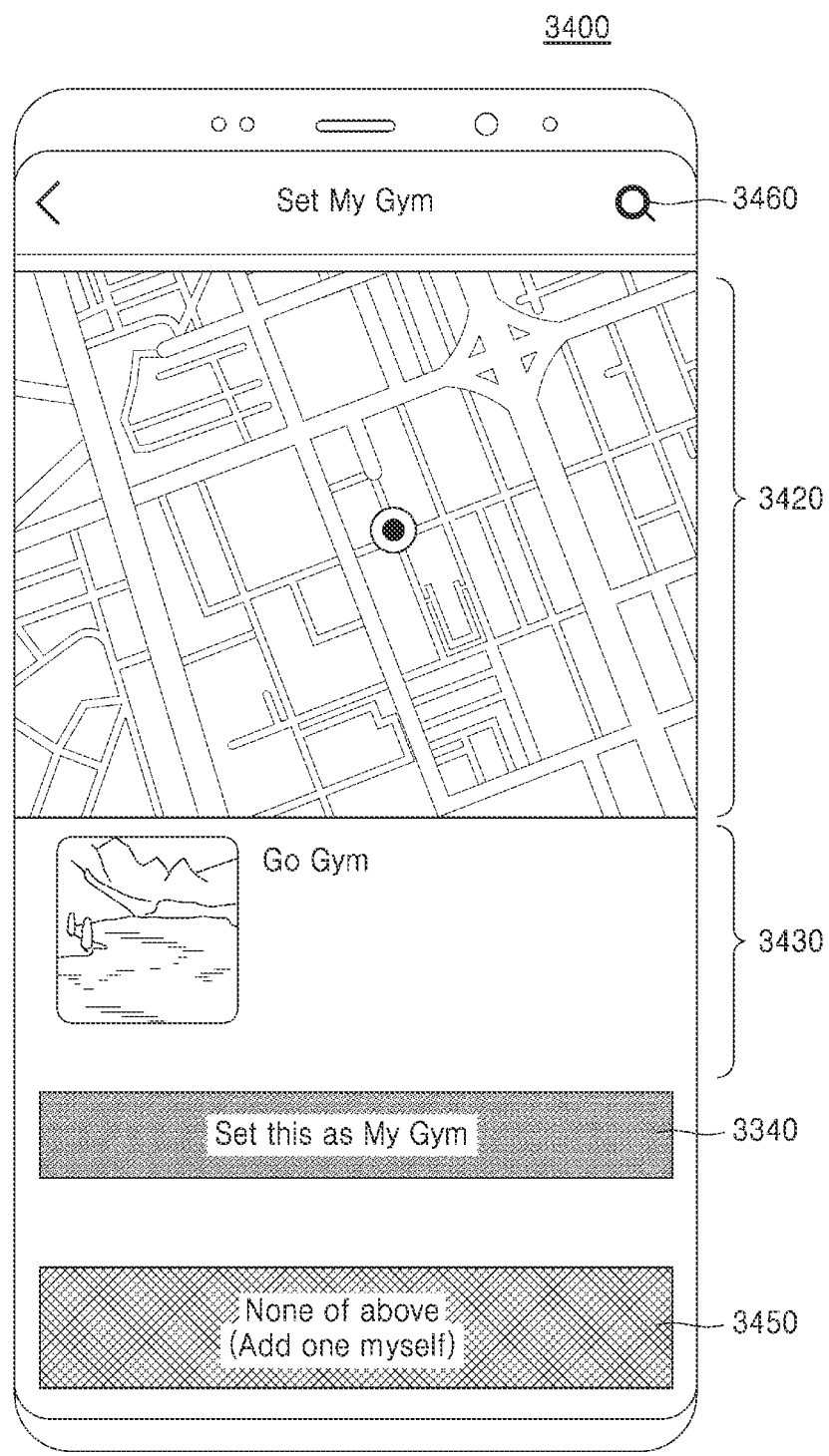

Next, when a birth month of the user is input to the user gender input portion 3250, as shown in FIG. 49, a color of the area of the user gender input portion 3250 is changed. In addition, since the input of all information is completed, the user information transmission portion 3260 is activated and displayed.

On the user information input page of the present disclosure, by implementing a method in which a color is filled whenever user information is input, it is possible to obtain an effect of guiding the input of user information intuitively and without boring.

<My-Gym Setup Page→

FIGS. 50 to 53 are views illustrating a my-gym setup page of the exercise history management system according to an embodiment of the present disclosure.

The my-gym setup page 3300 includes the gym list display area 3310, the map display area 3320, and the gym information display area 3330. In addition, the my-gym setup button 3340 may be further included.

Here, when my gym is initially set up only once, then my gym is automatically selected afterwards. However, when the current location of the user terminal 200 is significantly far from the location in my gym information, reselection may be required. Meanwhile, when the exercise log input and transmission portion 2620 (see FIG. 28) is pressed in a state in which my gym is not determined, a transmission/reception logic may not operate, and the exercise log input and transmission portion 2620 may be linked to the my-gym setup page 3300 first.

In the gym list display area 3310, gyms near the current location of the user are displayed in the transverse direction on a screen. The gym list display area 3310 may be scrolled in the transverse direction, and when one is clicked on from the gym list display area 3310, the corresponding gym is displayed in the center of the map display area 3320, and detailed information about the corresponding gym is displayed on the gym information display area 3330.

Predetermined map data is displayed on the map display area 3320. At the time when the application is executed, a current location 3321 of the user terminal 200 is displayed at the center of the screen in the map display area 3320, and nearby gyms 3322 are displayed at respective locations.

Information about the gym selected from the gym list display area 3310 or the map display area 3320 may be displayed on the gym information display area 3330. Alternatively, until an input is received from the user, a gym with a high probability of being "my gym" may be extracted in advance, and information about the gym may be displayed.

When the gym that the user wants to select is not included in the gyms displayed in the gym list display area 3310 or the map display area 3320, a direct input button 3450 (marked as "None of above (Add one myself)") hidden below appears when the screen is scrolled. When the direct input button 3450 is pressed, the direct input button 3450 is linked to the new gym add-page of FIG. 53. Alternatively, when a search button 3460 is pressed, the search button 3460 is linked to a gym search page of FIG. 52.

Figure 52:
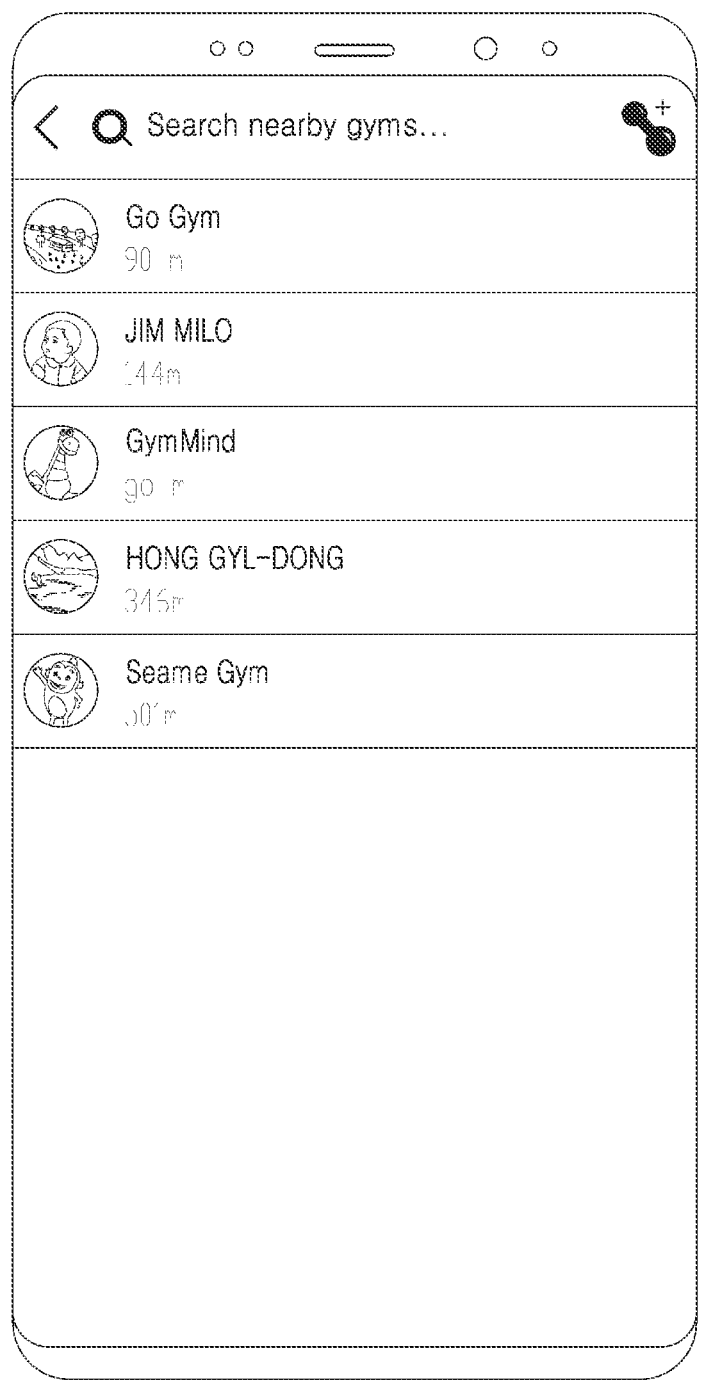

FIG. 52 is a view illustrating the gym search page.

As shown in FIG. 52, when a gym search page 3500 is accessed, by default, nearby gyms are displayed together with distance information in a list form, and keyword search is also possible.

Figure 53:
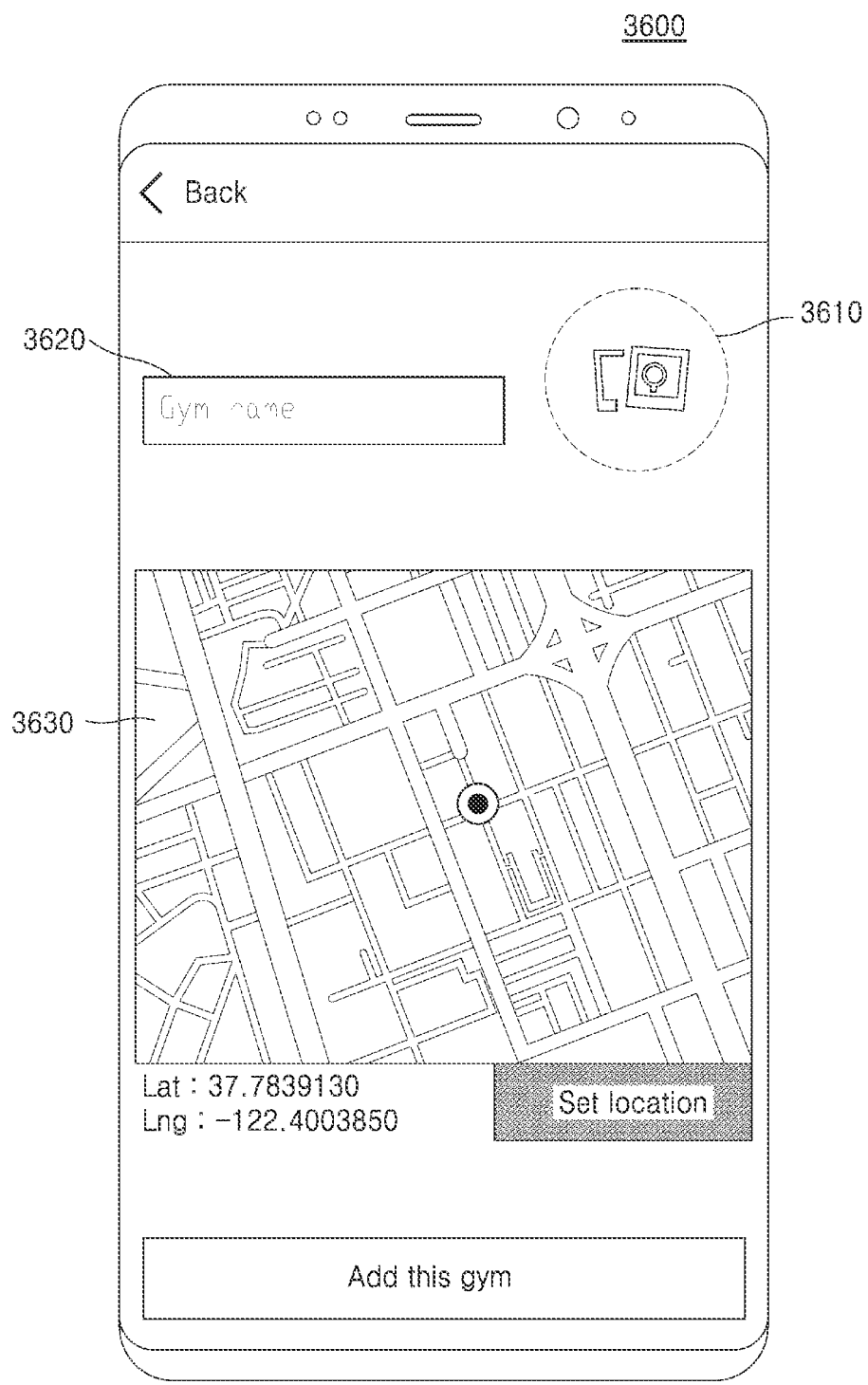

FIG. 53 is a view illustrating a new gym add-page.

Referring to FIG. 53, a new gym add-page 3600 of the exercise history management system includes a gym image input portion 3610, a gym name input portion 3620, a gym location input portion 3630, and a gym information transmission portion 3640. Here, a predetermined color may already be displayed on a border excluding the gym information input portions.

Here, in the new gym add-page of the present disclosure, like the user information input page (see FIGS. 44 to 49), an area to which the corresponding input portion belongs is displayed in different colors, brightness, and contrast so that an area in which information is not input is clearly expressed.

<User Page→

FIGS. 54 to 59 are views illustrating a user page of the exercise history management system according to an embodiment of the present disclosure.

A user page 3700 includes the user information display portion 3710, a user profile edit button 3720, and a user content display portion 3730.

The user information display portion 3710 displays a user image, an exercise count, the number of users who have been pooled (followed) by me, the number of users who have been pooled me, user comments, and the like. Meanwhile, although not shown in the drawings, my gym information of the user, a badge of a "birthday exerciser," and "Eve exerciser," or the like, a city badge that may be given according to the location of my gym (in which city the exercise was performed), and the like may be further displayed.

Figure 54:
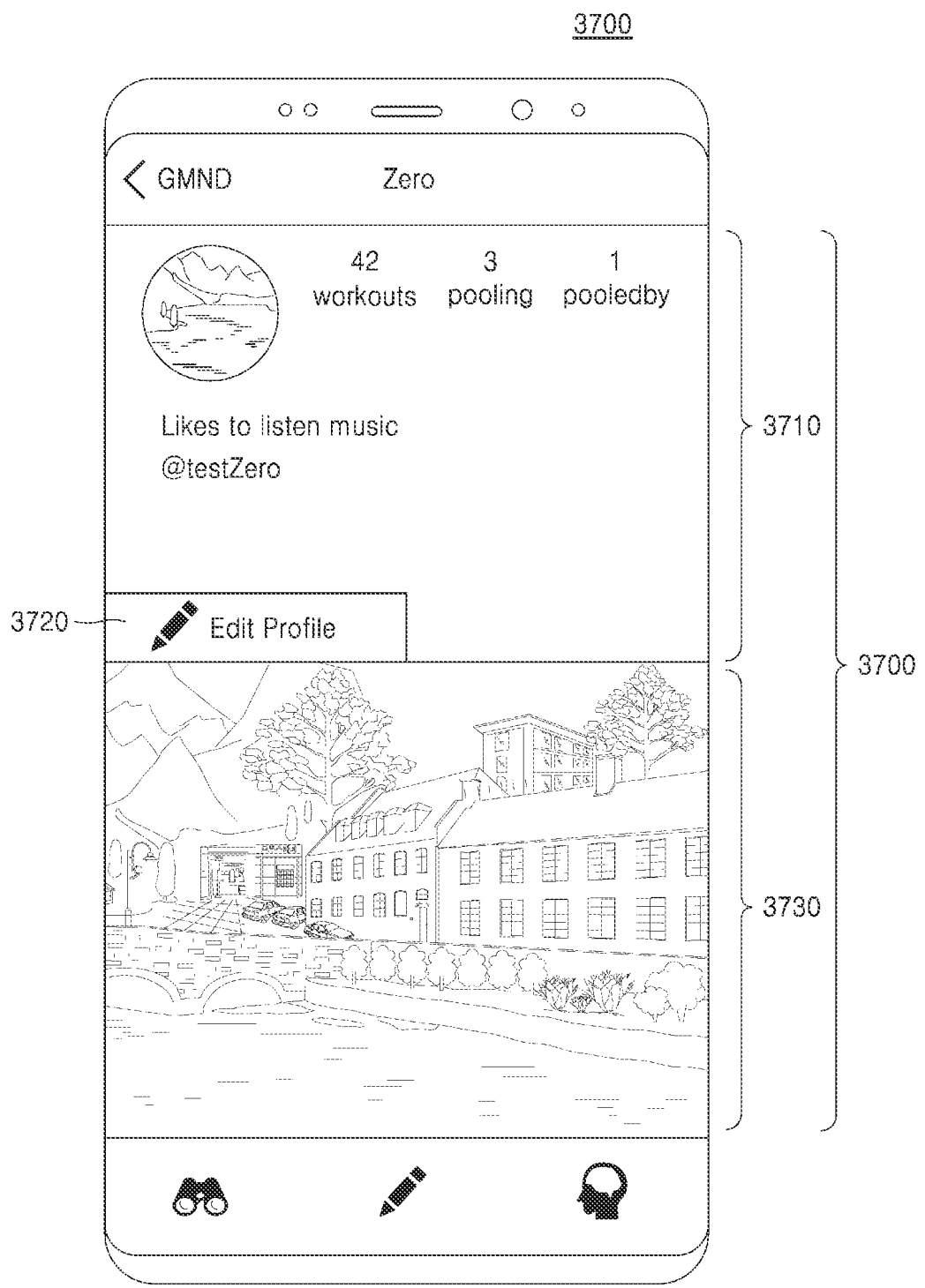
FIGS. 54 to 59 are views illustrating a user page of the exercise history management system according to an embodiment of the present disclosure.

In the case of a user page of the user himself/herself, the user profile edit button 3720 may be provided as shown in FIG. 54.

Figure 55:
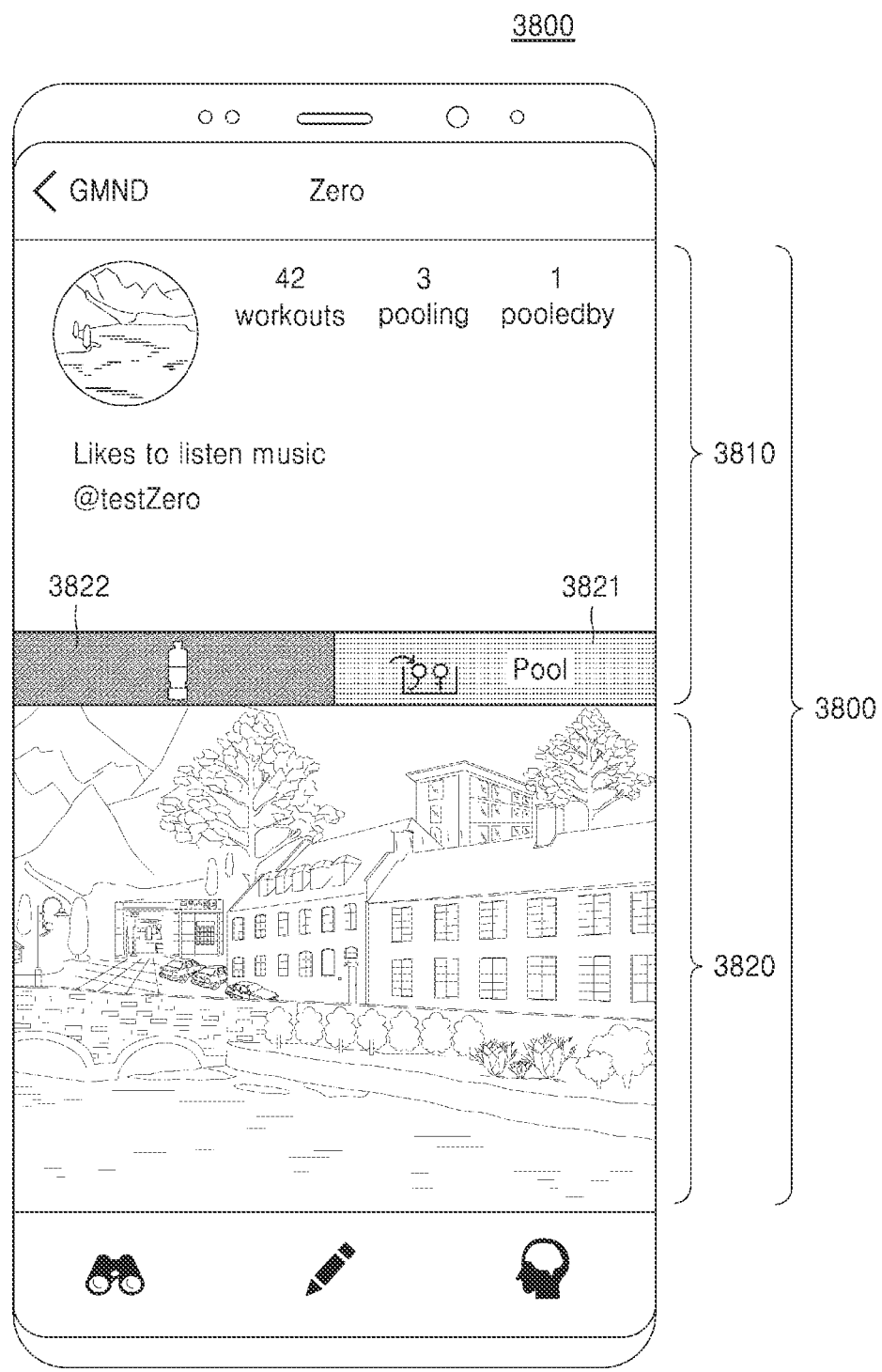

Alternatively, in the case of a user page of another user, a pool/un-pool button 3821 for the corresponding user may be provided as shown in FIG. 55.

In addition, when the page is a user page of another user and the user is currently exercising, a support button 3822 for the corresponding user may be provided as shown in FIG. 55.

Figure 56:
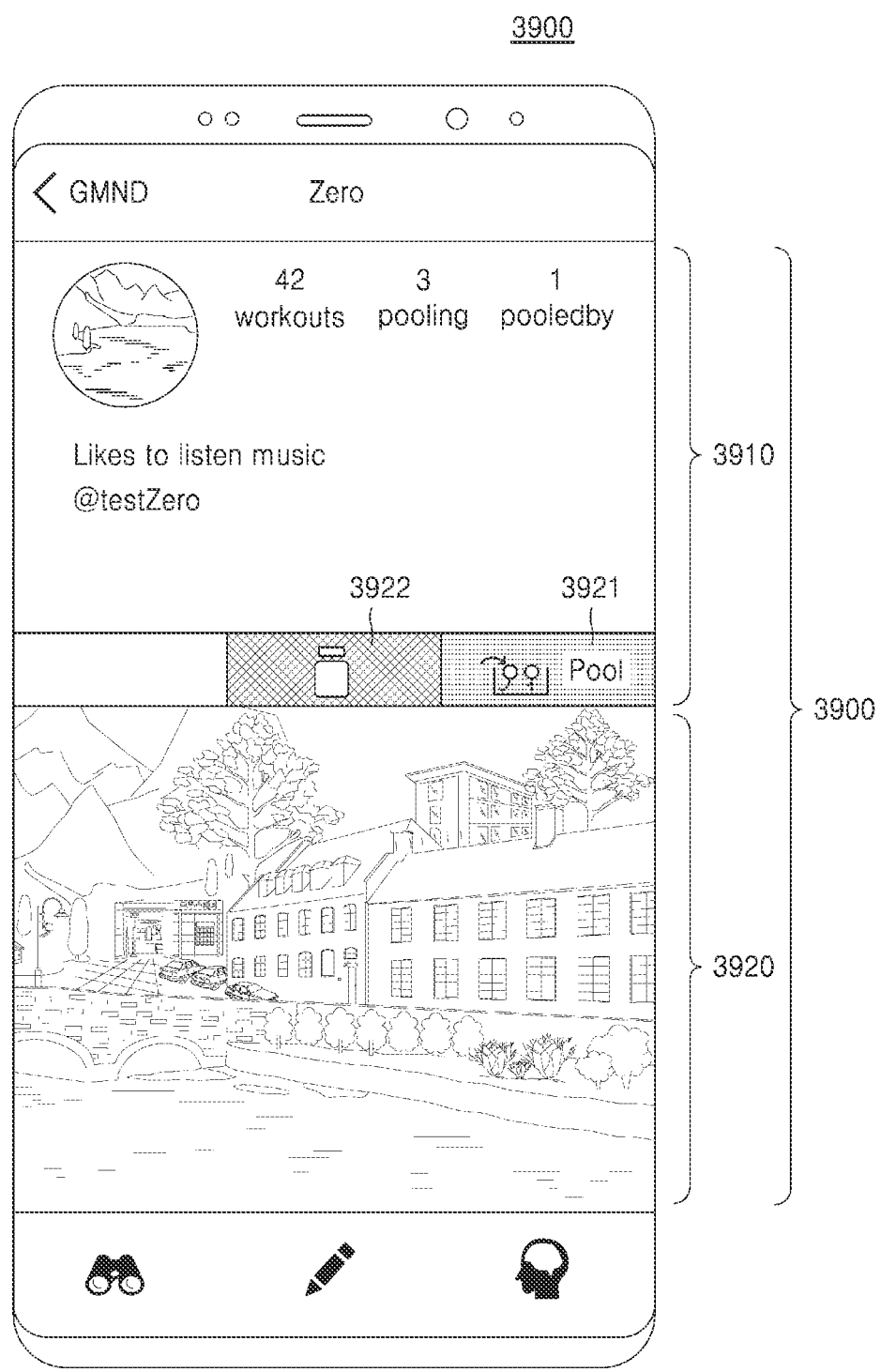

In addition, when the page is a user page of another user and the user is currently not exercising, a support button 3922 for the corresponding user may be provided as shown in FIG. 56.

Figure 57:
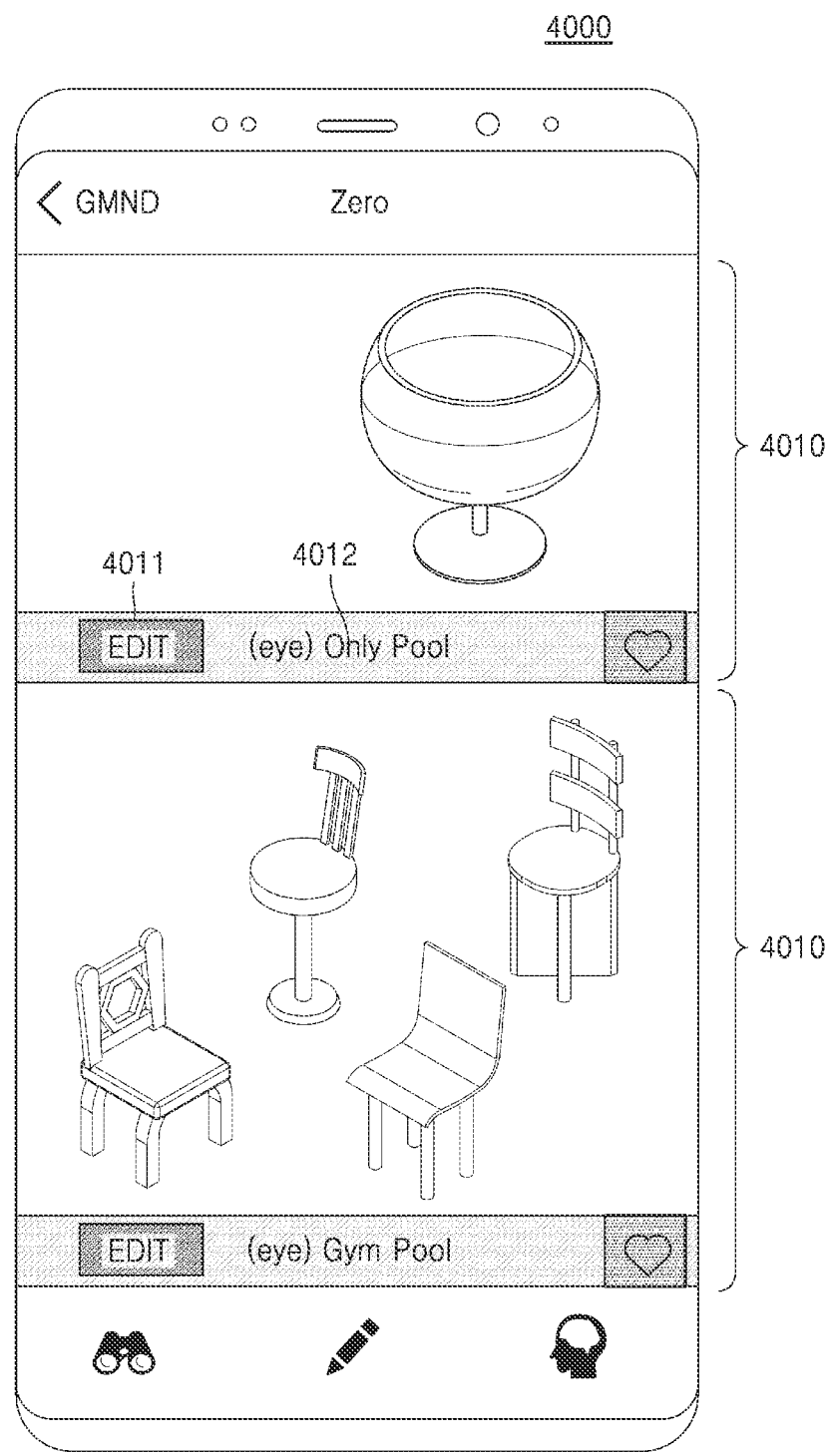

FIG. 57 is a view illustrating a case in which one or more user content display portions 4010 are displayed on a user page 4000.

As shown in FIG. 57, in the case of a user page of the user himself/herself, a user content edit button 4011 and a user content reading grade display portion 4012 may be displayed on each of the user content display portions 4010. Here, when the user content edit button 4011 is pressed, the user content edit button 4011 is linked to a user content edit page shown in FIG. 58.

Figure 58:
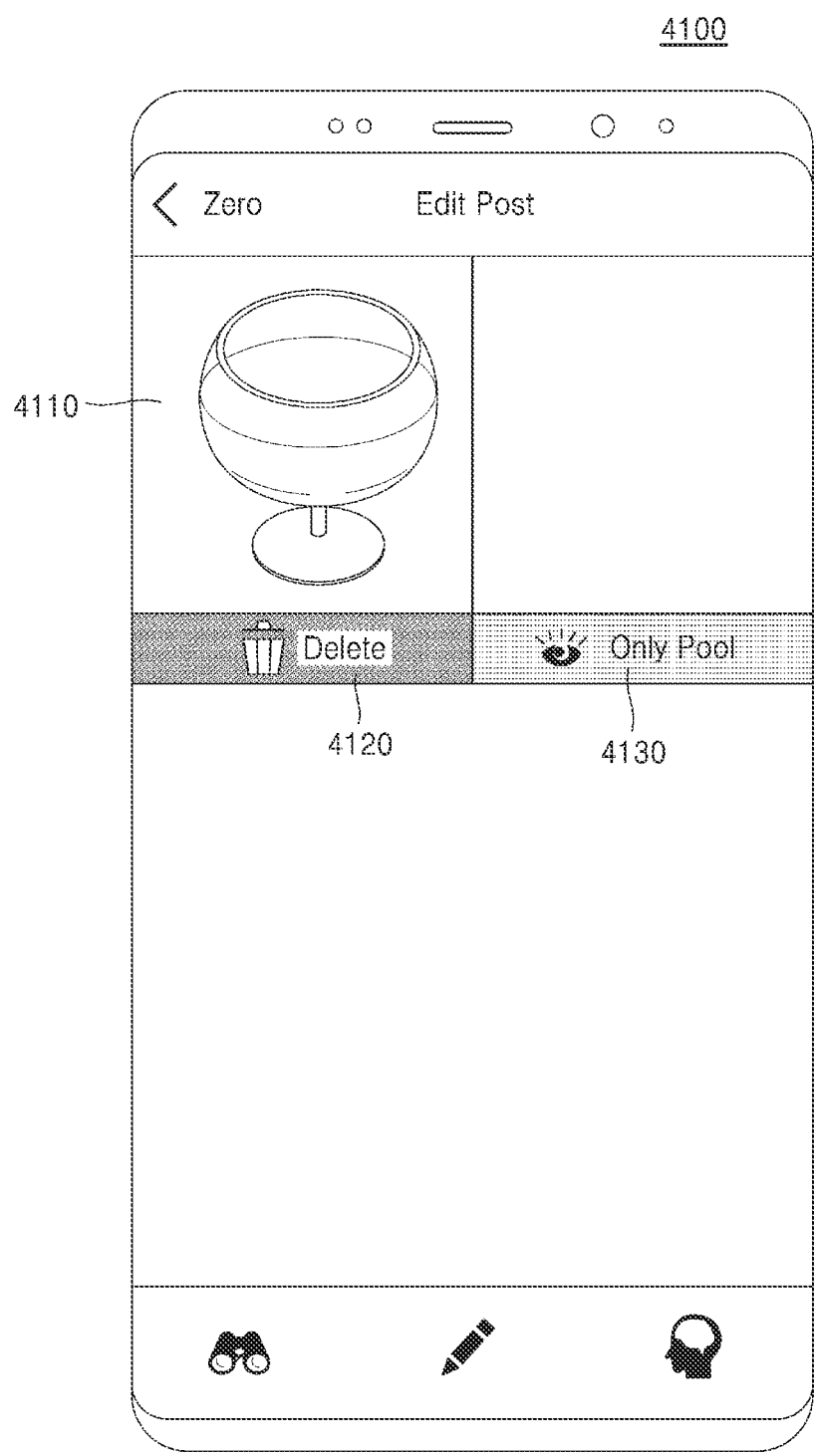

FIG. 58 illustrates the user content edit page. A user content 4110, a content deletion button 4120, and a content permission assignment portion 4130 are displayed on the user content edit page.

Figure 59:
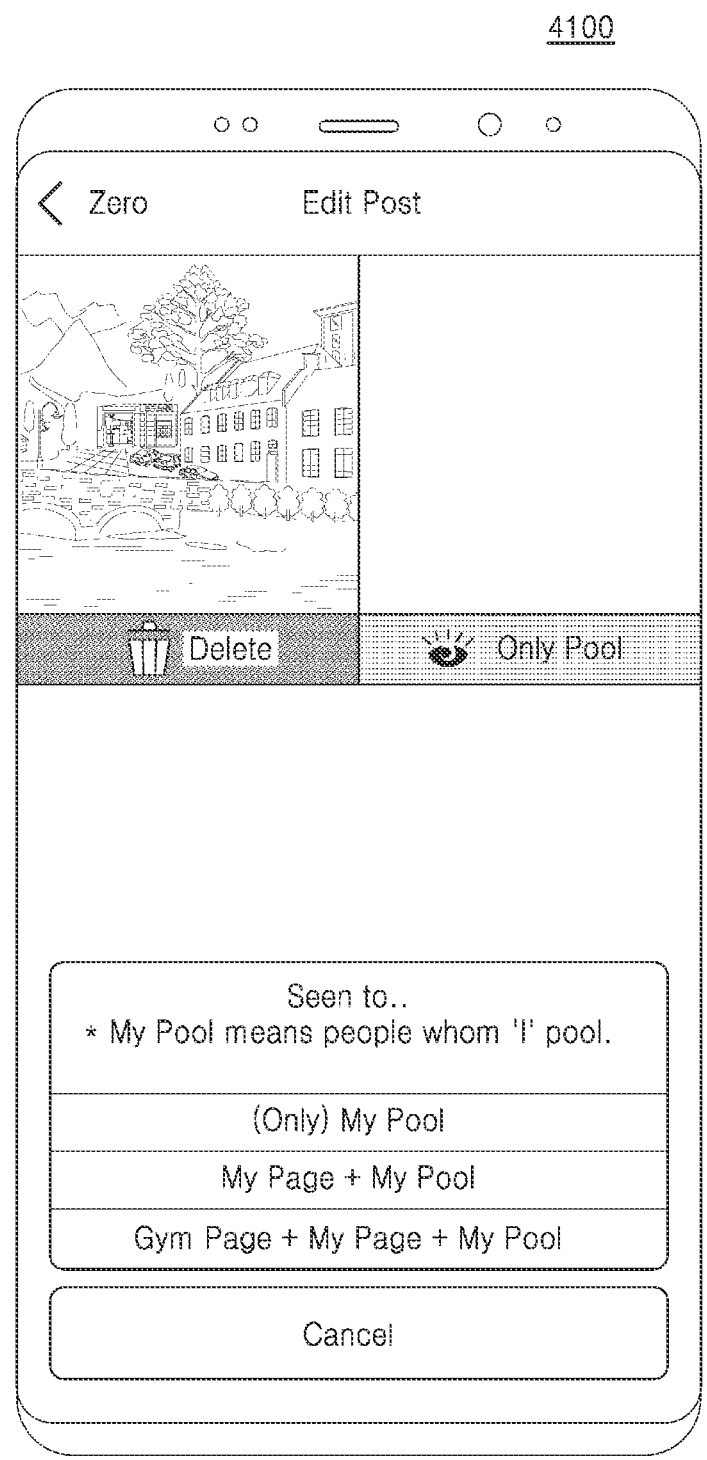

Here, when the content permission assignment portion 4130 is clicked, permissions to be assigned to the corresponding content are listed as shown in FIG. 59. Here, the permissions of the corresponding content may be given in the form of A/B+A/C+B+A.

That is, the permissions may be assigned differentially, such as visible to all (it is also displayed on the gym page that is set as my gym) (A), only visible by visiting my page (B+A), and only visible to users who have pooled by me (C+B+A).

As described above, the permission assignment is configured in such a manner in which as the content to be disclosed is small, the content is disclosed to fewer users, thereby increasing intuition.

Hereinafter, an exercise history managing method according to an embodiment of the present disclosure will be described.

Figure 60:
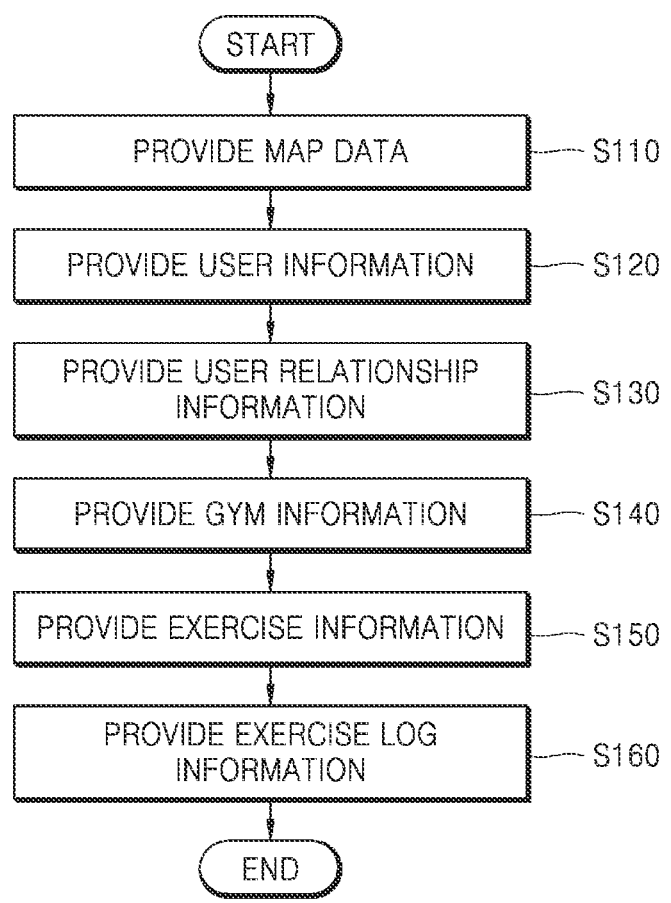
FIG. 60 is a flowchart illustrating an exercise history managing method according to an embodiment of the present disclosure.

FIG. 60 is a flowchart illustrating the exercise history managing method according to an embodiment of the present disclosure.

Referring to FIG. 60, the exercise history managing method according to an embodiment of the present disclosure includes providing map data to a user terminal (S110), providing user information to the user terminal (S120), providing user relationship information to the user terminal (S130), providing gym information to the user terminal (S140), providing exercise information to the user terminal (S150), and providing exercise log information to the user terminal (S160).

First, a map data providing unit 161 provides the map data to the user terminal (S110). In more detail, the map data providing unit 161 may serve to provide map data about a specific area, which is requested by a user terminal 200, to the user terminal 200. Here, the specific area may be an area corresponding to a gym location, which is included in the data transmitted from the user terminal 200, or may be an area including a current location of the user terminal 200. Alternatively, when the use of location information is not selected in the user terminal 200 (e.g., GPS is turned off), the specific area may be an area corresponding to the map data most recently received by the user.

Next, a user information managing unit 162 provides the user information to the user terminal (S120). In more detail, the user information managing unit 162 may receive predetermined user information transmitted from the user terminal 200, store the user information, and retrieve the user information in response to a request from the user terminal 200 and provide the retrieved user information to the user terminal 200. Here, the user information may include user authentication information (e.g., an email, a password, or the like), user personal information (e.g., a name of the user, a gender, a birth month, a photo, an exercise count, the number of users who have been pooled (followed) by me, the number of users who have been pooled me, user comments, and the like), user's preferred exercise information, user's gym information, and the like.

Next, a user relation managing unit 163 provides the user relationship information to the user terminal (S130). The user relation managing unit 163 manages the relationship between each user and other users, and may be referred to as a component that provides a name of social network service. That is, the user relation managing unit 163 manages a series of processes such as requesting, accepting, rejecting, and storing a pooling (or following) relationship between the users.

Next, a gym information managing unit 164 provides the gym information to the user terminal (S140). In more detail, the gym information managing unit 164 may receive information about gyms, store the received information, and retrieve the gym information in response to a request from the user terminal 200 and provide the retrieved gym information to the user terminal 200. Here, the gym information may include a name, a location, a photo, possible exercises, provided exercise equipment, registered users, and the like of the gym.

Next, an exercise information managing unit 165 provides the exercise information to the user terminal (S150). In more detail, the exercise information managing unit 165 may receive information about exercises, store the received information, and retrieve the exercise information in response to a request from the user terminal 200 and provide the retrieved exercise information to the user terminal 200. Here, the exercise information may include pieces of information on exercise names, first categories obtained by classifying the exercises belonging to each exercise name according to a first condition, second categories obtained by classifying the exercises belonging to the first category according to a second condition, and specific exercises belonging to the second category.

Next, an exercise log managing unit 166 provides the exercise log information to the user terminal (S160). In more detail, the exercise log managing unit 166 may receive predetermined exercise log information transmitted from the user terminal 200, store the exercise log information, and retrieve the exercise log information in response to a request from the user terminal 200 and provide the retrieved exercise log information to the user terminal 200. Here, the exercise log may include the name of exercise performed (per set), the weight of the exercise, an exercise count (per set), exercise duration (per set), comments, and the like. Here, the exercise log managing unit 166 may provide an exercise log of another user to the user terminal 200 so that the exercise log of another user is displayed on the user terminal 200 as an image representing an exercise. In addition, the exercise log managing unit 166 may provide each user terminal 200 with exercise logs of other users currently exercising, other users exercising in a preferred gym of the user, and other users having a pooling relationship with the user.

Hereinafter, a display control method according to an embodiment of the present disclosure will be described.

Figure 61:
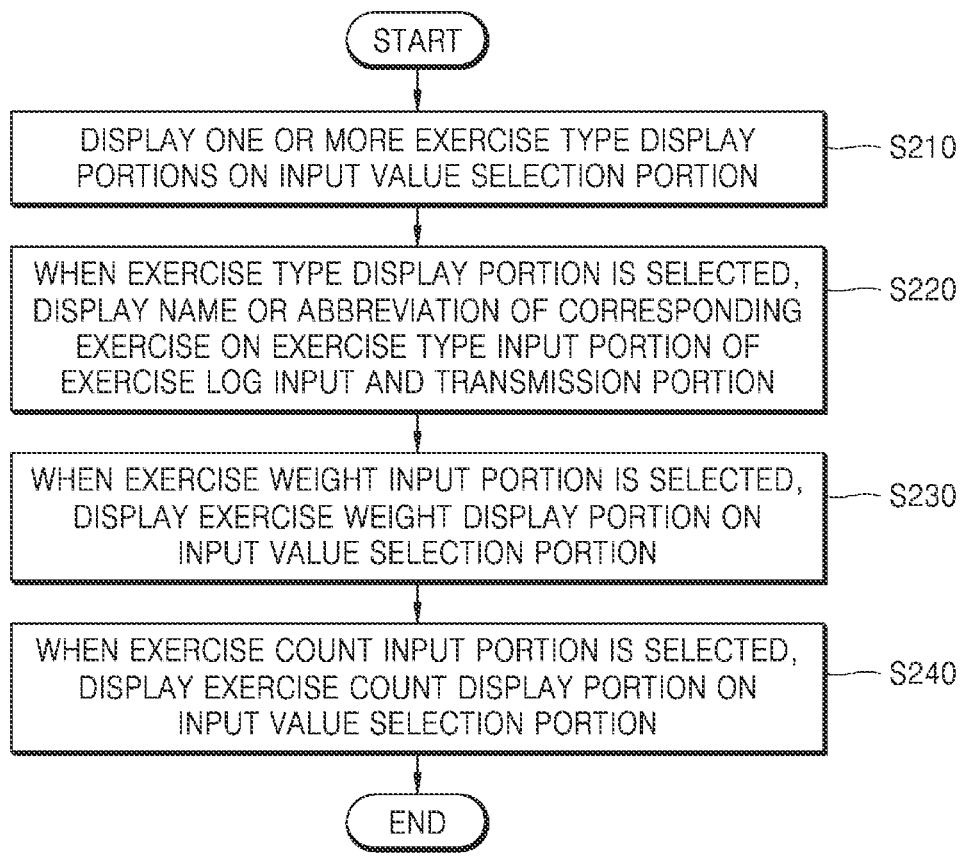
FIG. 61 to FIG. 64 are flowcharts illustrating a display control method according to an embodiment of the present disclosure.

FIG. 61 is a flowchart illustrating the display control method according to an embodiment of the present disclosure.

Referring to FIGS. 61 and 19 to 24, the display control method according to an embodiment of the present disclosure includes displaying one or more exercise name display portions on an input value selection portion (S210), when the exercise name display portion is selected, displaying the name or abbreviation of a corresponding exercise on an exercise name input portion of an exercise log input and transmission portion (S220), when an exercise weight input portion is selected, displaying an exercise weight display portion on the input value selection portion (S230), and when an exercise count input portion is selected, displaying an exercise count display portion on the input value selection portion (S240).

First, one or more exercise name display portions are displayed on the input value selection portion (S210). In more detail, as shown in FIG. 19, user's preferred exercises selected in advance by the user may be displayed on exercise name display portions 1831 and may be organized and displayed by category.

Next, when the exercise name display portion is selected, the name or abbreviation of the corresponding exercise is displayed on the exercise name input portion of the exercise log input and transmission portion (S220). In more detail, as shown in FIG. 19, when each of the exercise name display portions 1831 is selected, the name or abbreviation of the corresponding exercise may be displayed on an exercise name input portion 1821 of an exercise log input and transmission portion 1820. Alternatively, when a predetermined input, which is different from a general input such as a long press or a force touch, is performed on each of the exercise name display portions 1831, an exercise log input area 1800 disappears upward, and a detailed introduction page 2000 for the corresponding exercise may be displayed while moving upward.

Next, when the exercise weight input portion is selected, the exercise weight display portion is displayed on the input value selection portion (S230). In more detail, as shown in FIG. 22, when an exercise weight input portion 2122 is selected from an exercise log input and transmission portion 2120, an exercise weight display portion 2131 is displayed on an input value selection portion 2130. In addition, a unit-of-weight selection portion 2132 may be further displayed on the input value selection portion 2130. Here, the unit-of-weight selection portion 2132 may be provided in the form of a segmented control window and may be provided to change a unit of weight into a kilogram (kg) scale or a pound (lb) scale.

Next, when the exercise count input portion is selected, the exercise count display portion is displayed on the input value selection portion (S240). In more detail, as shown in FIG. 23, when an exercise count input portion 2223 is selected from an exercise log input and transmission portion

2220, an exercise count display portion 2231 is displayed on an input value selection portion 2230. In addition, a count/duration selection portion 2232 may be further displayed on the input value selection portion 2230. Here, the count/duration selection portion 2232 is provided in the form of a segmented control window to allow the user to select whether the exercise name is a counting exercise or a duration exercise (e.g., an isometric exercise) that maintains the same posture. Here, in the case of the duration exercise, a mark """, indicating units of seconds, may be displayed on the exercise count input portion 2223.

In addition, a tough set input portion 2233 may be further displayed on the input value selection portion 2230. Here, a tough set refers to a set that the user was able to complete with maximal or near-maximal effort. Here, when the user turns the tough set input portion 2233 on to display the tough set, the tough set input portion 2233 may be displayed by being changed as shown in FIG. 24.

According to the present disclosure, when an item to be entered is pressed in the exercise log input and transmission portion 1820, items displayed on the input value selection portion 1830 are changed and provided, so that the name, weight, and count of the exercise to be recorded may be quickly, accurately, and intuitively entered. In particular, the unit, the count/duration, and the like are changeable in one screen, and when the exercise weight input portion 1822 or the exercise count input portion 1823 is selected, the exercise weight input portion 1822 or the exercise count input portion 1823 is reset to display "0," so that user convenience may be further improved.

Hereinafter, a display control method according to another embodiment of the present disclosure will be described.

Figure 62:
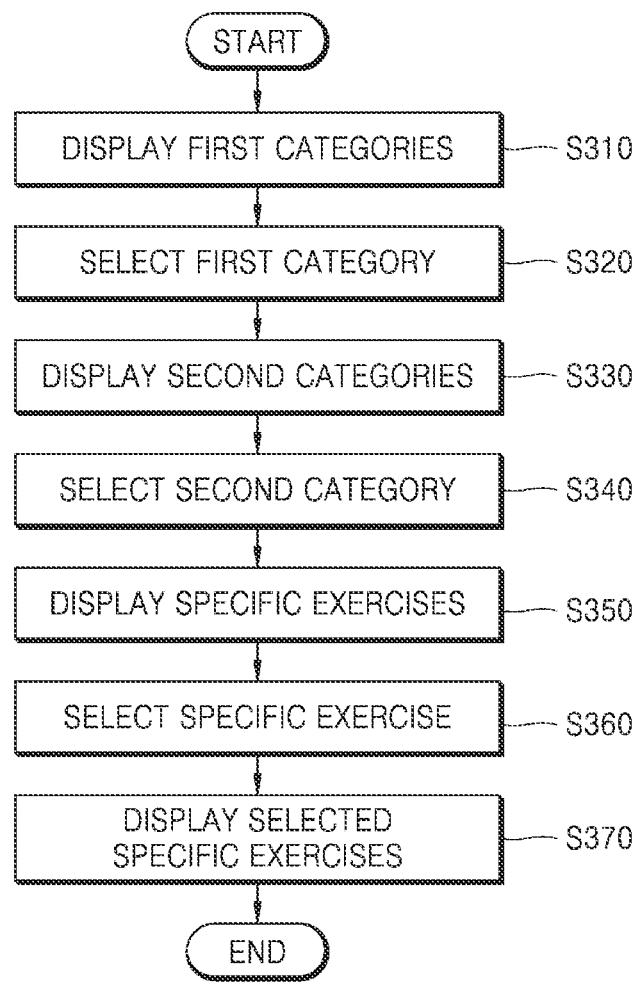

FIG. 62 is a flowchart illustrating the display control method according to another embodiment of the present disclosure.

Referring to FIGS. 62 and 25 to 27, a display control method according to an embodiment of the present disclosure includes displaying first categories (S310), selecting the first category (S320), displaying second categories (S330), selecting the second category (S340), displaying specific exercises (S350), selecting the specific exercise (S360), and displaying the specific exercises (S370).

First, as shown in FIG. 25, a user-preferred exercise setup page 2300 includes a preferred exercise display portion 2310 and a preferred exercise selection portion 2320.

In addition, an exercise name display portion 2330 and a first category selection portion 2340 may be displayed on the preferred exercise selection portion 2320 of each exercise name. Here, the name of the corresponding exercise name is displayed on the exercise name display portion 2330 (e.g., Weight Training, running, or the like). Here, when the exercise name display portion 2330 is pressed, other selectable exercise names may be listed.

In addition, the first categories obtained by classifying exercises belonging to the corresponding exercise name according to a first condition are displayed on the first category selection portion 2340 in the form of icons (S310). In FIG. 25, a core exercise, a lower body exercise, an upper body-pull exercise, an upper body-push exercise, a whole-body exercise, and the like are displayed in the form of icons as the first category of Weight Training. Here, the first categories of the corresponding exercise name may be displayed in the first direction (transverse direction on a screen) on the first category selection portion 2340. Here, FIG. 25 illustrates a state before the exercise names are selected so that only icons for the first categories of each exercise name are displayed.

Next, a specific icon is selected from the first category selection portion 2340 (S320). The first category may be selected by the following method. First, one icon in the first category selection portion 2440 may be tapped to select a desired first category. Alternatively, a slider 2442 of the first category selection portion 2440 may be dragged to select a desired first category. Alternatively, a desired first category may be selected by tapping one icon in the preferred exercise display portion 2410.

Next, when one of the plurality of displayed first categories is selected (S320), second categories 2451 obtained by classifying exercises belonging to the selected first category according to a second condition are displayed on a second category selection portion 2450 (S330). Here, the second category may also be referred to as a "family." Here, icons of the second categories of the corresponding exercise name may be displayed in the first direction (transverse direction on the screen) on the second category selection portion 2450.

The second category may be selected by the following method. First, one icon may be tapped from a second category selection portion 2450 to select a desired second category. Alternatively, a slider 2452 of the second category selection portion 2450 may be dragged to select a desired category.

Next, when one of the plurality of displayed second categories is selected (S340), one or more specific exercises belonging to the selected second category are displayed on the specific exercise selection portion 2460 (S350). Here, one or more specific exercises may be sequentially displayed in the second direction (longitudinal direction on the screen). Here, an on/off button of each of the specific exercises may be turned on to select the corresponding specific exercise.

Next, when the specific exercise is selected (S360), the selected specific exercise is included and displayed on one side of the corresponding first category icon of a preferred exercise display portion 2410 (S370), and when the specific exercise is included in the corresponding first category, a mark "?" displayed on an upper side of the first category icon may disappear. In another aspect, when all the icons have the mark "?" in the category, it means that there is no user-preferred exercise, and this may be interpreted as that the user is not exercising the whole body evenly. Thus, by displaying the mark "?," the user may be guided to exercise evenly for each part.

Here, in a user-preferred exercise setup page provided by an exercise history management system according to an embodiment of the present disclosure, the preferred exercise may be easily selected step by step on one screen. That is, first categories are displayed in the first direction (transverse direction on a screen). When one of the first categories is selected, second categories corresponding to the selected first category are displayed in the first direction (transverse direction on the screen). When one of the second categories is selected, specific exercises corresponding to the selected second category are displayed in the second direction (longitudinal direction on the screen). As a result, specific exercises to be added may be found with the minimum number of clicks on a small screen.

Further, according to the present disclosure, a user may more easily select a preferred exercise by arranging the exercises in the order of a name (kind)/a first category (division)/a second category (family)/a specific exercise (member exercise).

Hereinafter, a display control method according to another embodiment of the present disclosure will be described.

FIGS. 63 and 32 to 37 are views for describing a flow of a series of operations of a display control method according to another embodiment of the present disclosure.

Figure 63:
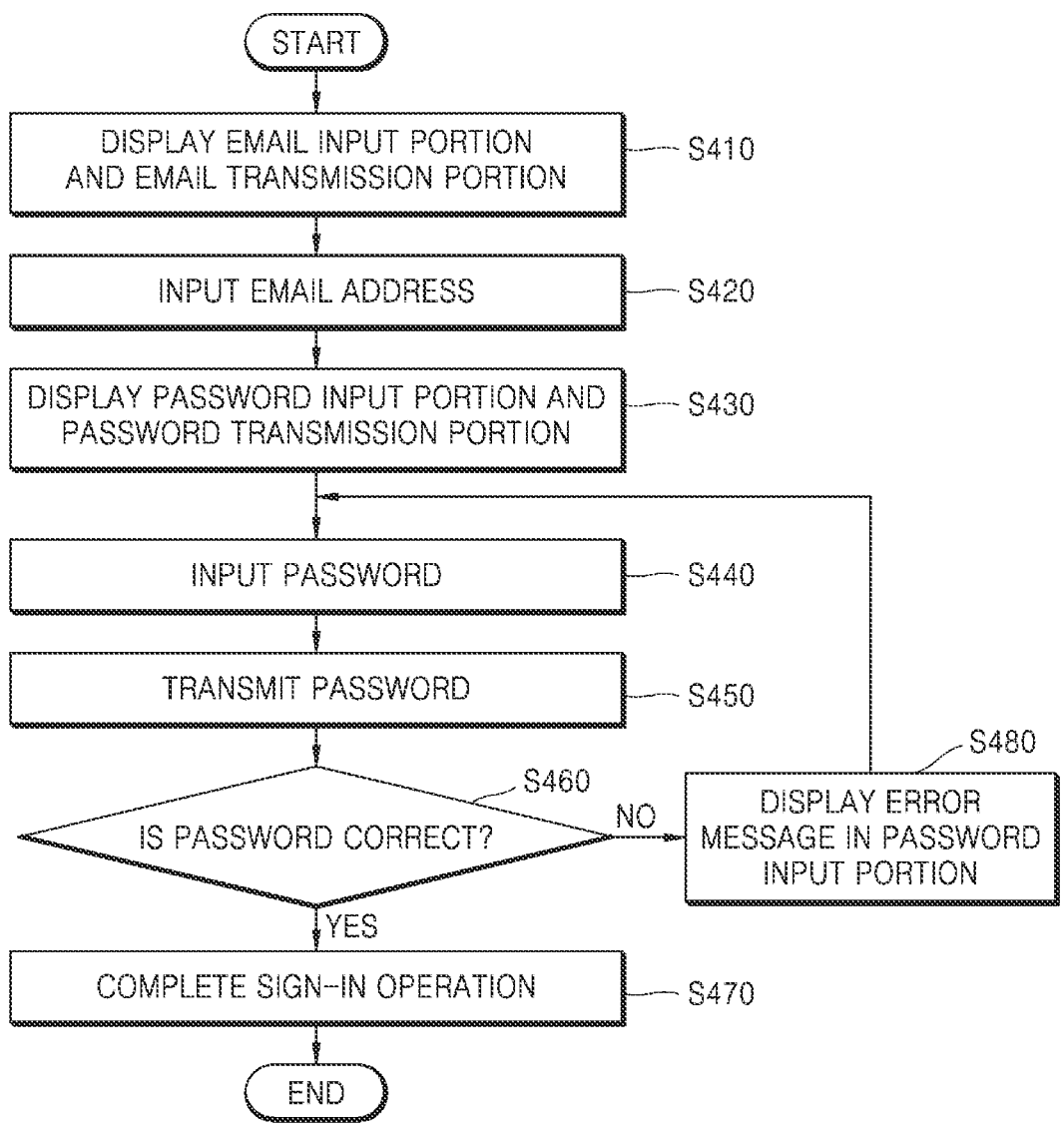

Referring to FIG. 63, a display control method according to an embodiment of the present disclosure includes displaying an email input portion and an email transmission portion (S410), inputting an email address (S420), displaying a password input portion and a password transmission portion (S430), inputting a password (S440), transmitting the password (S450), determining whether the password is a correct password (S460), completing a sign-in operation (S470), and displaying an error message in the password input portion (S480).

First, referring to FIG. 32, an email input portion 3010 and an email transmission portion 3020 are displayed on a sign-in page 3000 of the exercise history management system (S410).

The email transmission portion 3020 may be deactivated until an email address is input to the email input portion 3010. When the user inputs the email address to the email input portion 3010 (S420) and the input email address has a correct email format (for example, "@" is included), the email transmission portion 3020 may be activated.

When the user presses the activated email transmission portion 3020, the email input portion 3010 is switched to a password input window. That is, when the user presses the activated email transmission portion 3020, as shown in FIGS. 33 and 34, the email input portion 3010 and the email transmission portion 3020 disappear while moving in one direction (an arrow direction of FIG. 33), and a password input portion 3030 and a password transmission portion 3040 appear while moving in one direction (the arrow direction of FIG. 33) (S430).

The password transmission portion 3040 may be deactivated until the password is input to the password input portion 3030. In addition, when the user inputs the password to the password input portion 3030 (S440), the password transmission portion 3040 may be activated. In this state, the password transmission portion 3040 is pressed to transmit the password to a server (S450).

After determining whether the input password is a correct password (S460), if the input password is a wrong password, an input error message is displayed on the password input portion 3030 as shown in FIG. 35 (S480). At this point, the password input portion 3030 may be displayed in a changed color. At this point, the password transmission portion 3040 may be activated. In addition, a password reset request portion 3050 may be displayed at one side of the password transmission portion 3040, and when the password reset request portion 3050 is pressed, the password reset request portion 3050 may be linked to a password reset page of FIG. 36. When the email address to which the reset password is to be transmitted is input to an email input portion 3060 of FIG. 36, and then an email transmission portion 3070 is pressed, the password that is reset to correspond to the email address may be transmitted.

Meanwhile, when the password input portion 3030 on which the input error message is displayed is pressed in the state of FIG. 35, the state may return to the state of the password input window shown in FIG. 34.

Meanwhile, when the email address, which is input in FIG. 32, is an email address that does not exist in a user DB, as shown in FIG. 37, the input email address moves while animating upward of the email input portion 3010, and an error message is displayed in the email input portion 3010, and when the error message displayed in the email input portion 3010 is clicked, the page may return to the page of FIG. 32.

The sign-in page of the exercise history management system according to an embodiment of the present disclosure may show an email, password input and transmission, and an error message in one line, so that a user may use the sign-in page with a simple design and high immersion may be obtained.

Hereinafter, a display control method according to another embodiment of the present disclosure will be described.

FIGS. 64 and 44 to 49 are views for describing a flow of a series of operations of a display control method according to another embodiment of the present disclosure.

Figure 64:
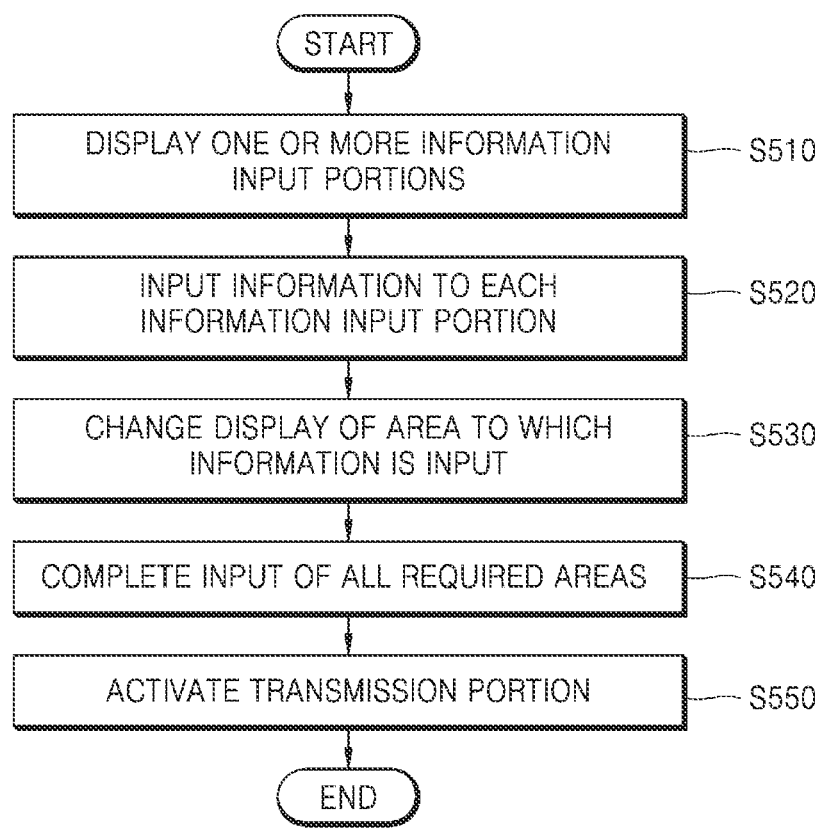

Referring to FIG. 64, a display control method according to an embodiment of the present disclosure includes displaying one or more information input portions (S510), inputting information to each of the information input portions (S520), changing a display of an area to which the information is input (S530), completing the input of all required areas (S540), and activating a transmission portion (S550).

First, referring to FIG. 44, a user image input portion 3210, a user's date pf birth input portion 3220, a user name input portion 3230, a terms display portion 3240, a user gender input portion 3250, and a user information transmission portion 3260 are displayed on a user information input page 3200 of the exercise history management system (S510). Here, a predetermined color may be already displayed on a border excluding the user's input portions.

Here, in the user information input page of the present disclosure, each time each piece of information is input, an area to which the corresponding input portion belongs is displayed in different colors, brightness, and contrast so that an area in which information is not input is clearly expressed.

Next, when information is input to each information input portion (S520), a display of the area to which the information is input is changed (S530). For example, when a user image is input to the user image input portion 3210, a color of the area of the user image input portion 3210 is changed as shown in FIG. 45.

Next, when a birth month of a user is input to the user's date pf birth input portion 3220, a color of the area of the user's date pf birth input portion 3220 is changed as shown in FIG. 46.

Next, when a user name is input to the user name input portion 3230, a color of the area of the user name input portion 3230 is changed as shown in FIG. 47.

Next, when an agreement button 3241 is clicked on the terms display portion 3240, as shown in FIG. 48, a color of the area of the terms display portion 3240 is changed. At this point, when the agreement button 3241 is clicked, a mark "Agree" may be changed to a mark "Agreed" and displayed. In this state, the gender has not been entered, and thus, it is possible to intuitively and clearly identify which information has not been input.

Next, when a birth month of the user is input to the user gender input portion 3250, as shown in FIG. 49, a color of the area of the user gender input portion 3250 is changed. In addition, since the input of all information is completed (S540), the user information transmission portion 3260 is activated and displayed (S550).

On the user information input page of the present disclosure, by implementing a method in which a color is filled whenever user information is input, it is possible to obtain an effect of guiding the input of user information intuitively and without boring.

FIGS. 65 to 73 are views illustrating a user page of the exercise history management system according to an embodiment of the present disclosure.

Here, FIGS. 65 to 71 views illustrating a screen for a user himself/herself to edit his/her user page.

Figure 65:
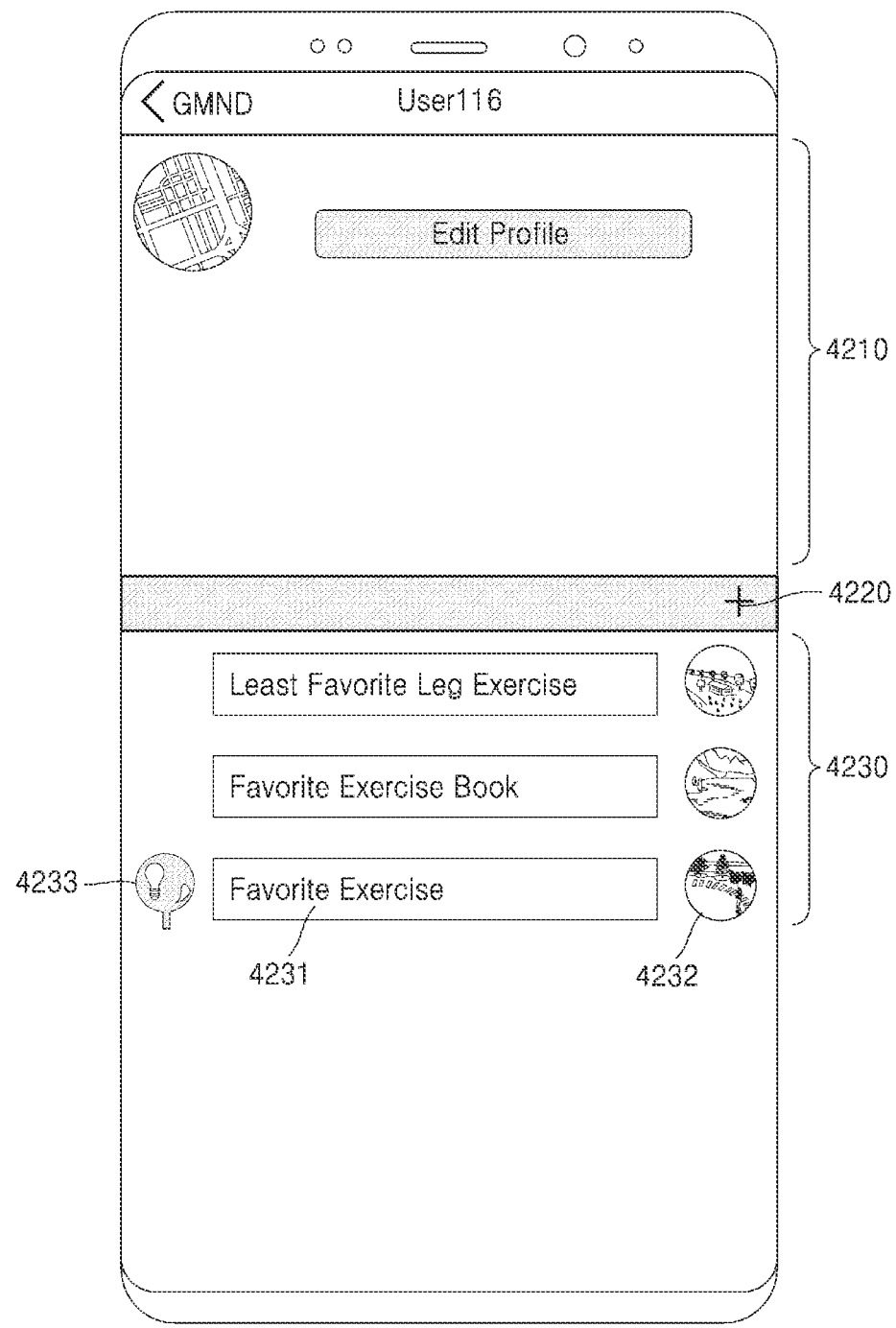
FIGS. 65 to 73 are views illustrating a user page of the exercise history management system according to an embodiment of the present disclosure.

Referring to FIG. 65, a user page 4200 includes a user profile display portion 4210, a user topic add button 4220, and a user topic display portion 4230.

A user image and a user profile edit button may be displayed on the user profile display portion 4210.

One or more user topics are displayed on the user topic display portion 4230. In more detail, the user topic display portion 4230 may include a topic text display portion 4231, a topic image display portion 4232, and a user-creation display portion 4233.

A type of topic or question from which a user's tendency or the like may be identified is displayed on the topic text display portion 4231. In addition, an image (photo or the like), which is uploaded as an answer to the topic (question) displayed on the topic text display portion 4231 by the user, is displayed on the topic image display portion 4232. That is, the question has a text format, and the answer has an image format. Here, when the topic image display portion 4232 is selected (touched or the like), the screen may be switched to a screen of FIG. 74.

Meanwhile, an icon indicating that the topic has been directly created by the user is displayed on the user-creation display portion 4233.

Figure 66:
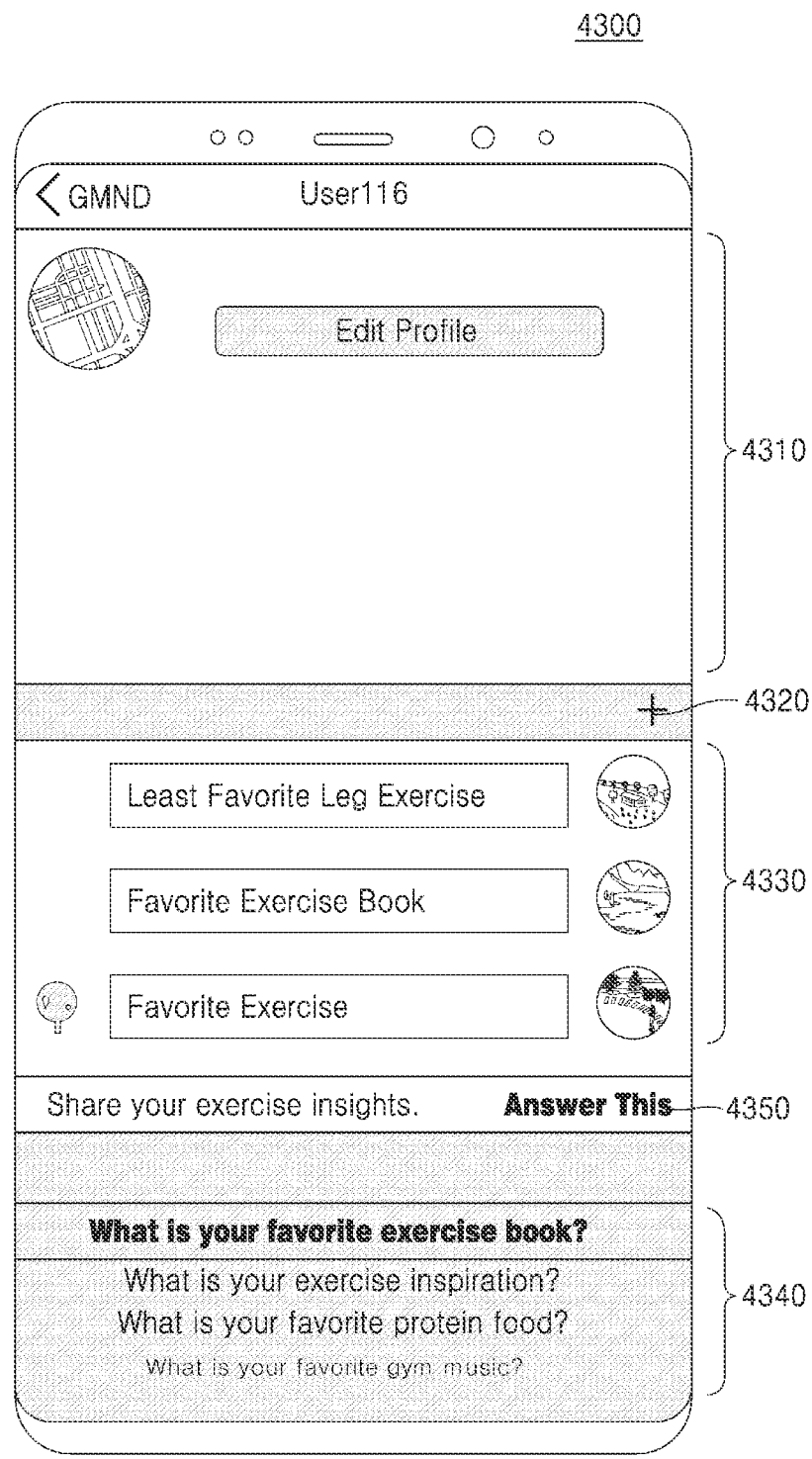

When the user topic add button 4220 is selected from the screen of FIG. 65, the screen is switched to a screen of FIG. 66. Referring to FIG. 66, a user page 4300 includes a user profile display portion 4310, a user topic add button 4320, and a user topic display portion 4330. In addition, the user page 4300 further includes a topic selection portion 4340 and an answer button 4350.

Topics provided as a default by the application may be displayed on the topic selection portion 4340.

The answer button 4350 is a button for selecting an image to be an answer to the corresponding topic. The phrase "Answer This" may be displayed on the answer button 4350, which is used for inputting answers to topics provided as a default by the application, as shown in FIG. 66.

Figure 67:
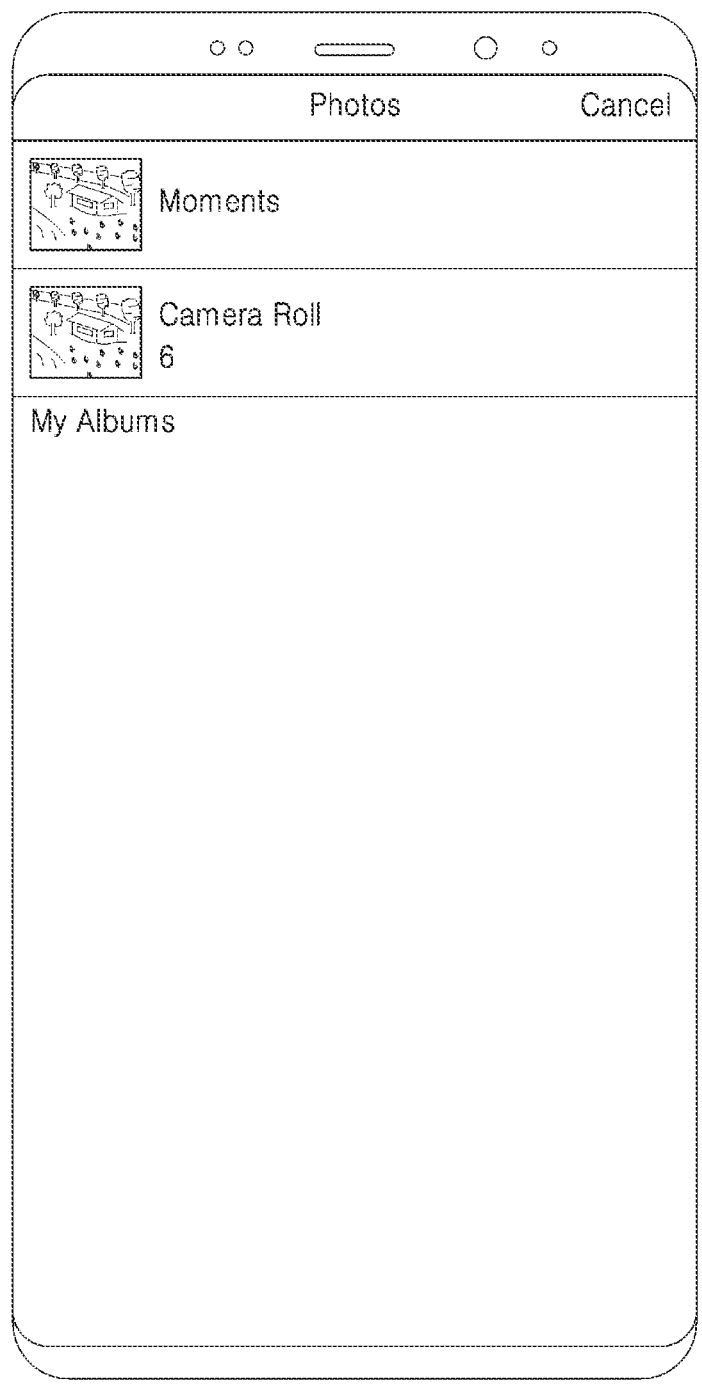

In this state, when the answer button 4350 is pressed, an image selection window shown in FIG. 67 is displayed. When an image is selected from the image selection window, the page returns to the page of FIG. 65, and the topic text and image selected at the image selection window may be added to the page of FIG. 65 and displayed.

Figure 68:
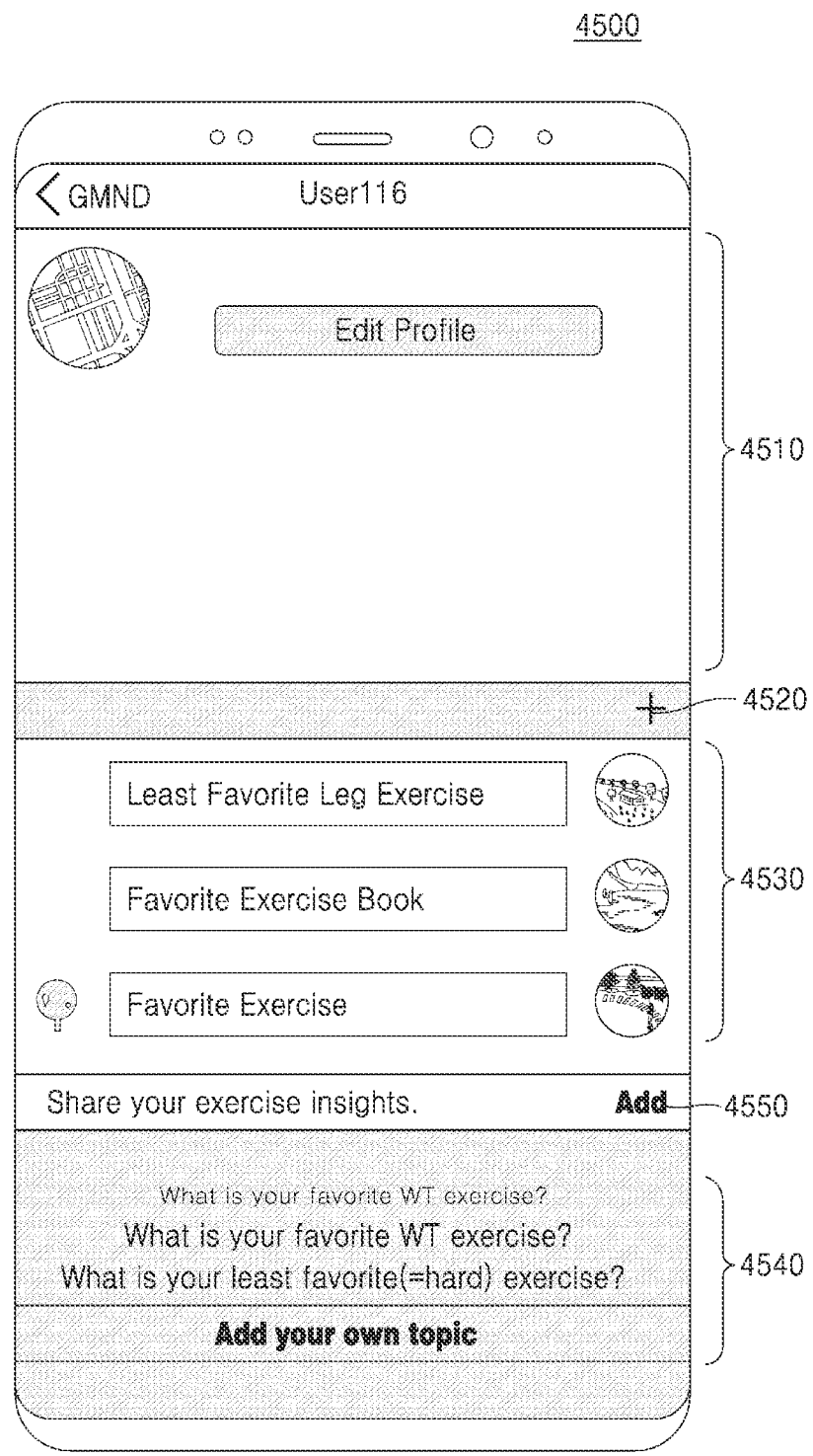

Meanwhile, instead of the topic provided as a default by the application, a topic created by the user himself/herself may also be added. Referring to FIG. 68, an item "Add your own topic" may be included in selectable items of a topic selection portion 4540 of a user page 4500. As described above, when the item "Add your own topic" is selected, the phrase "Add" may be displayed on an answer button 4550.

Figure 69:
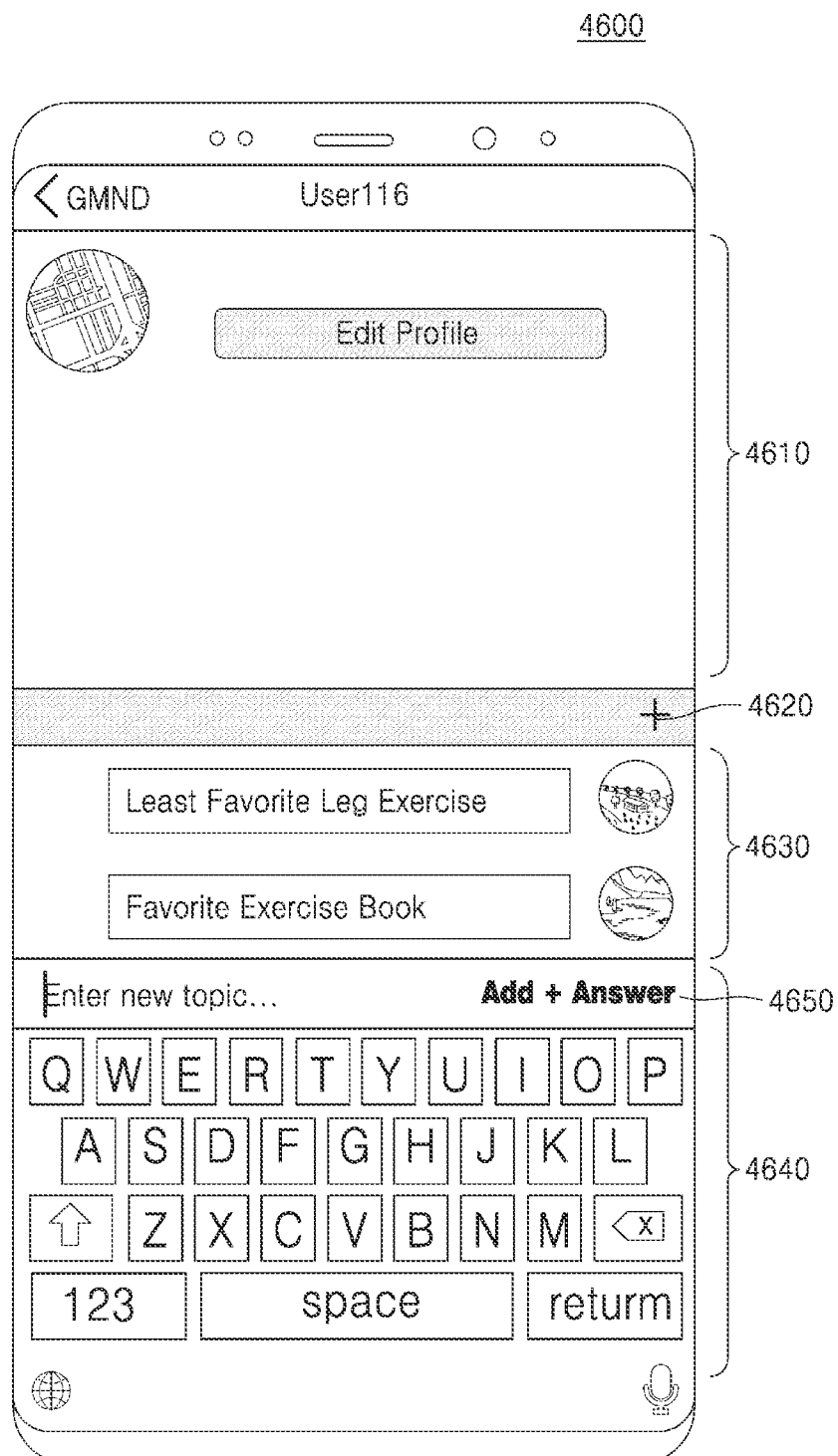

Here, when the answer button 4550 is pressed, as shown in FIG. 69, an input window 4640 is displayed so that the user himself/herself directly input a topic. At this point, the phrase "Add+Answer" may be marked on an answer button 4650. Here, when a topic (question) is input and the answer button 4650 is pressed, the image selection window shown in FIG. 67 is displayed. When an image is selected from the image selection window, the page returns to the page of FIG. 65, and the topic text and image selected at the image selection window may be added to the page of FIG. 65 and displayed.

In another aspect of the present disclosure, the phrase displayed on the answer button may be changed in the order of "Answer This"→"Add"→"Add+Answer" according to the operations.

Figure 70:
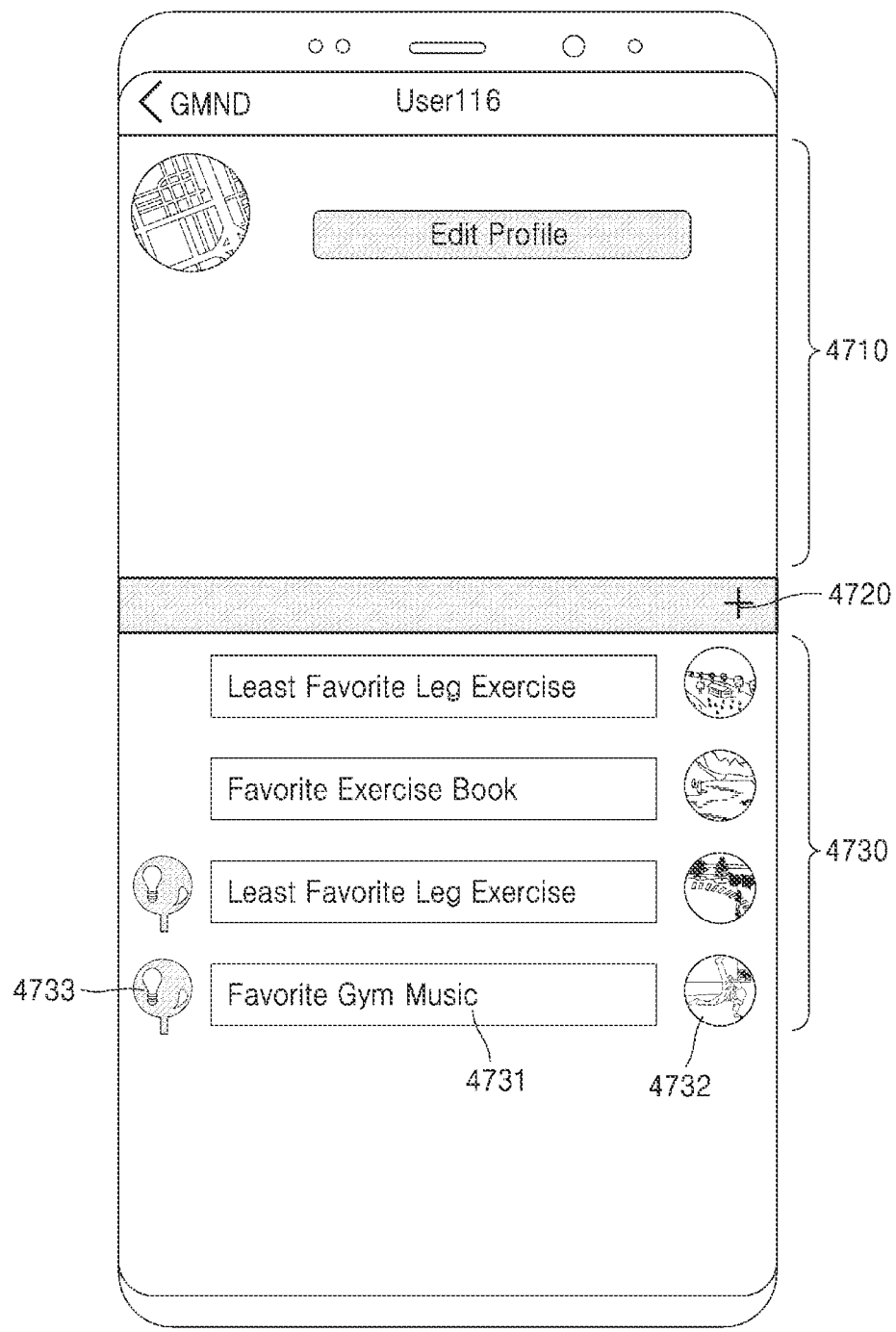

Meanwhile, for a topic created by the user himself/herself through the above process, a predetermined icon may be displayed on an area of a user-creation display portion 4733 as shown in FIG. 70.

Figure 71:
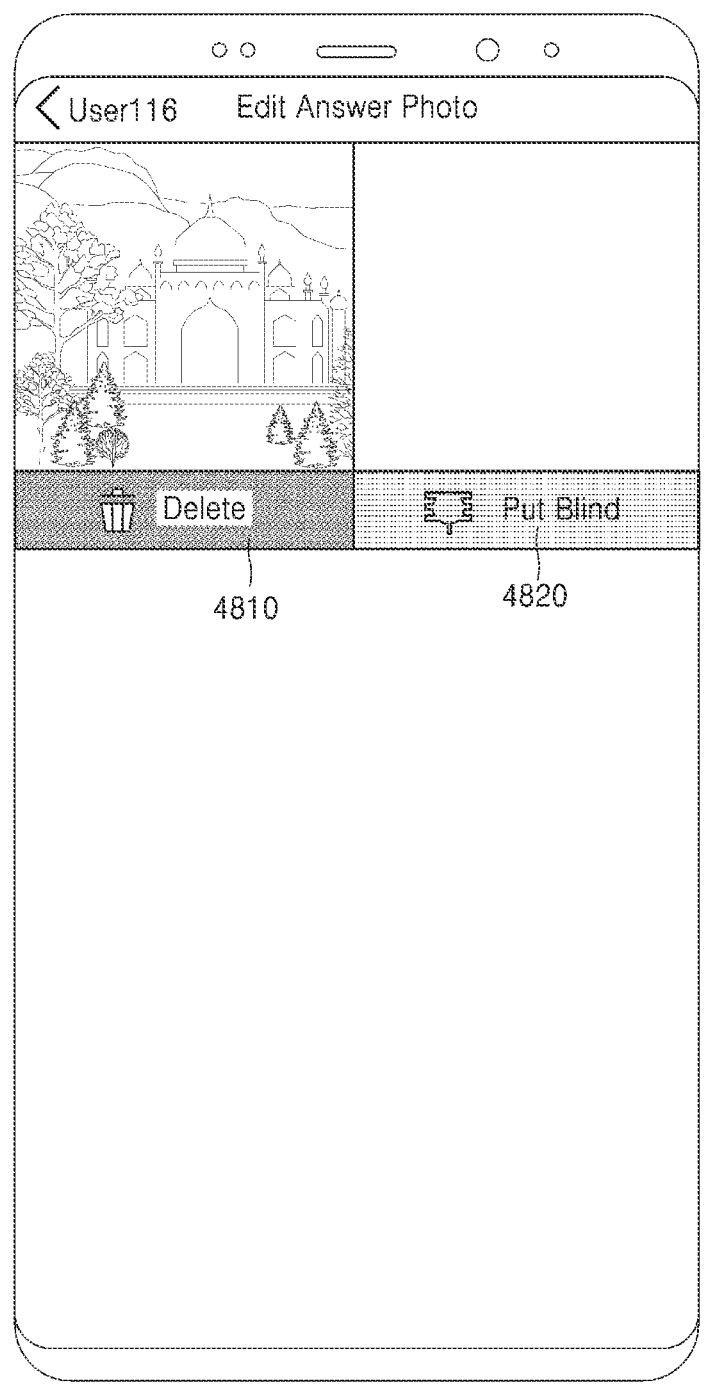

Meanwhile, when the topic text display portion 4231 is pressed on a user page 4700 shown in FIG. 70 presses, the page may be switched to a topic image editing page 4800 for editing the topic image as shown in FIG. 71.

The topic image editing page 4800 may include a delete button 4810 and a blind button 4820. Here, the blind button 4820 may provide a function of displaying a photo, so that other users may not view the photo before zooming in, by a manner such as horizontally forming several screens in the form of blinds or performing a mosaic treatment in a state in which the corresponding topic image is not zoomed in. This may be to lead other users to click the topic image by causing curiosity to other users.

Meanwhile, although not shown in the drawings, a setting of "on-the radar/off-the-radar" may be added for each topic image. In more detail, in the setting, each topic image may be set to an on-the radar (as a default) mode or an off-the-radar mode. In the case of the off-the-radar mode, the topic image of the user does not appear on a screen of another user, and the topic image of another user does not appear on the user's screen either (i.e., it is a mode in which neither my topic image nor other's topic images are visible and only a log-in function is used).

Furthermore, a stealth mode may be additionally present. This mode refers to a mode in which the user himself/herself may see the topic images of other users in the "on-the-radar mode," but the topic image of the user is not visible to other users. However, the topic image of the user in the off-the-radar mode is not visible to anyone.

The setting of "on-the radar/off-the-radar" may be applied to all contents of the present application as well as the topic image.

Figure 72:
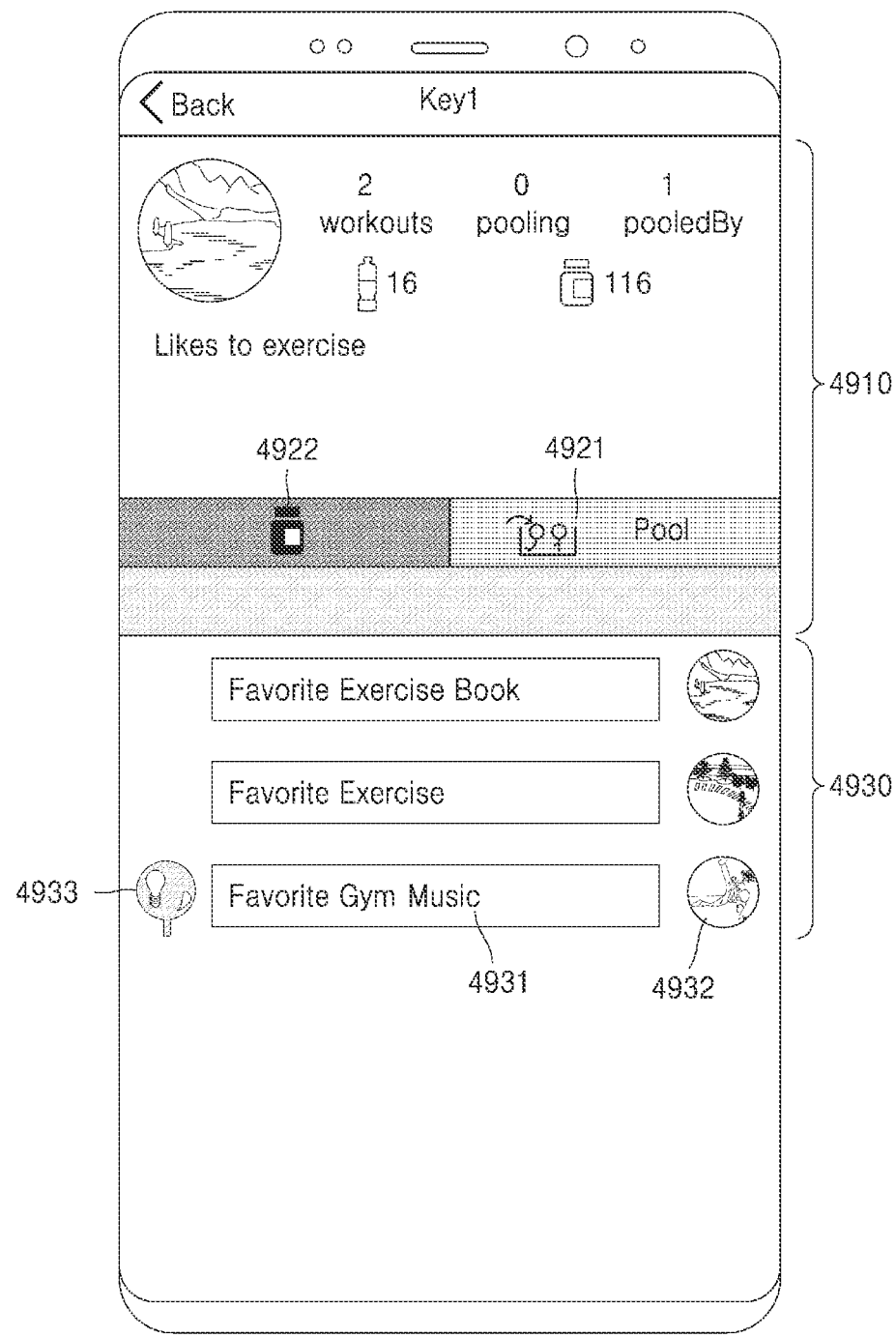

Meanwhile, FIG. 72 is a view illustrating a case in which one user accesses a user page of another user.

A user page 4900 includes a user information display portion 4910, a pool/un-pool button 4921, a support button 4922, and a user topic display portion 4930.

A user image, an exercise count, the number of users who have been pooled (followed) by me, the number of users who have been pooled me, user comments, and the like are displayed on the user information display portion 4910. Meanwhile, although not shown in the drawings, my gym information of the user, a badge of a "birthday exerciser," and "Eve exerciser," or the like, a city badge that may be given according to the location of my gym (in which city the exercise was performed), and the like may be further displayed.

In addition, in the case of a user page of another user, the pool/un-pool button 4921 for the corresponding user may be provided.

In addition, in the case of a user page of another user, the support button 4922 for the corresponding user may be provided. Here, the support button 4922 may be provided in the form of a water bottle when the corresponding user is currently exercising, and the support button 4922 may be provided in the form of a protein powder when the corresponding user is not currently exercising. This will be described in more detail later.

Figure 73:
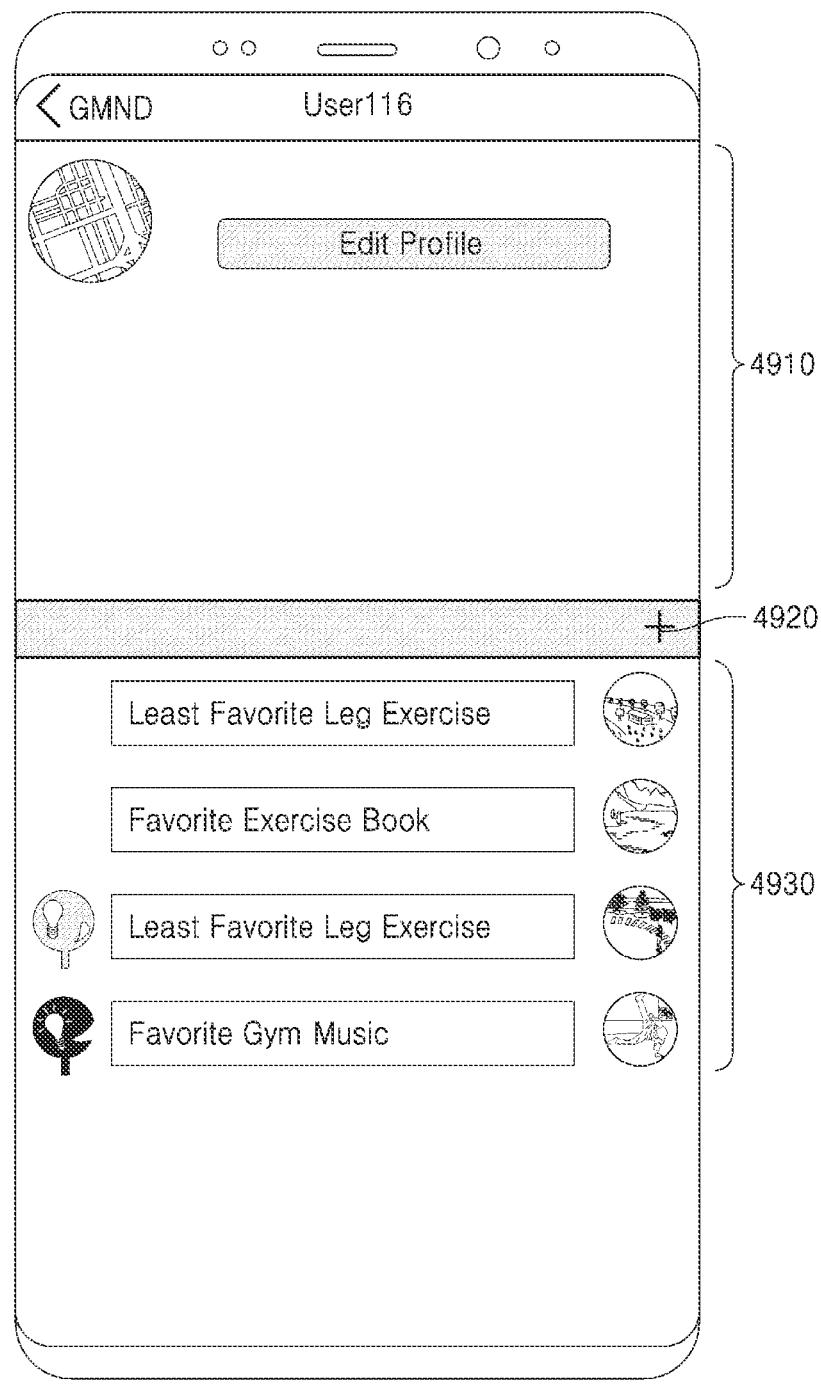

One or more user topics are displayed on the user topic display portion 4930. In more detail, the user topic display portion 4930 may include a topic text display portion 4931, a topic image display portion 4932, and a user preferred icon 4933. Here, when the user clicks the user preferred icon 4933 for a specific topic, the shape (color, shape, brightness, or the like) of the corresponding icon may be changed and displayed as shown in FIG. 73.

The user page of the present disclosure is configured such that a user answers the topic (question) expressed in a text form with an image. Also, in addition to simply answering the presented topics, a user may also create his/her own topic, and particular, at this point, the topic may be created on one screen without being switched between pages.

In addition, another user (content consumer) may evaluate (up-vote or down-vote) not only the content but also the topic (subject) itself, so that good topics (subjects) may be gathered or collected. In addition, the collected topics may be again adopted as default topics.

FIGS. 74 to 80 are views illustrating a photo zoom-in page of the exercise history management system according to an embodiment of the present disclosure and preference icons displayed on the photo zoom-in page.

Figure 74:
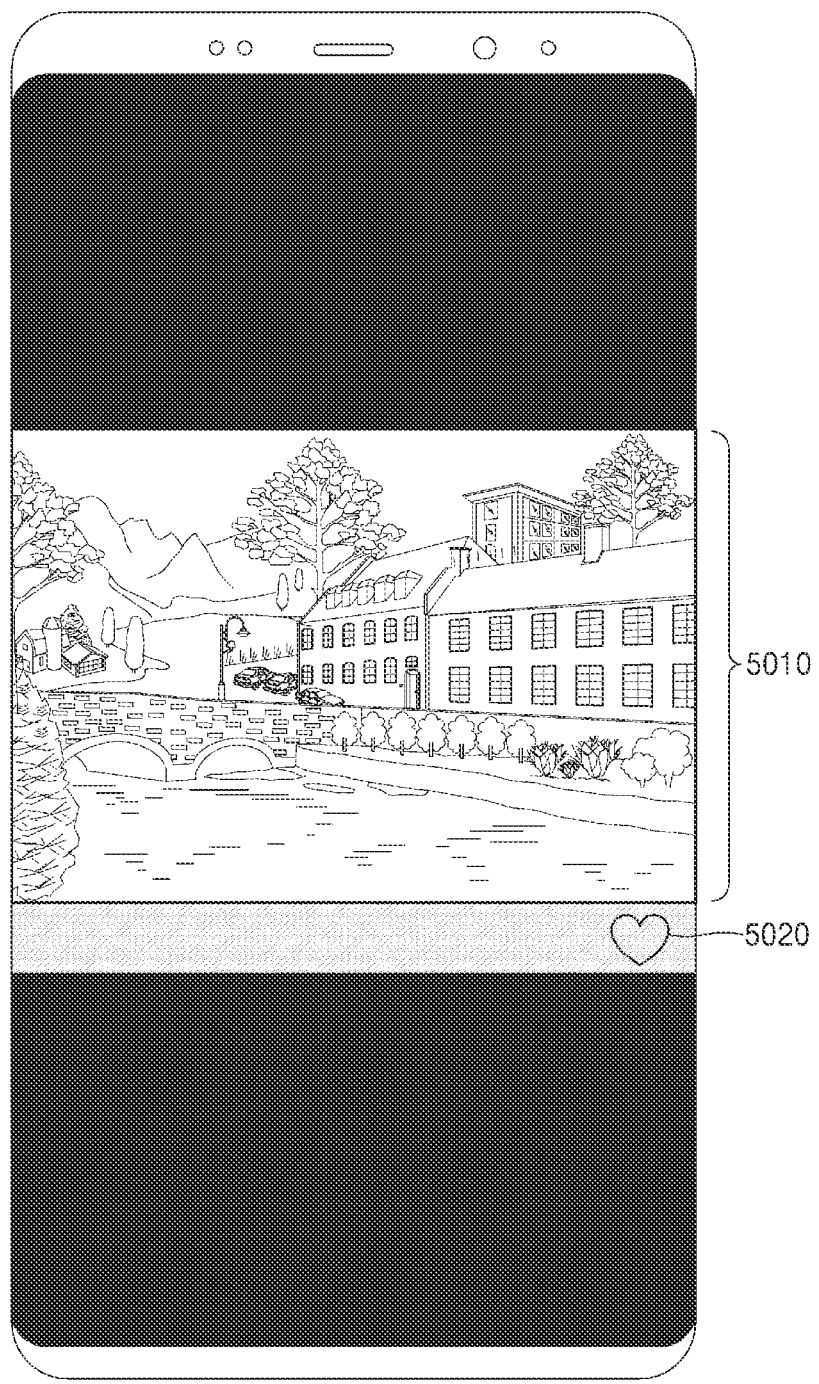

When the user image is clicked in FIG. 65, 72, or the like, the clicked image is zoomed in and displayed as an image 5010 shown in FIG. 74. In addition, a preference icon 5020 for the corresponding image 5010 is displayed on one side of the image 5010.

Initially, as shown in FIG. 74, a heart shape with an empty inside is displayed as the preference icon 5020. Here, whenever the preference icon 5020 is pressed one time, icons shown in FIGS. 74 to 79 are sequentially changed.

Figure 75:
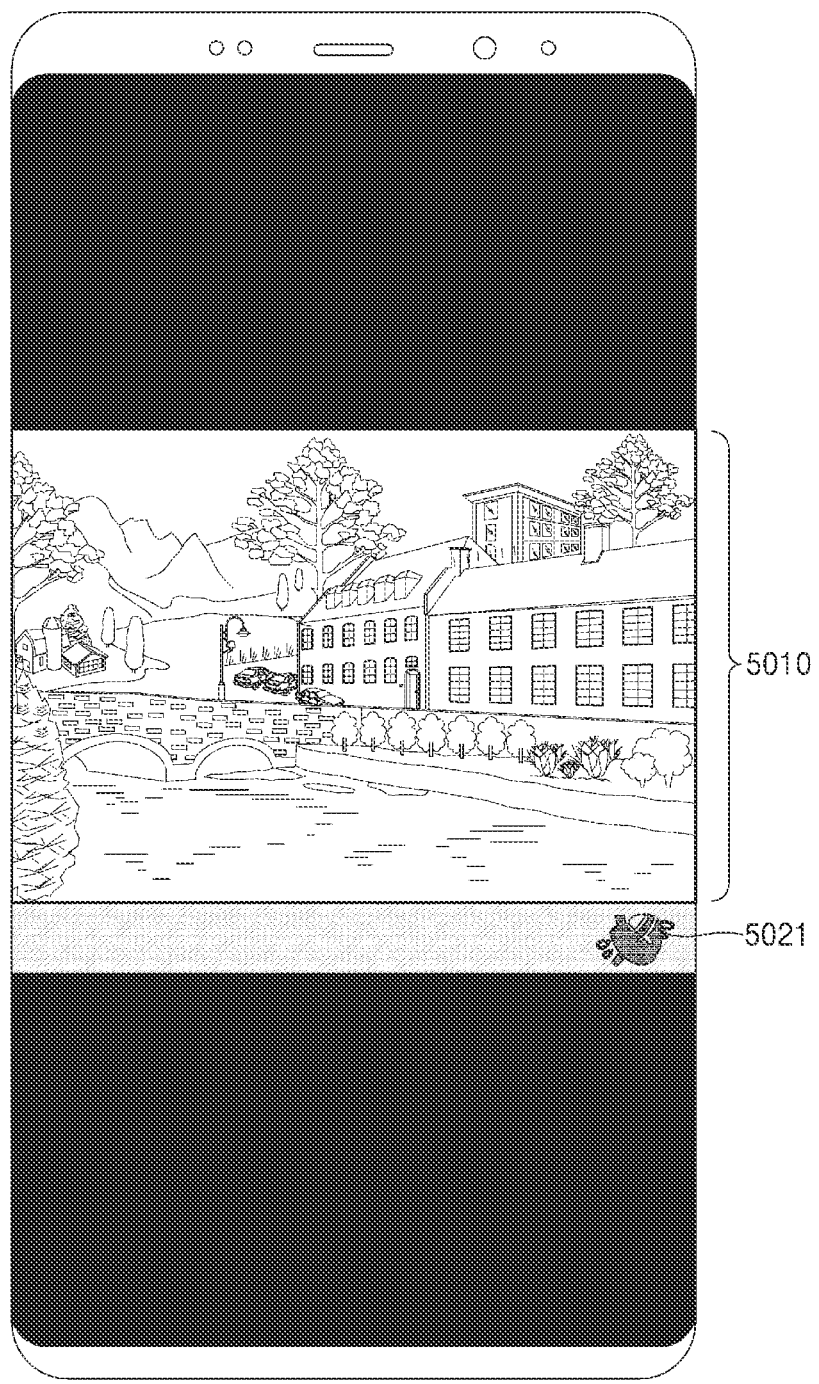
Figure 76:
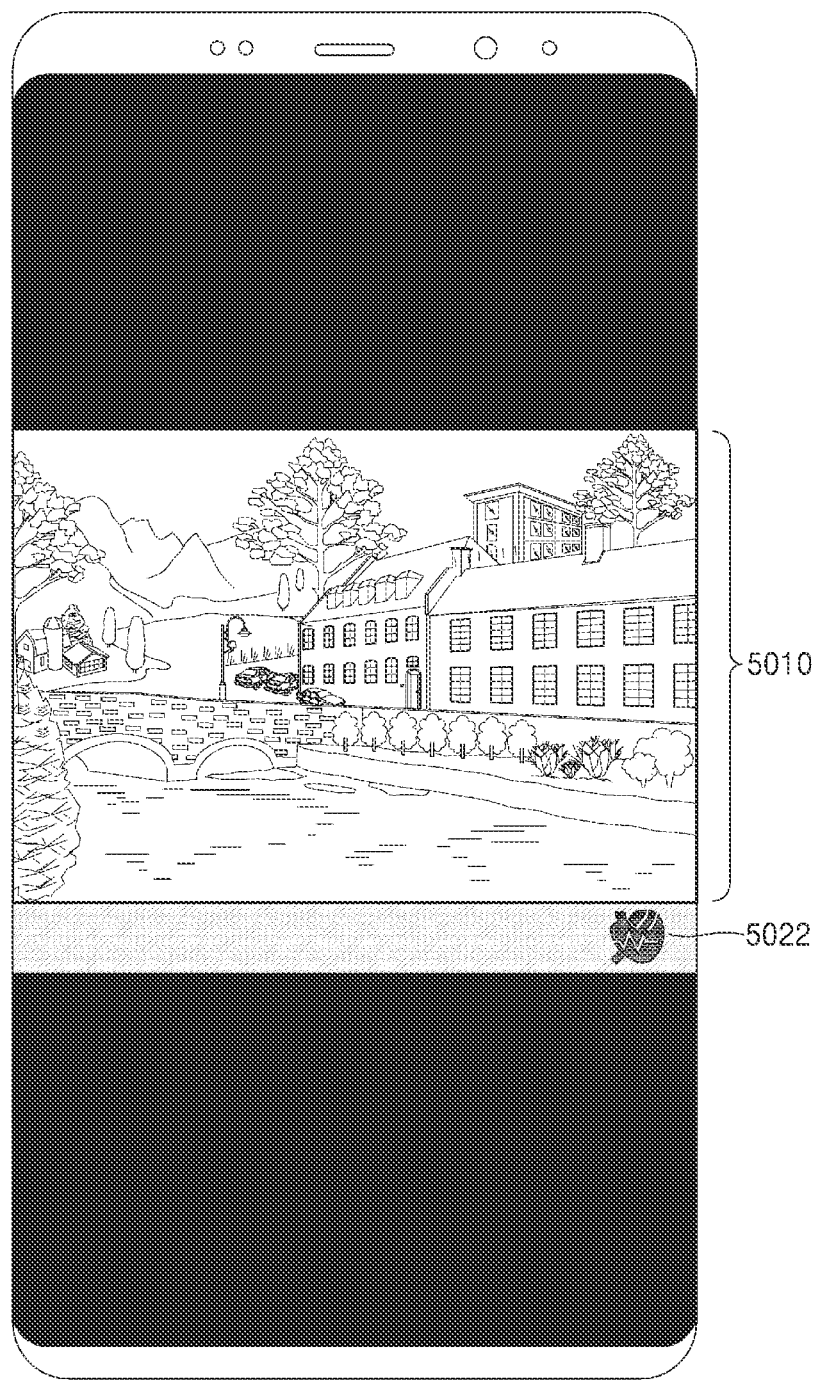
Figure 77:
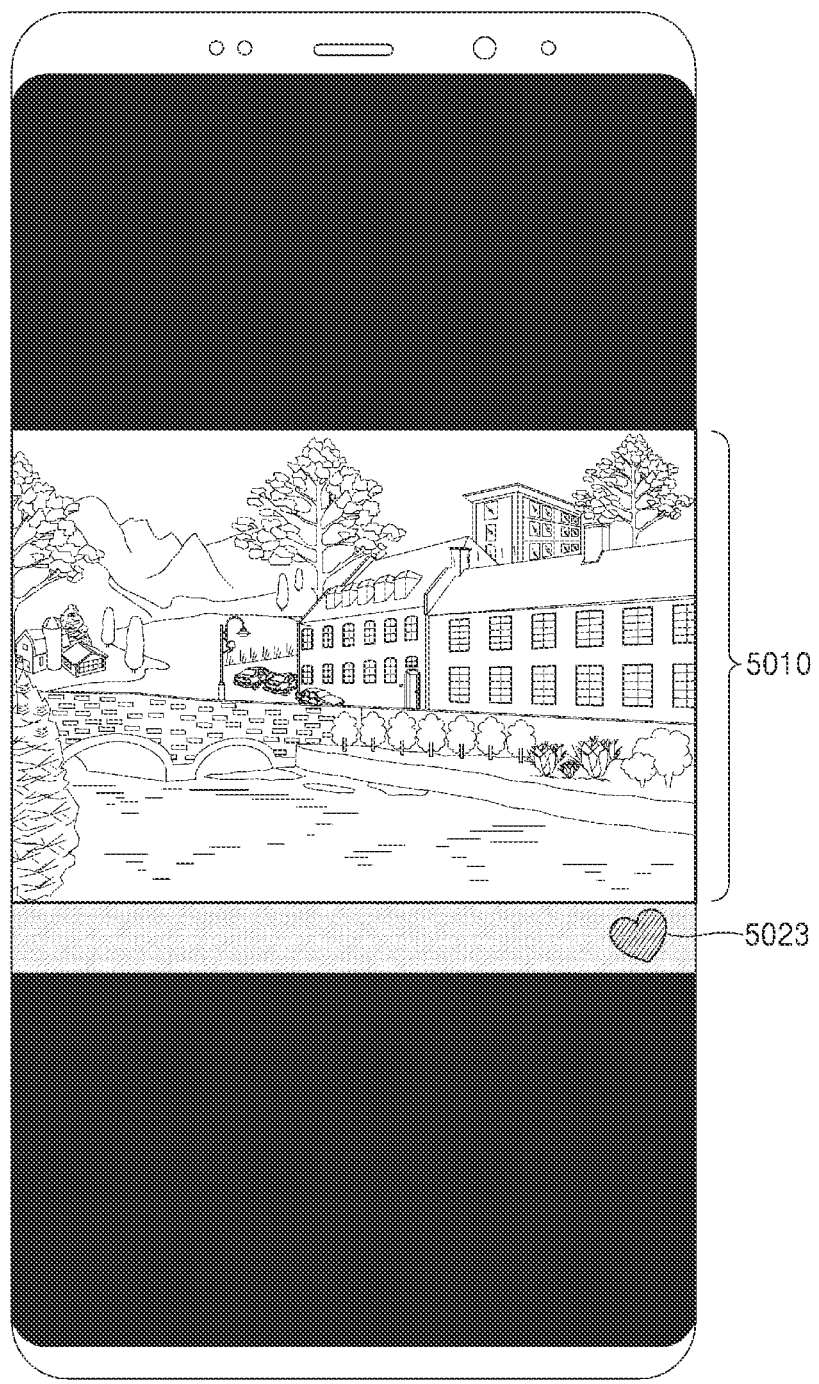
Figure 78:
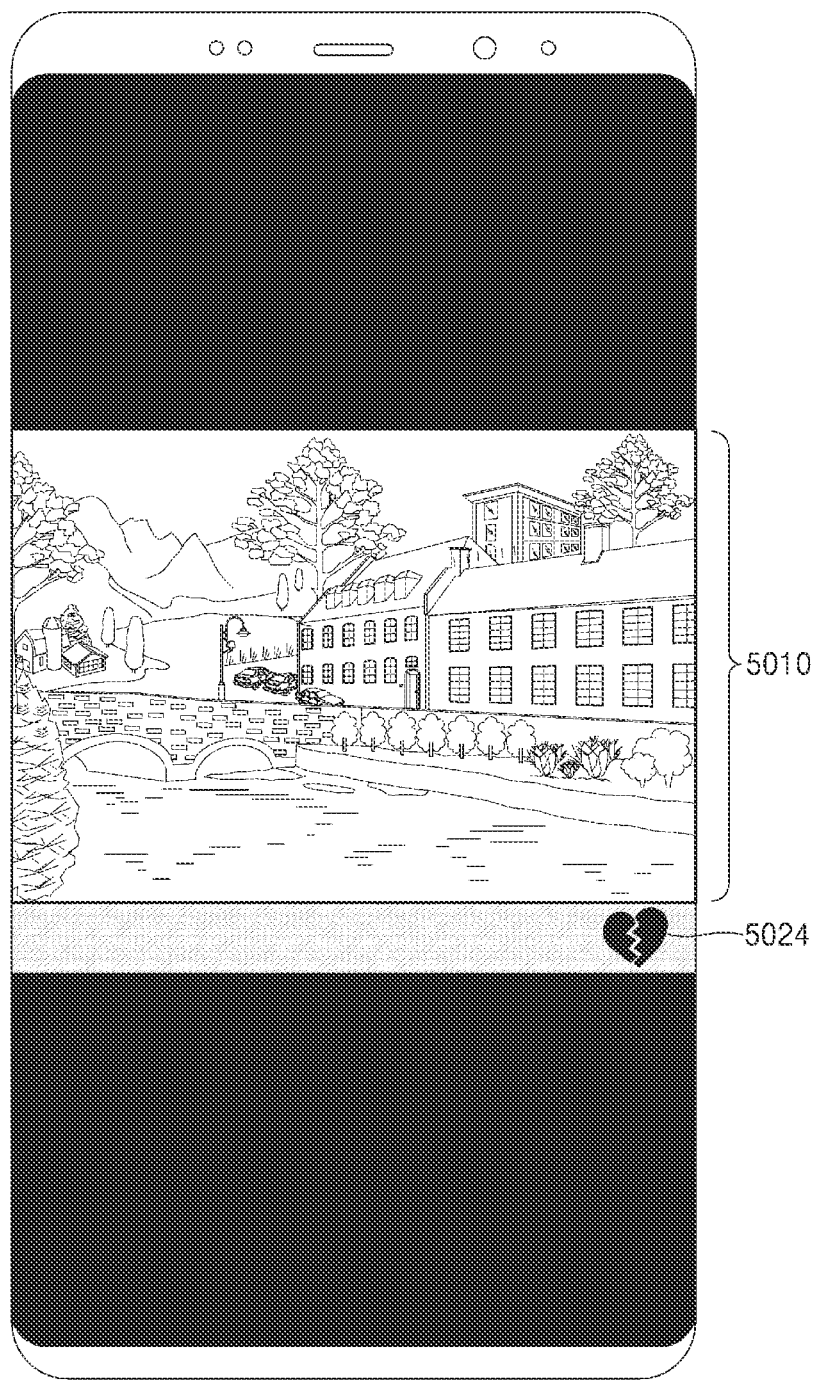
Figure 79:
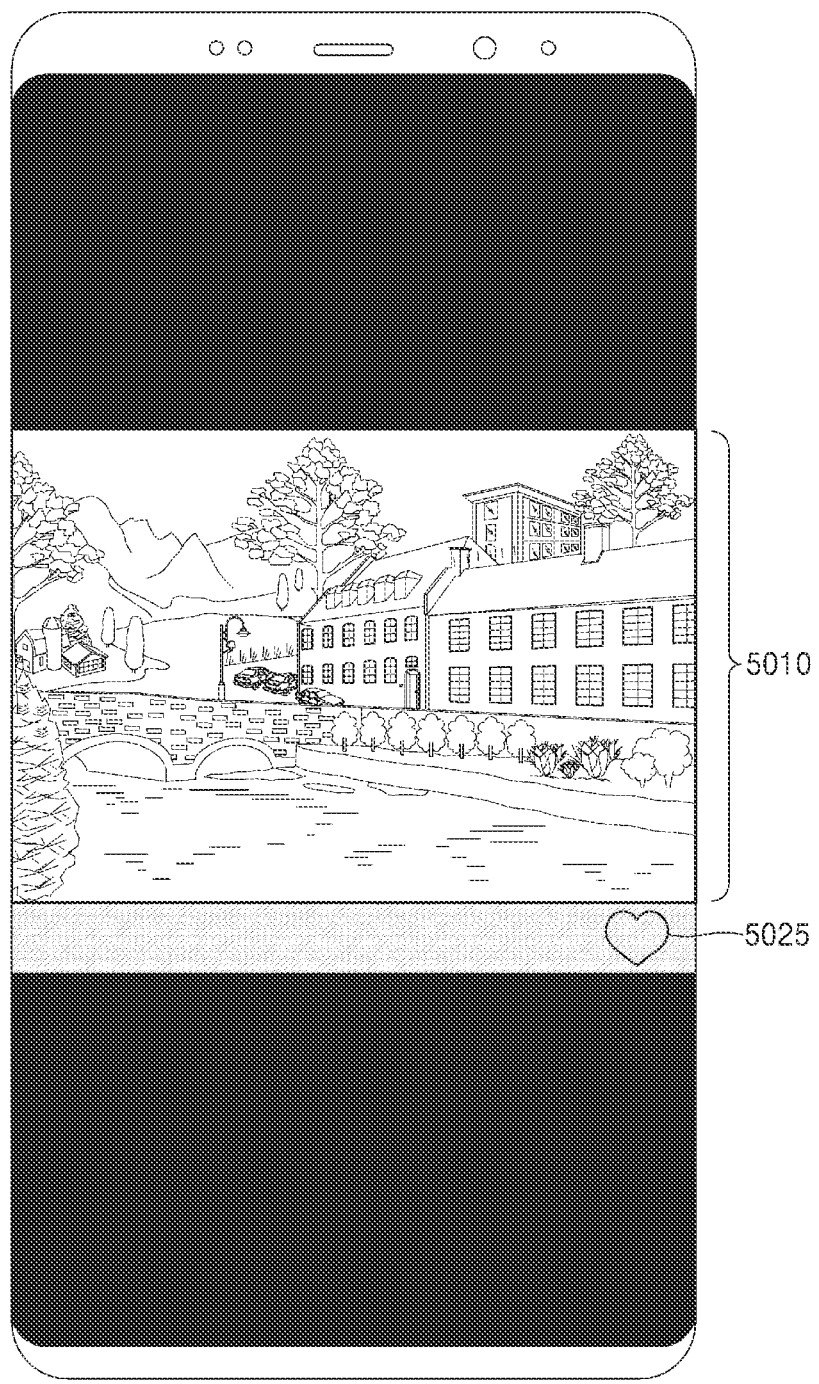

Here, a preference icon 5021 shown in FIG. 75 refers to a photo that makes the user want to exercise, a preference icon 5022 shown in FIG. 76 refers to a healthy photo (mainly food), a preference icon 5023 shown in FIG. 77 refers to a general like button, a preference icon 5024 shown in FIG. 78 refers to a dislike button, and a preference icon 5025 shown in FIG. 79 indicates an unselected state. FIG. 80 illustrates a screen that describes the meaning of each icon.

The "like/dislike" icon is generally expressed as a finger or a heart/empty heart, and in the present disclosure, user's preference may be evaluated with 'heart shapes' that are different from the heart/empty heart. That is, since the content may be evaluated while changing five types (or more) of icons (heart shape), there is an effect that various evaluation methods for the contents may be implemented.

FIGS. 81 to 86 are views illustrating a user page of the exercise history management system according to an embodiment of the present disclosure.

Figure 81:
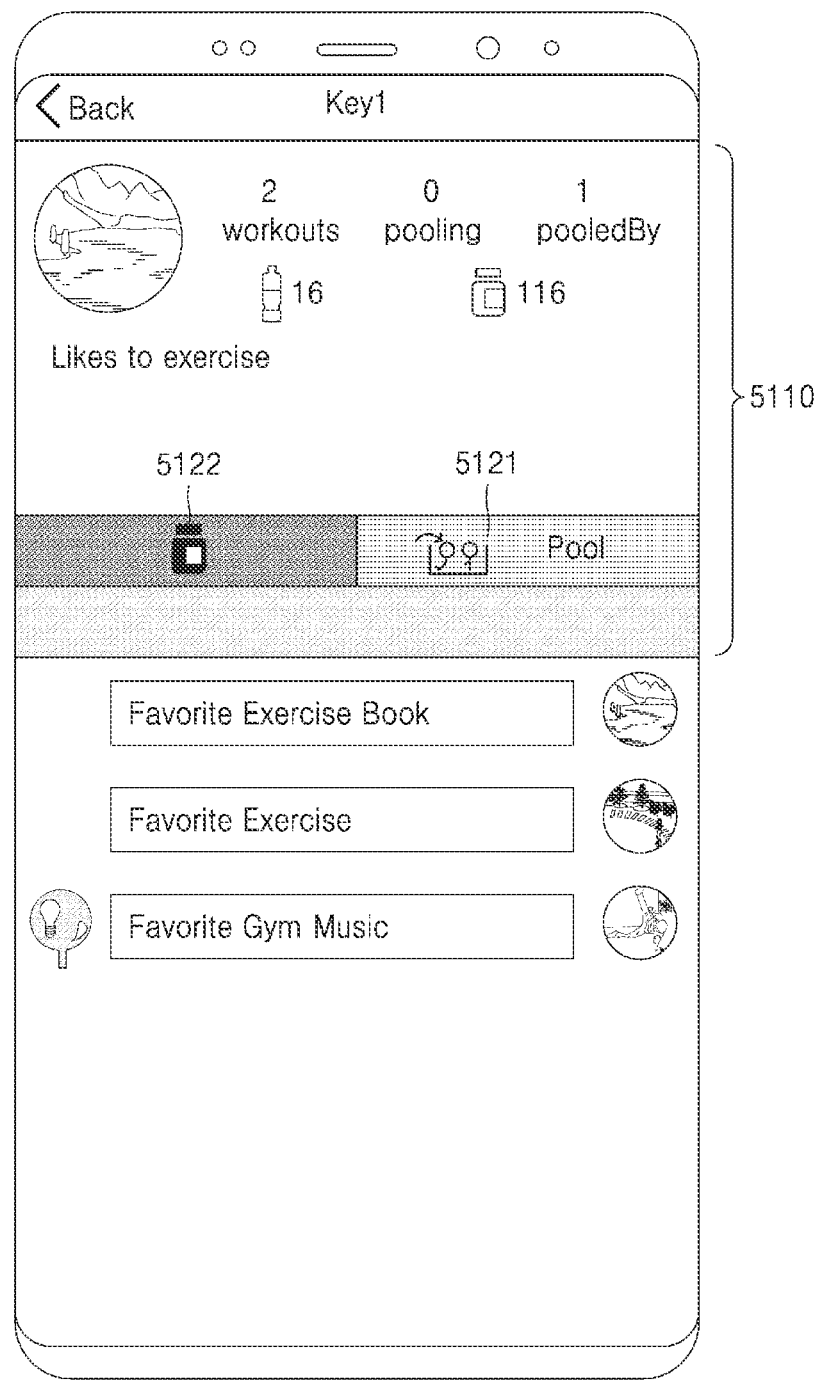
FIGS. 81 to 86 are views illustrating a user page of the exercise history management system according to an embodiment of the present disclosure.

First, referring to FIG. 81, a user page 5100 includes a user information display portion 5110, a pool/un-pool button 5121, a protein powder button 5122, and a user content display portion 5130.

A user image, an exercise count, the number of users who have been pooled (followed) by me, the number of users who have been pooled me, user comments, and the like are displayed on the user information display portion 5110. Meanwhile, although not shown in the drawings, my gym information of the user, a badge of a "birthday exerciser," and "Eve exerciser," or the like, a city badge that may be given according to the location of my gym (in which city the exercise was performed), and the like may be further displayed.

In addition, in the case of a user page of another user, the pool/un-pool button 5121 for the corresponding user may be provided.

In addition, when the page is a user page of another user and the corresponding user is currently not exercising, the protein powder button 5122 for the corresponding user may be provided. Here, the protein powder button 5122 performs a role of a type of support button.

Figure 82:
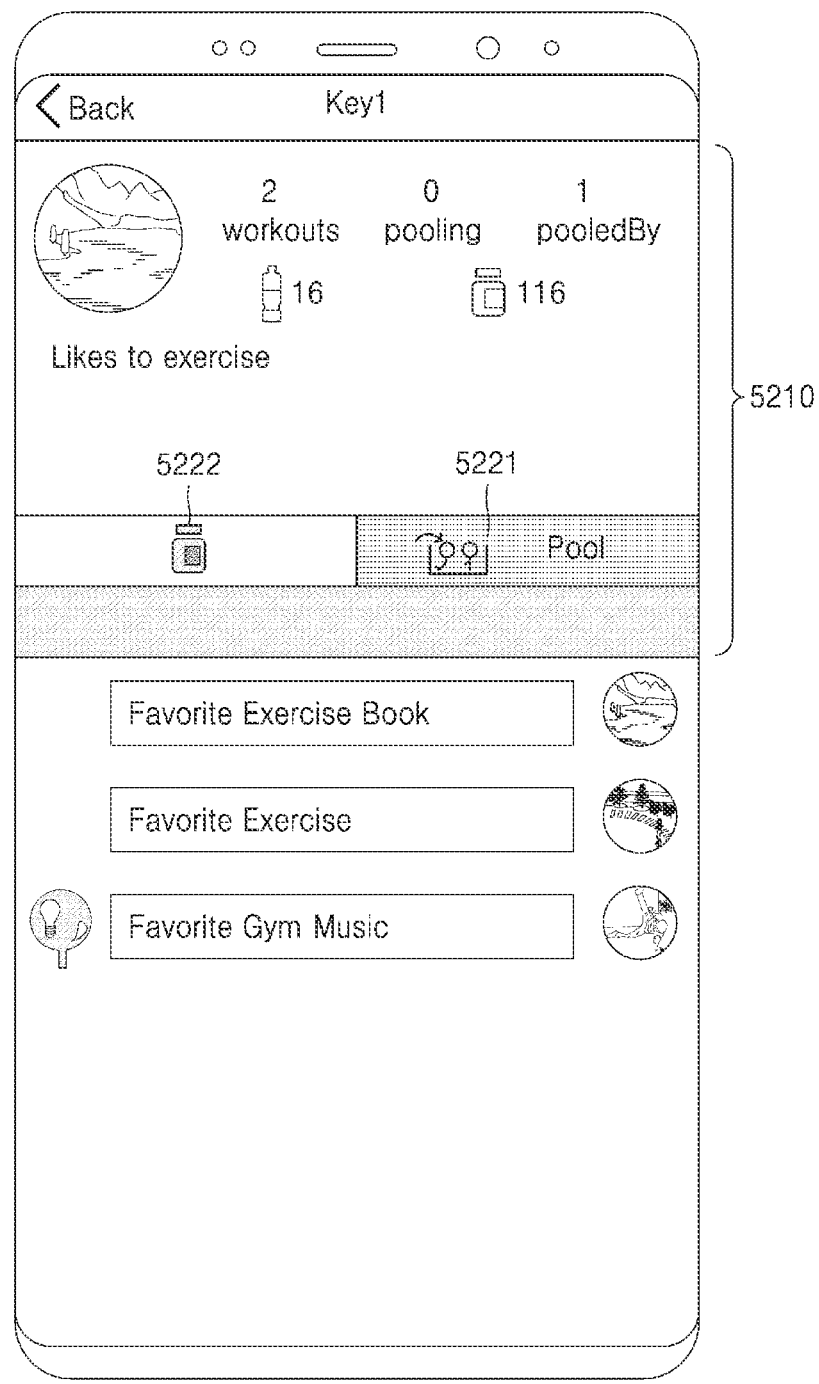

There is a limit to the number of times a user can provide a protein powder to another user per day (e.g., once a day), and when the number reaches the limit, the shape (color, shape, brightness, or the like) of the protein powder button 5122 may be changed and displayed as shown in FIG. 82. For example, whenever the user presents the protein powder, as shown in FIGS. 81 and 82, a lid of a protein powder container may gradually disappear or the color of the lid may become lighter.

Meanwhile, a stat of a support item such as the protein powder may be displayed on the user information display portion 5110, and all stats (workouts and the like) may be formed such that "on-the radar/off-the-radar" may be set on each state.

Figure 83:
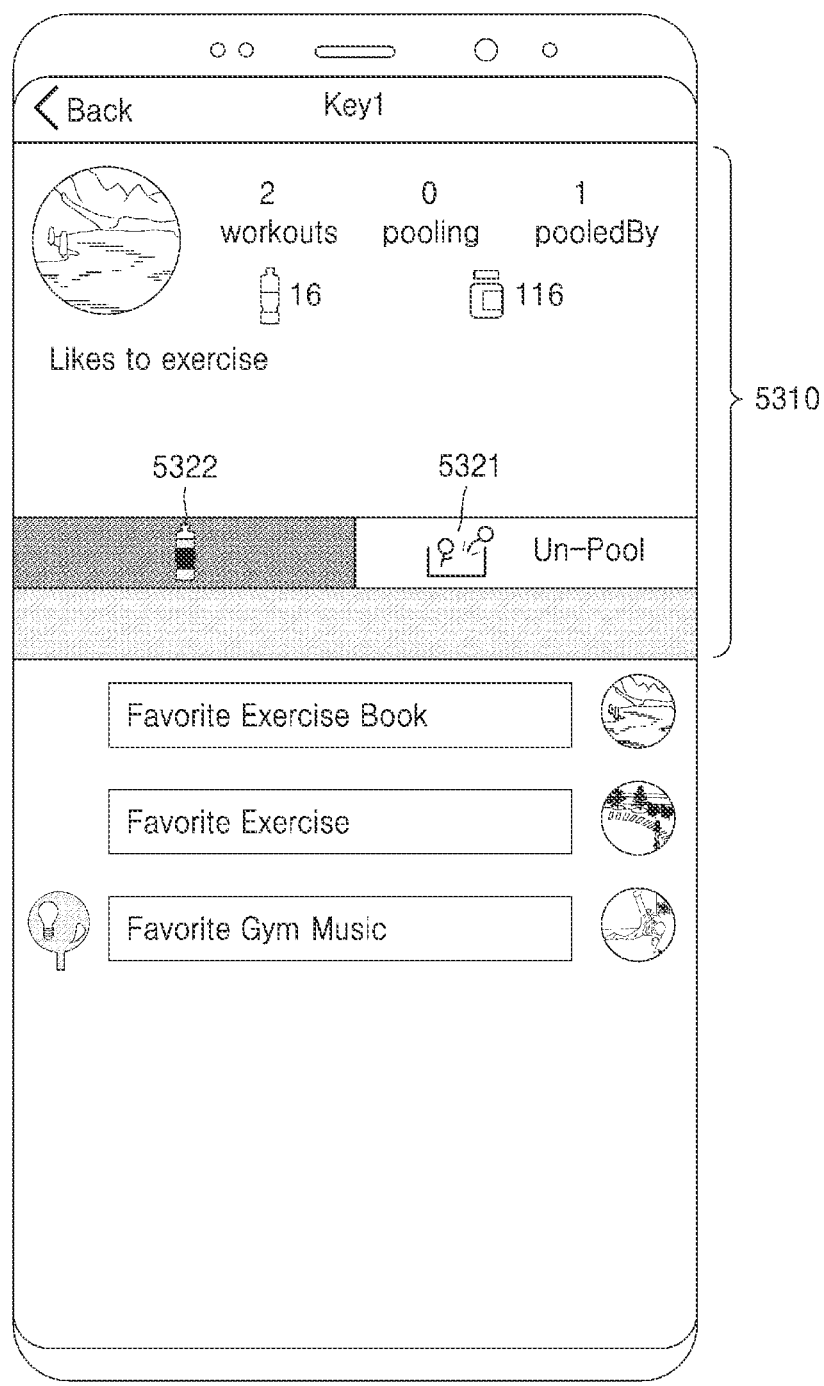
Figure 84:
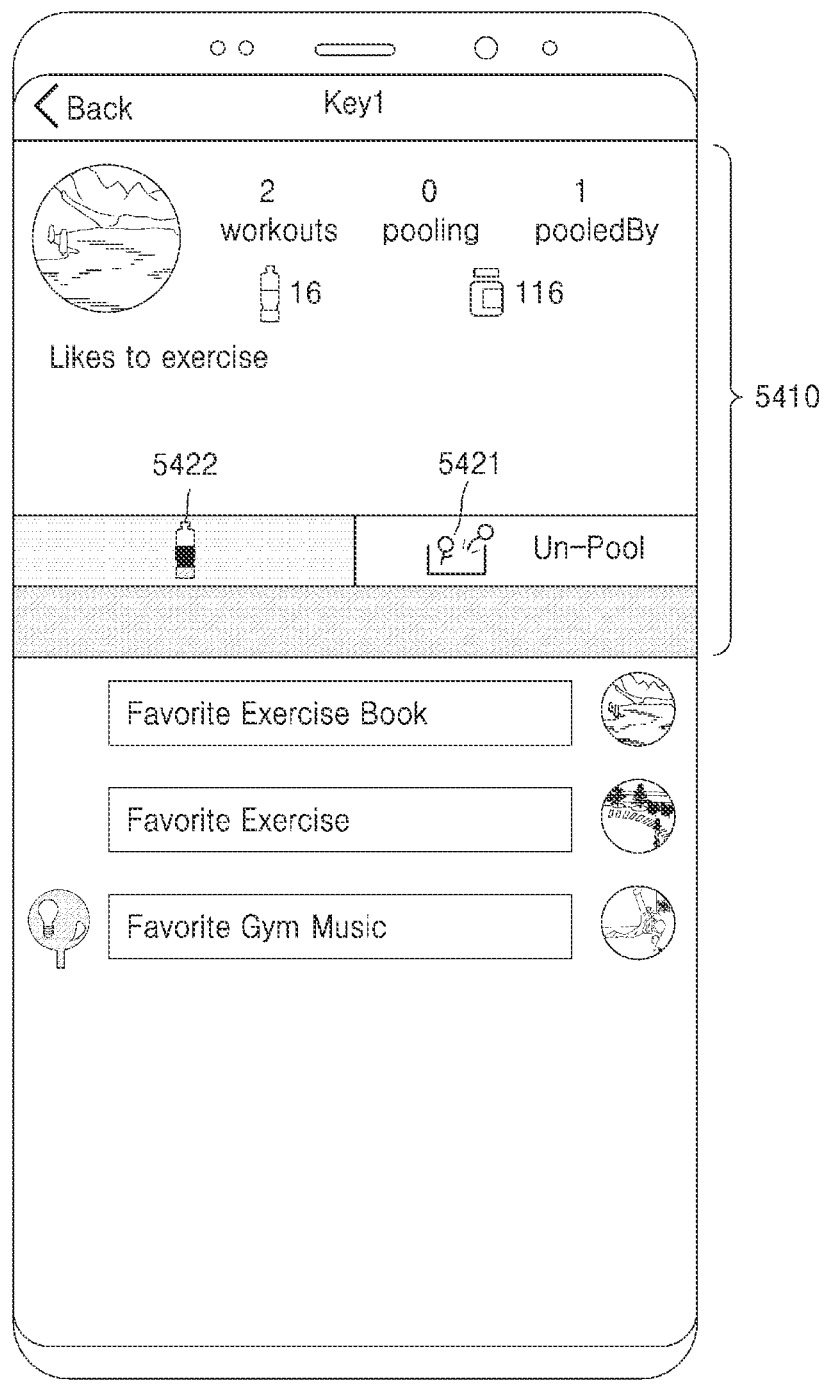
Figure 85:
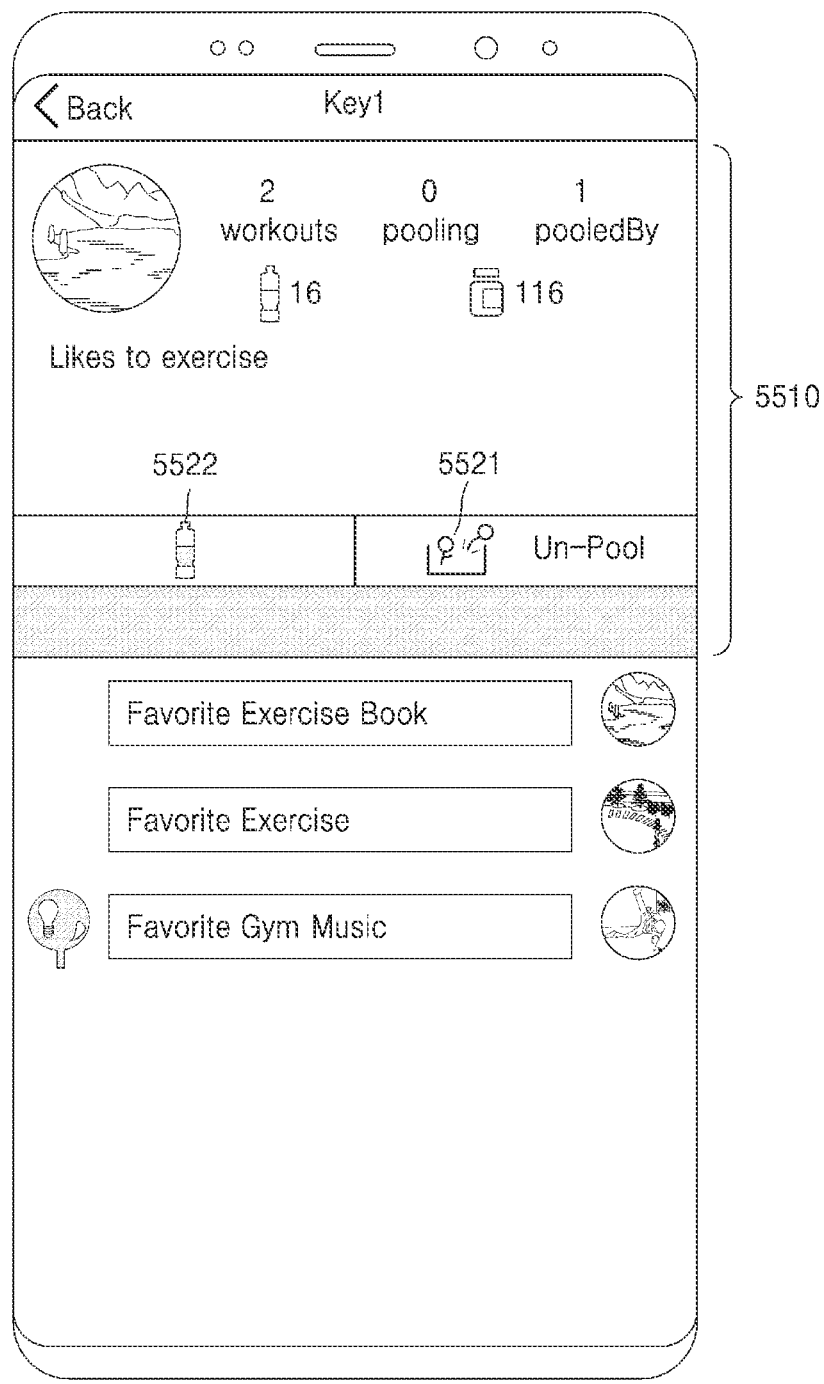

In addition, referring to FIG. 83, when the page is a user page of another user and the corresponding user is currently not exercising, a water bottle button 5322 for the corresponding user may be provided. Here, the water bottle button 5322 also performs a role of a type of support button.

In more detail, the water bottle button 5322 may be displayed on the user page of the corresponding user who is currently exercising. Here, the number of times the water bottle is given is also limited, for example, in the case of limiting the number of times the water bottle is given to two, the amount of water in the water bottle button 5322 may be gradually reduced, and the color of the button may gradually become lighter. That is, colors of the button which are not in harmony with the surroundings at first become lighter as a predetermined action is performed, and thus, eventually match the background behind the button.

Here, one water bottle and one protein powder may be given to all users per day, and may disappear when the water bottle and the protein powder are not used on the same day. Meanwhile, when the user starts to exercise, the system may additionally give one water bottle and one protein powder to the user.

Accordingly, the user may present a maximum of two water bottles and two protein powders to other users on a specific day. These may also disappear when not used on the same day, and may all be reset to one on the next day.

Here, a maximum of one water bottle and one protein powder per day may be set to be presented to each of other users. That is, networking may be encouraged to grow by allowing gifts to be sent to as many different people as possible.

Figure 86:
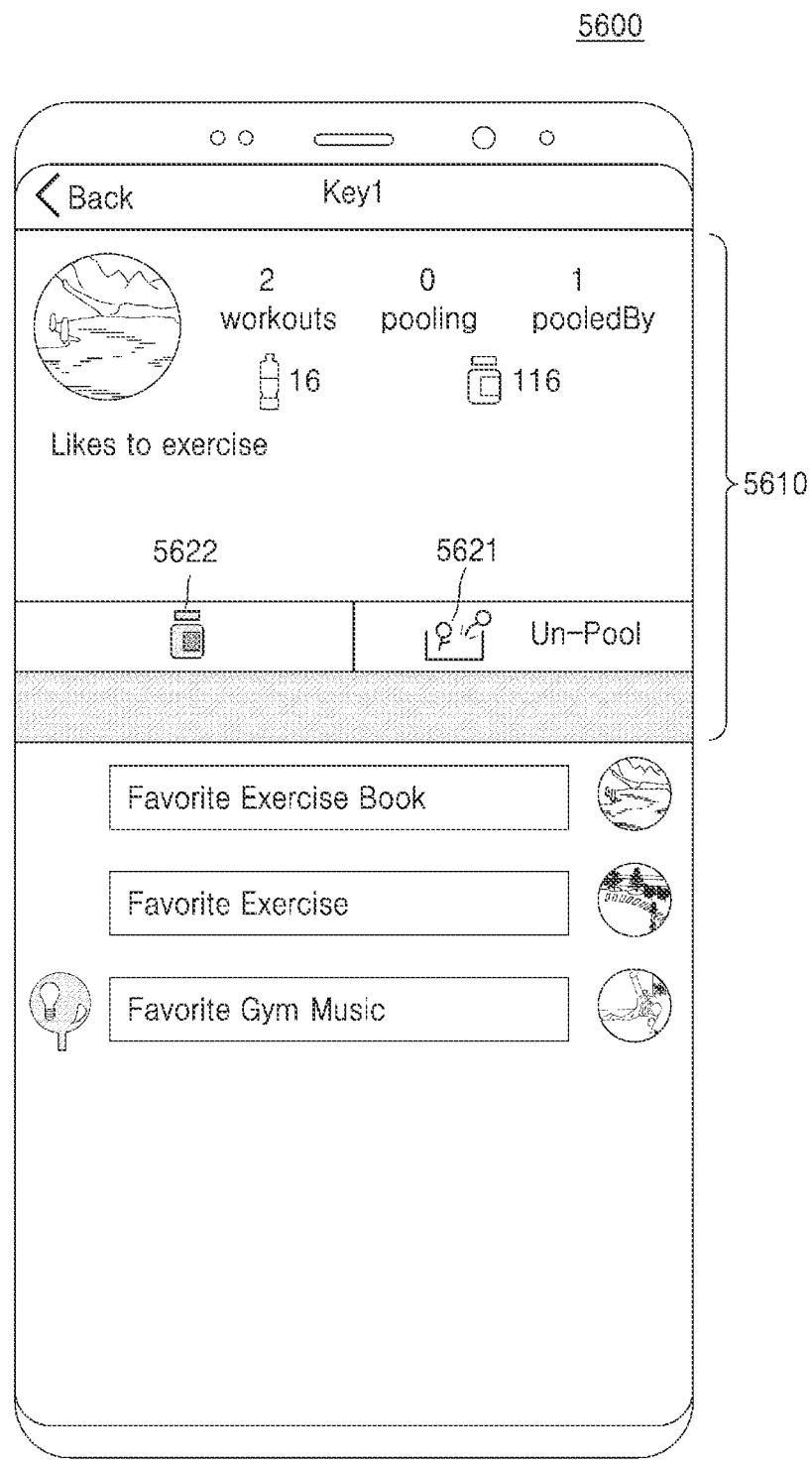

Meanwhile, when a pool/un-pool button 5221 is pressed in FIG. 82, the shape (color, shape, brightness, or the like) of the pool/un-pool button 5221 may be changed and displayed as shown in FIG. 86.

This is to encourage a pool and a gift (e.g., a protein powder, a water bottle, or the like) to be given to others. As described above, by allowing certain items (e.g., a water bottle) to be received only when an exercise is performed, there is an effect of encouraging the exercise to be performed more frequently.

As described above, the present disclosure may encourage an exercise to be performed by allowing a specific item to be received only when the exercise is performed. That is, a specific gift is given to a user who is currently exercising, so that the user should exercise to gather the corresponding item, thereby encouraging the user to exercise more frequently.

Meanwhile, a protein powder is provided to a user when the user is not currently exercising and water is provided to the user when the user is currently exercising, illustrating that the user drinks water during exercise and consumes protein when the exercise is not performed.

In addition, according to the present disclosure, whenever a water bottle is presented, the amount of water in a water bottle button gradually decreases and the color of the button gradually becomes lighter. Here, the amount of water may be reduced in the order of "full"-→"half"-→"empty." In addition, as a user repeatedly inputs, the color of the background screen gradually becomes lighter, so that an effect of encouraging a user's action may be obtained.

Figure 87:
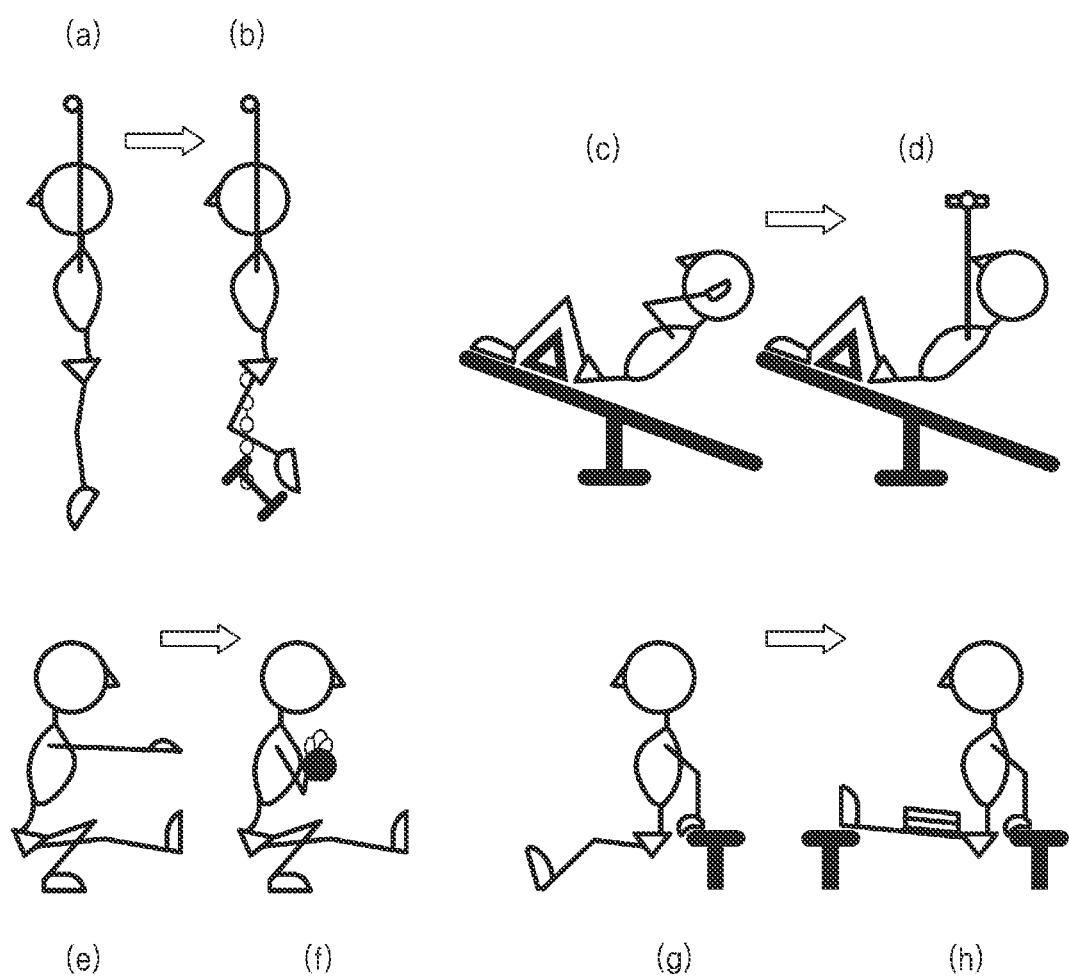
FIG. 87 is a view illustrating exercise icons of the exercise history management system according to an embodiment of the present disclosure.

FIG. 87 is a view illustrating exercise icons of the exercise history management system according to an embodiment of the present disclosure.

In general, in the case of a free-hand exercise, an exercise icon is also expressed as a body with nothing. In this case, when a weight is added to the weight input window shown in FIG. 22, as shown in FIG. 87, the exercise icon may be displayed by being changed to an icon in which the weight is added. That is, in a state of (a) OF FIG. 87, when the weight is added, the icon may be displayed by being changed to an icon of (b) of FIG. 87. Similarly, the icon may be displayed by being changed as (c)-→(d), (e)-→(f), (g)-→(h).

As described above, when the weight is added to the free-hand exercise, by changing the icon to an icon having the weight and displaying the icon, the exercise state of the user may be more accurately and intuitively identified.

Figure 88:
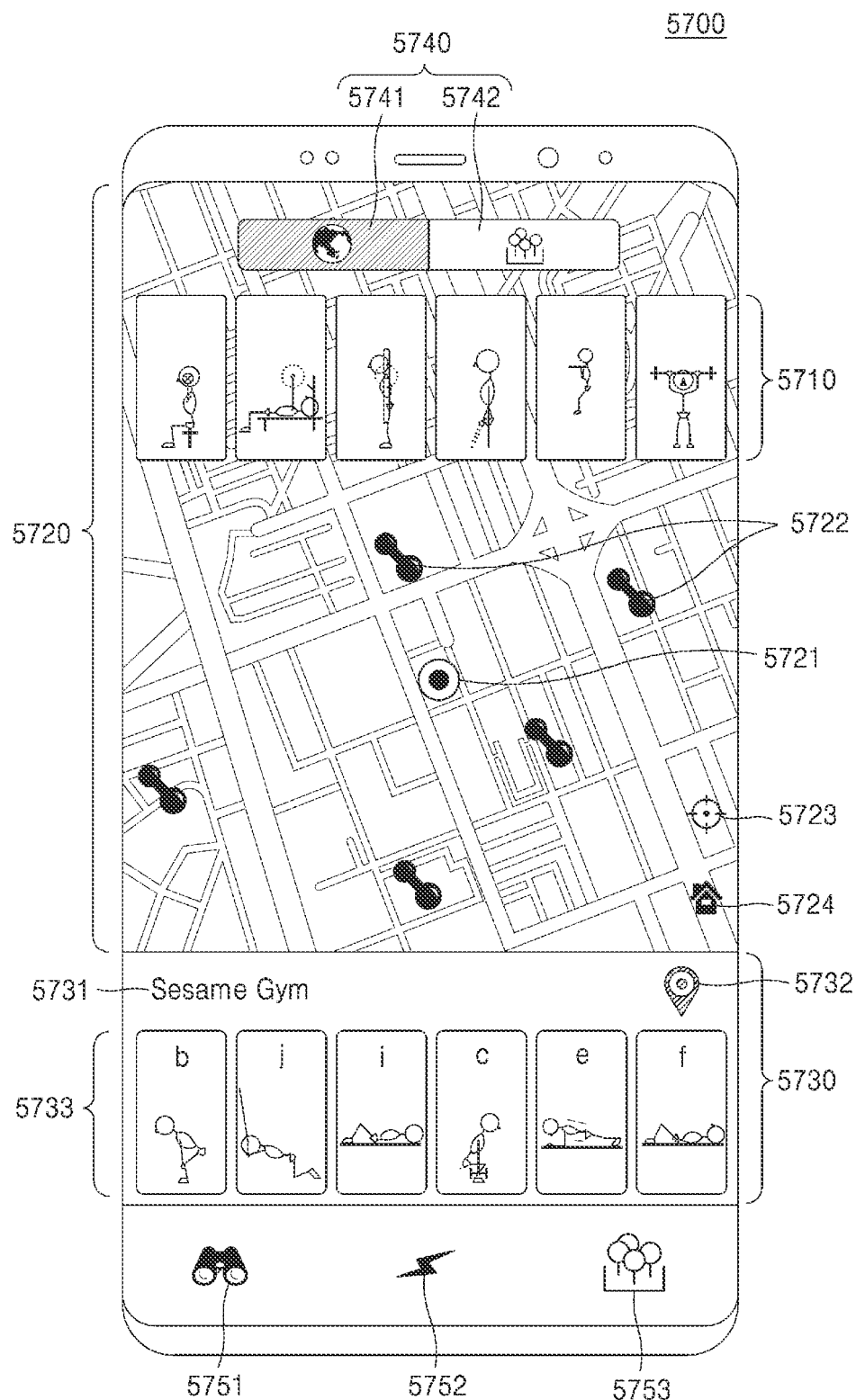
FIG. 88 is a view illustrating a map page displayed on the user terminal of the exercise history management system according to an embodiment of the present disclosure.

FIG. 88 is a view illustrating a map page according to another embodiment of the present disclosure, which is displayed on the user terminal of the exercise history management system. The map page of FIG. 88 is different from the map page of FIG. 4 in that a tab button at a lower end of FIG. 88 is different, which will be mainly described below.

A map page 5700 may be an initial screen of an application, which is provided to the user terminal 200 by the exercise history management system 1.

Three tab buttons are displayed at a lower end of the map page 5700. Among the three tabs at the lower end, a first tab on the left is a map page linking tab 5751 linked to the map page 5700, a second tab on the center is an exercise log input tab 5752 linked to a page for inputting an exercise history, and a third tab on the right is a pool page linking tab 5753 linked to the pool page 1200 (see FIG. 8).

Figure 89:
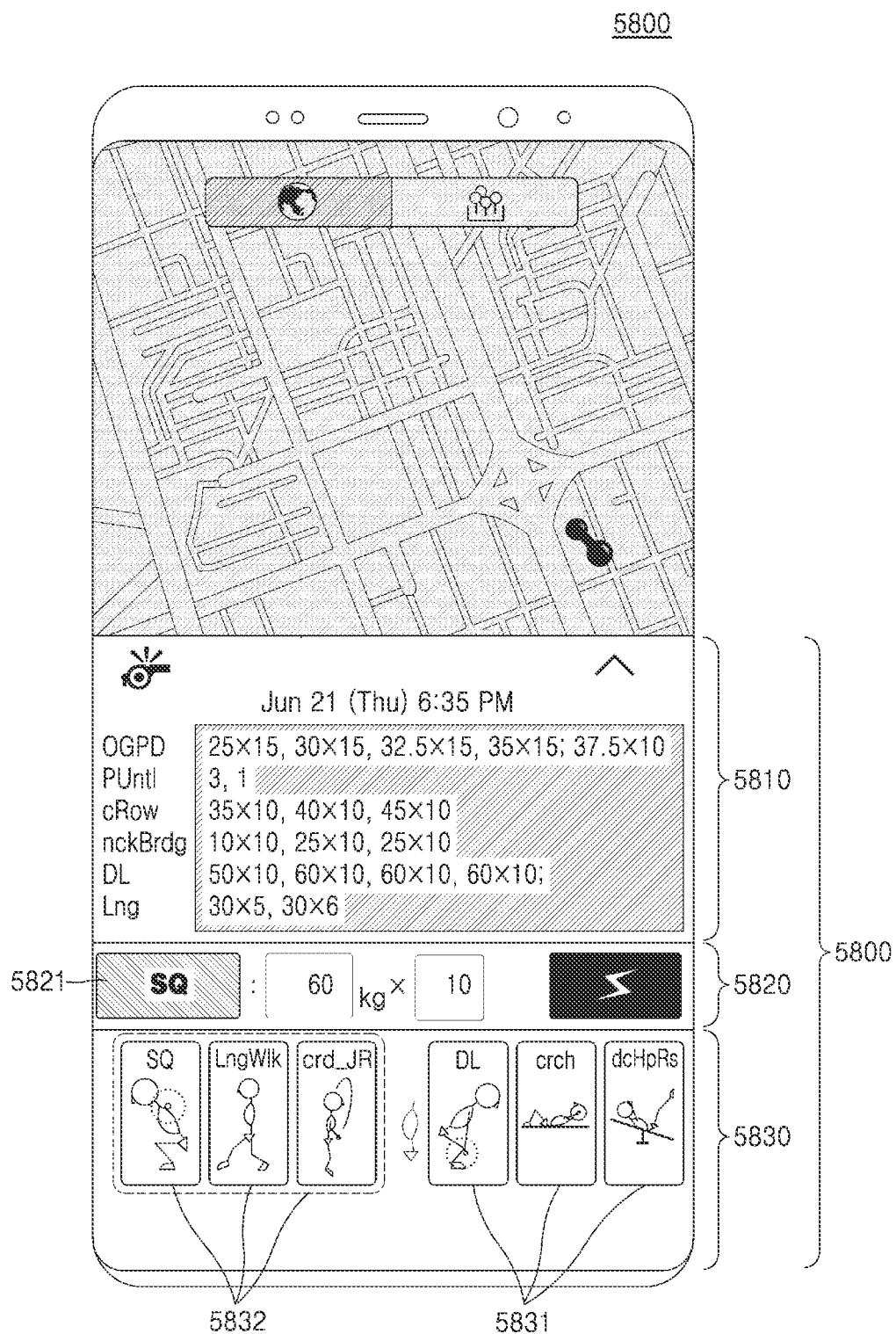
FIGS. 89 to 90 are views illustrating an exercise log input area displayed on the user terminal of the exercise history management system according to an embodiment of the present disclosure.

FIG. 89 is a view illustrating an exercise log input area according to another embodiment of the present disclosure, which is displayed on the user terminal of the exercise history management system. When the exercise log input tab 1152 (see FIG. 4) is selected from the map page 1100 (see FIG. 4), an exercise log input area 5800 may be displayed as shown in FIG. 89.

FIG. 89 is a view illustrating an initial screen of the exercise log input area. Referring to FIG. 89, the exercise log input area 5800 includes an exercise log display portion 5810, an exercise log input and transmission portion 5820, and an input value selection portion 5830. The exercise log input area of FIG. 89 is different from the exercise log input area of FIG. 19 in that the input value selection portion 5830 at a lower end of FIG. 89 is different, which will be mainly described below.

In a state in which an exercise name input portion 5821 is selected from the exercise log input and transmission portion 5820, one or more exercise name display portions 5831 may be displayed on the input value selection portion 5830. In addition, one or more recommended exercise display portions 5832 may be displayed on the input value selection portion 5830.

Here, in the present embodiment, as a user proceeds with an exercise, the exercise displayed on the recommended exercise display portion 5832 is organically changed.

In more detail, exercises that the user has performed at least once on a corresponding day may be displayed on the recommended exercise display portion 5832.

In response to the exercise performed by the user, on the recommended exercise display portion 5832, 1) exercises performed more than once on a corresponding day may be displayed, 2) a next exercise to be performed, which is predicted by the control unit, may be displayed, and 3) exercises that need to be performed by the user, even though the exercises are not included in the preferred exercise pool of the user, may be determined by the control unit and displayed.

Meanwhile, the exercise displayed on the recommended exercise display portion 5832 may be removed from the exercise name display portion 5831 or may be displayed on the exercise name display portion 5831 as it is.

For example, when a method in which the exercise displayed on the recommended exercise display portion 5832 is removed from the exercise name display portion 5831 is used, 1) since the exercise performed once is displayed on the recommended exercise display portion 5832, the user may easily find the performed exercise, or 2) since the exercise name display portion 5831 excludes the exercise performed once, it is easy to find the next exercise to be performed.

Here, when a predetermined input different from a general input such as a long press or a force touch is performed on each recommended exercise display portion 5832, the corresponding recommended exercise display portion 5832 may be deleted.

<Addition of Aerobic Exercise→

Figure 90:
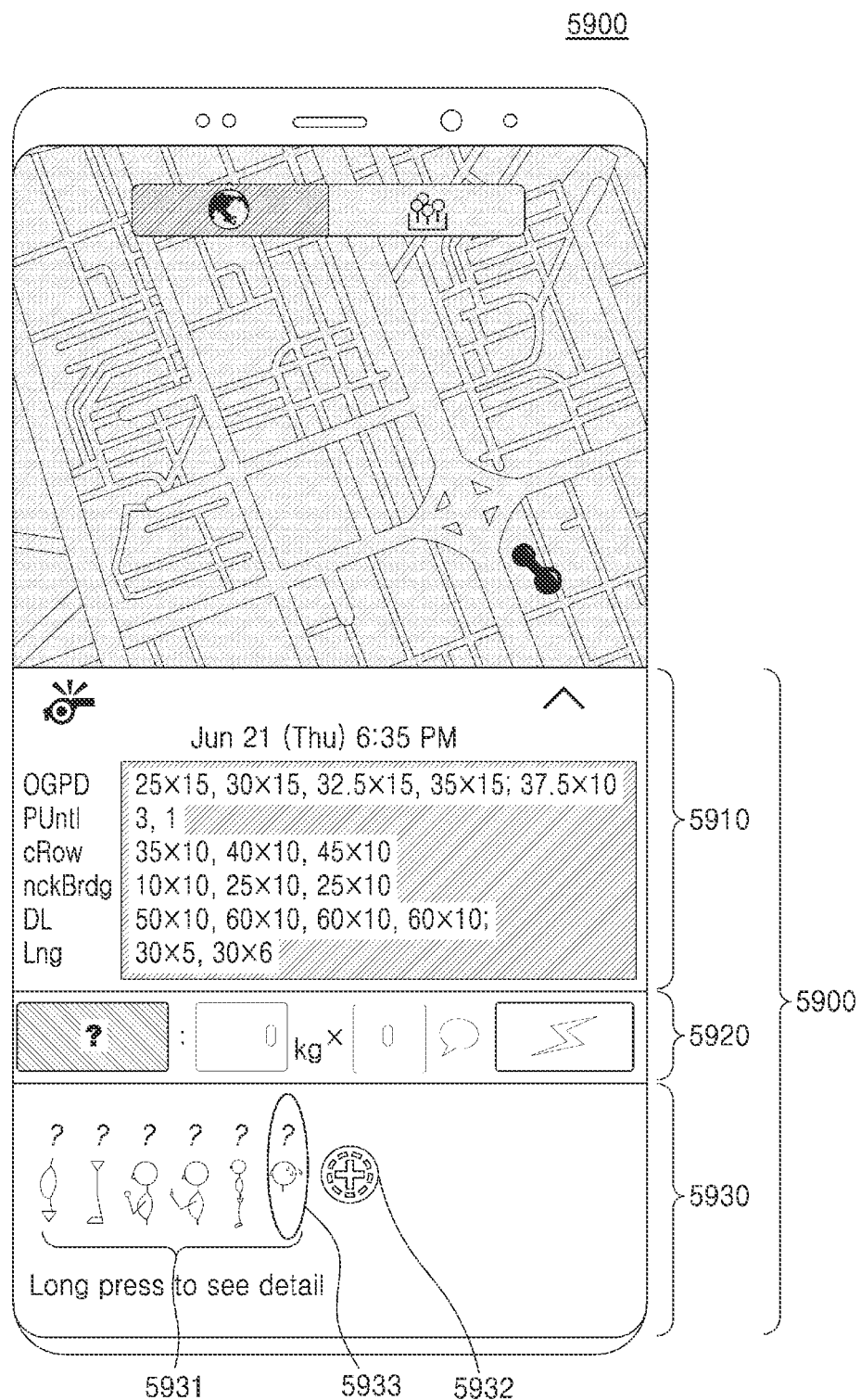

FIG. 90 is a view illustrating an exercise log input area according to another embodiment of the present disclosure, which is displayed on the user terminal of the exercise history management system. When the exercise log input tab 1152 (see FIG. 4) is selected from the map page 1100 (see FIG. 4), an exercise log input area 5900 may be displayed as shown in FIG. 90.

FIG. 90 is a view illustrating an initial screen of the exercise log input area.

Figure 93:
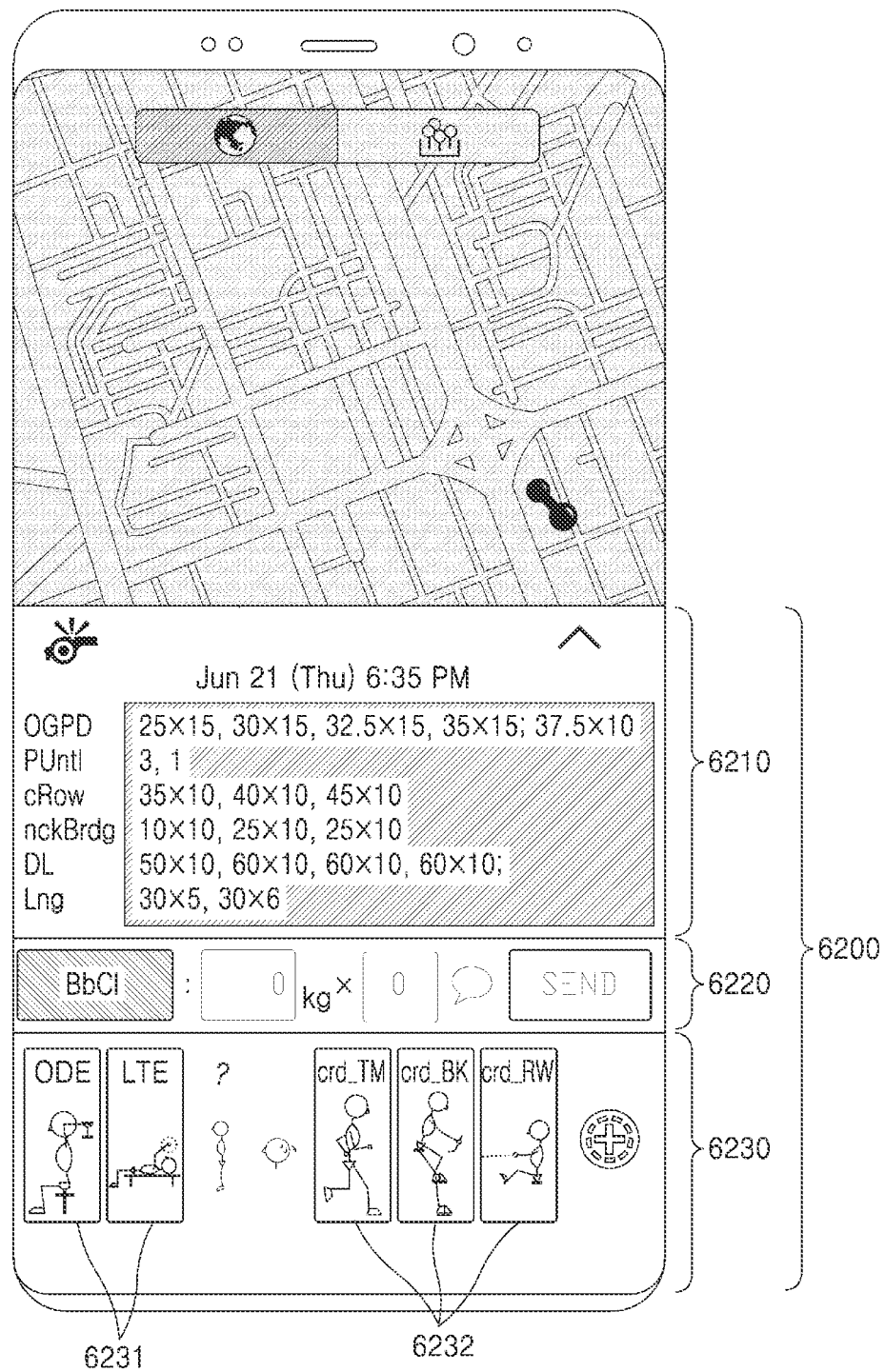
FIGS. 93 to 97 are views illustrating an exercise log input area displayed on the user terminal of the exercise history management system according to an embodiment of the present disclosure.

As shown in FIG. 90, when the application is executed for the first time, exercised-part blanked categories 5931 are displayed. In this state, when an exercise is added to the corresponding part by pressing an add button 5932 on the right to switch to a user-preferred exercise setup page 6000 (see FIG. 91) and setting the user's preferred exercise, a mark "?" disappears as shown in FIG. 93, and the user-preferred exercise may be displayed in ways such as images and abbreviations on corresponding exercise name display portions 6231.

Here, the exercise log input area of FIG. 90 is different from the exercise log input area of FIG. 20 in that an aerobic exercise category 5933 is added, which will be mainly described below.

Figure 91:
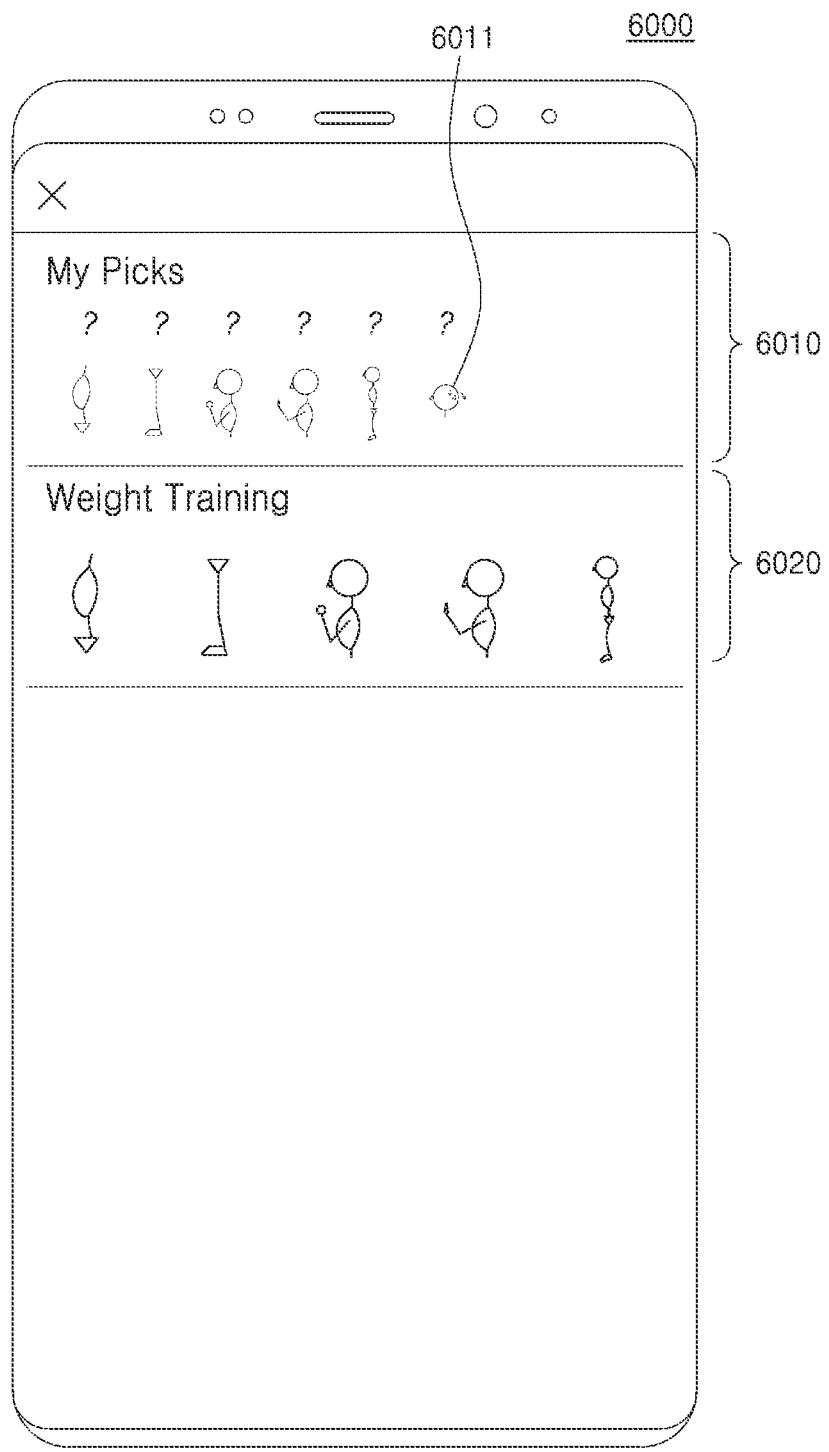
FIGS. 91 and 92 are views illustrating a user-preferred exercise setup page displayed on the user terminal of the exercise history management system according to an embodiment.

FIG. 91 is a view illustrating a user-preferred exercise setup page displayed on the user terminal of the exercise history management system of FIG. 90.

Referring to FIG. 91, the user-preferred exercise setup page 6000 includes a preferred exercise display portion 6010 and a preferred exercise selection portion 6020.

Here, FIG. 91 illustrates a screen (i.e., an initialized screen) at the time when the user-preferred exercise setup page 6000 is accessed for the first time after signing up for the service. Since preferred exercises are not yet set, a mark "?" is displayed on an upper end of each of first category icons of the preferred exercise display portion 6010.

Figure 92:
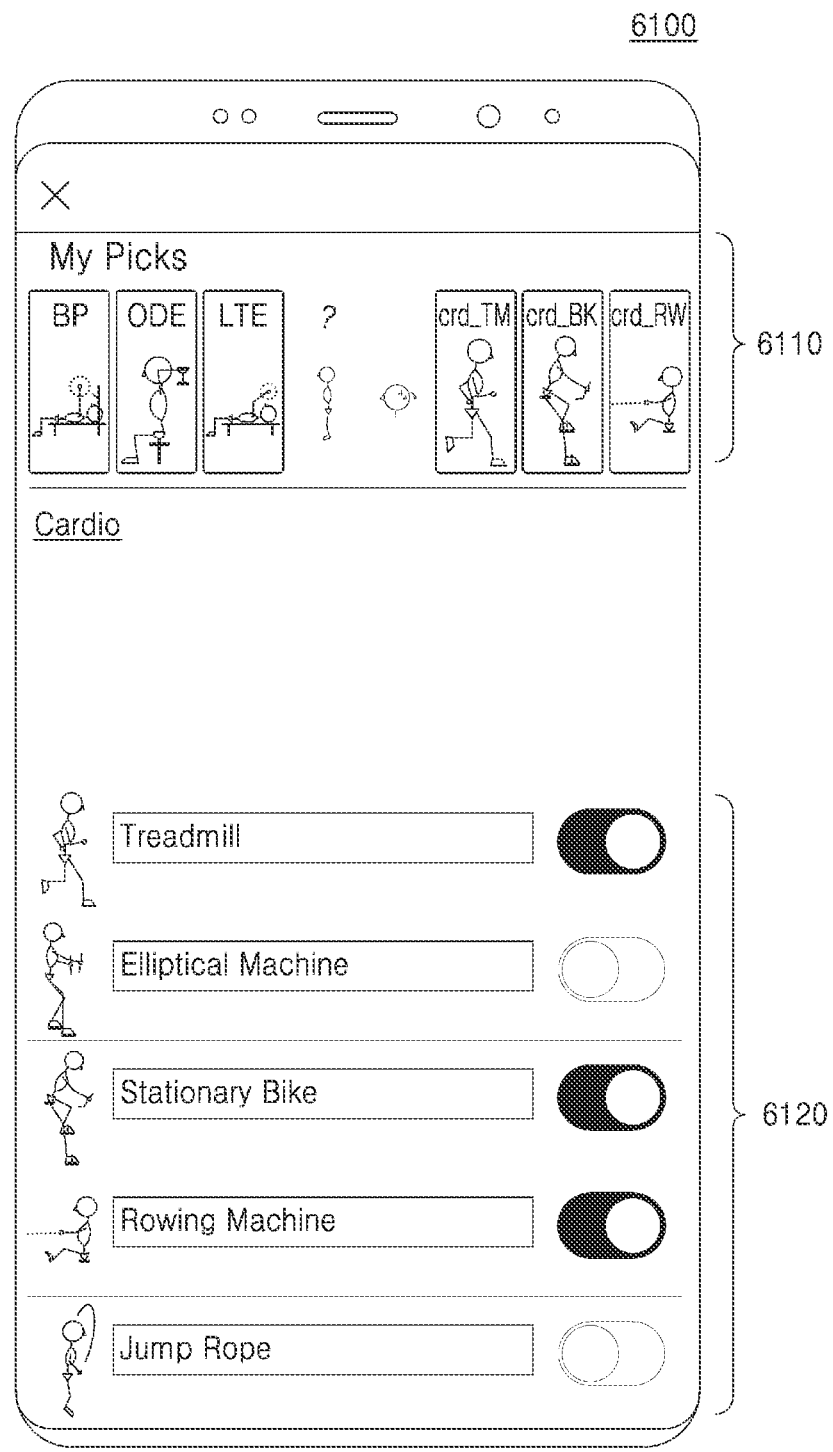

Here, when an aerobic exercise icon 6011 on the rightmost side of the preferred exercise display portion 6010 is selected, as shown in FIG. 92, exercises belonging to the aerobic exercise category are in a selectable state.

FIG. 92 is a view illustrating a process of setting a user-preferred exercise belonging to the aerobic exercise category on the user-preferred exercise setup page.

Referring to FIG. 92, a user-preferred exercise setup page 6100 includes a preferred exercise display portion 6110 and a preferred exercise selection portion 6120. In addition, one or more specific exercises are displayed on the preferred exercise selection portion 6120. Here, one or more specific exercises may be sequentially displayed in the second direction (longitudinal direction on the screen). Here, an on/off button of each of the specific exercises may be turned on to select the corresponding specific exercise.

FIG. 93 is a view illustrating an exercise log input area displayed on the user terminal of the exercise history management system of FIG. 90.

Referring to FIG. 93, an exercise log input area 6200 includes an exercise log display portion 6210, an exercise log input and transmission portion 6220, and an input value selection portion 6230.

Here, on the input value selection portion 6230, in addition to the one or more exercise name display portions 6231 related to Weight Training, one or more aerobic exercise name display portions 6232 may be displayed. Here, when one of the exercises displayed on the aerobic exercise name display portions 6232 is selected, the exercise log input and transmission portion 6220 is changed as shown in FIG. 94 and displayed.

Figure 94:
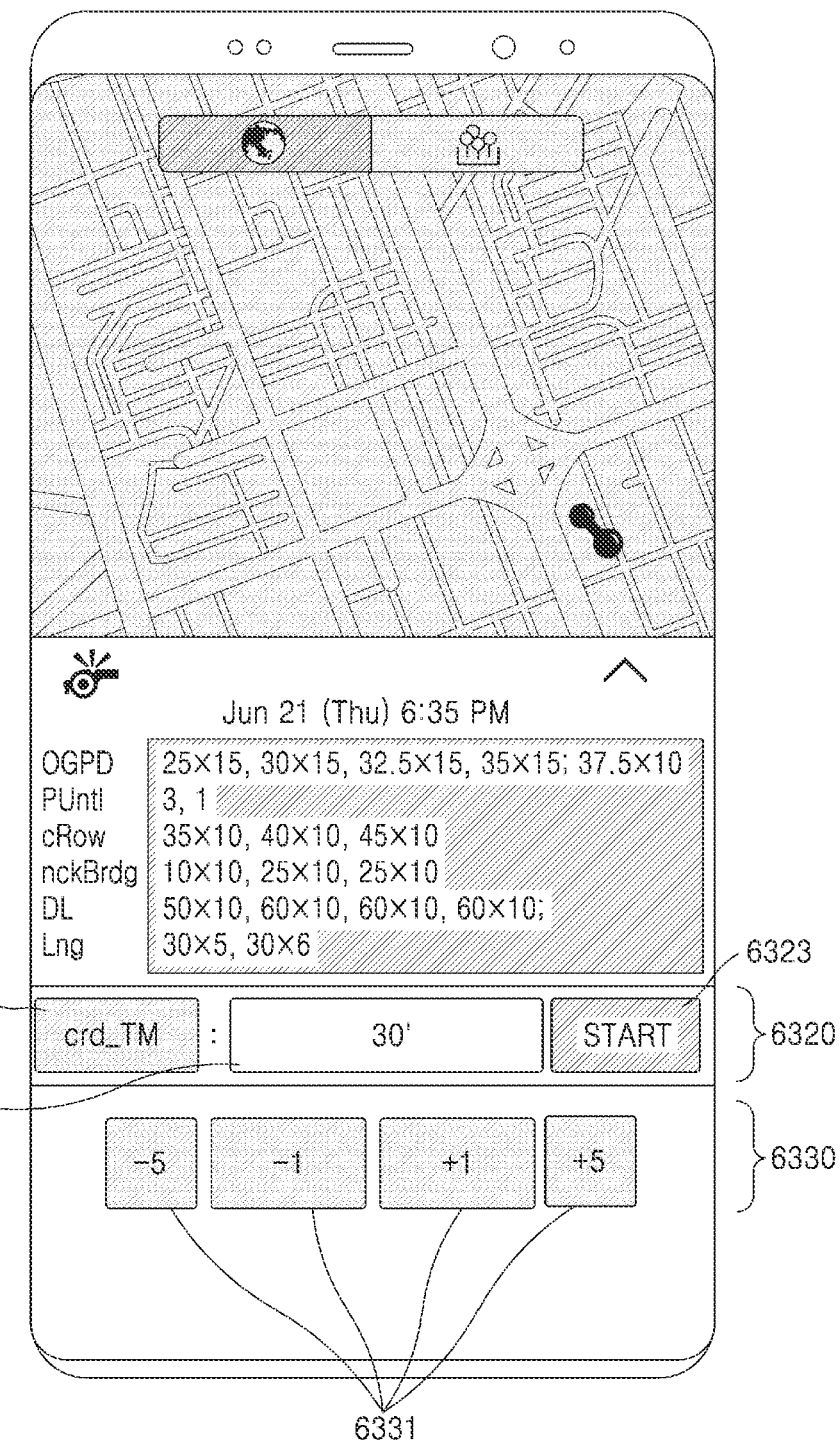

Referring to FIG. 94, when the respective aerobic exercise name display portions 6232 (see FIG. 93) are selected, a name or abbreviation of the corresponding exercise may be displayed on an exercise name input portion 6321 of an exercise log input and transmission portion 6320. In addition, a cardio box 6322 may be displayed on the exercise log input and transmission portion 6320. As shown in FIG. 94, in the previous step of starting the aerobic exercise, the cardio box 6322 may be a target time input portion to which a target time of the aerobic exercise is input. Although 30 minutes are input to the cardio box 6322 as a basic setting in FIG. 94, the basic setting may be changed according to user's exercise records or pre-setting. In addition, a transmission button of FIG. 93 is changed to a start button 6323 is displayed.

Meanwhile, when the cardio box 6322 is selected, an exercise duration adjusting portion 6331 is displayed on an input value selection portion 6330 below the cardio box 6322. The exercise duration adjusting portion 6331 may be selected to increase/decrease an exercise duration by five minutes/one minute. Here, a setting range of the target time may be limited. For example, the settings may be configured such that less than certain minutes or more than certain minutes may not be allowed. This may be for guiding an appropriate exercise amount to the user.

Figure 95:
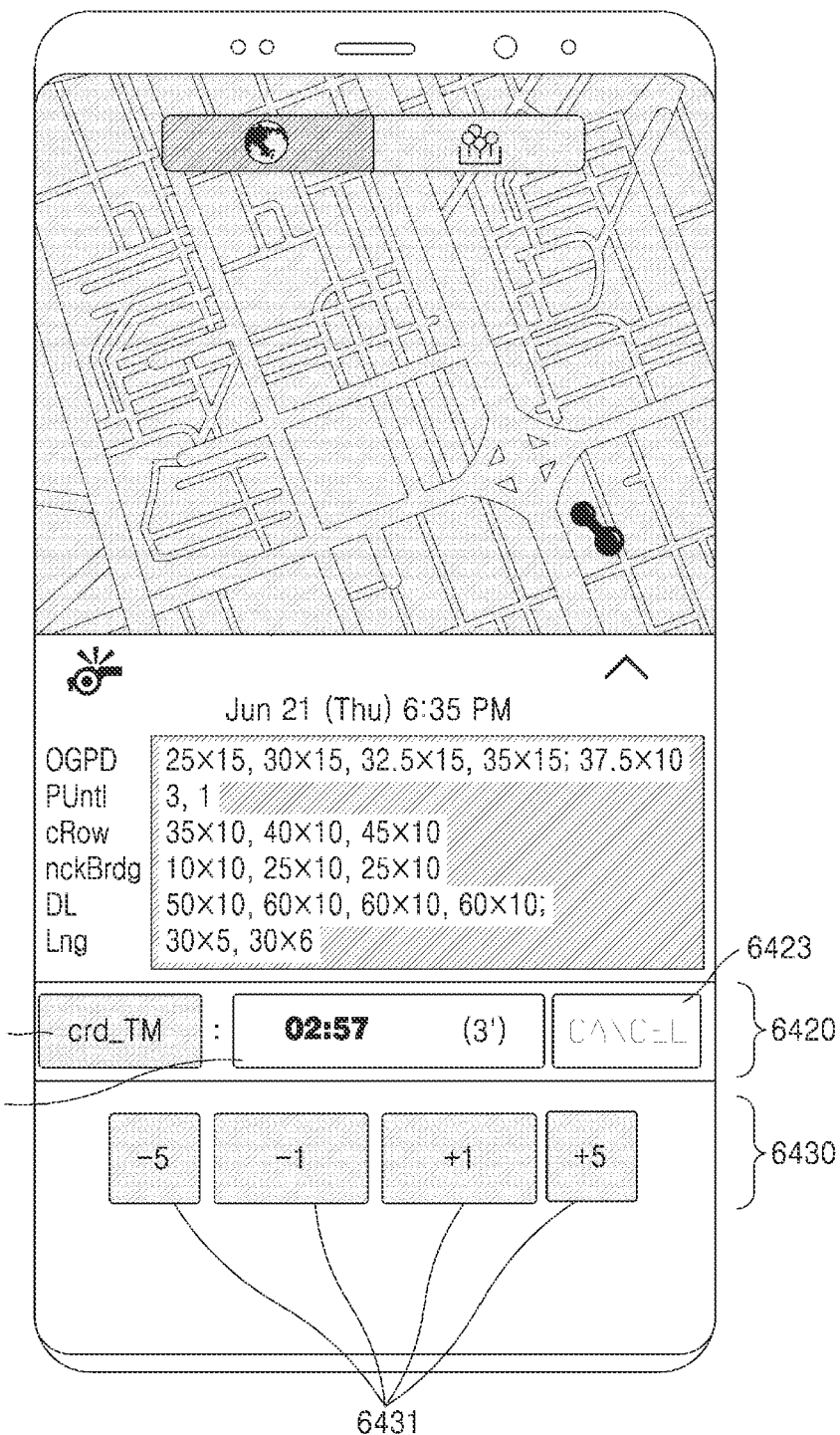

In this state, when the start button 6323 is pressed, the screen is changed as shown in FIG. 95, and a "remaining time" and a "target time" are displayed on a cardio box 6422. A situation of the target time of 3 minutes and the remaining time of 2 minutes and 57 seconds is displayed in FIG. 95. In addition, the start button 6323 (see FIG. 94) is changed to a cancel button 6423 and displayed.

In this state, when the cancel button 6423 is pressed, the corresponding aerobic exercise is canceled and may not remain in the user log.

Even after starting an exercise, the target time may be changed by using an exercise duration adjusting portion 6431 before the exercise ends. That is, the time may be increased or decreased. However, the target time may not be changed below the time at which the exercise is already performed.

Figure 96:
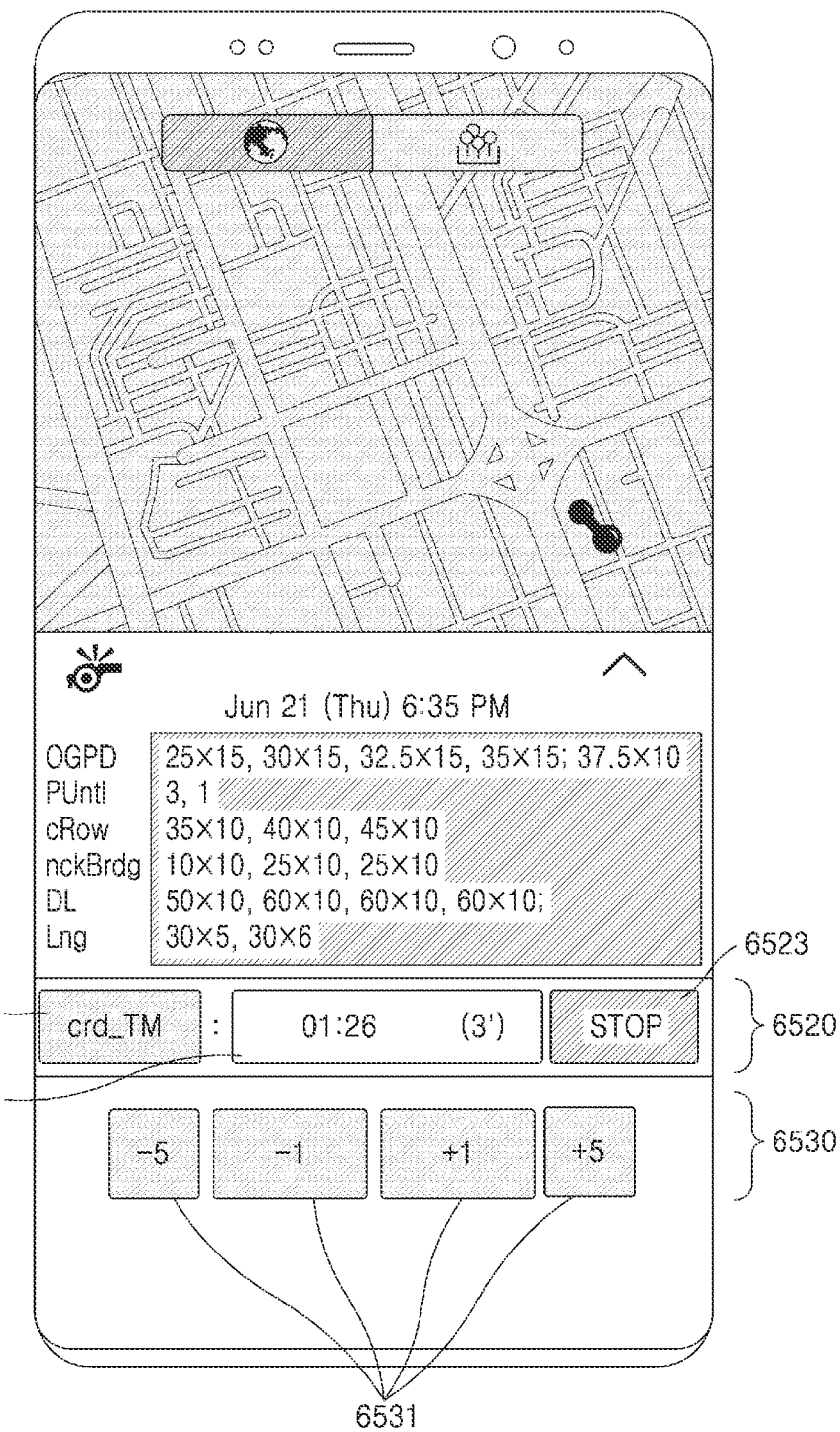

In this state, when a specific time elapses (for example, half of the target time elapses), the screen is changed to a screen shown in FIG. 96. That is, the cancel button 6423 (see FIG. 95) is changed to a stop button 6523, which is then displayed.

In addition, when half of the target time elapses as described above, the target time is input to the exercise log display portion 1410 (see FIG. 15). That is, when the exercise is performed more than half of the target time, it is admitted that the exercise has been achieved. In this case, the target time is input to the exercise log display portion 1410 (see FIG. 15). Here, the "target time" may be a final set target time.

Here, when the stop button 6523 is pressed, the screen returns to the initial exercise screen (see FIG. 94), and in the exercise log display portion 1410 (see FIG. 15), the state in which the "target time" is input is modified to a state the time (not the target time) actually exercised by the user is allowed to be input.

Figure 97:
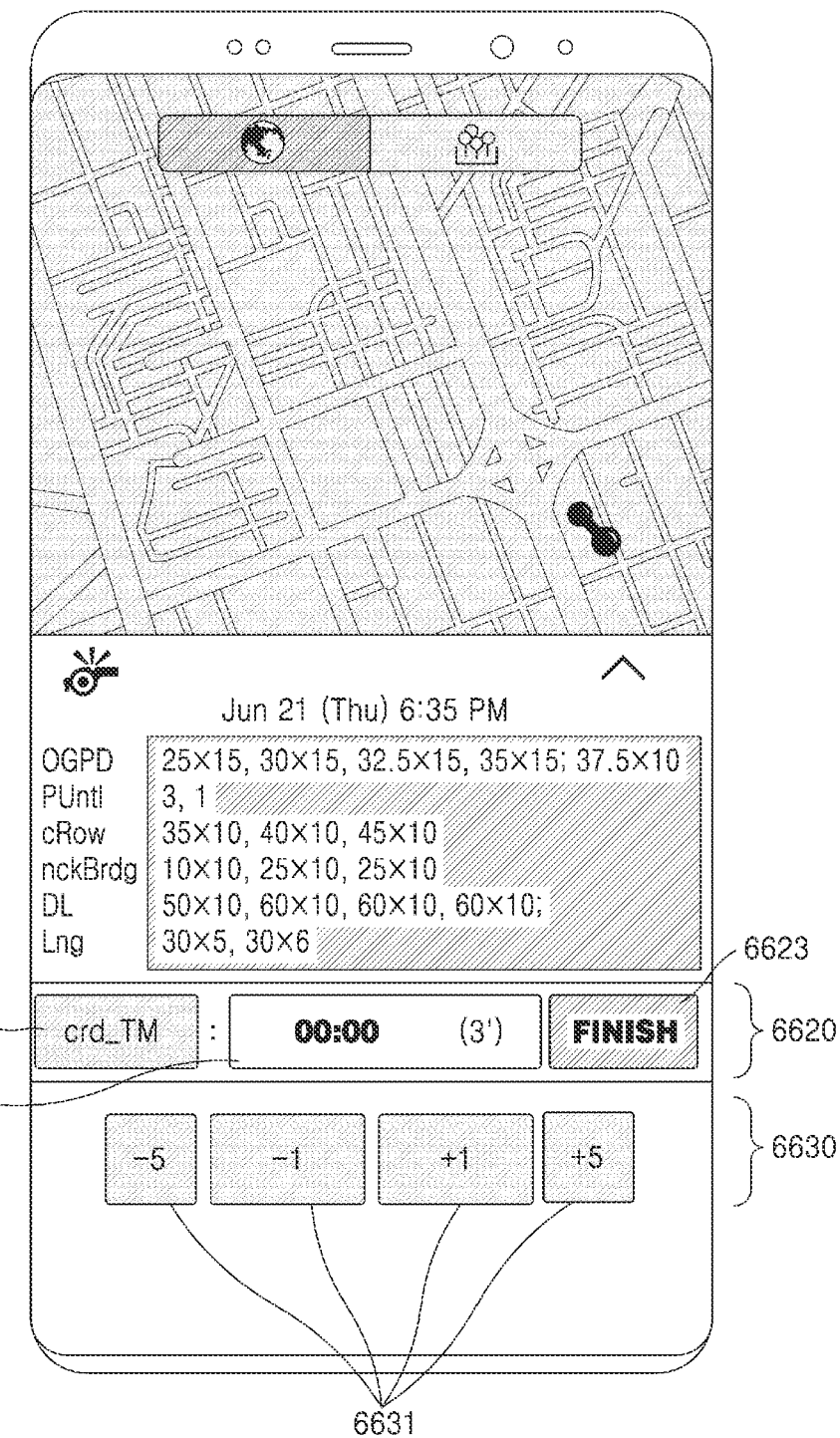

In this state, when it reaches the target time, the screen is changed to a screen shown in FIG. 97. That is, the stop button 6523 (see FIG. 95) is changed to an end button 6623, which is then displayed. At this time, the end button 6623 is displayed to blink, and along with this, through vibration or a notification sound, the user may be guided to press the end button 6623.

That is, the transmission portion 1425 (see FIG. 15) in Weight Training is changed to the start button 6323 (see FIG. 94), and at the beginning of the exercise, to the cancel button 6423 (see FIG. 95), after the aerobic exercise has progressed to a certain extent, to the stop button 6523 (see FIG. 96), and once reached the target, to the end button 6623 (see FIG. 97). In this way, the user may intuitively grasp the current situation.

Figure 98:
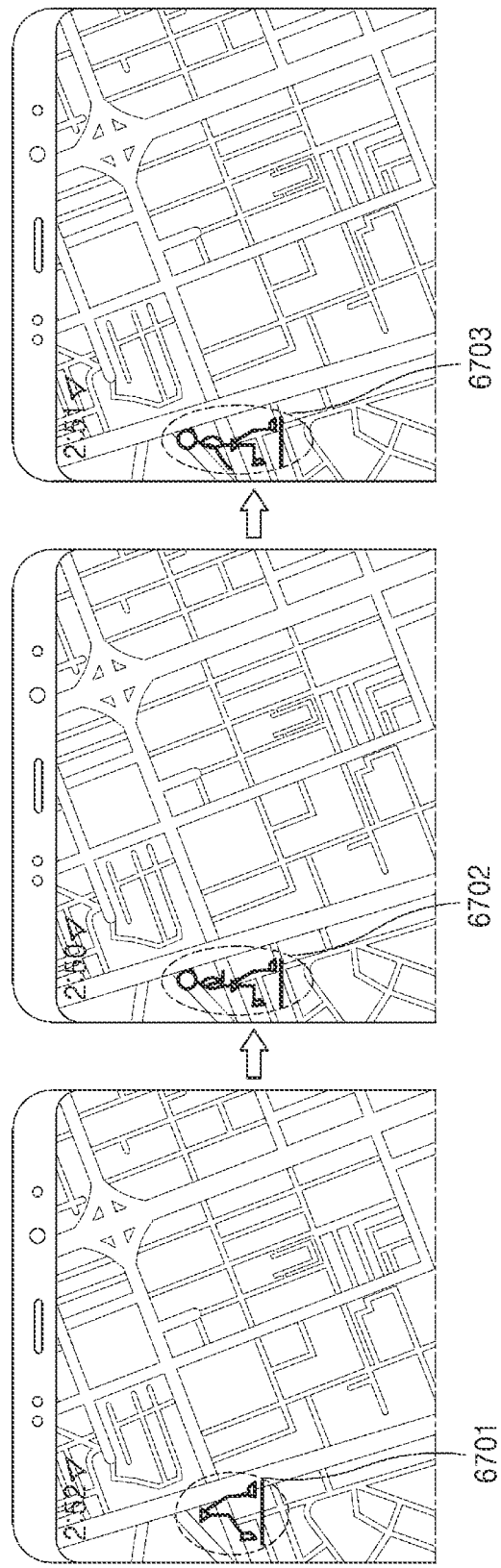
FIG. 98 is a view illustrating a map page of the exercise history management system according to an embodiment of the present disclosure.

Here, when the end button 6623 is pressed, the aerobic exercise ends. At this point, the end button 6623 is continuously displayed for five minutes, and when the end button 6623 is pressed, the aerobic exercise ends, the screen returns to an initial screen 6300 for the aerobic exercise, and a pose 6703 of achievement as shown in FIG. 98 may be displayed on the screen. As described above, the end button 6623 is displayed for a predetermined time, but a record remains in the log normally even when the end button 6623 is not pressed.

That is, when the user cancels the exercise, the exercise record is not left, when the user stops the exercise, an actual exercise duration is recorded, and when the user ends the exercise, the entire exercise duration is normally recorded.

Here, there may be differences in images displayed on each display area when it does not reach the target time, when it reaches the target time, and when the end button is pressed after reaching the target time. Here, when it reaches the target time means the situation of just running, that is, the situation in which it does not reach the target time.

That is, as shown in FIG. 98, 1) at first, when an aerobic exercise is started, a simply running image 6701 (in the case of running, the shape of legs) is displayed, and 2) when it reaches the target time, a cool-down image (6702) (image of sweating and running slowly) may be displayed. In addition, when the end button is pressed, the pose 6703 of inspiring may be displayed.

In addition, such a change may be reflected not only to the display area but also to the exercise display area 1221 (see FIG. 8) of the user who is exercising.

The particular implementations shown and described herein are illustrative examples of the embodiments and are not intended to otherwise limit the scope of the embodiments in any way. For the sake of brevity, conventional electronics, control systems, software development and other functional aspects of the systems may not be described in detail. Further, the connecting lines or connectors shown in the drawings are intended to represent example functional relationships and/or physical or logical couplings between the various elements. It should be noted that many alternative or additional functional relationships, physical connections, or logical connections may be present in a practical device. In addition, no item or element is essential to the practice of the present disclosure unless the element is specifically described as "essential" or "critical."

The use of the terms "a" and "an" and "the" and similar referents in the context of describing the present disclosure (especially in the context of the following claims) are to be construed to cover both the singular and the plural. Further, recitation of ranges of values herein is merely intended to serve as a shorthand method of referring individually to each separate value falling within the range, unless otherwise indicated herein, and each separate value is incorporated into the specification as if it were individually recited herein. Finally, operations of all methods described herein can be performed in any suitable order unless otherwise indicated herein or otherwise clearly contradicted by context. The present disclosure is not limited to the described order of the operations. The use of any and all examples, or exemplary terms (e.g., "such as") provided herein, is intended merely to better illuminate the present disclosure and does not pose a limitation on the scope of the present disclosure unless otherwise claimed. Also, numerous modifications and adaptations will be readily apparent to one of ordinary skill in the art without departing from the spirit and scope of the present disclosure.

Embodiments according to the present disclosure described above may be implemented in the form of program instructions that can be executed through various computer components and recorded on a computer-readable recording medium. The computer-readable recording medium may include program instructions, data files, data structures, and the like alone or in a combination thereof. The program instructions recorded on the computer-readable recording medium may be specially designed and configured for the present disclosure or may be available by those skilled in the art of computer software. Examples of the computer-readable recording medium include hardware devices specially configured to store and execute program instructions, including magnetic media such as a hard disk, a floppy disk, and a magnetic tape, optical media such as a compact disc read-only memory (CD-ROM) and a digital versatile disk (DVD), magneto-optical media such as a floptical disk, and solid state drives such as a read-only memory (ROM), a random access memory (RAM), and a flash memory. Examples of the program instructions include machine language codes generated by a compiler as well as high-level language codes which are executable by a computer using an interpreter or the like. The hardware devices may be modified with one or more software modules to perform processing in accordance with the present disclosure, and vice versa.

The present disclosure has been described above with specific details such as specific components, limited embodiments, and drawings. It should be understood, however, that there is no intent to limit the disclosure to the particular forms disclosed, but on the contrary, those skilled in the art to which this present disclosure pertains can make various modifications and changes from these descriptions.

Accordingly, it should be noted that the spirit of the present disclosure is not limited to the embodiments described above, and not only the claims to be described later, but also all ranges equivalent to or equivalently changed from the claims fall within the scope of the spirit of the present disclosure.

DESCRIPTION OF REFERENCE NUMERALS

100: Server
200: User terminal
300: Another User terminal

The invention claimed is:

1. A display control device comprising:
a network interface unit configured to provide a communication interface for a user to receive data including an exercise log of another different user;
an input/output unit configured to provide an input interface for receiving a user input signal from the user and an output interface for outputting a predetermined screen to the user; and
a display control unit configured to control a screen displayed on the input/output unit on the basis of the user input signal received by the input/output unit,
wherein the display control unit is further configured to control the screen displayed on the input/output unit such that an exercise motion of an exercise associated with the received exercise log is displayed on the input/output unit, and
wherein the display control unit is further configured to control the screen displayed on the input/output unit such that the exercise motion of the different user is expressed as a moving image of a drawing of a person composed of at least one of lines, curves, or dots, the moving image indicating a type of the exercise performed by the different user,
wherein the screen comprises an exercise log input area, wherein the exercise log input area comprises an exercise log display portion, wherein the exercise log display portion comprises a plurality of exercise log-by-date display portions each including a plurality of individual exercise log display portions respectively corresponding to a plurality of individual exercises,
wherein each of the plurality of individual exercise log display portions comprises one or more exercise records of the respective individual exercise, wherein the display control unit is further configured to display each of the plurality of individual exercise log display portions on a single row, and wherein, in response to an individual exercise log display portion of the plurality of individual exercise log display portions being selected, the display control unit is further configured to expand the selected individual exercise log display portion downward in a drop-down screen and display the expanded individual exercise log display portion such that each of the one or more exercise records of the selected individual exercise is displayed on a single row.

2. The display control device of claim 1, wherein the exercise log includes one or more pieces of information among an exercise name, an exercise weight, an exercise count, or an exercise duration of the exercise.

3. The display control device of claim 2, wherein the display control unit is further configured to control the screen displayed on the input/output unit such that the exercise motion is displayed together with at least one of the exercise count or the exercise duration.

4. The display control device of claim 3, wherein the display control unit is configured to control the screen such that an exercise log input area for receiving the exercise log is displayed on the input/output unit.

5. The display control device of claim 4,
wherein, in the exercise log input area, the display control unit is configured to control the screen such that an exercise log input and transmission portion is displayed, and
wherein the exercise log input and transmission portion includes some of an exercise name input portion for receiving the exercise name, whose exercise log is to be recorded, an exercise weight input portion for receiving the exercise weight, and an exercise count input portion for receiving the exercise count.

6. The display control device of claim 5, wherein the display control unit is configured to control the screen such that:
in the exercise log input area, an input value selection portion for displaying input values, which change as input items of the exercise log input and transmission portion are changed, is further displayed.

7. The display control device of claim 6, wherein the display control unit is configured to control the screen such that:
when the exercise name input portion is selected from the exercise log input and transmission portion through the input/output unit, an exercise name display portion is displayed on the input value selection portion,
when the exercise weight input portion is selected from the exercise log input and transmission portion through the input/output unit, an exercise weight display portion is displayed on the input value selection portion, and
when the exercise count input portion is selected from the exercise log input and transmission portion through the input/output unit, an exercise count display portion is displayed on the input value selection portion.

8. The display control device of claim 6, wherein the display control unit is configured to control the screen such that:
when the exercise weight input portion is selected from the exercise log input and transmission portion through the input/output unit,
the exercise weight input portion is initialized to display "0" while an exercise weight display portion is displayed on the input value selection portion.

9. The display control device of claim 6, wherein the display control unit is configured to control the screen such that:
when the exercise count input portion is selected from the exercise log input and transmission portion through the input/output unit,
a count/duration selection portion from which a count or duration is selected depending on whether the exercise name is a counting exercise or a duration exercise that maintains the same posture is further displayed on the input value selection portion.

10. The display control device of claim 6, wherein the display control unit is configured to control the screen such that a tough set input portion for recording a tough set that the user is able to complete with maximal or near-maximal effort is further displayed on the input value selection portion.

11. The display control device of claim 5, wherein the display control unit is configured to control the screen such that:
a transmission portion used for transmitting an input value to the outside is further displayed on the exercise log input and transmission portion, and
the transmission portion is activated when a valid count is input to the exercise count input portion through the input/output unit.

12. The display control device of claim 1, wherein the display control unit is configured to control the screen such that a user preferred exercise pool page for setting a user's preferred exercise is displayed on the input/output unit.

13. The display control device of claim 12,
wherein the display control unit is configured to control the screen such that a preferred exercise selection portion is displayed on the user preferred exercise pool page, and
wherein the preferred exercise selection portion includes at least some of an exercise name display portion for displaying a name of the exercise, a first category selection portion for displaying a plurality of first category icons, a second category selection portion for displaying a plurality of second category icons, and a specific exercise selection portion for displaying a plurality of specific exercise icons.

14. The display control device of claim 13, wherein the display control unit is configured to control the screen such that:
when one of the plurality of first category icons displayed on the first category selection portion is selected through the input/output unit,
a plurality of second category icons belonging to the selected first category are displayed on the second category selection portion.

15. The display control device of claim 14, wherein the display control unit is configured to control the screen such that:
when one of the plurality of second category icons displayed on the second category selection portion is selected through the input/output unit,
a plurality of specific exercise icons belonging to the selected second category are displayed on the specific exercise selection portion.

16. The display control device of claim 15, wherein the display control unit is configured to control the screen such that:
when one of the plurality of specific exercise icons displayed on the specific exercise selection portion is selected through the input/output unit, detailed information about the selected specific exercise is further displayed on the specific exercise selection portion.

17. The display control device of claim 16, wherein the display control unit is configured to control the screen such that:
a preferred exercise display portion is further displayed on the user preferred exercise pool page,
the plurality of first category icons are displayed on the preferred exercise display portion, and
when one of the plurality of specific exercise icons displayed on the specific exercise selection portion is selected through the input/output unit, the selected specific exercise icon is further displayed on one side of each of the first category icons of the preferred exercise display portion.

18. The display control device of claim 13, wherein the display control unit is configured to control the screen such that the first category icons and the second category icons are displayed along a first direction, and the specific exercise icons are displayed along a second direction different from the first direction.

19. The display control device of claim 13, wherein the display control unit is configured to control the screen such that:
a preferred exercise display portion is further displayed on the user preferred exercise pool page,
a plurality of first category icons are displayed on the preferred exercise display portion, and
a specific exercise icon selected from the corresponding first category is further displayed on one side of each of the first category icons.

20. A display control method comprising:
receiving, at a display control device of a user, data including an exercise log of another different user through a network interface unit of the display control device;
displaying an exercise motion of an exercise associated with the received exercise log on an input/output unit of the display control device by a display control unit of the display control device; and
controlling a screen displayed on the input/output unit such that the exercise motion of the different user is expressed as a moving image of a drawing of a person composed of at least one of lines, curves, or dots, the moving image indicating a type of the exercise performed by the different user,
wherein the screen comprises an exercise log input area, wherein the exercise log input area comprises an exercise log display portion, and wherein the exercise log display portion comprises a plurality of exercise log-by-date display portions each including a plurality of individual exercise log display portions,
the method further comprising:
displaying, by the display control unit, the plurality of exercise log-by-date display portions each including the plurality of individual exercise log display portions respectively corresponding to a plurality of individual exercises, wherein each of the plurality of individual exercise log display portions comprises one or more exercise records of the respective individual exercise;
displaying, by the display control unit, each of the plurality of individual exercise log display portions on a single row, and
in response to an individual exercise log display portion of the plurality of individual exercise log display portions being selected, expanding, by the display control unit, the selected individual exercise log display portion downward in a drop-down screen and displaying the expanded individual exercise log display portion such that each of the one or more exercise records of the selected individual exercise is displayed on a single row.

21. The display control method of claim 20, wherein the exercise log includes one or more pieces of information among an exercise name, an exercise weight, an exercise count, and an exercise duration of the exercise.

22. The display control method of claim 21, wherein the exercise motion is displayed on the input/output unit by the display control unit together with at least one of the exercise count or the exercise duration.

23. The display control method of claim 22, further comprising displaying, by the display control unit, an exercise log input area for receiving the exercise log on the input/output unit.

24. The display control method of claim 23,
wherein in the exercise log input area, an exercise log input and transmission portion is displayed, and
wherein the exercise log input and transmission portion includes two or more of an exercise name input portion for receiving the exercise name, whose exercise log is to be recorded, an exercise weight input portion for receiving the exercise weight, and an exercise count input portion for receiving the exercise count.

25. The display control method of claim 24, wherein:
in the exercise log input area,
an input value selection portion for displaying input values, which change as input items of the exercise log input and transmission portion are changed, is further displayed.

26. The display control method of claim 25, wherein:
when the exercise name input portion is selected from the exercise log input and transmission portion through the input/output unit, an exercise name display portion is displayed on the input value selection portion,
when the exercise weight input portion is selected from the exercise log input and transmission portion through the input/output unit, an exercise weight display portion is displayed on the input value selection portion, and
when the exercise count input portion is selected from the exercise log input and transmission portion through the input/output unit, an exercise count display portion is displayed on the input value selection portion.

27. The display control method of claim 25, wherein:
when the exercise weight input portion is selected from the exercise log input and transmission portion through the input/output unit,
the exercise weight input portion is initialized to display "0" while an exercise weight display portion is displayed on the input value selection portion.

28. The display control method of claim 25, wherein:
when the exercise name input portion is selected from the exercise log input and transmission portion through the input/output unit,
a count/duration selection portion for selecting a count or duration depending on whether the exercise name is a counting exercise or a duration exercise that maintains the same posture is further displayed on the input value selection portion.

29. The display control method of claim 25, wherein a tough set input portion through which a tough set that the user is able to complete with maximal or near-maximal effort is recorded is further displayed on the input value selection portion.

30. The display control method of claim 24, wherein:
a transmission portion used for transmitting an input value to the outside is further displayed on the exercise log input and transmission portion, and
the transmission portion is activated when a valid count is input to the exercise count input portion through the input/output unit.

31. The display control method of claim 20, wherein a user preferred exercise pool page for setting a user's preferred exercise is displayed on the input/output unit by the display control unit.

32. The display control method of claim 31, wherein:
a preferred exercise selection portion is displayed on the user preferred exercise pool page, and
the preferred exercise selection portion includes at least some of an exercise name display portion for displaying a name of the exercise, a first category selection portion for displaying a plurality of first category icons, a second category selection portion for displaying a plurality of second category icons, and a specific exercise selection portion for displaying a plurality of specific exercise icons.

33. The display control method of claim 32, wherein:
when one of the plurality of first category icons displayed on the first category selection portion is selected through the input/output unit,
a plurality of second category icons belonging to the selected first category are displayed on the second category selection portion.

34. The display control method of claim 33, wherein:
when one of the plurality of second category icons displayed on the second category selection portion is selected through the input/output unit,
a plurality of specific exercise icons belonging to the selected second category are displayed on the specific exercise selection portion.

35. The display control method of claim 34, wherein:
when one of the plurality of specific exercise icons displayed on the specific exercise selection portion is selected through the input/output unit,
detailed information about the selected specific exercise is further displayed on the specific exercise selection portion.

36. The display control method of claim 35, wherein:
a preferred exercise display portion is further displayed on the user preferred exercise pool page,
the plurality of first category icons are displayed on the preferred exercise display portion, and
when one of the plurality of specific exercise icons displayed on the specific exercise selection portion is selected through the input/output unit, the selected specific exercise icon is further displayed on one side of each of the first category icons of the preferred exercise display portion.

37. The display control method of claim 32, wherein the first category icons and the second category icons are displayed along a first direction, and the specific exercise icons are displayed along a second direction different from the first direction.

38. The display control method of claim 32, wherein:
a preferred exercise display portion is further displayed on the user preferred exercise pool page,
a plurality of first category icons are displayed on the preferred exercise display portion, and
a specific exercise icon selected from the corresponding first category is further displayed on one side of each of the first category icons.

39. A non-transitory computer readable medium storing instructions to perform a display control method, the method comprising:
receiving, at a display control device of a user, data including an exercise log of another different user through a network interface unit of the display control device;
displaying an exercise motion of an exercise associated with the received exercise log on an input/output unit of the display control device by a display control unit of the display control device; and
controlling a screen displayed on the input/output unit such that the exercise motion of the different user is expressed as a moving image of a drawing of a person composed of at least one of lines, curves, or dots, the moving image indicating a type of the exercise performed by the different user,
wherein the screen comprises an exercise log input area, wherein the exercise log input area comprises an exercise log display portion, and wherein the exercise log display portion comprises a plurality of exercise log-by-date display portions each including a plurality of individual exercise log display portions,
the method further comprising:
displaying, by the display control unit, the plurality of exercise log-by-date display portions each including the plurality of individual exercise log display portions respectively corresponding to a plurality of individual exercises, wherein each of the plurality of individual exercise log display portions comprises one or more exercise records of the respective individual exercise;
displaying, by the display control unit, each of the plurality of individual exercise log display portions on a single row, and
in response to an individual exercise log display portion of the plurality of individual exercise log display portions being selected, expanding, by the display control unit, the selected individual exercise log display portion downward in a drop-down screen and displaying the expanded individual exercise log display portion such that each of the one or more exercise records of the selected individual exercise is displayed on a single row.

40. The device of claim 1, wherein at least one of the one or more records of the selected individual exercise includes a weight and a number of the individual exercise.

41. The device of claim 1, wherein the screen further comprises a pool page, wherein the pool page comprises a user's-in-exercise-display area and a user's-not-in-exercise display area,
wherein the user's-in-exercise-display area is configured to display information on different users who are currently exercising and has been pooled by a selected user,
wherein the user's-not-in-exercise display area is configured to display information on other different users who are not currently exercising and has been pooled by the selected user, wherein the user's-not-in-exercise display areas comprises a time machine icon, and
wherein, in response to the time machine icon being selected, the user's-in-exercise display area is configured to display the most recent exercise of another different user exercising.

* * * * *